(12) United States Patent
Hardenbol et al.

(10) Patent No.: US 10,221,436 B2
(45) Date of Patent: Mar. 5, 2019

(54) PROCESSES AND SYSTEMS FOR PREPARATION OF NUCLEIC ACID SEQUENCING LIBRARIES AND LIBRARIES PREPARED USING SAME

(71) Applicant: 10X Genomics, Inc., Pleasanton, CA (US)

(72) Inventors: Paul Hardenbol, San Francisco, CA (US); Pranav Patel, Fremont, CA (US); Benjamin Hindson, Pleasanton, CA (US); Paul William Wyatt, Pleasanton, CA (US); Keith Bjornson, Fremont, CA (US); Indira Wu, San Carlos, CA (US); Kamila Belhocine, Fremont, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 310 days.

(21) Appl. No.: 14/990,276

(22) Filed: Jan. 7, 2016

(65) Prior Publication Data
US 2016/0257984 A1 Sep. 8, 2016

Related U.S. Application Data

(60) Provisional application No. 62/102,420, filed on Jan. 12, 2015, provisional application No. 62/262,769, filed on Dec. 3, 2015.

(51) Int. Cl.
*C40B 20/04* (2006.01)
*C12P 19/34* (2006.01)
*C12Q 1/6806* (2018.01)

(52) U.S. Cl.
CPC ............ *C12P 19/34* (2013.01); *C12Q 1/6806* (2013.01); *C40B 20/04* (2013.01); *B01J 2219/00547* (2013.01); *B01J 2219/00572* (2013.01); *B01J 2219/00722* (2013.01)

(58) Field of Classification Search
None
See application file for complete search history.

(56) References Cited

U.S. PATENT DOCUMENTS

| | | |
|---|---|---|
| 2,797,149 A | 6/1957 | Skeggs |
| 3,047,367 A | 7/1962 | Kessler |
| 3,479,141 A | 11/1969 | Smythe et al. |
| 4,124,638 A | 11/1978 | Hansen |
| 4,253,846 A | 3/1981 | Smythe et al. |
| 4,582,802 A | 4/1986 | Zimmerman et al. |
| 5,137,829 A | 8/1992 | Nag et al. |
| 5,149,625 A | 9/1992 | Church et al. |
| 5,185,099 A | 2/1993 | Delpuech et al. |
| 5,202,231 A | 4/1993 | Drmanac et al. |
| 5,270,183 A | 12/1993 | Corbett et al. |
| 5,413,924 A | 5/1995 | Kosak et al. |
| 5,418,149 A | 5/1995 | Gelfand et al. |
| 5,436,130 A | 7/1995 | Mathies et al. |
| 5,489,523 A | 2/1996 | Mathur |
| 5,512,131 A | 4/1996 | Kumar et al. |
| 5,558,071 A | 9/1996 | Ward et al. |
| 5,585,069 A | 12/1996 | Zanzucchi et al. |
| 5,587,128 A | 12/1996 | Wilding et al. |
| 5,605,793 A | 2/1997 | Stemmer |
| 5,618,711 A | 4/1997 | Gelfand et al. |
| 5,695,940 A | 12/1997 | Drmanac et al. |
| 5,700,642 A | 12/1997 | Monforte et al. |
| 5,705,628 A | 1/1998 | Hawkins |
| 5,708,153 A | 1/1998 | Dower et al. |
| 5,736,330 A | 4/1998 | Fulton |
| 5,739,036 A | 4/1998 | Parris |
| 5,744,311 A | 4/1998 | Fraiser et al. |
| 5,756,334 A | 5/1998 | Perler et al. |
| 5,834,197 A | 11/1998 | Parton |
| 5,842,787 A | 12/1998 | Kopf-Sill et al. |
| 5,846,719 A | 12/1998 | Brenner et al. |
| 5,846,727 A | 12/1998 | Soper et al. |
| 5,851,769 A | 12/1998 | Gray et al. |
| 5,856,174 A | 1/1999 | Lipshutz et al. |
| 5,872,010 A | 2/1999 | Karger et al. |

(Continued)

FOREIGN PATENT DOCUMENTS

| | | |
|---|---|---|
| EP | 0249007 A2 | 12/1987 |
| EP | 0271281 A2 | 6/1988 |

(Continued)

OTHER PUBLICATIONS

10X Genomics. 10x Genomics Chromium™ Single Cell 3' Solution Utilized for Perturb-seq Approach. Press Release. Dec. 19, 2016. Retrieved from https://www.10xgenomics.com/news/10x-genomics-chromium-single-cell-3-solution-utilized-perturb-seq-approach/.

Adamson, et al. A Multiplexed Single-Cell CRISPR Screening Platform Enables Systematic Dissection of the Unfolded Protein Response. Cell. Dec. 15, 2016;167(7):1867-1882.e21. doi: 10.1016/j.cell.2016.11.048.

Adey, et al. Rapid, low-input, low-bias construction of shotgun fragment libraries by high-density in vitro transposition. Genome Biology 11:R119 (2010).

(Continued)

*Primary Examiner* — Christopher M Gross
(74) *Attorney, Agent, or Firm* — Wilson Sonsini Goodrich & Rosati

(57) ABSTRACT

This disclosure provides methods for preparing a sequencing library including the steps of providing a template nucleic acid sequence, dNTPs, dUTP, a primer, a polymerase, a dUTP excising enzyme, and a plurality of beads including oligonucleotide adapter sequence segments; amplifying the template nucleic acid with the polymerase, dNTPs, dUTP and random hexamer to provide a complementary nucleic acid sequence including occasional dUTPs; and excising the incorporated dUTPs with the dUTP excising enzyme to provide nicks in the complementary nucleic acid sequence to provide a sequencing library.

37 Claims, 33 Drawing Sheets
Specification includes a Sequence Listing.

(56) References Cited

U.S. PATENT DOCUMENTS

| | | |
|---|---|---|
| 5,897,783 A | 4/1999 | Howe et al. |
| 5,900,481 A | 5/1999 | Lough et al. |
| 5,942,609 A | 8/1999 | Hunkapiller et al. |
| 5,958,703 A | 9/1999 | Dower et al. |
| 5,965,443 A | 10/1999 | Reznikoff et al. |
| 5,994,056 A | 11/1999 | Higuchi |
| 5,997,636 A | 12/1999 | Gamarnik et al. |
| 6,033,880 A | 3/2000 | Haff et al. |
| 6,046,003 A | 4/2000 | Mandecki |
| 6,051,377 A | 4/2000 | Mandecki |
| 6,057,107 A | 5/2000 | Fulton |
| 6,057,149 A | 5/2000 | Burns et al. |
| 6,103,537 A | 8/2000 | Ullman et al. |
| 6,133,436 A | 10/2000 | Koester et al. |
| 6,143,496 A | 11/2000 | Brown et al. |
| 6,159,717 A | 12/2000 | Savakis et al. |
| 6,171,850 B1 | 1/2001 | Nagle et al. |
| 6,172,218 B1 | 1/2001 | Brenner |
| 6,207,384 B1 | 3/2001 | Mekalanos et al. |
| 6,258,571 B1 | 7/2001 | Chumakov et al. |
| 6,265,552 B1 | 7/2001 | Schatz |
| 6,291,243 B1 | 9/2001 | Fogarty et al. |
| 6,294,385 B1 | 9/2001 | Goryshin et al. |
| 6,296,020 B1 | 10/2001 | McNeely et al. |
| 6,297,006 B1 | 10/2001 | Drmanac et al. |
| 6,297,017 B1 | 10/2001 | Schmidt et al. |
| 6,303,343 B1 | 10/2001 | Kopf-Sill |
| 6,306,590 B1 | 10/2001 | Mehta et al. |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,432,290 B1 | 8/2002 | Harrison et al. |
| 6,432,360 B1 | 8/2002 | Church |
| 6,485,944 B1 | 11/2002 | Church et al. |
| 6,492,118 B1 | 12/2002 | Abrams et al. |
| 6,511,803 B1 | 1/2003 | Church et al. |
| 6,524,456 B1 | 2/2003 | Ramsey et al. |
| 6,569,631 B1 | 5/2003 | Pantoliano et al. |
| 6,579,851 B2 | 6/2003 | Goeke et al. |
| 6,586,176 B1 | 7/2003 | Trnovsky et al. |
| 6,593,113 B1 | 7/2003 | Tenkanen et al. |
| 6,613,752 B2 | 9/2003 | Kay et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,723,513 B2 | 4/2004 | Lexow |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,880,576 B2 | 4/2005 | Karp et al. |
| 6,884,788 B2 | 4/2005 | Bulpitt et al. |
| 6,913,935 B1 | 7/2005 | Thomas |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,138,267 B1 | 11/2006 | Jendrisak et al. |
| 7,211,654 B2 | 5/2007 | Gao et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,297,485 B2 | 11/2007 | Bornarth et al. |
| 7,316,903 B2 | 1/2008 | Yanagihara et al. |
| 7,323,305 B2 | 1/2008 | Leamon et al. |
| 7,329,493 B2 | 2/2008 | Chou et al. |
| 7,425,431 B2 | 9/2008 | Church et al. |
| 7,536,928 B2 | 5/2009 | Kazuno |
| 7,544,473 B2 | 6/2009 | Brenner |
| 7,604,938 B2 | 10/2009 | Takahashi et al. |
| 7,608,434 B2 | 10/2009 | Reznikoff et al. |
| 7,608,451 B2 | 10/2009 | Cooper et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,700,325 B2 | 4/2010 | Cantor et al. |
| 7,708,949 B2 | 5/2010 | Stone et al. |
| 7,709,197 B2 | 5/2010 | Drmanac |
| 7,745,178 B2 | 6/2010 | Dong |
| 7,745,218 B2 | 6/2010 | Kim et al. |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,947,477 B2 | 5/2011 | Schroeder et al. |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,008,018 B2 | 8/2011 | Quake et al. |
| 8,053,192 B2 | 11/2011 | Bignell et al. |
| 8,067,159 B2 | 11/2011 | Brown et al. |
| 8,101,346 B2 | 1/2012 | Takahama |
| 8,124,404 B2 | 2/2012 | Alphey |
| 8,133,719 B2 | 3/2012 | Drmanac et al. |
| 8,137,563 B2 | 3/2012 | Ma et al. |
| 8,168,385 B2 | 5/2012 | Brenner |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,318,460 B2 | 11/2012 | Cantor et al. |
| 8,329,407 B2 | 12/2012 | Ismagilov et al. |
| 8,337,778 B2 | 12/2012 | Stone et al. |
| 8,361,299 B2 | 1/2013 | Sabin et al. |
| 8,420,386 B2 | 4/2013 | Ivics et al. |
| 8,461,129 B2 | 6/2013 | Bolduc et al. |
| 8,563,274 B2 | 10/2013 | Brenner et al. |
| 8,592,150 B2 | 11/2013 | Drmanac et al. |
| 8,598,328 B2 | 12/2013 | Koga et al. |
| 8,603,749 B2 | 12/2013 | Gillevet |
| 8,679,756 B1 | 3/2014 | Brenner et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagliov et al. |
| 8,829,171 B2 | 9/2014 | Steemers et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,927,218 B2 | 1/2015 | Forsyth |
| 8,986,286 B2 | 3/2015 | Tanghoj et al. |
| 9,005,935 B2 | 4/2015 | Belyaev |
| 9,012,390 B2 | 4/2015 | Holtze et al. |
| 9,017,948 B2 | 4/2015 | Agresti et al. |
| 9,029,083 B2 | 5/2015 | Griffiths et al. |
| 9,029,085 B2 | 5/2015 | Agresti et al. |
| 9,068,210 B2 | 6/2015 | Agresti et al. |
| 9,074,251 B2 | 7/2015 | Steemers et al. |
| 9,080,211 B2 | 7/2015 | Grunenwald et al. |
| 9,102,980 B2 | 8/2015 | Brenner et al. |
| 9,150,916 B2 | 10/2015 | Christen et al. |
| 9,175,295 B2 | 11/2015 | Kaminaka et al. |
| 9,238,671 B2 | 1/2016 | Goryshin et al. |
| 9,249,460 B2 | 2/2016 | Pushkarev et al. |
| 9,273,349 B2 | 3/2016 | Nguyen et al. |
| 9,290,808 B2 | 3/2016 | Fodor et al. |
| 9,328,382 B2 | 5/2016 | Drmanac et al. |
| 9,347,059 B2 | 5/2016 | Saxonov |
| 9,388,465 B2 | 7/2016 | Hindson et al. |
| 9,410,201 B2 | 8/2016 | Hindson et al. |

(56) References Cited

U.S. PATENT DOCUMENTS

| | | |
|---|---|---|
| 9,567,631 B2 | 2/2017 | Hindson et al. |
| 9,574,226 B2 | 2/2017 | Gormley et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,701,998 B2 | 7/2017 | Hindson et al. |
| 9,856,530 B2 | 1/2018 | Hindson et al. |
| 9,951,386 B2 | 4/2018 | Hindson et al. |
| 9,957,558 B2 | 5/2018 | Leamon et al. |
| 10,011,872 B1 | 7/2018 | Belgrader et al. |
| 10,137,449 B2 | 11/2018 | Bharadwaj et al. |
| 10,150,995 B1 | 12/2018 | Giresi et al. |
| 2001/0020588 A1 | 9/2001 | Adourian et al. |
| 2001/0036669 A1 | 11/2001 | Jedrzejewski et al. |
| 2001/0041357 A1 | 11/2001 | Fouillet et al. |
| 2001/0044109 A1 | 11/2001 | Mandecki |
| 2001/0048900 A1 | 12/2001 | Bardell et al. |
| 2002/0001856 A1 | 1/2002 | Chow et al. |
| 2002/0005354 A1 | 1/2002 | Spence et al. |
| 2002/0034737 A1 | 3/2002 | Drmanac |
| 2002/0043463 A1 | 4/2002 | Shenderov |
| 2002/0051971 A1 | 5/2002 | Stuelpnagel et al. |
| 2002/0051992 A1 | 5/2002 | Bridgham et al. |
| 2002/0058332 A1 | 5/2002 | Quake et al. |
| 2002/0068278 A1 | 6/2002 | Giese et al. |
| 2002/0089100 A1 | 7/2002 | Kawasaki |
| 2002/0092767 A1 | 7/2002 | Bjornson et al. |
| 2002/0113009 A1 | 8/2002 | O'Connor et al. |
| 2002/0119536 A1 | 8/2002 | Stern |
| 2002/0131147 A1 | 9/2002 | Paolini et al. |
| 2002/0160518 A1 | 10/2002 | Hayenga et al. |
| 2002/0164820 A1 | 11/2002 | Brown |
| 2002/0166582 A1 | 11/2002 | O'Connor et al. |
| 2002/0175079 A1 | 11/2002 | Christel et al. |
| 2002/0179849 A1 | 12/2002 | Maher et al. |
| 2003/0005967 A1 | 1/2003 | Karp |
| 2003/0007898 A1 | 1/2003 | Bohm et al. |
| 2003/0008285 A1 | 1/2003 | Fischer |
| 2003/0008323 A1 | 1/2003 | Ravkin et al. |
| 2003/0022231 A1 | 1/2003 | Wangh et al. |
| 2003/0027214 A1 | 2/2003 | Kamb |
| 2003/0027221 A1 | 2/2003 | Scott et al. |
| 2003/0028981 A1 | 2/2003 | Chandler et al. |
| 2003/0036206 A1 | 2/2003 | Chien et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0075446 A1 | 4/2003 | Culbertson et al. |
| 2003/0082587 A1 | 5/2003 | Seul et al. |
| 2003/0089605 A1 | 5/2003 | Timperman |
| 2003/0104466 A1 | 6/2003 | Knapp et al. |
| 2003/0108897 A1 | 6/2003 | Drmanac |
| 2003/0124509 A1 | 7/2003 | Kenis et al. |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0081962 A1 | 4/2004 | Chen et al. |
| 2004/0101880 A1 | 5/2004 | Rozwadowski et al. |
| 2004/0132122 A1 | 7/2004 | Banerjee et al. |
| 2004/0224331 A1 | 11/2004 | Cantor et al. |
| 2004/0258701 A1 | 12/2004 | Dominowski et al. |
| 2005/0019839 A1 | 1/2005 | Jespersen et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0272159 A1 | 12/2005 | Ismagilov et al. |
| 2005/0287572 A1 | 12/2005 | Mathies et al. |
| 2006/0002890 A1 | 1/2006 | Hersel et al. |
| 2006/0008799 A1 | 1/2006 | Cai et al. |
| 2006/0020371 A1 | 1/2006 | Ham et al. |
| 2006/0040382 A1 | 2/2006 | Heffron et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0177832 A1 | 8/2006 | Brenner |
| 2006/0177833 A1 | 8/2006 | Brenner |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0275782 A1 | 12/2006 | Gunderson et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0020640 A1 | 1/2007 | McCloskey et al. |
| 2007/0054119 A1 | 3/2007 | Garstecki et al. |
| 2007/0072208 A1 | 3/2007 | Drmanac |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0134277 A1 | 6/2007 | Chen et al. |
| 2007/0154903 A1 | 7/2007 | Marla et al. |
| 2007/0160503 A1 | 7/2007 | Sethu et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0207060 A1 | 9/2007 | Zou et al. |
| 2007/0228588 A1 | 10/2007 | Noritomi et al. |
| 2007/0231823 A1 | 10/2007 | McKernan et al. |
| 2007/0238113 A1 | 10/2007 | Kanda et al. |
| 2007/0259357 A1 | 11/2007 | Brenner |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0124726 A1 | 5/2008 | Monforte |
| 2008/0213766 A1 | 9/2008 | Brown et al. |
| 2008/0228268 A1 | 9/2008 | Shannon et al. |
| 2008/0241820 A1 | 10/2008 | Krutzik et al. |
| 2008/0242560 A1 | 10/2008 | Gunderson et al. |
| 2008/0268431 A1 | 10/2008 | Choy et al. |
| 2008/0268450 A1 | 10/2008 | Nam et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0048124 A1 | 2/2009 | Leamon et al. |
| 2009/0053169 A1 | 2/2009 | Castillo et al. |
| 2009/0068170 A1 | 3/2009 | Weitz et al. |
| 2009/0098555 A1 | 4/2009 | Roth et al. |
| 2009/0099041 A1 | 4/2009 | Church et al. |
| 2009/0105959 A1 | 4/2009 | Braverman et al. |
| 2009/0118488 A1 | 5/2009 | Drmanac et al. |
| 2009/0134027 A1 | 5/2009 | Jary |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155780 A1 | 6/2009 | Xiao et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0264299 A1 | 10/2009 | Drmanac et al. |
| 2009/0286687 A1 | 11/2009 | Dressman et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0035254 A1 | 2/2010 | Williams |
| 2010/0062494 A1 | 3/2010 | Church et al. |

(56) References Cited

U.S. PATENT DOCUMENTS

| | | |
|---|---|---|
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0113296 A1 | 5/2010 | Myerson |
| 2010/0120098 A1 | 5/2010 | Grunenwald et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston et al. |
| 2010/0187705 A1 | 7/2010 | Lee et al. |
| 2010/0210479 A1 | 8/2010 | Griffiths et al. |
| 2010/0248237 A1 | 9/2010 | Froehlich et al. |
| 2010/0248991 A1 | 9/2010 | Roesler et al. |
| 2010/0304982 A1 | 12/2010 | Hinz et al. |
| 2011/0000560 A1 | 1/2011 | Miller et al. |
| 2011/0008775 A1 | 1/2011 | Gao et al. |
| 2011/0028412 A1 | 2/2011 | Cappello et al. |
| 2011/0033548 A1 | 2/2011 | Lai et al. |
| 2011/0033854 A1 | 2/2011 | Drmanac et al. |
| 2011/0053798 A1 | 3/2011 | Hindson et al. |
| 2011/0059556 A1 | 3/2011 | Strey et al. |
| 2011/0071053 A1 | 3/2011 | Drmanac et al. |
| 2011/0086780 A1 | 4/2011 | Colston et al. |
| 2011/0092376 A1 | 4/2011 | Colston et al. |
| 2011/0092392 A1 | 4/2011 | Colston et al. |
| 2011/0160078 A1 | 6/2011 | Fodor et al. |
| 2011/0195496 A1 | 8/2011 | Muraguchi et al. |
| 2011/0201526 A1 | 8/2011 | Berka et al. |
| 2011/0217736 A1 | 9/2011 | Hindson |
| 2011/0218123 A1 | 9/2011 | Weitz et al. |
| 2011/0263457 A1 | 10/2011 | Krutzik et al. |
| 2011/0267457 A1 | 11/2011 | Weitz et al. |
| 2011/0281738 A1 | 11/2011 | Drmanac et al. |
| 2011/0287435 A1 | 11/2011 | Grunenwald et al. |
| 2011/0305761 A1 | 12/2011 | Shum et al. |
| 2011/0306141 A1 | 12/2011 | Bronchetti et al. |
| 2011/0319281 A1 | 12/2011 | Drmanac |
| 2012/0000777 A1 | 1/2012 | Garrell et al. |
| 2012/0010098 A1 | 1/2012 | Griffiths et al. |
| 2012/0010107 A1 | 1/2012 | Griffiths et al. |
| 2012/0014977 A1 | 1/2012 | Furihata et al. |
| 2012/0015382 A1 | 1/2012 | Weitz et al. |
| 2012/0015822 A1 | 1/2012 | Weitz et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0165219 A1 | 6/2012 | Van et al. |
| 2012/0172259 A1 | 7/2012 | Rigatti et al. |
| 2012/0190032 A1 | 7/2012 | Ness et al. |
| 2012/0190037 A1 | 7/2012 | Durin et al. |
| 2012/0196288 A1 | 8/2012 | Beer et al. |
| 2012/0208705 A1 | 8/2012 | Steemers et al. |
| 2012/0208724 A1 | 8/2012 | Steemers et al. |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0231972 A1 | 9/2012 | Golyshin et al. |
| 2012/0252012 A1 | 10/2012 | Armougom et al. |
| 2012/0253689 A1 | 10/2012 | Rogan et al. |
| 2012/0297493 A1 | 11/2012 | Cooper et al. |
| 2012/0309002 A1 | 12/2012 | Link |
| 2012/0316074 A1 | 12/2012 | Saxonov |
| 2013/0018970 A1 | 1/2013 | Woundy et al. |
| 2013/0022682 A1 | 1/2013 | Lee et al. |
| 2013/0028812 A1 | 1/2013 | Prieto et al. |
| 2013/0041004 A1 | 2/2013 | Drager et al. |
| 2013/0046030 A1 | 2/2013 | Rotem et al. |
| 2013/0059310 A1 | 3/2013 | Brenner et al. |
| 2013/0078638 A1 | 3/2013 | Berka et al. |
| 2013/0079231 A1 | 3/2013 | Pushkarev et al. |
| 2013/0084243 A1 | 4/2013 | Goetsch et al. |
| 2013/0096073 A1 | 4/2013 | Sidelman |
| 2013/0109575 A1 | 5/2013 | Kleinschmidt et al. |
| 2013/0109576 A1 | 5/2013 | Shuber et al. |
| 2013/0121893 A1 | 5/2013 | Delamarche et al. |
| 2013/0130919 A1 | 5/2013 | Chen et al. |
| 2013/0157870 A1 | 6/2013 | Pushkarev et al. |
| 2013/0157899 A1 | 6/2013 | Adler, Jr. et al. |
| 2013/0178368 A1 | 7/2013 | Griffiths et al. |
| 2013/0189700 A1 | 7/2013 | So et al. |
| 2013/0203605 A1 | 8/2013 | Shendure et al. |
| 2013/0203675 A1 | 8/2013 | Desimone et al. |
| 2013/0210639 A1 | 8/2013 | Link et al. |
| 2013/0210991 A1 | 8/2013 | Fonnum et al. |
| 2013/0211055 A1 | 8/2013 | Raines et al. |
| 2013/0225418 A1 | 8/2013 | Watson |
| 2013/0225623 A1 | 8/2013 | Buxbaum et al. |
| 2013/0274117 A1 | 10/2013 | Church et al. |
| 2013/0296173 A1 | 11/2013 | Callow et al. |
| 2013/0343317 A1 | 12/2013 | Etemad et al. |
| 2014/0030350 A1 | 1/2014 | Ashrafi et al. |
| 2014/0037514 A1 | 2/2014 | Stone et al. |
| 2014/0038178 A1 | 2/2014 | Otto et al. |
| 2014/0057799 A1 | 2/2014 | Johnson et al. |
| 2014/0065234 A1 | 3/2014 | Shum et al. |
| 2014/0093916 A1 | 4/2014 | Belyaev et al. |
| 2014/0120529 A1 | 5/2014 | Andersen et al. |
| 2014/0155295 A1 | 6/2014 | Hindson et al. |
| 2014/0194323 A1 | 7/2014 | Gillevet |
| 2014/0199730 A1 | 7/2014 | Agresti et al. |
| 2014/0199731 A1 | 7/2014 | Agresti et al. |
| 2014/0206554 A1 | 7/2014 | Hindson et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0287963 A1 | 9/2014 | Hindson et al. |
| 2014/0302503 A1 | 10/2014 | Lowe et al. |
| 2014/0315725 A1 | 10/2014 | Faham et al. |
| 2014/0315755 A1 | 10/2014 | Chen et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005188 A1 | 1/2015 | Levner et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov |
| 2015/0057163 A1 | 2/2015 | Rotem et al. |
| 2015/0072899 A1 | 3/2015 | Ward et al. |
| 2015/0111256 A1 | 4/2015 | Church et al. |
| 2015/0111788 A1 | 4/2015 | Fernandez et al. |
| 2015/0119280 A1 | 4/2015 | Srinivas et al. |
| 2015/0218633 A1 | 8/2015 | Hindson et al. |
| 2015/0224466 A1 | 8/2015 | Hindson et al. |
| 2015/0225777 A1 | 8/2015 | Hindson et al. |
| 2015/0225778 A1 | 8/2015 | Hindson et al. |
| 2015/0267191 A1 | 9/2015 | Steelman et al. |
| 2015/0291942 A1 | 10/2015 | Gloeckner et al. |
| 2015/0292988 A1 | 10/2015 | Bharadwaj et al. |
| 2015/0298091 A1 | 10/2015 | Weitz et al. |
| 2015/0299772 A1 | 10/2015 | Zhang |
| 2015/0299784 A1 | 10/2015 | Fan et al. |
| 2015/0329891 A1 | 11/2015 | Tan et al. |
| 2015/0337298 A1 | 11/2015 | Xi et al. |
| 2015/0353999 A1 | 12/2015 | Agresti et al. |
| 2015/0361418 A1 | 12/2015 | Reed et al. |
| 2015/0368638 A1 | 12/2015 | Steemers et al. |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0024558 A1 | 1/2016 | Hardenbol |
| 2016/0032282 A1 | 2/2016 | Vigneault et al. |
| 2016/0060621 A1 | 3/2016 | Agresti et al. |
| 2016/0060691 A1 | 3/2016 | Giresi et al. |
| 2016/0115474 A1 | 4/2016 | Jelinek et al. |
| 2016/0122753 A1 | 5/2016 | Mikkelsen et al. |
| 2016/0122817 A1 | 5/2016 | Jarosz et al. |

(56) References Cited

U.S. PATENT DOCUMENTS

| | | |
|---|---|---|
| 2016/0153005 A1 | 6/2016 | Zhang et al. |
| 2016/0160235 A1 | 6/2016 | Solodushko et al. |
| 2016/0177359 A1 | 6/2016 | Ukanis et al. |
| 2016/0208323 A1 | 7/2016 | Bernstein et al. |
| 2016/0231324 A1 | 8/2016 | Zhao et al. |
| 2016/0244742 A1 | 8/2016 | Linnarsson et al. |
| 2016/0244809 A1 | 8/2016 | Belgrader et al. |
| 2016/0244825 A1 | 8/2016 | Vigneault et al. |
| 2016/0281160 A1 | 9/2016 | Jarosz et al. |
| 2016/0289769 A1 | 10/2016 | Schwartz et al. |
| 2016/0304860 A1 | 10/2016 | Hindson et al. |
| 2016/0326583 A1 | 11/2016 | Johnson et al. |
| 2016/0348093 A1 | 12/2016 | Price et al. |
| 2016/0376663 A1 | 12/2016 | Brown |
| 2017/0009274 A1 | 1/2017 | Abate et al. |
| 2017/0016041 A1 | 1/2017 | Greenfield et al. |
| 2017/0114390 A1 | 4/2017 | Hindson et al. |
| 2017/0145476 A1 | 5/2017 | Ryvkin et al. |
| 2017/0183701 A1 | 6/2017 | Agresti et al. |
| 2017/0247757 A1 | 8/2017 | Hindson et al. |
| 2017/0260584 A1 | 9/2017 | Zheng et al. |
| 2017/0268056 A1 | 9/2017 | Vigneault et al. |
| 2017/0321252 A1 | 11/2017 | Hindson et al. |
| 2017/0335385 A1 | 11/2017 | Hindson et al. |
| 2017/0342404 A1 | 11/2017 | Hindson et al. |
| 2017/0348691 A1 | 12/2017 | Bharadwaj et al. |
| 2017/0356027 A1 | 12/2017 | Hindson et al. |
| 2017/0362587 A1 | 12/2017 | Hindson et al. |
| 2018/0008984 A1 | 1/2018 | Bharadwaj et al. |
| 2018/0015472 A1 | 1/2018 | Bharadwaj et al. |
| 2018/0015473 A1 | 1/2018 | Bharadwaj et al. |
| 2018/0016634 A1 | 1/2018 | Hindson et al. |
| 2018/0030512 A1 | 2/2018 | Hindson et al. |
| 2018/0030515 A1 | 2/2018 | Regev et al. |
| 2018/0057868 A1 | 3/2018 | Walder et al. |
| 2018/0087050 A1 | 3/2018 | Zheng et al. |
| 2018/0088112 A1 | 3/2018 | Fan et al. |
| 2018/0195112 A1 | 7/2018 | Lebofsky et al. |
| 2018/0267036 A1 | 9/2018 | Fan et al. |
| 2018/0282804 A1 | 10/2018 | Hindson et al. |
| 2018/0327839 A1 | 11/2018 | Hindson et al. |
| 2018/0340169 A1 | 11/2018 | Belhocine et al. |
| 2018/0340170 A1 | 11/2018 | Belhocine et al. |
| 2018/0340171 A1 | 11/2018 | Belhocine et al. |
| 2018/0340172 A1 | 11/2018 | Belhocine et al. |
| 2018/0346979 A1 | 12/2018 | Hindson et al. |

FOREIGN PATENT DOCUMENTS

| | | |
|---|---|---|
| EP | 0637996 B1 | 7/1997 |
| EP | 1019496 B1 | 9/2004 |
| EP | 1672064 A1 | 6/2006 |
| EP | 1482036 B1 | 10/2007 |
| EP | 1841879 A2 | 10/2007 |
| EP | 1944368 A1 | 7/2008 |
| EP | 1594980 B1 | 11/2009 |
| EP | 1967592 B1 | 4/2010 |
| EP | 2258846 A2 | 12/2010 |
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |
| EP | 2752664 A1 | 7/2014 |
| GB | 2097692 B | 5/1985 |
| GB | 2485850 A | 5/2012 |
| JP | S5949832 A | 3/1984 |
| JP | S60227826 A | 11/1985 |
| JP | 2006507921 A | 3/2006 |
| JP | 2006289250 A | 10/2006 |
| JP | 2007015990 A | 1/2007 |
| JP | 2007268350 A | 10/2007 |
| JP | 2009513948 A | 4/2009 |
| JP | 2009208074 A | 9/2009 |
| JP | 2012131798 A | 7/2012 |
| WO | WO-8402000 A1 | 5/1984 |
| WO | WO-9418218 A1 | 8/1994 |
| WO | WO-9419101 A1 | 9/1994 |
| WO | WO-9423699 A1 | 10/1994 |
| WO | WO-9530782 A1 | 11/1995 |
| WO | WO-9629629 A2 | 9/1996 |
| WO | 1996041011 A1 | 12/1996 |
| WO | WO-9802237 A1 | 1/1998 |
| WO | WO-9852691 A1 | 11/1998 |
| WO | 1999009217 A1 | 2/1999 |
| WO | WO-9952708 A1 | 10/1999 |
| WO | 2000008212 A1 | 2/2000 |
| WO | WO-0023181 A1 | 4/2000 |
| WO | WO-0026412 A1 | 5/2000 |
| WO | WO-0043766 A1 | 7/2000 |
| WO | WO-0070095 A2 | 11/2000 |
| WO | WO-0102850 A1 | 1/2001 |
| WO | WO-0114589 A2 | 3/2001 |
| WO | WO-0189787 A2 | 11/2001 |
| WO | WO-0190418 A1 | 11/2001 |
| WO | WO-0127610 A3 | 3/2002 |
| WO | WO-0231203 A2 | 4/2002 |
| WO | WO-02086148 A1 | 10/2002 |
| WO | WO-0218949 A3 | 1/2003 |
| WO | WO-03062462 A2 | 7/2003 |
| WO | WO-2004002627 A2 | 1/2004 |
| WO | WO-2004010106 A2 | 1/2004 |
| WO | WO-2004061083 A2 | 7/2004 |
| WO | WO-2004065617 A2 | 8/2004 |
| WO | WO-2004069849 A2 | 8/2004 |
| WO | 2004091763 A2 | 10/2004 |
| WO | WO-2004102204 A1 | 11/2004 |
| WO | 2004105734 A1 | 12/2004 |
| WO | WO-2004103565 A2 | 12/2004 |
| WO | WO-2005002730 A1 | 1/2005 |
| WO | 2005021151 A1 | 3/2005 |
| WO | WO-2005023331 A2 | 3/2005 |
| WO | WO-2005040406 A1 | 5/2005 |
| WO | 2005049787 A9 | 6/2005 |
| WO | 2005082098 A2 | 9/2005 |
| WO | WO-2006030993 A1 | 3/2006 |
| WO | WO-2006078841 A1 | 7/2006 |
| WO | 2006096571 A2 | 9/2006 |
| WO | WO-2007001448 A2 | 1/2007 |
| WO | WO-2007002490 A2 | 1/2007 |
| WO | WO-2007012638 A1 | 2/2007 |
| WO | WO-2007018601 A1 | 2/2007 |
| WO | WO-2007024840 A2 | 3/2007 |
| WO | 2007081387 A1 | 7/2007 |
| WO | WO-2007084192 A2 | 7/2007 |
| WO | WO-2007089541 A2 | 8/2007 |
| WO | WO-2007093819 A2 | 8/2007 |
| WO | 2007121489 A2 | 10/2007 |
| WO | WO-2007114794 A1 | 10/2007 |
| WO | 2007133710 A2 | 11/2007 |
| WO | 2007149432 A2 | 12/2007 |
| WO | WO-2007138178 A2 | 12/2007 |
| WO | WO-2007139766 A2 | 12/2007 |
| WO | WO-2007140015 A2 | 12/2007 |
| WO | WO-2007147079 A2 | 12/2007 |
| WO | WO-2008021123 A1 | 2/2008 |
| WO | WO-2008091792 A2 | 7/2008 |
| WO | WO-2008102057 A1 | 8/2008 |
| WO | WO-2008121342 A2 | 10/2008 |
| WO | 2007081385 | 11/2008 |
| WO | 2008109176 | 11/2008 |
| WO | WO-2008061193 A3 | 11/2008 |
| WO | WO-2008134153 A1 | 11/2008 |
| WO | WO-2008150432 A1 | 12/2008 |
| WO | 2009011808 A1 | 1/2009 |
| WO | WO-2009005680 A1 | 1/2009 |
| WO | WO-2009015296 A1 | 1/2009 |
| WO | WO-2009048532 A2 | 4/2009 |
| WO | WO-2009061372 A1 | 5/2009 |
| WO | 2009085215 A1 | 7/2009 |
| WO | WO-2009147386 A1 | 12/2009 |
| WO | WO-2010004018 A2 | 1/2010 |
| WO | 2010033200 A2 | 3/2010 |
| WO | WO-2010048605 A1 | 4/2010 |

(56) References Cited

FOREIGN PATENT DOCUMENTS

| WO | WO-2010104604 A1 | 9/2010 |
|---|---|---|
| WO | WO-2010115154 A1 | 10/2010 |
| WO | 2010148039 A2 | 12/2010 |
| WO | 2010151776 A2 | 12/2010 |
| WO | WO-2010117620 A3 | 2/2011 |
| WO | WO-2011028539 A1 | 3/2011 |
| WO | 2011047870 A1 | 4/2011 |
| WO | 2011056546 A1 | 5/2011 |
| WO | WO-2011074960 A1 | 6/2011 |
| WO | WO-2011140627 A1 | 11/2011 |
| WO | WO-2012012037 A1 | 1/2012 |
| WO | 2012048341 A1 | 4/2012 |
| WO | WO-2012047889 A2 | 4/2012 |
| WO | WO-2012061832 A1 | 5/2012 |
| WO | 2011066476 | 8/2012 |
| WO | WO-2012106546 A2 | 8/2012 |
| WO | WO-2012112804 A1 | 8/2012 |
| WO | WO-2012112970 A2 | 8/2012 |
| WO | 2012083225 | 9/2012 |
| WO | WO-2012136734 A1 | 10/2012 |
| WO | WO-2012142611 A2 | 10/2012 |
| WO | 2012149042 A2 | 11/2012 |
| WO | WO-2012148497 A2 | 11/2012 |
| WO | 2012166425 A2 | 12/2012 |
| WO | WO-2013019751 A1 | 2/2013 |
| WO | WO-2013036929 A1 | 3/2013 |
| WO | WO-2013055955 A1 | 4/2013 |
| WO | 2013122996 A1 | 8/2013 |
| WO | WO-2013123125 A1 | 8/2013 |
| WO | WO-2013126741 A1 | 8/2013 |
| WO | WO-2013134261 A1 | 9/2013 |
| WO | WO-2013150083 A1 | 10/2013 |
| WO | 2013177220 A1 | 11/2013 |
| WO | WO-2013188872 A1 | 12/2013 |
| WO | 2014028537 A1 | 2/2014 |
| WO | WO-2014053854 A1 | 4/2014 |
| WO | WO-2014071361 A1 | 5/2014 |
| WO | WO-2014074611 A1 | 5/2014 |
| WO | WO-2014093676 A1 | 6/2014 |
| WO | WO-2014108810 A2 | 7/2014 |
| WO | WO-2014140309 A1 | 9/2014 |
| WO | WO-2014144495 A1 | 9/2014 |
| WO | WO-2014150931 A1 | 9/2014 |
| WO | WO-2014189957 A2 | 11/2014 |
| WO | WO-2014210353 A2 | 12/2014 |
| WO | WO-2015044428 A1 | 4/2015 |
| WO | WO-2015164212 A1 | 10/2015 |
| WO | WO-2016040476 A1 | 3/2016 |
| WO | WO-2016126871 A2 | 8/2016 |
| WO | WO-2016191618 A1 | 12/2016 |
| WO | WO-2016207647 A1 | 12/2016 |
| WO | WO-2016207653 A1 | 12/2016 |
| WO | WO-2016207661 A1 | 12/2016 |
| WO | WO-2017015075 A1 | 1/2017 |
| WO | WO-2017025594 A1 | 2/2017 |
| WO | WO-2017053905 A1 | 3/2017 |
| WO | WO-2017075265 A1 | 5/2017 |
| WO | WO-2017156336 A1 | 9/2017 |
| WO | WO-2018045186 A1 | 3/2018 |
| WO | WO-2018058073 A2 | 3/2018 |

OTHER PUBLICATIONS

Buenrostro, et al. ATAC-seq: A Method for Assaying Chromatin Accessibility Genome-Wide. Curr Protoc Mol Biol.; 109: 21.29.1-21.29.9. doi:10.1002/0471142727.mb2129s109.
Buenrostro, et al. Single-cell chromatin accessibility reveals principles of regulatory variation. Nature. Jul. 23, 2015;523(7561):486-90. doi: 10.1038/nature14590. Epub Jun. 17, 2015.
Buenrostro, et al. "Transposition of native chromatin for fast and sensitive epigenomic profiling of open chromatin, DNA-binding proteins and nucleosome position." Nat Methods. Dec. 2013;10(12):1213-8. doi: 10.1038/nmeth.2688. Epub Oct. 6, 2013.
Caruccio N., Preparation of Next-Generation Sequencing Libraries Using Nextera Technology: Simultaneous DNA Fragmentation and Adaptor Tagging by In Vitro Transposition. Ch. 17 Methods in Microbiology 733:241 (2011).
Clark, et al. Single-cell epigenomics: powerful new methods for understanding gene regulation and cell identity. Genome Biol. Apr. 18, 2016;17:72. doi: 10.1186/s13059-016-0944-x.
Co-pending U.S. Appl. No. 15/825,740, filed Nov. 29, 2017.
Co-pending U.S. Appl. No. 15/831,726, filed Dec. 5, 2017.
Co-pending U.S. Appl. No. 15/832,183, filed Dec. 5, 2017.
Co-pending U.S. Appl. No. 15/832,547, filed Dec. 5, 2017.
Co-pending U.S. Appl. No. 15/842,550, filed Dec. 14, 2017.
Co-pending U.S. Appl. No. 15/842,687, filed Dec. 14, 2017.
Co-pending U.S. Appl. No. 15/842,713, filed Dec. 14, 2017.
Co-pending U.S. Appl. No. 15/847,659, filed Dec. 19, 2017.
Co-pending U.S. Appl. No. 15/847,752, filed Dec. 19, 2017.
Co-pending U.S. Appl. No. 15/848,714, filed Dec. 20, 2017.
Co-pending U.S. Appl. No. 15/850,241, filed Dec. 21, 2017.
Co-pending U.S. Appl. No. 15/872,499, filed Jan. 16, 2018.
Co-pending U.S. Appl. No. 15/875,899, filed Jan. 19, 2018.
Cusanovich; et al., "Multiplex single-cell profiling of chromatin accessibility by combinatorial cellular indexing. Sciencexpress, May 7, 2014, p. 1-9."
Cusanovich, et al. Supplementary materials for Multiplex single-cell profiling of chromatin accessibility by combinatorial cellular indexing. Science. May 22, 2015;348(6237):910-4. doi: 10.1126/science.aab1601. Epub May 7, 2015.
Dey, et al. Integrated genome and transcriptome sequencing of the same cell. Dey, Siddharth S. et al. "Integrated Genome and Transcriptome Sequencing from the Same Cell." Nature biotechnology 33.3 (2015): 285-289. PMC. Web. Dec. 18, 2017.
Dixit, et al. Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.
Lake, et al. "Integrative Single-Cell Analysis by Transcriptional and Epigenetic States in Human Adult Brain". Apr. 19, 2017. doi: https://doi.org/10.1101/128520.
Lennon; et al., "Lennon et al. A scalable, fully automated process for construction of sequence-ready barcoded libraries for 454. Genome Biology 11:R15 (2010)."
MacAulay; et al., "G&T-seq: parallel sequencing of single-cell genomes and transcriptomes. Nature Methods, 2015, p. 1-7."
MacAulay, et al. Single-Cell Multiomics: Multiple Measurements from Single Cells. Trends in Genetics 33.2 (2017): 155-168. PMC. Web. Dec. 18, 2017.
Pott, et al. Single-cell ATAC-seq: strength in numbers. Genome Biol. Aug. 21, 2015;16:172. doi: 10.1186/s13059-015-0737-7.
Preissl, et al. Single nucleus analysis of the chromatin landscape in mouse forebrain development. Posted Jul. 4, 2017. bioRxiv 159137; doi: https://doi.org/10.1101/159137.
Syed, et al. Nature Methods 2 pgs (Nov. 2009).
Adamson et al., "Production of arrays of chemically distinct nanolitre plugs via repeated splitting in microfluidic devices", Lab Chip 6(9): 1178-1186 (Sep. 2006).
Kolodeziejczyk et al., "The technology and biology of single-cell RNA sequencing", Molecular Cell, vol. 58 (May 21, 2015).
Xia and Whitesides, Soft Lithography, Angew. Chem. Int. Ed. 37:550-575 (1998).
Baret, et al. Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.
BD. BD Rhapsody™ Single-Cell Analysis System: Analyze hundreds of genes across tens of thousands of single cells in parallel. BD, Becton, Dickinson and Company. BDGM1012 Rev. 1. 2017. 8 pages.
Buchman GW, et al. Selective RNA amplification: a novel method using dUMP-containing primers and uracil DNA glycosylase. PCR Methods Appl. Aug. 1993; 3(1):28-31.
Co-pending U.S. Appl. No. 15/687,357, filed Aug. 25, 2017.
Co-pending U.S. Appl. No. 15/687,856, filed Aug. 28, 2017.
Co-pending U.S. Appl. No. 15/693,374, filed Aug. 31, 2017.
Co-pending U.S. Appl. No. 15/717,840, filed Sep. 27, 2017.

(56) References Cited

OTHER PUBLICATIONS

Co-pending U.S. Appl. No. 15/717,847, filed Sep. 27, 2017.
Co-pending U.S. Appl. No. 15/717,871, filed Sep. 27, 2017.
Co-pending U.S. Appl. No. 15/718,764, filed Sep. 28, 2017.
Co-pending U.S. Appl. No. 15/718,893, filed Sep. 28, 2017.
Co-pending U.S. Appl. No. 15/719,459, filed Sep. 28, 2017.
Co-pending U.S. Appl. No. 15/720,085, filed Sep. 29, 2017.
Dressman et al. Supplementary Information pp. 1-2 of article published 2003, PNAS 100(15:8817-22).
Hosono S, et al. Unbiased whole-genome amplification directly from clinical samples. Genome Res. May 2003; 13(5):954-64. Epub Apr. 14, 2003.
Kamperman, et al. Centering Single Cells in Microgels via Delayed Crosslinking Supports Long-Term 3D Culture by Preventing Cell Escape. Small. Jun. 2017;13(22). doi: 10.1002/smll.201603711. Epub Apr. 28, 2017.
Lienemann, et al. Single cell-laden protease-sensitive microniches for long-term culture in 3D. Lab Chip. Feb. 14, 2017;17(4):727-737. doi: 10.1039/c6lc01444e.
Lo, et al. On the design of clone-based haplotyping. Genome Biol. 2013;14(9):R100.
Maricic T, et al. Optimization of 454 sequencing library preparation from small amounts of DNA permits sequence determination of both DNA strands. Biotechniques. Jan. 2009; 46(1):51-2, 54-7.
Perrott, Jimmy. Optimization and Improvement of Emulsion PCR for the Ion Torrent Next-Generation Sequencing Platform. (2011) Thesis.
Shahi, et al. Abseq: Ultrahigh-throughput single cell protein profiling with droplet microfluidic barcoding. Sci Rep. 2017; 7: 44447. Published online Mar. 14, 2017. doi: 10.1038/srep44447.
Skerra A. Phosphorothioate primers improve the amplification of DNA sequences by DNA polymerases with proofreading activity. Nucleic Acids Res. Jul. 25, 1992; 20(14):3551-4.
Stoeckius, et al. Simultaneous epitope and transcriptome measurement in single cells. Nature methods. Jul. 31, 2017. Supplemental Materials.
Co-pending U.S. Appl. No. 15/831,847, filed Dec. 5, 2017.
Hamilton, A.J. "microRNA in erythrocytes" Biochem. Soc. Trans. (2010) 38, 229-231.
miRNA (http://www.exiqon.com/what-are-microRNAs) accessed Oct. 19, 2017.
Orakdogen, N. "Novel responsive poly(N,N-dimethylaminoethyl methacrylate) gel beads: preparation, mechanical properties and pH-dependent swelling behavior" J Polym Res (2012) 19:9914.
"Portable Water Filters" (http://www.portablewaterfilters.org/water-filter-guide/particle-contaminant-size-chart-microns/) 2015, accessed Oct. 19, 2017.
Abate, et al. Beating Poisson encapsulation statistics using close-packed ordering. Lab Chip. Sep. 21, 2009;9(18):2628-31 . doi: 10.1039/b909386a. Epub Jul. 28, 2009.
Aitman, et al. Copy number polymorphism in Fcgr3 predisposes to glomerulonephritis in rats and humans. Nature. Feb. 16, 2006;439(7078):851-5.
Akselband, "Enrichment of slow-growing marine microorganisms from mixed cultures using gel microdrop (GMD) growth assay and fluorescence-activated cell sorting", J. Exp. Marine Bioi., 329: 196-205 (2006).
Akselband, "Rapid mycobacteria drug susceptibility testing using gel microdrop (GMD) growth assay and flow cytometry", J. Microbiol. Methods, 62:181-197 (2005).
Altemos et al., "Genomic Characterization of Large Heterochromatic Gaps in the Human Genome Assembly," PLOS Computational Biology, May 15, 2014, vol. 10, Issue 5, 14 pages.
Amini, S. et al. "Haplotype-resolved whole-genome sequencing by contiguity-preserving transposition and combinatorial indexing" Nature Genetics (2014) 46:1343-1349 doi:10.1038/ng.3119.
Anonymous, "Oligo(dT)25 cellulose beads" NEB (2012) Retrieved from the Internet:https://www.neb.com/~/media/Catalog/All-Products/286CA51268E24DE1B06F1CB288698B54/Datacards%20or%Manuals/S1408Datasheet-Lot0011205.pdf.

Anonymous, "Oligotex Handbook" Qiagen (2012) XP055314680, Retrieved from the Internet: URL:http://www.qiagen.com/de/resources/download.apsx?id=f9fald98-d54d-47e7-a20b-8b0cb8975009&lang=en.
Anonymous: "Viscosity-Basic concepts" (2004) XP055314117, Retrieved from the Internet: URL:http://lhtc.epfl.ch/webdav/site/lhtc/shared/import/migration/2 VISCOSITY.pdf.
Attia, et al. Micro-injection moulding of polymer microfluidic devices. Microfluidics and nanofluidics. 2009; 7(1):1-28.
Zong, et al. Genome-wide detection of single-nucleotide and copy-number variations of a single human cell. Science. Dec. 21, 2012;338(6114):1622-6. doi: 10.1126/science.1229164.
Balikova, et al. Autosomal-dominant microtia linked to five tandem copy-number-variable region at chromosome 4p16. Am J Hum Genet. Jan. 2008;82(1):181-7. doi: 10.1016/j.ajhg.2007.08.001.
Berkum, et al. Hi-C: a method to study the three-dimensional architecture of genomes. J Vis Exp. May 6, 2010;(39). pii: 1869. doi: 10.3791/1869.
Biles et al., Nucl. Acids Res. 32(22):e176 2004.
Bodi, K. et al. "Comparison of Commercially Available Target Enrichment Methods for Next-Generation Sequencing" J Biomolecular Techniques (2013) 24:73-86.
Boone, et al. Plastic advances microfluidic devices. The devices debuted in silicon and glass, but plastic fabrication may make them hugely successful in biotechnology application. Analytical Chemistry. Feb. 2002; 78A-86A.
Braeckmans et al., Scanning the Code. Modern Drug Discovery. 2003:28-32.
Bransky, et al. A microfluidic droplet generator based on a piezoelectric actuator. Lab Chip. Feb. 21, 2009;9(4):516-20. doi: 10.1039/b814810d. Epub Nov. 20, 2008.
Briggs, et al. "Tumor-infiltrating immune repertoires captures by single-cell barcoding in emulsion" with Supplementary material. bioRxiv 134841; doi: https://doi.org/10.1101/134841. Posted May 5, 2017.
Brouzes, et al. Droplet microfluidic technology for single-cell high-throughput screening. Proc Natl Acad Sci U S A. Aug. 25, 2009;106(34):14195-200. doi: 10.1073/pnas.0903542106. Epub Jul. 15, 2009.
Browning, et al. Haplotype phasing: existing methods and new developments. Nat Rev Genet. Sep. 16, 2011;12(10):703-14. doi: 10.1038/nrg3054. Review.
Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.
Carroll, "The selection of high-producing cell lines using flow cytometry and cell sorting", Exp. Op. Bioi. Therp., 4:11 1821-1829 (2004).
Chaudhary "A rapid method of cloning functioNal variable-region antibody genese in *Escherichia coli* as single-chain imrnunotoxins" Proc. Nat!. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;I8(1):83-101.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Choi, et al. Identification of novel isoforms of the EML4-ALK transforming gene in non-small cell lung cancer. Cancer Res. Jul. 1, 2008;68(13):4971-6. doi: 10.1158/0008-5472.CAN-07-6158.
Chokkalingam, et al. Probing cellular heterogeneity in cytokine-secreting immune cells using droplet-based microfluidics. Lab Chip. Dec. 21, 2013;13(24):4740-4. doi: 10.1039/c3lc50945a.
Christian M, et al. Targeting DNA double-strand breaks with TAL effector nucleases. Genetics. 2010;186:757-761.
Chu, et al. Controllable monodisperse multiple emulsions. Angew Chem Int Ed Engl. 2007;46(47):8970-4.
Chung, et al. Structural and molecular interrogation of intact biological systems. Nature. May 16, 2013;497(7449):332-7. doi: 10.1038/nature12107. Epub Apr. 10, 2013.

(56) References Cited

OTHER PUBLICATIONS

Cong, et al. Multiplex genome engineering using CRISPR/Cas systems. Science. Feb. 15, 2013;339(6121):819-23. doi: 10.1126/science.1231143. Epub Jan. 3, 2013.
Cook, et al. Copy-number variations associated with neuropsychiatric conditions. Nature. Oct. 16, 2008;455(7215):919-23. doi: 10.1038/nature07458.
Co-pending U.S. Appl. No. 15/355,542, filed Nov. 18, 2016.
Co-pending U.S. Appl. No. 15/392,557, filed Dec. 28, 2016.
Co-pending U.S. Appl. No. 15/430,298, filed Feb. 10, 2017.
Co-pending U.S. Appl. No. 15/440,772, filed Feb. 23, 2017.
Co-pending U.S. Appl. No. 15/449,741, filed Mar. 3, 2017.
Co-pending U.S. Appl. No. 15/470,814, filed Mar. 27, 2017.
Co-pending U.S. Appl. No. 15/588,519, filed May 5, 2017.
Coufal, et al. L1 retrotransposition in human neural progenitor cells. Nature. Aug. 27, 2009;460(7259):1127-31. doi: 10.1038/nature08248. Epub Aug. 5, 2009.
De Bruin et al., UBS Investment Research. Q-Series®: DNa Sequencing. UBS Securities LLC. Jul. 12, 2007. 15 pages.
Dekker, et al. Capturing chromosome conformation. Science. Feb. 15, 2002;295(5558):1306-11.
Doshi, et al. Red blood cell-mimicking synthetic biomaterial particles. Proceedings of the National Academy of Sciences 106.51 (2009): 21495-21499.
Draper, et al. Compartmentalization of electrophoretically separated analytes in a multiphase microfluidic platform. Anal Chem. Jul. 3, 2012;84(13):5801-8. doi: 10.1021/ac301141x. Epub Jun. 13, 2012.
Dressler, et al. Droplet-based microfluidics enabling impact on drug discovery. J Biomol Screen. Apr. 2014;19(4):483-96. doi: 10.1177/1087057113510401. Epub Nov. 15, 2013.
"Dressman et al. Transforming single DNA molecules into fluorescent magnetic particles for detection and enumeration of genetic variations. Proc. Natl. Acad. Sci. 2003. 100(15):8817-8822."
"Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013."
Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun. 14, 2010:1059.
Fan, et al. Noninvasive diagnosis of fetal aneuploidy by shotgun sequencing DNA from maternal blood. Proc Natl Acad Sci U S A. Oct. 21, 2008;105(42)16266-71. doi: 10.1073/pnas.0808319105. Epub Oct. 6, 2008.
Fan, et al. Whole-genome molecular haplotyping of single cells. Nature Biotechnology, vol. 29, No. 1. Jan. 1, 2011. pp. 51-57.
Fang, et al. Fluoride-cleavable biotinylation phosphoramidite for 5'-end-labeling and affinity purification of synthetic oligonucleotides. Nucleic Acids Res. Jan. 15, 2003;31(2):708-15.
Frampton, G.M. et al. "Development and validation of a clinical cancer genomic profiling test based on massively parallel DNA sequencing" Nature Biotechnology (2013) 31(11):1023-1031. doi:10.1038/nbr.2696.
Fredrickson, et al. Macro-to-micro interfaces for microfluidic devices. Lab Chip. Dec. 2004;4(6):526-33. Epub Nov. 10, 2004.
Fu, "A micro fabricated fluorescence-activated cell sorter", Nature Biotech., 17:1109-1111 (1997).
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.
Gericke, et al. Functional cellulose beads: preparation, characterization, and applications. Chemical reviews 113.7 (2013): 4812-4836.
Ghadessy, et al. Directed evolution of polymerase function by compartmentalized self-replication. Proc Natl Acad Sci U S A. Apr. 10, 2001;98(8):4552-7. Epub Mar. 27, 2001.
Gonzalez, et al. The influence of CCL3L1 gene-containing segmental duplications on HIV-1/AIDS susceptibility. Science. Mar. 4, 2005;307(5714):1434-40. Epub Jan. 6, 2005.
Granieri, Lucia. Droplet-based microfluidics and engineering of tissue plasminogen activator for biomedical applications. Ph.D. Thesis, Nov. 13, 2009 (131 pages).
Grasland-Mongrain, et al. Droplet coalescence in microfluidic devices. Jan.-Jul. 2003. 31 pages. http://www.eleves.ens.fr/home/grasland/rapports/stage4.pdf.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
He, J. et al. "Genotyping-by-sequencing (GBS), an ultimate marker-assisted selections (MAS) tool to accelerate plant breeding" Frontiers in Plant Sci (Sep. 30, 2014) 5:1-8.
Hjerten, et al. General methods to render macroporous stationary phases nonporous and deformable, exemplified with agarose and silica beads and their use in high-performance ion-exchange and hydrophobic-interaction chromatography of proteins. Chromatographia 31.1-2 (1991): 85-94.
"Sigma. Streptavidin-agarose (S1638) product information sheet. www.sigma-aldrich.com".
Illumina Nextera Enrichment Sample Preparation Guide. Feb. 2013.
Illumina TruSeq Custom Enrichment Kit Data Sheet. (c) 2014.
Ioannidis, N. Manufacturing of Agarose-Based Chromatographic Adsorbents With Controlled Pore and Particle Sizes. A thesis submitted to The University of Birmingham for the degree of Doctor of Philosophy. 2009.
Jena, et al. Cyclic olefin copolymer based microfluidic devices for biochip applications: Ultraviolet surface grafting using 2-methacryloyloxyethyl phosphorylcholine. Biomicrofluidics. Mar. 2012;6(1):12822-1282212. doi: 10.1063/1.3682098. Epub Mar. 15, 2012.
Jung, et al. Micro machining of injection mold inserts for fluidic channel of polymeric biochips. Sensors. 2007; 7(8):1643-1654.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
"Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013."
Karmakar, et al. Organocatalytic removal of formaldehyde adducts from RNA and DNA bases. Nat Chem. Sep. 2015;7(9):752-8. doi: 10.1038/nchem.2307. Epub Aug. 3, 2015.
Kebschull, et al. High-Throughput Mapping of Single-Neuron Projections by Sequencing of Barcoded RNA. Neuron. Sep. 7, 2016;91(5):975-87. doi: 10.1016/j.neuron.2016.07.036. Epub Aug. 18, 2016.
Khomiakov A et al., [Analysis of perfect and mismatched DNA duplexes by a generic hexanucleotide microchip]. Mol Bioi (Mosk). Jul.-Aug. 2003;37(4):726-41. Russian. Abstract only.
Kim et al., Albumin loaded microsphere of amphiphilic poly(ethylene glycol)/poly(a-ester) multiblock copolymer. Eu. J. Pharm. Sci. 2004;23:245-51. Available online Sep. 27, 2004.
Kim, et al. Fabrication of monodisperse gel shells and functioNal microgels in microfluidic devices. Angew Chem Int Ed Engl. 2007;46(11):1819-22.
Kim, et al. Rapid prototyping of microfluidic systems using a PDMS/polymer tape composite. Lab Chip. May 7, 2009;9(9):1290-3. doi: 10.1039/b818389a. Epub Feb. 10, 2009.
Kitzman, et al. Noninvasive whole-genome sequencing of a human fetus. Sci Transl Med. Jun. 6, 2012;4(137):137ra76. doi: 10.1126/scitranslmed.3004323.
Kivioj a, et al., "Counting Absolute Numbers of Molecules Using Unique Molecular Identifiers", Nature Methods 9, 72-74 (2012).
Klein, et al. Droplet barcoding for single-cell transcriptomics applied to embryonic stem cells. Cell. May 21, 2015;161(5):1187-201. doi: 10.1016/j.cell.2015.04.044.

(56) References Cited

OTHER PUBLICATIONS

Knight, et al. Subtle chromosomal rearrangements in children with unexplained mental retardation. Lancet. Nov. 13, 1999;354(9191):1676-81.
Korlach et al., Methods in Enzymology, Real-Time DNA Sequencing from Single Polymerase Molecules, (2010) 472:431-455.
Kutyavin, et al. Oligonucleotides containing 2-aminoadenine and 2-thiothymine act as selectively binding complementary agents. Biochemistry. Aug. 27, 1996;35(34):11170-6.
Lagus, et al. A review of the theory, methods and recent applications of high-throughput single-cell droplet microfluidics. J. Phys. D: Appl. Phys. (2013) 46:114005. (21 pages).
Lee, et al. ACT-PRESTO: Rapid and consistent tissue clearing and labeling method for 3-dimensional (3D) imaging. Sci Rep. Jan. 11, 2016;6:18631. doi: 10.1038/srep18631.
Lee; et al., "Highly multiplexed subcellular RNA sequencing in situ. Science. Mar. 21, 2014;343(6177):1360-3. doi: 10.1126/science. 1250212. Epub Feb. 27, 2014."
Lee, J-H. et al. "Fluorescent in situ sequencing (FISSEQ) of RNA for gene expression profiling in intact cells and tissues" Nature Protocols (Feb. 12, 2015) 10(3):442-458.
Li, et al. A single-cell-based platform for copy number variation profiling through digital counting of amplified genomic DNA fragments. ACS Appl Mater Interfaces. Mar. 24, 2017. doi: 10.1021/acsami.7b03146. [Epub ahead of print].
Li, Y., et al., "PEGylated PLGA Nanoparticles as protein carriers: synthesis, preparation and biodistribution in rats," JourNal of Controlled Release, vol. 71, pp. 203-211 (2001).
Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.
Liu, et al. Smart thermo-triggered squirting capsules for Nanoparticle delivery. Soft Matter. 2010; 6(16):3759-3763.
Loscertales, I.G., et al., "Micro/Nano Encapsulation via Electrified Coaxial Liquid Jets," Science, vol. 295, pp. 1695-1698 (2002).
Love, "A microengraving method for rapid selection of single cells producing antigen-specific antibodies", Nature Biotech, 24:6 703 (Jun. 2006).
Lowe, Adam J. Norbornenes and [n]polynorbornanes as molecular scaffolds for anion recognition. Ph.D. Thesis (May 2010). (361 pages).
Lupski. Genomic rearrangements and sporadic disease. Nat Genet. Jul. 2007;39(7 Suppl):S43-7.
Macosko, et al. Highly Parallel Genome-wide Expression Profiling of Individual Cells Using Nanoliter Droplets. Cell. May. 21, 2015;161(5):1202-14. doi: 10.1016/j.cell.2015.05.002.
Mair, et al. Injection molded microfluidic chips featuring integrated interconnects. Lab Chip. Oct. 2006;6(10):1346-54. Epub Jul. 31, 2006.
Makino, et al. Preparation of hydrogel microcapsules: Effects of preparation conditions upon membrane properties. Colloids and Surfaces B: Biointerfaces. Nov. 1998; 12(2), 97-104.
Marcus. Gene method offers diagnostic hope. The Wall Street JourNal. Jul. 11, 2012.
Matochko, et al. Uniform amplification of phage display libraries in monodisperse emulsions. Methods. Sep. 2012;58(1):18-27. doi: 10.1016/j.ymeth.2012.07.012. Epub Jul. 20, 2012.
Mazutis, et al. Selective droplet coalescence using microfluidic systems. Lab Chip. Apr. 24, 2012;12(10):1800-6. doi: 10.1039/c2lc40121e. Epub Mar. 27, 2012.
Merriman, et al. Progress in ion torrent semiconductor chip based sequencing. Electrophoresis. Dec. 2012;33(23):3397-417. doi: 10.1002/elps.201200424.
Microfluidic ChipShop. Microfluidic product catalogue. Mar. 2005.
Microfluidic ChipShop. Microfluidic product catalogue. Oct. 2009.
Miller JC, et al. An improved zinc-finger nuclease architecture for highly specific genome editing. Nat. Biotechnol. 2007;25:778-785.

Mirzabekov, "DNA Sequencing by Hybridization—a Megasequencing Method and a Diagnostic Tool?" Trends in Biotechnology 12(1): 27-32 (1994).
Moore, et al. Behavior of capillary valves in centrifugal microfluidic devices prepared by three-dimensional printing. Microfluidics and Nanofluidics. 2011; 10(4):877-888.
Morgan, et al. Chapter 12: Human microbiome analysis. PLoS Comput Biol. 2012;8(12):e1002808. doi: 10.1371/journal.pcbi. 1002808. Epub Dec. 27, 2012.
Mouritzen et al., Single nucleotide polymorphism genotyping using locked nucleic acid (LNa). Expert Rev Mol Diagn. Jan. 2003;3(1):27-38.
Mozhanova, A.A. et al. "Local elastic properties of biological materials studied by SFM" (2003) XP055314108, Retrieved from the Internet: URL:http://www.ntmdt.com/data/media/files/publications/2003/08.08_a.a.mozhanova_n.i.n_english.pdf.
Muotri, et al. L1 retrotransposition in neurons is modulated by MeCP2. Nature. Nov. 18, 2010;468(7322):443-6. doi: 10.1038/nature09544.
Nagano, et al. Single-cell Hi-C reveals cell-to-cell variability in chromosome structure. Nature. Oct. 3, 2013;502(7469):59-64. doi: 10.1038/nature12593. Epub Sep. 25, 2013.
Nagashima, et al. Preparation of monodisperse poly (acrylamide-co-acrylic acid) hydrogel microspheres by a membrane emulsification technique and their size-dependent surface properties. Colloids and Surfaces B: Biointerfaces. Jun. 15, 1998; 11(1-2), 47-56.
Navin. The first five years of single-cell cancer genomics and beyond. Genome Res. Oct. 2015;25(10):1499-507. doi: 10.1101/gr. 191098.115.
Nguyen, et al. In situ hybridization to chromosomes stabilized in gel microdrops. Cytometry. 1995; 21:111-119.
Novak, et al. Single cell multiplex gene detection and sequencing using microfluidicallygenerated agarose emulsions. Angew Chem Int Ed Engl. Jan. 10, 2011;50(2):390-5. doi: 10.1002/anie. 201006089.
Oberholzer, et al. Polymerase chain reaction in liposomes. Chem Biol. Oct. 1995;2(10):677-82.
Ogawa, et al. Production and characterization of O/W emulsions containing cationic droplets stabilized by lecithin-chitosan membranes. J Agric Food Chem. Apr. 23, 2003;51(9):2806-12.
Okushima, S., et al,. "Controlled Production ofMonodisperse Double Emulsions by Two-Step Droplet Breakup in Microfluidic Devices," Langmuir, vol. 20, pp. 9905-9908 (2004).
Oligotex Handbook. For purification of poly A+ RNA from total RNA and directly from cultured cells or tissues as well as purification of polyadenylated in vitro transcripts. Jun. 2012.
Pantel, et al. Detection methods of circulating tumor cells. J Thorac Dis. Oct. 2012;4(5):446-7. doi: 10.3978/j.issn.2072-1439.2012.08. 15.
Patel, et al. Single-cell RNA-seq highlights intratumoral heterogeneity in primary glioblastoma. Science. Jun. 20, 2014;344(6190):1396-401. doi: 10.1126/science.1254257. Epub Jun. 12, 2014.
Perez, C., et al., "Poly(lactic acid)-poly(ethylene glycol) Nanoparticles as new carriers for the delivery ofplasmid DNa," JourNal of Controlled Release, vol. 75, pp. 211-224 (2001).
Peters, et al. Accurate whole-genome sequencing and haplotyping from 10 to 20 human cells. Nature. Jul. 11, 2012;487(7406):190-5. doi: 10.1038/Nature11236.
Picot, J. et al. "A biomimetic microfluidic chip to study the circulation and mechanical retention of red blood cells in the spleen" Am J Hematology (Jan. 12, 2015) 90(4):339-345.
Pinto, et al. Functional impact of global rare copy number variation in autism spectrum disorders. Nature. Jul. 15, 2010;466(7304):368-72. doi: 10.1038/nature09146. Epub Jun. 9, 2010.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Porteus MH, Baltimore D. Chimeric nucleases stimulate gene targeting in human cells. Science. 2003;300:763.

(56) References Cited

OTHER PUBLICATIONS

Ram, et al. Strategy for microbiome analysis using 16S rRNA gene sequence analysis on the Illumina sequencing platform. Syst Biol Reprod Med. Jun. 2011;57(3):162-70. doi: 10.3109/19396368.2011. 555598. Epub Mar. 1, 2011.
Ran, et al., Genome Engineering Using the CRISPR-Cas9 System, Nature Protocol, (2013), 8(11):2281-2308.
Richardson, et al. Novel inhibition of archaeal family-D DNA polymerase by uracil. Nucleic acids research 41.7 (2013): 4207-4218.
Rogozin, et al. A highly conserved family of inactivated archaeal B family DNA polymerases. Biol Direct. Aug. 6, 2008;3:32. doi: 10.1186/1745-6150-3-32.
Ropers. New perspectives for the elucidation of genetic disorders. Am J Hum Genet. Aug. 2007;81(2):199-207. Epub Jun. 29, 2007.
Rotem, et al. High-Throughput Single-Cell Labeling (Hi-SCL) for RNA-Seq Using Drop-Based Microfluidics. PLoS One. May 22, 2015;10(5):e0116328. doi: 10.1371/journal.pone.0116328. eCollection 2015.
Rotem, et al. Single Cell Chip-Seq Using Drop-Based Microfluidics. Abstract #50. Frontiers of Single Cell Analysis, Stanford University Sep. 5-7, 2013.
Rotem, et al. Single-cell ChIP-seq reveals cell subpopulations defined by chromatin state. Nat Biotechnol. Nov. 2015;33(11):1165-72. doi: 10.1038/nbt.3383. Epub Oct. 12, 2015.
Ryan, "Rapid assay for mycobacterial growth and antibiotic susceptibility using gel microdrop and encapsulation", J. Clinical Microbial., 33:7 1720-1726 (1995).
Sander JD, et al. Selection-free zinc-finger-nuclease engineering by context-dependent assembly (CoDA). Nat. Methods. 2011;8:67-69.
Schirinzi et al., Combinatorial sequencing-by-hybridization: aNalysis of the NFI gene. Genet Test. 2006 Spring;10(1):8-17.
Schmeider, et al. Fast identification and removal of sequence contamination from genomic and metagenomic datasets. PLoS One. Mar. 9, 2011;6(3):e17288. doi: 10.1371/journal.pone.0017288.
Schmitt, "Bead-based multiplex genotyping of human papillomaviruses", J. Clinical Microbial., 44:2 504-512 (2006).
Sebat, et al. Strong association of de novo copy number mutations with autism. Science. Apr. 20, 2007;316(5823):445-9. Epub Mar. 15, 2007.
Seiffert, et al. Smart microgel capsules from macromolecular precursors. J Am Chem Soc. May 12, 2010;132(18):6606-9. doi: 10.1021/ja102156h.
Shimkus, et al. A chemically cleavable biotinylated nucleotide: usefulness in the recovery of protein—DNA complexes from avidin affinity columns. Proc Natl Acad Sci U S A. May 1985;82(9):2593-7.
Shlien, et al. Copy number variations and cancer. Genome Med. Jun. 16, 2009;1(6):62. doi: 10.1186/gm62.
Shlien, et al. Excessive genomic DNA copy number variation in the Li-Fraumeni cancer predisposition syndrome. Proc Natl Acad Sci U S A. Aug. 12, 2008;105(32):11264-9. doi: 10.1073/pnas. 0802970105. Epub Aug. 6, 2008.
Shuttleworth, et al. Recognition of the pro-mutagenic base uracil by family B DNA polymerases from archaea. J Mol Biol. Mar. 26, 2004;337(3):621-34.
Simeonov et al., Single nucleotide polymorphism genotyping using short, fluorescently labeled locked nucleic acid (LNa) probes and fluorescence polarization detection. Nucleic Acids Res. Sep. 1, 2002;30(17):e91.
Sorokin et al., DiscrimiNation between perfect and mismatched duplexes with oligonucleotide gel microchips: role of thermodyNamic and kinetic effects during hybridization. J Biomol Struct Dyn. Jun. 2005;22(6):725-34.
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese JourNal Experimental Surgery. May 2005;22(5):639-40.
Susaki, et al. Whole-brain imaging with single-cell resolution using chemical cocktails and computational analysis. Cell. Apr. 24, 2014;157(3):726-39. doi: 10.1016/j.cell.2014.03.042. Epub Apr. 17, 2014.
Tayyab, S. et al. "Size exclusion chromatography and size exclusion HPLC of proteins" Biochem Ed, Pergamon, (1991) 19(3):149-152.
Tewhey, et al. Microdroplet-based PCR enrichment for large-scale targeted sequencing. Nat Biotechnol. Nov. 2009;27(11):1025-31. doi: 10.1038/nbt.1583. Epub Nov. 1, 2009.
Tomer, et al. Advanced CLARITY for rapid and high-resolution imaging of intact tissues. Nat Protoc. Jul. 2014;9(7):1682-97. doi: 10.1038/nprot.2014.123. Epub Jun. 19, 2014.
Tonelli, et al. Perfluoropolyether functional oligomers: unusual reactivity in organic chemistry. Journal of fluorine chemistry. 2002; 118(1) 107-121.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093/protein/gzq032. Epub May 31, 2010.
Turner, et al. Methods for genomic partitioning. Annu Rev Genomics Hum Genet. 2009;10:263-84. doi: 10.1146/annurev-genom-082908-150112. Review.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Wang, et al. A novel thermo-induced self-bursting microcapsule with magnetic-targeting property. Chemphyschem. Oct. 5, 2009;10(14):2405-9.
Wang, et al. Digital karyotyping. Proc Natl Acad Sci U S A. Dec. 10, 2002;99(25):16156-61. Epub Dec. 2, 2002.
Wang et al., Single nucleotide polymorphism discrimiNation assisted by improved base stacking hybridization using oligonucleotide microarrays. Biotechniques. 2003;35:300-08.
Wesolowska, et al. Cost-effective multiplexing before capture allows screening of 25 000 clinically relevant SNPs in childhood acute lymphoblastic leukemia. Leukemia. Jun. 2011;25(6):1001-6. doi: 10.1038/leu.2011.32. Epub Mar. 18, 2011.
Whitesides, "Soft lithography in biology and biochemistry", Annual Review of Biomedical Engineering, 3:335-373 (2001).
Woo, et al. G/C-modified oligodeoxynucleotides with selective complementarity: synthesis and hybridization properties. Nucleic Acids Res. Jul. 1, 1996;24(13):2470-5.
Wood AJ, et al. Targeted genome editing across species using ZFNs and TALENs. Science. 2011;333:307.
Xia and Whitesides, Soft Lithography, Ann. Rev. Mat. Sci. 28:153-184 (1998).
Yamamoto, et al. Chemical modification of Ce(IV)/EDTA-base artificial restriction DNa cutter for versatile manipulation of doulbe-stranded DNa. Nucleic Acids Research. 2007; 35(7):e53.
Zhang, "Combinatorial marking of cells and organelles with reconstituted fluorescent proteins", Cell, 119:137-144 (Oct. 1, 2004).
Zhang, et al. Degradable disulfide core-cross-linked micelles as a drug delivery system prepared from vinyl functioNalized nucleosides via the RAFT process. Biomacromolecules. Nov. 2008;9(11):3321-31. doi: 10.1021/bm800867n. Epub Oct. 9, 2008.
Zhang F, et al. Efficient construction of sequence-specific TAL effectors for modulating mammalian transcription. Nat. Biotechnol. 2011;29:149-153.
Zhao, J., et al., "Preparation of hemoglobin-loaded Nano-sized particles with porous structure as oxygen carriers," Biomaterials, vol. 28, pp. 1414-1422 (2007).
Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.

(56) References Cited

OTHER PUBLICATIONS

Zhu et al. Hydrogel Droplet Microfluidics for High-Throughput Single Molecule/Cell Analysis. Accounts of Chemical Research Article ASAP. DOI: 10.1021/acs.accounts.6b00370.
Zhu, et al. Synthesis and self-assembly of highly incompatible polybutadienepoly(hexafluoropropoylene oxide) diblock copolymers. Journal of Polymer Science Part B: Polymer Physics. 2005; 43(24):3685-3694.
Zimmermann et at., Microscale production of hybridomas by hypoosmolar electrofusion. Hum• Antibodies Hybridomas. Jan. 1992;3(1 ): 14-8.
Brenner, et al. In vitro cloning of complex mixtures of DNA on microbeads: physical separation of differentially expressed cDNAs. Proc Natl Acad Sci U S A. Feb. 15, 2000;97(4):1665-70.
Chang et al. Droplet-based microfluidic platform for heterogeneous enzymatic assays, 2013, Lab Chip, 13, 1817-1822 (Year: 2013).
Co-pending U.S. Appl. No. 15/887,711, filed Feb. 2, 2018.
Co-pending U.S. Appl. No. 15/887,947, filed Feb. 2, 2018.
JPK "Determining the elastic modulus of biological samples using atomic force microscopy" (https://www.jpk.com/ app-technotes-img/AFM/pdf/jpk-app-elastic-modulus.14-1.pdf) 2009, pp. 1-9 (Year: 2009).
Lasken, et al. (1996) Archaebacterial DNA Polymerases Tightly Bind Uracil-containing DNA. The Journal of Biological Chemistry, 271(30):17692-17696 (Year: 1996).
Lee et al. Alginate: Properties and biomedical applications. Prog Polym Sci 37(1):106-126 (2012).
Miller-Stephenson Chemicals 157 FS Series catalog, www.miller-stephenon.com.
Morimoto, et al. Monodisperse semi-permeable microcapsules for continuous observation of cells. 2009. Lab Chip 9(15):2217-2223.
Narayanan, J. et al. "Determination of agarose gel pore size: Absorbance measurements vis a vis other techniques" Journal of Physics: Conference Series 28 (2006) 83-86 (Year: 2006).
Sakaguchi, et al. (1996) Cautionary Note on the Use of dUMP-Containing PCR Primers with Pfu and VentR. Biotechniques, 21(3): 369-370 (Year: 1996).
Spormann Laboratory, Polymerase Chain Reaction (PCR), Alfred Spormann Laboratory, 2009, 1-3. (Year: 2009).
ThermoFisher, Protocols, M-270 Streptavidin, ThermoFisherScientific, 2007, 1-5. (Year: 2007).
Zhou, Y. et al. "Development of an enzyme activity screening system for p-glucosidase-displaying yeasts using calcium alginate micro-beads and flow sorting" Appl Microbiol Biotechnol (2009) 84:375-382 (Year: 2009).
Ahern, "Biochemical, Reagents Kits Offer Scientists Good Return on Investment" The Scientist (1995) 9(15):1-7.
Bentzen, et al. Large-scale detection of antigen-specific T cells using peptide-MHC-I multimers labeled with DNA barcodes. Nat Biotechnol. Oct. 2016;34(10):1037-1045. doi: 10.1038/nbt.3662. Epub Aug. 29, 2016.
Boulanger, et al, "Massively parallel haplotyping on microscopic beads for the high-throughput phase analysis of single molecules", PLoS One, vol. 7:1-10, 2012.
Brown, K., Targeted Sequencing Using Droplet-Based Microfluidics, RainDance Technologies, 2009, 1-18.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-5. Epub Aug. 9, 2001.
Casbon, et al, "Reflex: intramolecular barcoding of long-range PCR products for sequencing multiple pooled DNAs", Nucleic Acids Res., pp. 1-6, 2013.
Co-pending U.S. Appl. No. 15/596,754, filed May 16, 2017.
Co-pending U.S. Appl. No. 15/598,898, filed May 18, 2017.
Curcio. Improved Techniques for High-Throughput Molecular Diagnostics. PhD Thesis. 2002.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
Han, X. et al. "CRISPR-Cas9 delivery to hard-to-transfect cells via membrane deformation" Science Advances (2015) 1(7): E1500454 (8 pages).
Hiatt, et al. Parallel, tag-directed assembly of locally derived short sequence reads. Nat Methods. Feb. 2010;7(2):119-22. doi: 10.1038/nmeth.1416. Epub Jan. 17, 2010.
Hirsch et al. (2002) "Easily reversible desthiobiotin binding to streptavidin, avidin, and other biotin-binding proteins: uses for protein labeling, detection, and isolation." Analytical of Biochemistry 308(2):343-357.
Hosokawa, et al. Massively parallel whole genome amplification for single-cell sequencing using droplet microfluidics. Scientific Reports 7, Article No. 5199 (2017).
Imburgio, et al, "Studies of promoter recognition and start site selection by T7 RNA polymerase using a comprehensive collection of promoter variants", Biochemistry., 39:10419-30, 2000.
Katsura, et al. Indirect micromanipulation of single molecules in water-in-oil emulsion. Electrophoresis. Jan. 2001;22(2):289-93.
Kenis, et al. Microfabrication Inside Capillaries Using Multiphase Laminar Flow Patterning. Science. Jul. 2, 1999;285(5424):83-5.
Kirkness et al. "Sequencing of isolated sperm cells for direct haplotyping of a human genome," Genome Res (2013) 23:826-832.
Kitzman et al. "Haplotype-resolved genome sequencing of a Gujarati Indian individual." Nat Biotechnol (2011) 29:59-63.
Kozarewa, et al, "96-plex molecular barcoding for the Illumina Genome Analyzer", Methods Mol Biol., 733:279-98, 2011.
Kozarewa, et al. "Amplification-free Illumina sequencing-library preparation facilitates improved mapping and assembly of GC-biased genomes", Nat Methods., 6: 291-5, 2009.
Kwok, et al, "Single-molecule analysis for molecular haplotyping", Hum Mutat., 23:442-6, 2004.
Lagally, et al. Single-Molecular DNA Amplification and Analysis in an Integrated Microfluidic Device. Anal Chem. Feb. 1, 2001;73(3):565-70.
Laird et al, Hairpin-bisulfite PCR: Assessing epigenetic methylation patterns on complementary strands of individual DNA molecules, 2004, PNAS, 101, 204-209.
Lan, et al. "Single-cell genome sequencing at ultra-high-throughput with microfluidic droplet barcoding" with Supplementary Material. Nat Biotechnol. May 29, 2017. doi: 10.1038/nbt.3880. [Epub ahead of print].
Linch, et al. Bone marrow processing and cryopreservation. Journal of Clinical Pathology; Feb. 1982, vol. 35, No. 2; pp. 186-190.
Lundin, et al, "Hierarchical molecular tagging to resolve long continuous sequences by massively parallel sequencing", Sci Rep., 3:1186, 2003.
Man. Monolithic Structures for Integrated Microfluidic Analysis. PhD Thesis. 2001.
Myllykangas et al., Targeted Sequencing Library Preparation by Genomic DNA Circularization, BMC Biotechnology, 2011, 11(122), 1-12.
Nisisako, et al. Droplet formation in a microchannel network. Lab Chip. Feb. 2002;2(1):24-6. Epub Jan. 18, 2002.
Nisisako, T. et al. "Droplet Formation in a Microchannel on PMMA Plate" Abstract. 2001 Kluwer Academic Publishers. p. 137-138.
Oyola, et al, "Optimizing Illumina next-generation sequencing library preparation for extremely AT-biased genomes", BMC Genomics. ,13:1, 2012.
PCT/IB2010/002243, International Search Report and Written Opinion, dated Feb. 9, 2011, 13pgs.
Rakszewska, A. et al. "One drop at a time: toward droplet microfluidics as a versatile tool for single-cell analysis" NPG Asia Materials (2014) 6(10):e133 (12 pages).
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Reis, A. et al. "CRISPR/Cas9 and Targeted Genome Editing: A New Era in Molecular Biology" (2014) XP002766825: URL:https://ww.

(56) References Cited

OTHER PUBLICATIONS neb.com/tools-and-resources/feabture-articles/crispr-cas9-and-targeted-genome-editing-a-new-era-in-molecular-biology.

Reisner, et al, "Single-molecule denaturation mapping of DNA in nanofluidic channels", Proc Natl Acad Sci U.S.A., 107: 13294-9, 2010.

Repp et al. "Genotyping by Multiplex Polymerase Chain Reaction for Detection of Endemic Hepatitis B Virus Transmission" J Clinical Microbiology (1993) 31:1095-1102.

Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-7. URL:http://454.com/downloads/my454/documentation/technical-bulletins/TCB-09004 Using MultiplexIdentifierAdaptorsForTheGSFLXTitaniumSeriesChemistry-BasicMIDSet.pdf.

Roche. Using Multiplex Identifier (MID) Adaptors for the GS FLX Titanium Chemistry Extended MID Set Genome Sequencer FLX System, Technical Bulletin 005-2009, (Apr. 1, 2009) pp. 1-7. URL:http://454.com/downloads/my454/documentation/technical-bulletins/TCB-09005 UsingMultiplexIdentifierAdaptorsForTheGSFLXTitaniumChemistry-ExtendedMIDSet.pdf.

Rodrigue, S. et al. "Whole genome amplification and de novo assembly of single bacterial cells" PLoS One. Sep. 2, 2009;4(9):e6864. doi: 10.1371/journal.pone.0006864.

Schubert, et al. Microemulsifying fluorinated oils with mixtures of fluorinated and hydrogenated surfactants. Colloids and Surfaces A; Physicochemical and Engineering Aspects, 84(1994) 97-106.

Schwartz, et al., "Capturing native long-range contiguity by in situ library construction and optical sequencing", PNAS (Nov. 2012), 109(46)18749-18754.

Song, et al. Reactions in droplets in microfluidic channels. Angew Chem Int Ed Engl. Nov. 13, 2006;45(44):7336-56.

Stoeckius, et al. Large-scale simultaneous measurement of epitopes and transcriptomes in single cells. bioRxiv 113068; doi: https://doi.org/10.1101/113068.

Tewhey et al., Supplementary Materials, Nature Biotechnology, 2009, 27(11), 1-22.

Thorsen, et al. Dynamic pattern formation in a vesicle-generating microfluidic device. Physical Review Letters. American Physical Society. 2001; 86(18):4163-4166.

Turner, et al. Assaying chromosomal inversions by single-molecule haplotyping. Nat Methods. Jun. 2006;3(6):439-45.

Turner, et al, "High-throughput haplotype determination over long distances by haplotype fusion PCR and ligation haplotyping", Nat Protoc., 4:1771-83, 2009.

Ushijima et al, Detection and interpretation of altered methylation patterns in cancer cells, 2005, Nature reviews, 5, 223-231.

Van Nieuwerburgh, et al, "Illumina mate-paired DNA sequencing-library preparation using Cre-Lox recombination", Nucleic Acids Res., 40:1-8, 2012.

Wang, et al., "Self-Formed Adaptor PCR: a Simple and Efficient Method for Chromosome Walking", Applied and Environmental Microbiology (Aug. 2007), 73(15):5048-5051.

Ward, et al. Microfluidic flow focusing: Drop size and scaling in pressure versus flow-rate-driven pumping. Electrophoresis. Oct. 2005;26(19):3716-24.

Weigl, et al. Microfluidic Diffusion-Based Separation and Detection. Science. 1999; pp. 346-347.

Wiseman, R.W. et al. "Major histocompatibility complex genotyping with massively parallel pyrosequencing" Nature Medicine (Oct. 11, 2009) 15(11):1322-1326.

Xiao, et al, "Determination of haplotypes from single DNA molecules: a method for single-molecule barcoding", Hum Mutat., 28:913-21, 2007.

Yan, Pu et al. "Rapid one-step construction of hairpin RNA" Biochem and Biophys Res Comm (Jun. 12, 2009) 383(4):464-468.

Zeng, et al. High-performance single cell genetic analysis using microfluidic emulsion generator arrays. Anal Chem. Apr. 15, 2010;82(8):3183-90. doi: 10.1021/ac902683t.

Zhang. Genomics of inherited bone marrow failure and myelodysplasia. Dissertation [online]. University of Washington. 2015 [Retrieved on May 3, 2017].

Xi, et al. New library construction method for single-cell genomes. PLoS One. Jul. 19, 2017;12(7):e0181163. doi: 10.1371/journal.pone.0181163. eCollection 2017.

Abate et al., Valve-based flow focusing for drop formation. Appl Phys Lett. 2009;94. 3 pages.

Abate, et al. High-throughput injection with microfluidics using picoinjectors. Proc Natl Acad Sci U S A. Nov. 9, 2010;107(45):19163-6. doi: 10.1073/pNas.1006888107. Epub Oct. 20, 2010.

Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.

Anna et al., "Formation of dispersions using 'flow focusing' in microchannels", Appln. Phys. Letts. 82:3 364 (2003).

Chou, H-P. et al. "Disposable Microdevices for DNA Analysis and Cell Sorting" Proc. Solid-State Sensor and Actuator Workshop Hilton Head, SC Jun. 8-11, 1998, pp. 11-14.

Christiansen et al. "The Covalent Eukaryotic Topoisomerase I-DNA Intermediate Catalyzes pH-dependent Hydrolysis and Alcoholysis" J Biol Chem (Apr. 14, 1994) 269(15)11367-11373.

Clausell-Tormos et al., "Droplet-based microfluidic platforms for the encapsulation and screening of mammalian cells and multicellular organisms", Chem. Biol. 15:427-437 (2008).

Demirci, et al. "Single cell epitaxy by acoustic picolitre droplets" Lab Chip. Sep. 2007;7(9):1139-45. Epub Jul. 10, 2007.

Doerr, "The smallest bioreactor", Nature Methods, 2:5 326 (2005).

Dowding, et al. "Oil core/polymer shell microcapsules by interNal phase separation from emulsion droplets. II: controlling the release profile of active molecules" Langmuir. Jun. 7, 2005;21(12):5278-84.

Drmanac et al., Sequencing by hybridization (SBH): advantages, achievements, and opportunities. Adv Biochem Eng Biotechnol. 2002;77 :75-101.

Droplet Based Sequencing (slides) dated (Mar. 12, 2008).

Esser-Kahn, et al. Triggered release from polymer capsules. Macromolecules. 2011; 44:5539-5553.

Fisher, S. et al. "A Scalable, fully automated process for construction of sequence-ready human exome targeted capture libraries" Genome Biology (2011) 2:R1-R15. doi: 10.1186/gb-2011-12-1-r1. Epub Jan. 4, 2011.

Freiberg, et al. "Polymer microspheres for controlled drug release" Int J Pharm. Sep. 10, 2004;282(1-2):1-18.

Fu. A.Y. et al. "A microfabricated fluorescence-activated cell sorter" Nature Biotech (Nov. 1999) 17:1109-1111.

Fulton et al., "Advanced multiplexed analysis with the FlowMetrix system" Clin Chem. Sep. 1997;43(9): 1749-56.

Garstecki, P. et al. "Formation of monodisperse bubbles in a microfluidic flow-focusing device" Appl. Phys. Lett (2004) 85(13):2659-2651. DOI: 10.1063/1.1796526.

Hashimshony, T et al. "CEL-Seq: Single-Cell RNa-Seq by Multiplexed Linear Amplification" Cell Rep. Sep. 27, 2012;2(3):666-73. doi: 10.1016/j.celrep.2012.08.003. Epub Aug. 30, 2012.

He "Selective Encapsulation of Single Cells and Subcellular Organelles into Picoliter- and Femtoliter—Volume Droplets" Anal. Chem 77: 1539-1544 (2005).

Holtze, C. et al. Biocompatible surfactants for water-in-fluorocarbon emulsions. Lab Chip. Oct. 2008;8(10):1632-9. doi: 10.1039/b806706f. Epub Sep. 2, 2008.

Huebner, "Quantitative detection of protein expression in single cells using droplet microfluidics", Chem. Commun. 1218-1220 (2007).

Hug, H. et al. "Measurement of the number of molecules of a single mRNA species in a complex mRNA preparation" J Theor Biol. Apr. 21, 2003;221(4):615-24.

Koster et al., "Drop-based microfluidic devices for encapsulation of single cells", Lab on a Chip The Royal Soc. of Chem. 8: 1110-1115 (2008).

Shah, "Fabrication of mono disperse thermosensitive microgels and gel capsules in micro fluidic devices", Soft Matter, 4:2303-2309 (2008).

(56) References Cited

OTHER PUBLICATIONS

Tawfik, D.S. et al. "Man-made cell-like compartments for molecular evolution" Nature Biotech (Jul. 1998) 16:652-656.
Theberge, A.B, et al. Microdropelts in microfluidics: an evolving platform for discoveries in chemsitry and biology. Angew Chem Int Ed Engl. Aug. 9, 2010;49(34):5846-68. doi: 10.1002/anie. 200906653.
Weaver, J.C. et al. "Rapid clonal growth measurements at the single-cell level: gel microdroplets and flow cytometry", Biotechnology, 9:873-877 (1991).
Williams, R. et al. "Amplification of complex gene libraries by emulsion PCR" Nature Methods (Jul. 2006) 3(7):545-550.
Adey, et al., "Ultra-low-input, tagmentation-based whole-genome bisulfite sequencing", Genome Research, 2012, 22 ;6): 1139-1143.
Ason et al. DNA sequence bias during Tn5 transposition. Journal of molecular biology 335.5 (2004): 1213-1225.
Bjornsson et al., Intra-individual change over time in DNA methylation with familial clustering, JAMA, Jun. 25, 2008, vol. 299 No. 24, pp. 2877-2883.
Boyle, et al. "High-resolution genome-wide in vivo footprinting of diverse transcription factors in human cells", Genome Res. Mar. 2011;21(3):456-64.
Buenrostro, et al., "Tranposition of native chromatin for fast and sensitive epigenomic profiling of open chromatin, DNA-binding proteins and nucleosome position", Nature Methods, 2013, 10(12): 1213-1218.
Co-pending U.S. Appl. No. 15/933,299, filed Mar. 22, 2018.
Co-pending U.S. Appl. No. 15/975,468, filed May 9, 2018.
Co-pending U.S. Appl. No. 15/980,473, filed May 15, 2018.
Co-pending U.S. Appl. No. 15/985,388, filed May 21, 2018.
Co-pending U.S. Appl. No. 16/000,803, filed Jun. 5, 2018.
Co-pending U.S. Appl. No. 16/045,474, filed Jul. 25, 2018.
Co-pending U.S. Appl. No. 16/052,431, filed Aug. 1, 2018.
Co-pending U.S. Appl. No. 16/052,486, filed Aug. 8, 2018.
Co-pending U.S. Appl. No. 16/056,231, filed Aug. 6, 2018.
Depristo et al. A framework for variation discovery and genotyping using next-generation DNA sequencing data. Nature Genet 43:491-498 (2011).
Zhu, et al. Reverse transcriptase template switching: a SMART approach for full-length cDNA library construction. Biotechniques. Apr. 2001;30(4):892-7.
Gangadharan et al., DNA transposon Hermes insert into DNA in nucleosome-free regions in vivo, Proc nat Ad Sci, Dec. 21, 2010, vol. 107, No. 51, pp. 1966-1972.
Green et al. Insertion site preference of Mu, Tn5, and Tn7 transposons. Mobile DNA 3.1 (2012): 3.
Han, SW et al. "Targeted Sequencing of Cancer-Related Genes in Colorectal Cancer Using Next-Generation Sequencing" PLOS One (2013) 8(5):e64271.
Haring, et al. Chromatin immunoprecipitation: optimization, quantitative analysis and data normalization. Plant Methods. 2007; 3: 11.
Joneja, et al. Linear nicking endonuclease-mediated strand-displacement DNA amplification. Anal Biochem. Jul. 1, 2011;414(1):58-69. doi: 10.1016/j.ab.2011.02.025. Epub Feb. 20, 2011.
Knapp, et al. Generating barcoded libraries for multiplex high-throughput sequencing. Methods Mol Biol. 2012;840:155-70. doi: 10.1007/978-1-61779-516-9_19.
Lai; et al., ""Characterization and Use of Laser-Based Lysis for Cell Analysis On-Chip", Journal of the Royal Society, Interface, vol. 5, Supplement 2, pp. S113-S121, Oct. 2008, (Year:2008)", Journal of the Royal Society, Interface, Oct. 2008, vol. 5, Supplement 2, S113-S121.
Lander, et al. Initial sequencing and analysis of the human genome. Nature, 409 (Feb. 15, 2001): 860-921.
Park. ChIP—seq: advantages and challenges of a maturing technology. Nature Reviews Genetics vol. 10, pp. 669-680 (2009).
"U.S. Appl. No. 61/982,001, filed Apr. 21, 2014 (Year:2014)".
Shaikh, et al. A modular microfluidic architecture for integrated biochemical analysis. Proc Natl Acad Sci U S A. Jul. 12, 2005;102(28):9745-50. Epub Jun. 28, 2005.
Simon, et al., "Using formaldehyde-assisted isolation of regulatory elements (FAIRE) to isolate active regulatory DNA", Nature Protocols, 2012, 7(2): 256-267.
Smith, et al. Highly-multiplexed barcode sequencing: an efficient method for parallel analysis of pooled samples. Nucleic Acids Research, 38(13): e142 (2010).
Song, et al., "DNase-seq: A High-Resolution Technique for Mapping Active Gene Regulatory Elements across the Senome from Mammalian Cells", Cold Spring Harbor Laboratory Press, 2010, 2010(2), doi:10.1101/pdb.prot5384.
Holmberg, et al. The biotin-streptavidin interaction can be reversibly broken using water at elevated temperatures. Feb. 2, 2005. Electrophoresis, 26:501-510.
Invitrogen Dynal. Dynabeads M-280 Streptavidin 2006 product sheet.
Morton. Parameters of the human genome. Apr. 23, 1991. Proceedings of the National Academy of Sciences of the United States of America, 88: 7474-7476.
National Human Genome Research Institute (NHGRI). The Human Genome Project Completion: Frequently Asked Questions. Last Updated: Oct. 30, 2010.
Qiagen. Omniscript Reverse Transcription Handbook. Oct. 2010.
Seiffert, et al. Microfluidic fabrication of smart microgels from macromolecular precursors. 2010. Polymer.
Wong, et al. Multiplexed Barcoded CRISPR-Cas9 Screening Enabled by CombiGEM. PNAS. Mar. 1, 2016, vol. 113, pp. 2544-2549.
Zentner, et al. Surveying the epigenomic landscape, one base at a time. Genome Biol. Oct. 22, 2012;13(10):250. doi: 10.1186/gb4051.
Co-pending U.S. Appl. No. US16/160,576, filed Oct. 15, 2018.
Co-pending U.S. Appl. No. US16/160,719, filed Oct. 15, 2018.
Co-pending U.S. Appl. No. US16/165,389, filed Oct. 19, 2018.
Co-pending U.S. Appl. No. US16/170,980, filed Oct. 25, 2018.
Co-pending U.S. Appl. No. US16/196,684, filed Nov. 20, 2018.
Co-pending U.S. Appl. No. US16/206,168, filed Nov. 30, 2018.
Co-pending U.S. Appl. No. US16/212,441, filed Dec. 6, 2018.
Delehanty, et al. Peptides for specific intracellular delivery and targeting of nanoparticles: implications for developing nanoparticle-mediated drug delivery. Ther Deliv. Sep. 2010;1(3):411-33.
Epicentre., "EZ-Tn5TM Custom Transposome Construction Kits", http://www.epicentre.com, pp. 1-17, 2012.
Jin, et al. Genome-wide detection of DNase I hypersensitive sites in single cells and FFPE tissue samples. Nature. Dec 3, 2015;528(7580):142-6. doi: 10.1038/nature15740.
Lebedev, A. et al. "Hot Start PCR with heat-activatable primers: a novel approach for improved PCR performance" NAR (2008) 36(20):E131-1.
Margulies 2005 Supplementary methods (Year: 2005).
Thaxton, C.S. et al. "A Bio-Bar-Code Assay Based Upon Dithiothreitol Oligonucleotide Release" Anal Chem (2005) 77:8174-8178.
Zhang, et al. One-step fabrication of supramolecular microcapsules from microfluidic droplets. Science.Feb. 10, 2012;335(6069):690-4. doi: 10.1126/science.1215416.

| Sample Description | Sample ID | Mean Depth Deduped | DPCV Deduped on Confident Regions | BAC Aware Amplification Rate (Full Coverage) |
|---|---|---|---|---|
| GEM_No heat #1 | 9929 | 90.1 | 0.201 | 0.271 |
| GEM_No heat #2 | 9930 | 95.7 | 0.191 | 0332 |
| GEM_NaOH denature #1 | 9931 | 128.8 | 0.236 | 0.683 |
| GEM_NaOH denature #2 | 9932 | 150.1 | 0.241 | 0.669 |
| GEM_heat #1 | 9933 | 149.7 | 0.218 | 0.842 |
| GEM_heat #2 | 9934 | 196.5 | 0.219 | 0.916 |

Fig. 10

| Sample Description | Sample ID | Mean Depth Deduped | Mean Dup Rate (0.25X ign BC) | DPCV Deduped on Conf Reg |
|---|---|---|---|---|
| All Human Non-Targeted | | | | < 0.7 |
| 500nM adapt-12 | 10723 | 10.5 | 1.000180 | 0.29 |
| 400nM adapt-12 | 10724 | 9.9 | 1.000188 | 0.29 |
| 320nM adapt-12 | 10725 | 13.8 | 1.000371 | 0.29 |
| 256nM adapt-12 | 10726 | 10.6 | 1.000183 | 0.29 |
| 205nM adapt-12 | 10727 | 12.1 | 1.000184 | 0.28 |
| 164nM adapt-12 | 10728 | 12.3 | 1.000186 | 0.28 |
| 131nM adapt-12 | 10729 | 11.7 | 1.000188 | 0.28 |
| 105nM adapt-12 | 10730 | 9.8 | 1.000187 | 0.28 |
| 84nM adapt-12 | 10731 | 11.6 | 1.000182 | 0.27 |
| 67nM adapt-12 | 10732 | 12.1 | 1.000376 | 0.27 |
| 54nM adapt-12 | 10733 | 14.1 | 1.000182 | 0.27 |
| LL-ctrl | 10734 | 5.8 | 1.000178 | 0.17 |

Fig. 11

| Ligase | Template kind | Adaptor | Adap conc | P5/P7 quant |
|---|---|---|---|---|
| No ligase | NTC | Phos degenerate | 0.2 | 0.17 |
| No ligase | NTC | Phos inline | 0.2 | 0.52 |
| No ligase | NTC | No Phos inline | 0.2 | 0.9 |
| No ligase | NTC | No Phos degenerate | 2 | 0.38 |
| No ligase | NTC | Phos inline | 2 | 0.78 |
| No ligase | NTC | No Phos inline | 2 | 1.8 |
| No ligase | BACS | No adap | 0 | 0.25 |
| No ligase | BACS | Phos degenerate | 0.2 | 0.47 |
| No ligase | BACS | Phos inline | 0.2 | 0.67 |
| No ligase | BACS | No Phos inline | 0.2 | 0.97 |
| No ligase | BACS | No Phos degenerate | 2 | 0.36 |
| No ligase | BACS | Phos inline | 2 | 1.03 |
| No ligase | BACS | No Phos inline | 2 | 2.74 |
| + ligase | NTC | Phos degenerate | 0.2 | 0.66 |
| + ligase | NTC | Phos inline | 0.2 | 1.01 |
| + ligase | NTC | No Phos inline | 0.2 | 1.42 |
| + ligase | NTC | No Phos degenerate | 2 | 0.5 |
| + ligase | NTC | Phos inline | 2 | 2.28 |
| + ligase | NTC | No Phos inline | 2 | 2.99 |
| + ligase | BACS | No adap | 0 | 2.37 |
| + ligase | BACS | No Phos inline | 0.2 | 43.55 |
| + ligase | BACS | Phos degenerate | 0.2 | 53.39 |
| + ligase | BACS | Phos inline | 0.2 | 104.2 |
| + ligase | BACS | No Phos degenerate | 2 | 10.78 |
| + ligase | BACS | No Phos inline | 2 | 85.99 |
| + ligase | BACS | Phos inline | 2 | 106.56 |

Fig. 13

PROCESSES AND SYSTEMS FOR PREPARATION OF NUCLEIC ACID SEQUENCING LIBRARIES AND LIBRARIES PREPARED USING SAME

CROSS-REFERENCE TO RELATED APPLICATIONS

This application claims the benefit of U.S. Provisional Patent Application No. 62/102,420, filed Jan. 12, 2015, and U.S. Provisional Patent Application No. 62/262,769, filed Dec. 3, 2015, said applications being incorporated herein by reference in their entirety for all purposes.

SEQUENCE LISTING

The instant application contains a Sequence Listing which has been submitted electronically in ASCII format and is hereby incorporated by reference in its entirety. Said ASCII copy, created Feb. 16, 2016, is named 100-080902US_S-L.txt and is 1 KB in size.

BACKGROUND

Nucleic acid sequencing technology has experienced rapid and massive advances over recent years. As compared to gel based separation methods where nested sets of terminated sequence extension products were interpreted visually by scientists, today's sequencing technologies produce enormous amounts of sequence data, allow illumination of never before sequenced genomes and genome regions, and provide throughput and costs that allow the widespread adoption of sequencing into routine biological research and diagnostics.

Genomic sequencing can be used to obtain information in a wide variety of biomedical contexts, including diagnostics, prognostics, biotechnology, and forensic biology. Sequencing may involve basic methods including Maxam-Gilbert sequencing and chain-termination methods, or de novo sequencing methods including shotgun sequencing and bridge PCR, or next-generation methods including polony sequencing, 454 pyrosequencing, Illumina sequencing, SOLiD sequencing, Ion Torrent semiconductor sequencing, HeliScope single molecule sequencing, SMRT® sequencing, and others. For most sequencing applications, a sample such as a nucleic acid sample is processed prior to introduction to a sequencing machine. A sample may be processed, for example, by amplification or by attaching a unique identifier. Often unique identifiers are used to identify the origin of a particular sample.

Despite the huge advances in sequencing technology, or perhaps illuminated by such huge advances, there exists a need to be able to create broad, diverse and representative sequencing libraries from samples of nucleic acids. Further, as the applications of sequencing technologies expands, the needs for these library preparation methods to address widely divergent sample types also increases. For example, the ability to uniformly interrogate the entire genome, or at least the entire portion of the genome that is of interest is a significant source of difficulty for molecular biologists. The lack of uniformity emanates from numerous process inputs into all of the various sequencing technologies. For example, fragment size biases may make it more likely that a sequencing technology will sequence only short fragments of the genome. Likewise, specific sequence context may increase or decrease the likelihood that portions of the genome will not be primed and sequenced, or amplified in pre-sequencing steps, leading to uneven sequence coverage in the resulting sequence data. Finally, a host of other characteristics of the sequences, e.g., secondary or tertiary structures, or the sequencing technologies, e.g., long read vs. short read technologies, can lead to biased representation of the originating sequence within a sequencing library.

With these challenges, the process of converting sample nucleic acids into sequenceable libraries has taken on significant complexity and time commitments, e.g., in fragmentation, separation, amplification, incorporation of sequencer specific library components, and clean up. Methods and systems are provided herein for preparing improved sequencing libraries, as well as the libraries prepared, that have additional benefits of simplified workflows.

SUMMARY

Provided are improved methods and systems for preparing libraries of nucleic acids for use as sequencing libraries, as well as the libraries prepared using these methods. The libraries described herein have advantages of improved coverage, low error rates, and applicability for generation of long range sequence information from shorter read sequence data.

The present disclosure generally provides methods for the preparation of sequencing libraries, for example barcode sequencing libraries, useful, for example, with approaches employing NGS (Next Generation Sequencing). Sequencing libraries produced as described herein using a priming free amplification by polymerization at nick sites (priming free amplification), provide superior sequencing results, e.g., whole genome sequencing results, when compared to conventional primer based amplification (primed amplification) library preparation approaches.

In general in one aspect a method of creating a sequencing library is provided, including creating a plurality of barcoded nucleic acid fragments from a template nucleic acid, each of the plurality of barcoded nucleic acid fragments including a common barcode sequence; and appending a first adapter sequence to each of the plurality of barcoded nucleic acid fragments, the first adapter comprising one or more functional sequences.

In one embodiment the creating step includes contacting the template nucleic acid with a first set of oligonucleotides, the first set of oligonucleotides comprising a plurality of barcode oligonucleotides, each of the plurality of barcode oligonucleotides having the common barcode sequence and a primer sequence at its 3' terminus; and annealing the primer sequences on the plurality of barcode oligonucleotides to the template nucleic acid and extending the plurality of barcode oligonucleotides along the template nucleic acid to create the plurality of barcoded nucleic acid fragments from the template nucleic acid.

In another embodiment the appending step includes contacting the plurality of barcoded nucleic acid fragments with a second set of oligonucleotides, the second set of oligonucleotides comprising a plurality of primer sequences complementary to at least a portion of the plurality of barcoded nucleic acid fragments, and at least one functional sequence; and annealing the second set of oligonucleotides to the plurality of barcoded nucleic acid fragments and extending the second set of oligonucleotides along the plurality of barcoded nucleic acid fragments, to create replicate barcoded fragments including the at least one functional sequence.

In yet another embodiment the appending step includes ligating the first adapter sequence to each of the plurality of barcoded nucleic acid fragments. It is envisioned that the step of ligating the first adapter sequence to each of the plurality of barcoded nucleic acid fragments includes shearing each of the plurality of barcoded nucleic acid fragments to create sheared fragments and ligating the first adapter sequence to a 3' terminus of the sheared fragments.

In general, in one aspect a method of preparing a sequencing library is provided including the steps of: (a) providing a template nucleic acid sequence, dNTPs, dUTP, a primer, a polymerase, a dUTP excising enzyme, and a plurality of beads including oligonucleotide adapter sequence segments; (b) amplifying the template nucleic acid with the polymerase, dNTPs, dUTP and random hexamer to provide a complementary nucleic acid sequence including occasional dUTPs; and (c) excising the incorporated dUTPs with the dUTP excising enzyme to provide nicks in the complementary nucleic acid sequence to provide a sequencing library.

In one embodiment the method further includes a step (d) of amplifying the nicked complementary nucleic acid sequence, and a step (e) of extending the sequence of the amplified nucleic acid sequence using a nucleic acid extension means. In some embodiments the steps of the method above are performed in a single reaction.

In another embodiment the plurality of beads is a pooled bead population. In a specific embodiment the beads of the pooled bead population are co-partitioned with one or more of the components listed in step (a), and wherein the partition optionally comprises a droplet in an emulsion.

In some embodiments the beads including degradable beads selected from chemically degradable beads, photodegradable beads and thermally degradable beads. In a specific embodiment the beads include chemically reducible cross-linkers. More specifically the chemically reducible cross-linkers can include disulfide linkages.

In another embodiment the amplification in step (b) is isothermal.

In a further embodiment the polymerase is phi29 DNA polymerase.

In a different embodiment the nucleic acid extension means is selected from the group consisting of a ligating enzyme, a nucleic acid extension enzyme and a transposase. In a related embodiment the library of amplified nucleic acid sequences includes single stranded DNA and the ligating enzyme includes an ATP independent enzyme. The ATP independent enzyme can include thermostable 5' App DNA/RNA ligase. In another related embodiment the ligating enzyme includes a topoisomerase. Specifically the topoisomerase can be topoisomerase I. In still another related embodiment the ligating enzyme includes T4 DNA ligase.

In general, in another aspect a method of preparing a barcode sequencing library is provided, including: (a) providing a template nucleic acid sequence, dNTPs, dUTP, a primer, a polymerase, a dUTP excising enzyme, a nucleic acid extension means and a plurality of beads comprising oligonucleotide barcode sequence segments; (b) amplifying the template nucleic acid with the polymerase, dNTPs, dUTP and random hexamer to provide a complementary nucleic acid sequence including occasional dUTPs; and (c) excising the incorporated dUTPs with the dUTP excising enzyme to provide nicks in the complementary nucleic acid sequence; (d) amplifying the nicked complementary nucleic acid sequence to provide a library of amplified nucleic acid sequences; and (e) releasing the barcode sequence segments from the pooled bead population; and (f) extending the sequence of the amplified nucleic acid sequences using the barcode sequence segments and the nucleic acid extension means to provide a barcode library or alternatively, ligating the barcode sequence segments, using a nucleic acid ligating enzyme, to the library of amplified nucleic acid sequences to provide a barcode library.

In some embodiments of the method, the steps are performed in a single reaction. In one embodiment the plurality of beads is a pooled bead population. In another embodiment the beads of the pooled bead population are co-partitioned with one or more of the components listed in step (a), and wherein the partition optionally includes a droplet in an emulsion. In a further embodiment the beads include degradable beads selected from chemically degradable beads, photodegradable beads and thermally degradable beads. In a particular embodiment the beads include chemically reducible cross-linkers. The chemically reducible cross-linkers can include disulfide linkages.

In other embodiments the amplification in step (b) is isothermal. In some embodiments the polymerase is phi29 DNA polymerase. In other embodiments the nucleic acid extension means is selected from the group consisting of a ligating enzyme, a nucleic acid extension enzyme and a transposase. In some embodiments the library of amplified nucleic acid sequences includes single stranded DNA and the ligating enzyme includes an ATP independent enzyme. In a specific embodiment the ATP independent enzyme includes thermostable 5' App DNA/RNA ligase. In a different embodiment the ligating enzyme includes a topoisomerase. It is contemplated that the topoisomerase can be topoisomerase I.

In yet another embodiment the ligating enzyme includes T4 DNA ligase.

In one embodiment the barcode sequence segments include at least 4 nucleotides at least 10 nucleotides or at least 20 nucleotides. In another embodiment the barcode sequence segments include at least 1000 different barcode sequence segments. In some embodiments at least 1,000,000 oligonucleotide molecules are attached to each bead. In other embodiments the pooled bead population includes at least 10 different bead populations. In a different embodiment the pooled bead population includes at least 100 different bead populations. In one specific embodiment the pooled bead population includes at least 500 different bead populations.

In a further embodiment the oligonucleotide barcode sequence segments include at least one functional sequence. In one embodiment the functional sequence is selected from an adapter, a primer sequence, a primer annealing sequence, an attachment sequence, and a sequencing primer sequence. In a particular embodiment the functional sequence is sequestered and releasable in a releasing step including a stimulus selected from the list consisting of thermal increase and chemical cleavage. In a different embodiment the releasing step includes degrading at least a portion the beads of the bead population including oligonucleotide barcode sequence segments. In a specific embodiment degrading the beads includes cleaving a chemical linkage including a disulfide bridge linkage between the barcode sequence segments and the bead, and the releasing step includes exposing the beads to a reducing agent. In a particular embodiment the reducing agent includes a reducing agent selected from the group consisting of DTT and TCEP.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 10 shows DPCV and amplification rates with and without denaturation steps.

FIG. 11 shows the effect of adaptor concentration on dup rate (measure of library complexity), and DPCV.

FIG. 13 shows the results of control experiments to test the specificity of T4 ligase based barcoding.

DETAILED DESCRIPTION

I. General Overview
Library Preparation Using Priming Free Amplification by Polymerization at Nick Sites Sequencing libraries produced as described herein using a priming free amplification by polymerization at nick sites (priming free amplification), provide superior sequencing results, e.g., whole genome sequencing results, when compared to conventional primer based amplification (primed amplification) library preparation approaches. Advantageously, for example, the priming free amplification approach results in more even sequencing coverage across a broad range of GC base content when compared to primed amplification results. Additionally, an improved sequencing coverage evenness is achieved in priming free amplification, resulting in a more poissonian distribution when compared to the distribution for primped amplification.

Figure 1:
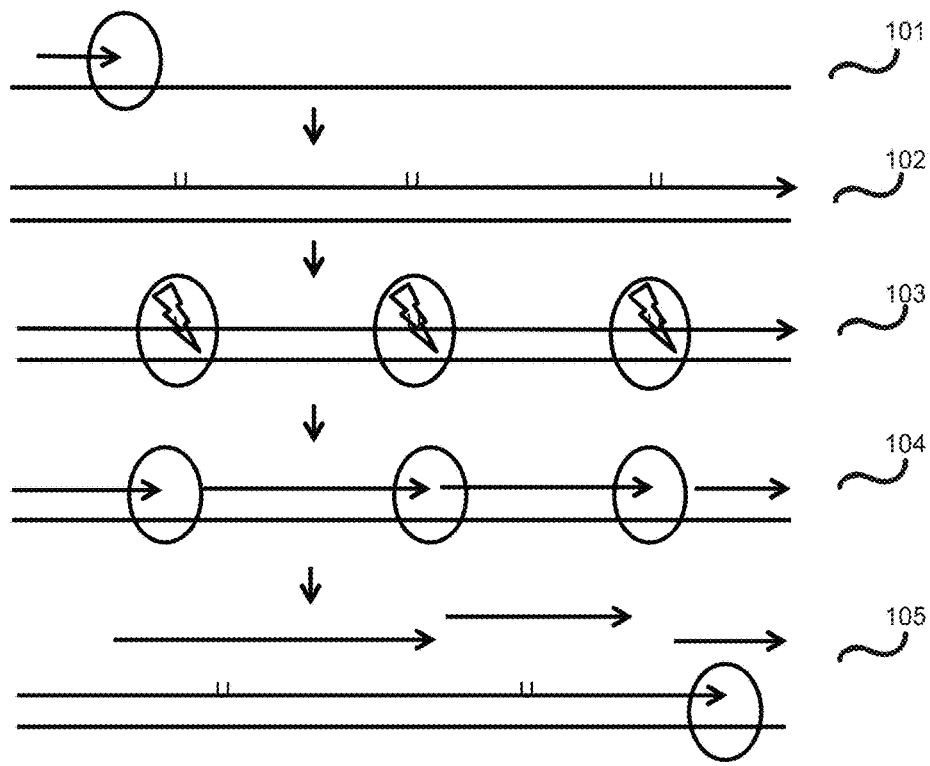
FIG. 1 is a diagram illustrating the process of priming free amplification of templates.

The design of the invention generally is shown in FIG. 1, which illustrates the process of library preparation using priming free amplification of templates. The approach illustrated is also employed in the experimental or prophetic exemplary support as disclosed in the Examples below. In some embodiments, the sequencing libraries are tagged with molecular barcodes and are suitable for use in NGS (Next Generation Sequencing) reactions.

Although illustrated as a series of panels in FIG. 1, the reaction processes illustrated can be performed simultaneously with all the reagents present together in the priming free amplification by polymerization process. This process can be contrasted with a standard primed amplification process for preparing a sequencing library.

In general, one method of the invention is shown in FIG. 1. At FIG. 1 (101), a DNA polymerase, for example, phi29 DNA Polymerase (New England Biolabs® Inc. (NEB), Ipswich, Mass.) used to perform isothermal amplification is shown including: initiation using a hexamer (short arrow) and phi29 DNA polymerase (oval) which has very high processivity and fidelity that results in even coverage and low error rates. As the polymerase processes along the target sequence (long line) a copied DNA template is produced. FIG. 1 (102) illustrates the polymerase based incorporation of dUTP (U) in a growing template strand (long arrow) upon initial amplification in the presence of all dNTPs and a small amount of dUTP. FIG. 1 (103) shows the inclusion in the reaction of an enzyme (oval with bolt) capable of excising dUTP and creating nicks in the copied template DNA strand (long arrow), but not the original target sequence (long line). FIG. 1 (104) shows the result of nicking by the enzyme capable of excising dUTP wherein the original amplified strand from (103) is now, for example, four shorter amplified strands (short arrows). Additionally, phi29 DNA polymerase (oval) is shown engaging at the nick sites for additional amplification in a priming independent amplification process. FIG. 1 (105) illustrates recycling of the original target sequence as a template (long line) upon strand displacement of released amplified fragments (short arrows) owing to the highly processive phi29 DNA polymerase (oval). Subsequent amplifications mirror the process shown in (102) to produce additional released amplified fragments (short arrows).

This disclosure provides methods, systems and compositions useful in the processing of sample materials through the controlled delivery of reagents to subsets of sample components, followed by analysis of those sample components employing, in part, the delivered reagents. In many cases, the methods and compositions are employed for sample processing, particularly for nucleic acid analysis applications, generally, and nucleic acid sequencing applications, in particular. Included within this disclosure are bead compositions that include diverse sets of reagents, such as diverse libraries of beads attached to large numbers of oligonucleotides containing barcode sequences, and methods of making and using the same.

Methods of making beads can generally include, e.g. combining bead precursors (such as monomers or polymers), primers, and cross-linkers in an aqueous solution, combining said aqueous solution with an oil phase, sometimes using a microfluidic device or droplet generator, and causing water-in-oil droplets to form. In some cases, a catalyst, such as an accelerator and/or an initiator, may be added before or after droplet formation. In some cases, initiation may be achieved by the addition of energy, such, as for example via the addition of heat or light (e.g., UV light). A polymerization reaction in the droplet can occur to generate a bead, in some cases covalently linked to one or more copies of an oligonucleotide (e.g., primer). Additional sequences can be attached to the functionalized beads using a variety of methods. In some cases, the functionalized beads are combined with a template oligonucleotide (e.g., containing a barcode) and partitioned such that on average one or fewer template oligonucleotides occupy the same partition as a functionalized bead. While the partitions may be any of a variety of different types of partitions, e.g., wells, microwells, tubes, vials, microcapsules, etc., in preferred aspects, the partitions may be droplets (e.g., aqueous droplets) within an emulsion. The oligonucleotide (e.g., barcode) sequences can be attached to the beads within the partition by a reaction such as a primer extension reaction, ligation reaction, or other methods. For example, in some cases, beads functionalized with primers are combined with template barcode oligonucleotides that comprise a binding site for the primer, enabling the primer to be extended on the bead. After multiple rounds of amplification, copies of the single barcode sequence are attached to the multiple primers attached to the bead. After attachment of the barcode sequences to the beads, the emulsion can be broken and the barcoded beads (or beads linked to another type of amplified product) can be separated from beads without amplified barcodes. Additional sequences, such as a random sequence (e.g., a random N-mer) or a targeted sequence, can then be added to the bead-bound barcode sequences, using, for example, primer extension methods or other amplification reactions. This process can generate a large and diverse library of barcoded beads.

Functional sequences are envisioned to include, for example, immobilization sequences for immobilizing barcode containing sequences onto surfaces, e.g., for sequencing applications. For ease of discussion, a number of specific functional sequences are described below, such as P5, P7, R1, R2, sample indexes, random Nmers, etc., and partial sequences for these, as well as complements of any of the foregoing. However, it will be appreciated that these descriptions are for purposes of discussion, and any of the various functional sequences included within the barcode containing oligonucleotides may be substituted for these specific sequences, including without limitation, different attachment sequences, different sequencing primer regions, different n-mer regions (targeted and random), as well as sequences having different functions, e.g., secondary structure forming, e.g., hairpins or other structures, probe sequences, e.g., to allow interrogation of the presence or absence of the oligonucleotides or to allow pull down of resulting amplicons, or any of a variety of other functional sequences.

Also included within this disclosure are methods of sample preparation for nucleic acid analysis, and particularly for sequencing applications Sample preparation can generally include, e.g. obtaining a sample comprising sample nucleic acid from a source, optionally further processing the sample, combining the sample nucleic acid with barcoded beads, and forming emulsions containing fluidic droplets comprising the sample nucleic acid and the barcoded beads. Droplets may be generated, for example, with the aid of a microfluidic device and/or via any suitable emulsification method. The fluidic droplets can also comprise agents capable of dissolving, degrading, or otherwise disrupting the barcoded beads, and/or disrupting the linkage to attached sequences, thereby releasing the attached barcode sequences from the bead. The barcode sequences may be released either by degrading the bead, detaching the oligonucleotides from the bead such as by a cleavage reaction, or a combination of both. By amplifying (e.g., via amplification methods described herein) the sample nucleic acid in the fluidic droplets, for example, the free barcode sequences can be attached to the sample nucleic acid. The emulsion comprising the fluidic droplets can then be broken and, if desired, additional sequences (e.g., sequences that aid in particular sequencing methods, additional barcode sequences, etc.) can then be added to the barcoded sample nucleic acid using, for example, additional amplification methods. Sequencing can then be performed on the barcoded, amplified sample nucleic acid and one or more sequencing algorithms applied to interpret the sequencing data. As used herein, the sample nucleic acids may include any of a wide variety of nucleic acids, including, e.g., DNA and RNA, and specifically including for example, genomic DNA, cDNA, mRNA total RNA, and cDNA created from a mRNA or total RNA transcript.

The methods and compositions of this disclosure may be used with any suitable digital processor. The digital processor may be programmed, for example, to operate any component of a device and/or execute methods described herein. In some embodiments, bead formation may be executed with the aid of a digital processor in communication with a droplet generator. The digital processor may control the speed at which droplets are formed or control the total number of droplets that are generated. In some embodiments, attaching barcode sequences to sample nucleic acid may be completed with the aid of a microfluidic device and a digital processor in communication with the microfluidic device. In some cases, the digital processor may control the amount of sample and/or beads provided to the channels of the microfluidic device, the flow rates of materials within the channels, and the rate at which droplets comprising barcode sequences and sample nucleic acid are generated.

The methods and compositions of this disclosure may be useful for a variety of different molecular biology applications including, but not limited to, nucleic acid sequencing, protein sequencing, nucleic acid quantification, sequencing optimization, detecting gene expression, quantifying gene expression, epigenetic applications, and single-cell analysis of genomic or expressed markers. Moreover, the methods and compositions of this disclosure have numerous medical applications including identification, detection, diagnosis, treatment, staging of, or risk prediction of various genetic and non-genetic diseases and disorders including cancer.

II. Beads or Particles

The methods, compositions, devices, and kits of this disclosure may be used with any suitable bead or particle, including gel beads and other types of beads. Beads may serve as a carrier for reagents that are to be delivered in accordance with the methods described herein. In particular, these beads may provide a surface to which reagents are releasably attached, or a volume in which reagents are entrained or otherwise releasably partitioned. These reagents may then be delivered in accordance with a desired method, for example, in the controlled delivery of reagents into discrete partitions. A wide variety of different reagents or reagent types may be associated with the beads, where one may desire to deliver such reagents to a partition. Non-limiting examples of such reagents include, e.g., enzymes, polypeptides, antibodies or antibody fragments, labeling reagents, e.g., dyes, fluorophores, chromophores, etc., nucleic acids, polynucleotides, oligonucleotides, and any combination of two or more of the foregoing. In some cases, the beads may provide a surface upon which to synthesize or attach oligonucleotide sequences. Various entities including oligonucleotides, barcode sequences, primers, crosslinkers and the like may be associated with the outer surface of a bead. In the case of porous beads, an entity may be associated with both the outer and inner surfaces of a bead. The entities may be attached directly to the surface of a bead (e.g., via a covalent bond, ionic bond, van der Waals interactions, etc.), may be attached to other oligonucleotide sequences attached to the surface of a bead (e.g. adaptor or primers), may be diffused throughout the interior of a bead and/or may be combined with a bead in a partition (e.g. fluidic droplet). In preferred embodiments, the oligonucleotides are covalently attached to sites within the polymeric matrix of the bead and are therefore present within the interior and exterior of the bead. In some cases, an entity such as a cell or nucleic acid is encapsulated within a bead. Other entities including amplification reagents (e.g., PCR reagents, primers) may also be diffused throughout the bead or chemically-linked within the interior (e.g., via pores, covalent attachment to polymeric matrix) of a bead.

Beads may serve to localize entities or samples. In some embodiments, entities (e.g. oligonucleotides, barcode sequences, primers, crosslinkers, adaptors and the like) may be associated with the outer and/or an inner surface of the bead. In some cases, entities may be located throughout the bead. In some cases, the entities may be associated with the entire surface of a bead or with at least half the surface of the bead.

Beads may serve as a support on which to synthesize oligonucleotide sequences. In some embodiments, synthesis of an oligonucleotide may comprise a ligation step. In some cases, synthesis of an oligonucleotide may comprise ligating two smaller oligonucleotides together. In some cases, a primer extension or other amplification reaction may be used to synthesize an oligonucleotide on a bead via a primer attached to the bead. In such cases, a primer attached to the bead may hybridize to a primer binding site of an oligonucleotide that also contains a template nucleotide sequence. The primer can then be extended by a primer extension reaction or other amplification reaction, and an oligonucleotide complementary to the template oligonucleotide can thereby be attached to the bead. In some cases, a set of identical oligonucleotides associated with a bead may be ligated to a set of diverse oligonucleotides, such that each identical oligonucleotide is attached to a different member of the diverse set of oligonucleotides. In other cases, a set of diverse oligonucleotides associated with a bead may be ligated to a set of identical oligonucleotides.

Bead Characteristics

The methods, compositions, devices, and kits of this disclosure may be used with any suitable bead. In some embodiments, a bead may be porous, non-porous, solid, semi-solid, semi-fluidic, or fluidic. In some embodiments, a bead may be dissolvable, disruptable, or degradable. In some cases, a bead may not be degradable. In some embodiments, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the beads are silica beads. In some cases, the beads are rigid. In some cases, the beads may be flexible.

In some embodiments, the bead may contain molecular precursors (e.g., monomers or polymers), which may form a polymer network via polymerization of the precursors. In some cases, a precursor may be an already polymerized species capable of undergoing further polymerization via, for example, a chemical cross-linkage. In some cases, a precursor comprises one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers.

A bead may comprise natural and/or synthetic materials, including natural and synthetic polymers. Examples of natural polymers include proteins and sugars such as deoxyribonucleic acid, rubber, cellulose, starch (e.g. amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly (ethylene terephthalate), polyethylene, polyisobutylene, poly(methyl methacrylate), poly(oxymethylene), polyformaldehyde, polypropylene, polystyrene, poly(tetrafluoroethylene), poly(vinyl), poly(vinyl alcohol), poly(vinyl chloride), poly(vinylidene dichloride), poly(vinylidene diflu acetate oride materials), poly(vinyl fluoride) and combinations (e.g., copolymers) thereof. Beads may also be formed from other than polymers, including lipids, micelles, ceramics, glass-ceramics, material composites, metals, other inorganic materials, and others.

In some cases, a chemical cross-linker may be a precursor used to cross-link monomers during polymerization of the monomers and/or may be used to functionalize a bead with a species. In some cases, polymers may be further polymerized with a cross-linker species or other type of monomer to generate a further polymeric network. Non-limiting examples of chemical cross-linkers (also referred to as a "crosslinker" or a "crosslinker agent" herein) include cystamine, gluteraldehyde, dimethyl suberimidate, N-Hydroxysuccinimide crosslinker BS3, formaldehyde, carbodiimide (EDC), SMCC, Sulfo-SMCC, vinylsilance, N,N'diallyltartardiamide (DATD), N,N'-Bis(acryloyl)cystamine (BAC), or homologs thereof. In some cases, the crosslinker used in the present disclosure contains cystamine.

Crosslinking may be permanent or reversible, depending upon the particular crosslinker used. Reversible crosslinking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine. In some embodiments, disulfide linkages may be formed between molecular precursor units (e.g. monomers, oligomers, or linear polymers). In some embodiments, disulfide linkages may be may be formed between molecular precursor units (e.g. monomers, oligomers, or linear polymers) or precursors incorporated into a bead and oligonucleotides.

Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In at least one alternative example, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some embodiments, the bead may comprise covalent or ionic bonds between polymeric precursors (e.g. monomers, oligomers, linear polymers), oligonucleotides, primers, and other entities. In some cases, the covalent bonds comprise carbon-carbon bonds or thioether bonds.

In some cases, a bead may comprise an acrydite moiety, which in certain aspects may be used to attach one or more species (e.g., barcode sequence, primer, other oligonucleotide) to the bead. In some cases, an acrydite moiety can refer to an acrydite analogue generated from the reaction of acrydite with one or more species, such as, for example, the reaction of acrydite with other monomers and cross-linkers during a polymerization reaction. Acrydite moieties may be modified to form chemical bonds with a species to be attached, such as an oligonucleotide (e.g., barcode sequence, primer, other oligonucleotide). For example, acrydite moieties may be modified with thiol groups capable of forming a, disulfide bond or may be modified with groups already comprising a disulfide bond. The thiol or disulfide (via disulfide exchange) may be used as an anchor point for a species to be attached or another part of the acrydite moiety may be used for attachment. In some cases, attachment is reversible, such that when the disulfide bond is broken (e.g., in the presence of a reducing agent), the agent is released from the bead. In other cases, an acrydite moiety comprises a reactive hydroxyl group that may be used for attachment.

Functionalization of beads for attachment of other species, e.g., nucleic acids, may be achieved through a wide range of different approaches, including activation of chemical groups within a polymer, incorporation of active or activatable functional groups in the polymer structure, or attachment at the pre-polymer or monomer stage in bead production.

For example, in some examples, precursors (e.g., monomers, cross-linkers) that are polymerized to form a bead may comprise acrydite moieties, such that when a bead is generated, the bead also comprises acrydite moieties. Often, the acrydite moieties are attached to an oligonucleotide sequence, such as a primer (e.g., a primer for one or more of amplifying target nucleic acids and/or sequencing target nucleic acids barcode sequence, binding sequence, or the like)) that is desired to be incorporated into the bead. In some cases, the primer comprises a P5 sequence. For example, acrylamide precursors (e.g., cross-linkers, monomers) may comprise acrydite moieties such that when they are polymerized to form a bead, the bead also comprises acrydite moieties.

In some cases, precursors such as monomers and cross-linkers may comprise, for example, a single oligonucleotide (e.g., such as a primer or other sequence) or other species. In some cases, precursors such as monomers and cross-linkers may comprise multiple oligonucleotides, other sequences, or other species. The inclusion of multiple acrydite moieties or other linker species in each precursor may improve loading of a linked species (e.g., an oligonucleotide) into beads generated from the precursors because each precursor can comprise multiple copies of a species to be loaded.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange)) such that the species can be linked to the beads (e.g., via a generated disulfide bond). In some cases, though, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as, for example, N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent:gel bead ratios of less than about 10000, 100000, 1000000, 10000000, 100000000, 1000000000, 10000000000, or 100000000000) of reducing agent may be used for reduction. Controlling the number of disulfide linkages that are reduced to free thiols may be useful in ensuring bead structural integrity during functionalization. In some cases, optically-active agents, such as fluorescent dyes may be may be coupled to beads via free thiol groups of the beads and used to quantify the number of free thiols present in a bead and/or track a bead.

In some cases, addition of moieties to a gel bead after gel bead formation may be advantageous. For example, addition of a species after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in species (e.g., a primer, a P5 primer) infiltration into the bead during subsequent functionalization of the bead with the species. Post-production functionalization may also be useful in controlling loading ratios of species in beads, such that, for example, the variability in loading ratio is minimized. Also, species loading may be performed in a batch process such that a plurality of beads can be functionalized with the species in a single batch.

In some cases, acrydite moieties linked to precursors, another species linked to a precursor, or a precursor itself comprise a labile bond, such as, for example, chemically, thermally, or photo-sensitive bonds e.g., disulfide bonds, UV sensitive bonds, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule. Moreover, the addition of multiple types of labile bonds to a gel bead may result in the generation of a bead capable of responding to varied stimuli. Each type of labile bond may be sensitive to an associated stimulus (e.g., chemical stimulus, light, temperature, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both. In general, the barcodes that are releasable as described herein, may generally be referred to as being activatable, in that they are available for reaction once released. Thus, for example, an activatable barcode may be activated by releasing the barcode from a bead (or other suitable type of partition described herein). As will be appreciated, other activatable configurations are also envisioned in the context of the described methods and systems. In particular, reagents may be provided releasably attached to beads, or otherwise disposed in partitions, with associated activatable groups, such that once delivered to the desired set of reagents, e.g., through co-partitioning, the activatable group may be reacted with the desired reagents. Such activatable groups include caging groups, removable blocking or protecting groups, e.g., photolabile groups, heat labile groups, or chemically removable groups.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)).

A bead may be linked to a varied number of acrydite moieties. For example, a bead may comprise about 1, 10, 100, 1000, 10000, 100000, 1000000, 10000000, 100000000, 1000000000, or 10000000000 acrydite moieties linked to the beads. In other examples, a bead may comprise at least 1, 10, 100, 1000, 10000, 100000, 1000000, 10000000, 100000000, 1000000000, or 10000000000 acrydite moieties linked to the beads. For example, a bead may comprise about 1, 10, 100, 1000, 10000, 100000, 1000000, 10000000, 100000000, 1000000000, or 10000000000 oligonucleotides covalently linked to the beads, such as via an acrydite moiety. In other examples, a bead may comprise at least 1, 10, 100, 1000, 10000, 100000, 1000000, 10000000, 100000000, 1000000000, or 10000000000 oligonucleotides covalently linked to the beads, such as via an acrydite moiety.

Species that do not participate in polymerization may also be encapsulated in beads during bead generation (e.g., during polymerization of precursors). Such species may be entered into polymerization reaction mixtures such that generated beads comprise the species upon bead formation. In some cases, such species may be added to the gel beads after formation. Such species may include, for example, oligonucleotides, species necessary for a nucleic acid amplification reaction (e.g., primers, polymerases, dNTPs, co-factors (e.g., ionic co-factors)) including those described herein, species necessary for enzymatic reactions (e.g., enzymes, co-factors, substrates), or species necessary for a nucleic acid modification reaction such as polymerization, ligation, or digestion. Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead.

Beads may be of uniform size or heterogeneous size. In some cases, the diameter of a bead may be about 1 µm, 5 µm, 10 µm, 20 µm, 30 µm, 40 µm, 45 µm, 50 µm, 60 µm, 65 µm, 70 µm, 75 µm, 80 µm, 90 µm, 100 µm, 250 µm, 500 µm, or 1 mm. In some cases, a bead may have a diameter of at least about 1 µm, 5 µm, 10 µm, 20 µm, 30 µm, 40 µm, 45 µm, 50 µm, 60 µm, 65 µm, 70 µm, 75 µm, 80 µm, 90 µm, 100 µm, 250 µm, 500 µm, 1 mm, or more. In some cases, a bead may have a diameter of less than about 1 µm, 5 µm, 10 µm, 20 µm, 30 µm, 40 µm, 45 µm, 50 µm, 60 µm, 65 µm, 70 µm, 75 µm, 80 µm, 90 µm, 100 µm, 250 µm, 500 µm, or 1 mm. In some cases, a bead may have a diameter in the range of about 40-75 µm, 30-75 µm, 20-75 µm, 40-85 µm, 40-95 µm, 20-100 µm, 10-100 µm, 1-100 µm, 20-250 µm, or 20-500 µm.

In certain preferred aspects, the beads are provided as a population of beads having a relatively monodisperse size distribution. As will be appreciated, in some applications, where it is desirable to provide relatively consistent amounts of reagents within partitions, maintaining relatively consistent bead characteristics, such as size, contributes to that overall consistency. In particular, the beads described herein may have size distributions that have a coefficient of variation in their cross-sectional dimensions of less than 50%, less than 40%, less than 30%, less than 20%, and in some cases less than 15%, less than 10%, or even less than 5%.

Beads may be of a regular shape or an irregular shape. Examples of bead shapes include spherical, non-spherical, oval, oblong, amorphous, circular, cylindrical, and homologs thereof.

Degradable Beads

In addition to, or as an alternative to the cleavable linkages between the beads and the associated molecules, e.g., barcode containing oligonucleotides, described above, the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental changes, such as, for example, temperature, or pH. For example, a gel bead may be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid species) may result in release of the species from the bead.

A degradable bead may comprise one or more species with a labile bond such that when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond is broken and the bead is degraded. For example, a polyacrylamide gel bead may comprise cystamine crosslinkers. Upon exposure of the bead to a reducing agent, the disulfide bonds of the cystamine are broken and the bead is degraded.

A degradable bead may be useful in more quickly releasing an attached species (e.g., an oligonucleotide, a barcode sequence) from the bead when the appropriate stimulus is applied to the bead. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

A degradable bead may be introduced into a partition, such as a droplet of an emulsion or a well, such that the bead degrades within the partition and any associated species are released within the droplet when the appropriate stimulus is applied. The free species may interact with other species. For example, a polyacrylamide bead comprising cystamine and linked, via a disulfide bond, to a barcode sequence, may be combined with a reducing agent within a droplet of a water-in-oil emulsion. Within the droplet, the reducing agent breaks the various disulfide bonds resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

As will be appreciated, where degradable beads are provided, it may be desirable to avoid exposing such beads to the stimulus or stimuli that cause such degradation prior to the desired time, in order to avoid premature bead degradation and issues that arise from such degradation, including for example poor flow characteristics, clumping and aggregation. By way of example, where beads comprise reducible cross-linking groups, such as disulfide groups, it will be desirable to avoid contacting such beads with reducing agents, e.g., DTT or other disulfide cleaving reagents. In such cases, treatments to the beads described herein will, in some cases be provided to be free of reducing agents, such as DTT. Because reducing agents are often provided in commercial enzyme preparations, it is often desirable to provide reducing agent free (or DTT free) enzyme preparations in treating the beads described herein. Examples of such enzymes include, e.g., polymerase enzyme preparations, ligase enzyme preparations, as well as many other enzyme preparations that may be used to treat the beads described herein. By "reducing agent free" or "DTT free" preparations means that the preparation will have less than $1/10$th, less than $1/50^{th}$, and even less than $1/100^{th}$ of the lower ranges for such materials used in degrading the beads. For example, for DTT, the reducing agent free preparation will typically have less than 0.01 mM, 0.005 mM, 0.001 mM DTT, 0.0005 mM DTT, or even less than 0.0001 mM DTT or less. In many cases, the amount of DTT will be undetectable.

Methods for Degrading Beads

In some cases, a stimulus may be used to trigger degrading of the bead, which may result in the release of contents from the bead. Generally, a stimulus may cause degradation of the bead structure, such as degradation of the covalent bonds or other types of physical interaction. These stimuli may be useful in inducing a bead to degrade and/or to release its contents. Examples of stimuli that may be used include chemical stimuli, thermal stimuli, light stimuli and any combination thereof, as described more fully below.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degrading the bead.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

The methods, compositions, devices, and kits of this disclosure may be used with any suitable agent to degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at 0.1 mM, 0.5 mM, 1 mM, 5 mM, or 10 mM. The reducing agent may be present at more than 0.1 mM, 0.5 mM, 1 mM, 5 mM, 10 mM, or more. The reducing agent may be present at less than 0.1 mM, 0.5 mM, 1 mM, 5 mM, or 10 mM.

Timing of Degrading Step

Beads may be degraded to release contents attached to and contained within the bead. This degrading step may occur simultaneously as the sample is combined with the bead. This degrading step may occur simultaneously when the sample is combined with the bead within a fluidic droplet that may be formed in a microfluidic device. This degrading step may occur after the sample is combined with the bead within a fluidic droplet that may be formed in a microfluidic device. As will be appreciated, in many applications, the degrading step may not occur.

The reducing agent may be combined with the sample and then with the bead. In some cases, the reducing agent may be introduced to a microfluidic device as the same time as the sample. In some cases, the reducing agent may be introduced to a microfluidic device after the sample is introduced. In some cases, the sample may be mixed with the reducing agent in a microfluidic device and then contacted with the gel bead in the microfluidic device. In some embodiments, the sample may be pre-mixed with the reducing agent and then added to the device and contacted with the gel bead.

A degradable bead may degrade instantaneously upon application of the appropriate stimuli. In other cases, degradation of the bead may occur over time. For example, a bead may degrade upon application of an appropriate stimulus instantaneously or within about 0, 0.01, 0.1, 0.5, 1, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 11, 12, 13, 14, 15 or 20 minutes. In other examples, a bead may degrade upon application of a proper stimulus instantaneously or within at most about 0, 0.01, 0.1, 0.5, 1, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 11, 12, 13, 14, 15 or 20 minutes.

Beads may also be degraded at different times, relative to combining with a sample. For example, the bead may be combined with the sample and subsequently degraded at a point later in time. The time between combining the sample with the bead and subsequently degrading the bead may be about 0.0001, 0.001, 0.01, 1, 10, 30, 60, 300, 600, 1800, 3600, 18000, 36000, 86400, 172800, 432000, or 864000 seconds. The time between combining the sample with the bead and subsequently degrading the bead may be more than about 0.0001, 0.001, 0.01, 1, 10, 30, 60, 300, 600, 1800, 3600, 18000, 36000, 86400, 172800, 432000, 864000 seconds or more. The time between combining the sample with the bead and subsequently degrading the bead may be less than about 0.0001, 0.001, 0.01, 1, 10, 30, 60, 300, 600, 1800, 3600, 18000, 36000, 86400, 172800, 432000, or 864000 seconds.

Preparing Beads Pre-functionalized with Oligonucleotides

The beads described herein may be produced using a variety of methods. Suitable beads are described in U.S. Patent Application Publication No. 20140378350, filed Jun. 26, 2014, the contents of which are incorporated herein by reference. In some cases, beads may be formed from a liquid containing molecular precursors (e.g. linear polymers, monomers, cross-linkers). The liquid is then subjected to a polymerization reaction, and thereby hardens or gels into a bead (or gel bead). The liquid may also contain entities such as oligonucleotides that become incorporated into the bead during polymerization. This incorporation may be via covalent or non-covalent association with the bead. For example, in some cases, the oligonucleotides may be entrained within a bead during formation. Alternatively, they may be coupled to the bead or the bead framework either during formation or following formation. Often, the oligonucleotides are connected to an acrydite moiety that becomes cross-linked to the bead during the polymerization process. In some cases, the oligonucleotides are attached to the acrydite moiety by a disulfide linkage. As a result, a composition comprising a bead-acrydite-S—S-oligonucleotide linkage is formed.

In one exemplary process, functionalized beads may be generated by mixing a plurality of polymers and/or monomers with one or more oligonucleotides, such as, for example, one or more oligonucleotides that comprises a primer (e.g., a universal primer, a sequencing primer). The polymers and/or monomers may comprise acrylamide and may be crosslinked such that disulfide bonds form between the polymers and/or monomers, resulting in the formation of hardened beads. The oligonucleotides may be covalently linked to the plurality of polymers and/or monomers during the formation of the hardened beads (e.g., contemporaneously) or may be covalently linked to the plurality of polymers and/or monomers after the formation of the hardened beads (e.g., sequentially). In some cases, the oligonucleotides may be linked to the beads via an acrydite moiety.

In most cases, a population of beads is pre-functionalized with the identical oligonucleotide such as a universal primer or primer binding site. In some cases, the beads in a population of beads are pre-functionalized with multiple different oligonucleotides. These oligonucleotides may optionally include any of a variety of different functional sequences, e.g., for use in subsequent processing or application of the beads. Functional sequences may include, e.g., primer sequences, such as targeted primer sequences, universal primer sequences, e.g., primer sequences that are sufficiently short to be able to hybridize to and prime extension from large numbers of different locations on a sample nucleic acid, or random primer sequences, attachment or immobilization sequences, ligation sequences, hairpin sequences, tagging sequences, e.g., barcodes or sample index sequences, or any of a variety of other nucleotide sequences.

By way of example, in some cases, the universal primer (e.g., P5 or other suitable primer) may be used as a primer on each bead, to attach additional content (e.g., barcodes, random N-mers, other functional sequences) to the bead. In some cases, the universal primer (e.g., P5) may also be compatible with a sequencing device, and may later enable attachment of a desired strand to a flow cell within the sequencing device. For example, such attachment or immobilization sequences may provide a complementary sequence to oligonucleotides that are tethered to the surface of a flow cell in a sequencing device, to allow immobilization of the sequences to that surface for sequencing. Alternatively, such attachments sequences may additionally be provided within, or added to the oligonucleotide sequences attached to the beads. In some cases, the beads and their attached species may be provided to be compatible with subsequent analytical process, such as sequencing devices or systems. In some cases, more than one primer may be attached to a bead and more than one primer may contain a universal sequence, in order to, for example, allow for differential processing of the oligonucleotide as well as any additional sequences that are coupled to that sequence, in different sequential or parallel processing steps, e.g., a first primer for amplification of a target sequence, with a second primer for sequencing the amplified product. For example, in some cases, the oligonucleotides attached to the beads will comprise a first primer sequence for conducting a first amplification or replication process, e.g., extending the primer along a target nucleic acid sequence, in order to generate an amplified barcoded target sequence(s). By also including a sequencing primer within the oligonucleotides, the resulting amplified target sequences will include such primers, and be readily transferred to a sequencing system. For example, in some cases, e.g., where one wishes to sequence the amplified targets using, e.g., an Illumina sequencing system, an R1 primer or primer binding site may also be attached to the bead.

Entities incorporated into the beads may include oligonucleotides having any of a variety of functional sequences as described above. For example, these oligonucleotides may include any one or more of P5, R1, and R2 sequences, non cleavable 5'acrydite-P5, a cleavable 5' acrydite-SS-P5, R1c, sequencing primer, read primer, universal primer, P5_U, a universal read primer, and/or binding sites for any of these primers. In some cases, a primer may contain one or more modified nucleotides nucleotide analogues, or nucleotide mimics. For example, in some cases, the oligonucleotides may include peptide nucleic acids (PNAs), locked nucleic acid (LNA) nucleotides, or the like. In some cases, these oligonucleotides may additionally or alternatively include nucleotides or analogues that may be processed differently, in order to allow differential processing at different steps of their application. For example, in some cases one or more of the functional sequences may include a nucleotide or analogue that is not processed by a particular polymerase enzyme, thus being uncopied in a process step utilizing that enzyme. For example, e.g., in some cases, one or more of the functional sequence components of the oligonucleotides will include, e.g., a uracil containing nucleotide, a nucleotide containing a non-native base, a blocker oligonucleotide, a blocked 3' end, 3'ddCTP. As will be appreciated, sequences of any of these entities may function as primers or primer binding sites depending on the particular application.

Polymerization may occur spontaneously. In some cases, polymerization may be initiated by an initiator and/or an accelerator, by electromagnetic radiation, by temperature changes (e.g., addition or removal of heat), by pH changes, by other methods, and combinations thereof. An initiator may refer to a species capable of initiating a polymerization reaction by activating (e.g., via the generation of free radicals) one or more precursors used in the polymerization reaction. An accelerator may refer to a species capable of accelerating the rate at which a polymerization reaction occurs. In some cases, an accelerator may speed up the activation of an initiator (e.g., via the generation of free radicals) used to then activate monomers (e.g., via the generation of free radicals) and, thus, initiate a polymerization reaction. In some cases, faster activation of an initiator can give rise to faster polymerization rates. In some cases, though, acceleration may also be achieved via non-chemical means such as thermal (e.g., addition and removal of heat) means, various types of radiative means (e.g., visible light, UV light, etc.), or any other suitable means. To create droplets containing molecular precursors, which may then polymerize to form hardened beads, an emulsion technique may be employed. For example, molecular precursors may be added to an aqueous solution. The aqueous solution may then be emulsified with an oil (e.g., by agitation, microfluidic droplet generator, or other method). The molecular precursors may then be polymerized in the emulsified droplets to form the beads.

An emulsion may be prepared, for example, by any suitable method, including methods known in the art, such as bulk shaking, bulk agitation, flow focusing, and microsieve (See e.g., Weizmann et al., Nature Methods, 2006, 3(7):545-550; Weitz et al. U.S. Pub. No. 2012/0211084). In some cases, an emulsion may be prepared using a microfluidic device. In some cases, water-in-oil emulsions may be used. These emulsions may incorporate fluorosurfactants such as Krytox FSH with a PEG-containing compound such as bis krytox peg (BKP). In some cases, oil-in-water emulsions may be used. In some cases, polydisperse emulsions may be formed. In some cases, monodisperse emulsions may be formed. In some cases, monodisperse emulsions may be formed in a microfluidic flow focusing device. (Gartecki et al., Applied Physics Letters, 2004, 85(13):2649-2651).

In at least one example, a microfluidic device for making the beads may contain channel segments that intersect at a single cross intersection that combines two or more streams of immiscible fluids, such as an aqueous solution containing molecular precursors and an oil.

Combining two immiscible fluids at a single cross intersection may cause fluidic droplets to form. The size of the fluidic droplets formed may depend upon the flow rate of the fluid streams entering the fluidic cross, the properties of the two fluids, and the size of the microfluidic channels. Initiating polymerization after formation of fluidic droplets exiting the fluidic cross may cause hardened beads to form from the fluidic droplets. Examples of microfluidic devices, channel networks and systems for generating droplets, both for bead formation and for partitioning beads into discrete droplets as discussed elsewhere herein, are described for example in U.S. Pub. No. 20150292988, and incorporated herein by reference in its entirety for all purposes.

To manipulate when individual molecular precursors, oligomers, or polymers begin to polymerize to form a hardened bead, an initiator and/or accelerator may be added at different points in the bead formation process. An accelerator may be an agent which may initiate the polymerization process (e.g., in some cases, via activation of a polymerization initiator) and thus may reduce the time for a bead to harden. In some cases, a single accelerator or a plurality of accelerators may be used for polymerization. Careful tuning of acceleration can be important in achieving suitable polymerization reactions. For example, if acceleration is too fast, weight and excessive chain transfer events may cause poor gel structure and low loading of any desired species. If acceleration is too slow, high molecular weight polymers can generate trapped activation sites (e.g., free radicals) due to polymer entanglement and high viscosities. High viscosities can impede diffusion of species intended for bead loading, resulting in low to no loading of the species. Tuning of accelerator action can be achieved, for example, by selecting an appropriate accelerator, an appropriate combination of accelerators, or by selecting the appropriate accelerator(s) and any stimulus (e.g., heat, electromagnetic radiation (e.g., light, UV light), another chemical species, etc.) capable of modulating accelerator action. Tuning of initiator action may also be achieved in analogous fashion.

An accelerator may be water-soluble, oil-soluble, or may be both water-soluble and oil-soluble. For example, an accelerator may be tetramethylethylenediamine (TMEDA or TEMED), dimethylethylenediamine, N,N,N,'N'-tetramethylmethanediamine, N,N'-dimorpholinomethane, or N,N,N', N'-Tetrakis(2-Hydroxypropyl)ethylenediamine Azo-based initiators may be used in the absence of TEMED and APS and can function as thermal based initiators. A thermal based initiator can activate species (e.g., via the generation of free radicals) thermally and, thus, the rate of initiator action can be tuned by temperature and/or the concentration of the initiator. A polymerization accelerator or initiator may include functional groups including phosphonate, sulfonate, carboxylate, hydroxyl, albumin binding moieties, N-vinyl groups, and phospholipids. A polymerization accelerator or initiator may be a low molecular weight monomeric-compound. An accelerator or initiator may be a) added to the oil prior to droplet generation, b) added in the line after droplet generation, c) added to the outlet reservoir after droplet generation, or d) combinations thereof.

Polymerization may also be initiated by electromagnetic radiation. Certain types of monomers, oligomers, or polymers may contain light-sensitive properties. Thus, polymerization may be initiated by exposing such monomers, oligomers, or polymers to UV light, visible light, UV light combined with a sensitizer, visible light combined with a sensitizer, or combinations thereof. An example of a sensitizer may be riboflavin.

The time for a bead to completely polymerize or harden may vary depending on the size of the bead, whether an accelerator may be added, when an accelerator may be added, the type of initiator, when electromagnetic radiation may be applied, the temperature of solution, the polymer composition, the polymer concentration, and other relevant parameters. For example, polymerization may be complete after about 5, 6, 7, 8, 9, 10, 11, 12, 13, 14, 15, 16, 17, 18, 19, or 20 minutes. Polymerization may be complete after more than about 5, 6, 7, 8, 9, 10, 11, 12, 13, 14, 15, 16, 17, 18, 19, 20 minutes or more. Polymerization may be complete in less than about 5, 6, 7, 8, 9, 10, 11, 12, 13, 14, 15, 16, 17, 18, 19, or 20 minutes.

Beads may be recovered from emulsions (e.g. gel-water-oil) by continuous phase exchange. Excess aqueous fluid may be added to the emulsion (e.g. gel-water-oil) and the hardened beads may be subjected to sedimentation, wherein the beads may be aggregated and the supernatant containing excess oil may be removed. This process of adding excess aqueous fluid followed by sedimentation and removal of excess oil may be repeated until beads are suspended in a given purity of aqueous buffer, with respect to the continuous phase oil. The purity of aqueous buffer may be about 80%, 90%, 95%, 96%, 97%, 98%, or 99% (v/v). The purity of aqueous buffer may be more than about 80%, 90%, 95%, 96%, 97%, 98%, 99% or more (v/v). The purity of aqueous buffer may be less than about 80%, 90%, 95%, 96%, 97%, 98%, or 99% (v/v). The sedimentation step may be repeated about 2, 3, 4, or 5 times. The sedimentation step may be repeated more than about 2, 3, 4, 5 times or more. The sedimentation step may be repeated less than about 2, 3, 4, or 5 times. In some cases, sedimentation and removal of the supernatant may also remove un-reacted starting materials.

Examples of droplet generators may include single flow focuser, parallel flow focuser, and microsieve membrane, such as those used by Nanomi B. V., and others. Preferably, a microfluidic device is used to generate the droplets.

Barcode and Random N-mers (Introduction)

Certain applications, for example polynucleotide library sequencing, may rely on unique identifiers ("barcodes") to identify a sequence and, for example, to assemble a larger sequence from sequenced fragments. Therefore, it may be desirable to add barcodes to polynucleotide fragments before sequencing. In the case of nucleic acid applications, such barcodes are typically comprised of a relatively short sequence of nucleotides attached to a sample sequence, where the barcode sequence is either known, or identifiable by its location or sequence elements. In some cases, a unique identifier may be useful for sample indexing. In some cases, though, barcodes may also be useful in other contexts. For example, a barcode may serve to track samples throughout processing (e.g., location of sample in a lab, location of sample in plurality of reaction vessels, etc.); provide manufacturing information; track barcode performance over time (e.g., from barcode manufacturing to use) and in the field; track barcode lot performance over time in the field; provide product information during sequencing and perhaps trigger automated protocols (e.g., automated protocols initiated and executed with the aid of a computer) when a barcode associated with the product is read during sequencing; track and troubleshoot problematic barcode sequences or product lots; serve as a molecular trigger in a reaction involving the barcode, and combinations thereof. In particularly preferred aspects, and as alluded to above, barcode sequence segments as described herein, can be used to provide linkage information as between two discrete determined nucleic acid sequences. This linkage information may include, for example, linkage to a common sample, a common reaction vessel, e.g., a well or partition, or even a common starting nucleic acid molecule. In particular, by attaching common barcodes to a specific sample component, or subset of sample components within a given reaction volume, one can attribute the resulting sequences bearing that barcode to that reaction volume. In turn, where the sample is allocated to that reaction volume based upon its sample of origin, the processing steps to which it is subsequently exposed, or on an individual molecule basis, one can better identify the resulting sequences as having originated from that reaction volume.

Barcodes may be generated from a variety of different formats, including bulk synthesized polynucleotide barcodes, randomly synthesized barcode sequences, microarray based barcode synthesis, native nucleotides, partial complement with N-mer, random N-mer, pseudo random N-mer, or combinations thereof. Synthesis of barcodes is described herein, as well as in, for example, in U.S. Pub. No. 20140228255, the full disclosure of which is hereby incorporated herein by reference in its entirety for all purposes.

As described above, oligonucleotides incorporating barcode sequence segments, which function as a unique identifier, may also include additional sequence segments. Such additional sequence segments may include functional sequences, such as primer sequences, primer annealing site sequences, immobilization sequences, or other recognition or binding sequences useful for subsequent processing, e.g., a sequencing primer or primer binding site for use in sequencing of samples to which the barcode containing oligonucleotide is attached. Further, as used herein, the reference to specific functional sequences as being included within the barcode containing sequences also envisioned the inclusion of the complements to any such sequences, such that upon complementary replication will yield the specific described sequence.

In some examples, barcodes or partial barcodes may be generated from oligonucleotides obtained from or suitable for use in an oligonucleotide array, such as a microarray or bead array. In such cases, oligonucleotides of a microarray may be cleaved, (e.g., using cleavable linkages or moieties that anchor the oligonucleotides to the array (such as photoclevable, chemically cleavable, or otherwise cleavable linkages)) such that the free oligonucleotides are capable of serving as barcodes or partial barcodes. In some cases, barcodes or partial barcodes are obtained from arrays are of known sequence. The use of known sequences, including those obtained from an array, for example, may be beneficial in avoiding sequencing errors associated with barcodes of unknown sequence. A microarray may provide at least about 10,000,000, at least about 1,000,000, at least about 900,000, at least about 800,000, at least about 700,000, at least about 600,000, at least about 500,000, at least about 400,000, at least about 300,000, at least about 200,000, at least about 100,000, at least about 50,000, at least about 10,000, at least about 1,000, at least about 100, or at least about 10 different sequences that may be used as barcodes or partial barcodes.

The beads provided herein may be attached to oligonucleotide sequences that may behave as unique identifiers (e.g., barcodes). Often, a population of beads provided herein contains a diverse library of barcodes, wherein each bead is attached to multiple copies of a single barcode sequence. In some cases, the barcode sequences are pre-synthesized and/or designed with known sequences. In some cases, each bead within the library is attached to a unique barcode sequence. In some cases, a plurality of beads will have the same barcode sequence attached to them. For example, in some cases about 1%, 2%, 3%, 4%, 5%, 10%, 20%, 25%, 30%, 50%, 75%, 80%, 90%, 95%, or 100% of the beads in a library are attached to a barcode sequence that is identical to a barcode sequence attached to a different bead in the library. Sometimes, about 1%, 2%, 3%, 4%, 5%, 10%, 20%, 25%, or 30% of the beads are attached to the same barcode sequence.

The length of a barcode sequence may be any suitable length, depending on the application. In some cases, a barcode sequence may be about 2 to about 500 nucleotides in length, about 2 to about 100 nucleotides in length, about 2 to about 50 nucleotides in length, about 2 to about 20 nucleotides in length, about 6 to about 20 nucleotides in length, or about 4 to 16 nucleotides in length. In some cases, a barcode sequence is about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, or 500 nucleotides in length. In some cases, a barcode sequence is greater than about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, 500, 750, 1000, 5000, or 10000 nucleotides in length. In some cases, a barcode sequence is less than about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, 500, 750, or 1000 nucleotides in length.

The barcodes may be loaded into beads so that one or more barcodes are introduced into a particular bead. In some cases, each bead may contain the same set of barcodes. In other cases, each bead may contain different sets of barcodes. In other cases, each bead may comprise a set of identical barcodes. In other cases, each bead may comprise a set of different barcodes.

The beads provided herein may be attached to oligonucleotide sequences that are random, pseudo-random, or targeted N-mers capable of priming a sample (e.g., genomic sample) in a downstream process. In some cases, the same n-mer sequences will be present on the oligonucleotides attached to a single bead or bead population. This may be the case for targeted priming methods, e.g., where primers are selected to target certain sequence segments within a larger target sequence. In other cases, each bead within a population of beads herein is attached to a large and diverse number of N-mer sequences to, among other things, diversify the sampling of these primers against template molecules, as such random n-mer sequences will randomly prime against different portions of the sample nucleic acids.

The length of an N-mer may vary. In some cases, an N-mer (e.g., a random N-mer, a pseudo-random N-mer, or a targeted N-mer) may be between about 2 and about 100 nucleotides in length, between about 2 and about 50 nucleotides in length, between about 2 and about 20 nucleotides in length, between about 5 and about 25 nucleotides in length, or between about 5 and about 15 nucleotides in length. In some cases, an N-mer (e.g., a random N-mer, a pseudo-random N-mer, or a targeted N-mer) may be about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, or 500 nucleotides in length. In some cases, an N-mer (e.g., a random N-mer, a pseudo-random N-mer, or targeted a N-mer) may be greater than about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, 500, 750, 1000, 5000, or 10000 nucleotides in length. In some cases, an N-mer (e.g., a random N-mer, a pseudo-random N-mer, or a targeted N-mer) may be less than about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, 500, 750, or 1000 nucleotides in length.

N-mers (including random N-mers) can be engineered for priming a specific sample type. For example, N-mers of different lengths may be generated for different types of sample nucleic acids or different regions of a sample nucleic acid, such that each N-mer length corresponds to each different type of sample nucleic acid or each different region of a sample nucleic acid. For example, an N-mer of one length may be generated for sample nucleic acid originating from the genome of one species (e.g., for example, a human genome) and an N-mer of another length may be generated for a sample nucleic acid originating from another species (e.g., for example, a yeast genome). In another example, an N-mer of one length may be generated for sample nucleic acid comprising a particular sequence region of a genome and an N-mer of another length may be generated for a sample nucleic acid comprising another sequence region of the genome. Moreover, in addition or as an alternative to N-mer length, the base composition of the N-mer (e.g., GC content of the N-mer) may also be engineered to correspond to a particular type or region of a sample nucleic acid. Base content may vary in a particular type of sample nucleic acid or in a particular region of a sample nucleic acid, for example, and, thus, N-mers of different base content may be useful for priming different sample types of nucleic acid or different regions of a sample nucleic acid.

Populations of beads described elsewhere herein can be generated with an N-mer engineered for a particular sample type or particular sample sequence region. In some cases, a mixed population of beads (e.g., a mixture of beads comprising an N-mer engineered for one sample type or sequence region and beads comprising another N-mer engineered for another sample type or sequence region) with respect to N-mer length and content may be generated. In some cases, a population of beads may be generated, where one or more of the beads can comprise a mixed population of N-mers engineered for a plurality of sample types or sequence regions.

As noted previously, in some cases, the N-mers, whether random or targeted, may comprise nucleotide analogues, mimics, or non-native nucleotides, in order to provide primers that have improved performance in subsequent processing steps. For example, in some cases, it may be desirable to provide N-mer primers that have different melting/annealing profiles when subjected to thermal cycling, e.g., during amplification, in order to enhance the relative priming efficiency of the n-mer sequence. In some cases, nucleotide analogues or non-native nucleotides may be incorporated into the N-mer primer sequences in order to alter the melting temperature profile of the primer sequence as compared to a corresponding primer that includes native nucleotides. In certain cases, the primer sequences, such as the N-mer sequences described herein, may include modified nucleotides or nucleotide analogues, e.g., LNA bases, at one or more positions within the sequence, in order to provide elevated temperature stability for the primers when hybridized to a template sequence, as well as provide generally enhanced duplex stability. In some cases, LNA nucleotides are used in place of the A or T bases in primer synthesis to replace those weaker binding bases with tighter binding LNA analogues. By providing enhanced hybridizing primer sequences, one may generate higher efficiency amplification processes using such primers, as well as be able to operate within different temperature regimes.

Other modifications may also be provided to the oligonucleotides described above. For example, in some cases, the oligonucleotides may be provided with protected termini or other regions, in order to prevent or reduce any degradation of the oligonucleotides, e.g., through any present exonuclease activity. In one example, the oligonucleotides may be provided with one or more phosphorothioate nucleotide analogue at one or more positions within the oligonucleotide sequence, e.g., adjacent or proximal to the 3' and/or 5' terminal position. These phosphorothioate nucleotides typically provide a sulfur group in place of the non-linking oxygen in an internucleotide linkage within the oligonucleotide to reduce or eliminate nuclease activity on the oligonucleotides, including, e.g., 3'-5' and/or 5'-3' exonucleases. In general, phosphorothioate analogues are useful in imparting exo and/or endonuclease resistance to oligonucleotides that include them, including providing protection against, e.g., 3'-5' and/or 5'-3' exonuclease digestion of the oligonucleotides. Accordingly, in some aspects, these one or more phosphorothioate linkages will be in one or more of the last 5 to 10 internucleotide linkages at either the 3' or the 5' terminus of the oligonucleotides, and preferably include one or more of the last 3' or 5' terminal internucleotide linkage and second to last 5' terminal internucleotide linkage, in order to provide protection against 3'-5' or 5'-3' exonuclease activity. Other positions within the oligonucleotides may also be provided with phosphorothiate linkages as well. In addition to providing such protection on the oligonucleotides that comprise the barcode sequences (and any associated functional sequences), the above described modifications are also useful in the context of the blocker sequences described herein, e.g., incorporating phosphorothioate analogues within the blocker sequences, e.g., adjacent or proximal to the 3' and/or 5' terminal position as well as potentially other positions within the oligonucleotides.

Attaching Content to Pre-functionalized Beads

A variety of content may be attached to the beads described herein, including beads functionalized with oligonucleotides. Often, oligonucleotides are attached, particularly oligonucleotides with desired sequences (e.g., barcodes, random N-mers). In many of the methods provided herein, the oligonucleotides are attached to the beads through a primer extension reaction. Beads pre-functionalized with primer can be contacted with oligonucleotide template. Amplification reactions may then be performed so that the primer is extended such that a copy of the complement of the oligonucleotide template is attached to the primer. Other methods of attachment are also possible such as ligation reactions.

In some cases, oligonucleotides with different sequences (or the same sequences) are attached to the beads in separate steps. For example, in some cases, barcodes with unique sequences are attached to beads such that each bead has multiple copies of a first barcode sequence on it. In a second step, the beads can be further functionalized with a second sequence. The combination of first and second sequences may serve as a unique barcode, or unique identifier, attached to a bead. The process may be continued to add additional sequences that behave as barcode sequences (in some cases, greater than 1, 2, 3, 4, 5, 6, 7, 8, 9, or 10 barcode sequences are sequentially added to each bead). The beads may also be further functionalized random N-mers that can, for example, act as a random primer for downstream whole genome amplification reactions.

In some cases, after functionalization with a certain oligonucleotide sequence (e.g., barcode sequence), the beads may be pooled and then contacted with a large population of random Nmers that are then attached to the beads. In some cases, particularly when the beads are pooled prior to the attachment of the random Nmers, each bead has one barcode sequence attached to it, (often as multiple copies), but many different random Nmer sequences attached to it.

Limiting dilution may be used to attach oligonucleotides to beads, such that the beads, on average, are attached to no more than one unique oligonucleotide sequence such as a barcode. Often, the beads in this process are already functionalized with a certain oligonucleotide, such as primers. For example, beads functionalized with primers (e.g., such as universal primers) and a plurality of template oligonucleotides may be combined, often at a high ratio of beads: template oligonucleotides, to generate a mixture of beads and template oligonucleotides. The mixture may then be partitioned into a plurality of partitions (e.g., aqueous droplets within a water-in-oil emulsion), such as by a bulk emulsification process, emulsions within plates, or by a microfluidic device, such as, for example, a microfluidic droplet generator. In some cases, the mixture can be partitioned into a plurality of partitions such that, on average, each partition comprises no more than one template oligonucleotide.

The barcodes may be loaded into the beads at an expected or predicted ratio of barcodes per bead to be barcoded. In some cases, the barcodes are loaded such that a ratio of about 0.0001, 0.001, 0.1, 1, 2, 3, 4, 5, 6, 7, 8, 9, 10, 20, 50, 100, 500, 1000, 5000, 10000, 20000, 50000, 100000, 500000, 1000000, 5000000, 10000000, 50000000, 100000000, 500000000, 1000000000, 5000000000, 10000000000, 50000000000, or 100000000000 barcodes are loaded per bead. In some cases, the barcodes are loaded such that a ratio of more than 0.0001, 0.001, 0.1, 1, 2, 3, 4, 5, 6, 7, 8, 9, 10, 20, 50, 100, 500, 1000, 5000, 10000, 20000, 50000, 100000, 200000, 300000, 400000, 500000, 600000, 700000, 800000, 900000, 1000000, 2000000, 3000000, 4000000, 5000000, 6000000, 7000000, 8000000, 9000000, 10000000, 20000000, 30000000, 40000000, 50000000, 60000000, 70000000, 80000000, 90000000, 100000000, 200000000, 300000000, 400000000, 500000000, 600000000, 700000000, 800000000, 900000000, 1000000000, 2000000000, 3000000000, 4000000000, 5000000000, 6000000000, 7000000000, 8000000000, 9000000000, 10000000000, 20000000000, 30000000000, 40000000000, 50000000000, 60000000000, 70000000000, 80000000000, 90000000000, 100000000000 or more barcodes are loaded per bead. In some cases, the barcodes are loaded such that a ratio of less than about 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.1, 0.2, 0.3, 0.4, 0.5, 0.6, 0.7, 0.8, 0.9, 1, 2, 3, 4, 5, 6, 7, 8, 9, 10, 20, 50, 100, 500, 1000, 5000, 10000, 20000, 50000, 100000, 500000, 1000000, 5000000, 10000000, 50000000, 100000000, 500000000, 1000000000, 5000000000, 10000000000, 50000000000, or 100000000000 barcodes are loaded per bead.

Beads, including those described herein (e.g., substantially dissolvable beads, in some cases, substantially dissolvable by a reducing agent), may be covalently or non-covalently linked to a plurality of oligonucleotides, wherein at least a subset of the oligonucleotides comprises a constant region or domain (e.g., a barcode sequence, a barcode domain, a common barcode domain, or other sequence that is constant among the oligonucleotides of the subset) and a variable region or domain (e.g., a random sequence, a random N-mer, or other sequence that is variable among the oligonucleotides of the subset). In some cases, the oligonucleotides may be releasably coupled to a bead, as described elsewhere herein. Oligonucleotides may be covalently or non-covalently linked to a bead via any suitable linkage, including types of covalent and non-covalent linkages described elsewhere herein. In some cases, an oligonucleotide may be covalently linked to a bead via a cleavable linkage such as, for example, a chemically cleavable linkage (e.g., a disulfide linkage), a photocleavable linkage, or a thermally cleavable linkage. Beads may comprise more than about or at least about 1, 10, 50, 100, 500, 1000, 5000, 10000, 50000, 100000, 500000, 1000000, 5000000, 10000000, 50000000, 100000000, 500000000, 1000000000, 5000000000, 10000000000, 50000000000, 100000000000, 500000000000, or 1000000000000 oligonucleotides comprising a constant region or domain and a variable region or domain.

In some cases, the oligonucleotides may each comprise an identical constant region or domain (e.g., an identical barcode sequence, identical barcode domain, a common domain, etc.). In some cases, the oligonucleotides may each comprise a variable domain with a different sequence. In some cases, the percentage of the oligonucleotides that comprise an identical constant region (or common domain) may be at least about 0.01%, 0.1%, 1%, 5%, 10%, 15%, 20%, 25%, 30%, 35%, 40%, 45%, 50%, 55%, 60%, 65%, 70%, 75%, 80%, 85%, 90%, 95%, or 100%. In some cases, the percentage of the oligonucleotides that comprise a variable region with a different sequence may be at least about 0.01%, 0.1%, 1%, 5%, 10%, 15%, 20%, 25%, 30%, 35%, 40%, 45%, 50%, 55%, 60%, 65%, 70%, 75%, 80%, 85%, 90%, 95%, or 100%. In some cases, the percentage of beads in a plurality of beads that comprise oligonucleotides with different nucleotide sequences (including those comprising a variable and constant region or domain) is at least about 0.01%, 0.1%, 1%, 5%, 10%, 15%, 20%, 25%, 30%, 35%, 40%, 45%, 50%, 55%, 60%, 65%, 70%, 75%, 80%, 85%, 90%, 95%, or 100%. In some cases, the oligonucleotides may also comprise one or more additional sequences, such as, for example a primer binding site (e.g., a sequencing primer binding site), a universal primer sequence (e.g., a primer sequence that would be expected to hybridize to and prime one or more loci on any nucleic acid fragment of a particular length, based upon the probability of such loci being present within a sequence of such length) or any other desired sequence including types of additional sequences described elsewhere herein.

As described elsewhere herein, a plurality of beads may be generated to form, for example, a bead library (e.g., a barcoded bead library). In some cases, the sequence of a common domain (e.g., a common barcode domain) or region may vary between at least a subset of individual beads of the plurality. For example, the sequence of a common domain or region between individual beads of a plurality of beads may be different between 2 or more, 10 or more, 50 or more, 100 or more, 500 or more, 1000 or more, 5000 or more, 10000 or more, 50000 or more, 100000 or more, 500000 or more, 1000000 or more, 5000000 or more, 10000000 or more, 50000000 or more, 100000000 or more, 500000000 or more, 1000000000 or more, 5000000000 or more, 10000000000 or more, 50000000000 or more, or 100000000000 or more beads of the plurality. In some cases, each bead of a plurality of beads may comprise a different common domain or region. In some cases, the percentage of individual beads of a plurality of beads that comprise a different common domain or region may be at least about 0.01%, 0.1%, 1%, 5%, 10%, 15%, 20%, 25%, 30%, 35%, 40%, 45%, 50%, 55%, 60%, 65%, 70%, 75%, 80%, 85%, 90%, 95%, or 100%. In some cases, a plurality of beads may comprise at least about 2, 10, 50, 100, 500, 1000, 5000, 10000, 50000, 100000, 500000, 1000000, 5000000, 10000000, 50000000, 100000000, 500000000, or more different common domains coupled to different beads in the plurality.

As an alternative to limiting dilution (e.g., via droplets of an emulsion), other partitioning methods may be used to attach oligonucleotides to beads. For example, the wells of a plate may be used. Beads comprising a primer (e.g., P5, primer linked to the bead via acrydite and, optionally, a disulfide bond) may be combined with a template oligonucleotide (e.g., a template oligonucleotide comprising a barcode sequence) and amplification reagents in the wells of a plate. Each well can comprise one or more copies of a unique template barcode sequence and one or more beads. Thermal cycling of the plate extends the primer, via hybridization of the template oligonucleotide to the primer, such that the bead comprises an oligonucleotide with a sequence complementary to the oligonucleotide template. Thermal cycling may continue for a desired number of cycles (e.g., at least about 1, 2, 5, 10, 15, 20, 25, 30, 35, 40, 45, 50 or more cycles) up until all primers have been extended.

Upon completion of thermal cycling, the beads may be pooled into a common vessel, washed (e.g., via centrifugation, magnetic separation, etc.), complementary strands denatured, washed again, and then subject to additional rounds of bulk processing if desired. For example, a random N-mer sequence may be added to the bead-bound oligonucleotides using the primer extension method described above for limiting dilution.

The PCR reagents may include any suitable PCR reagents. In some cases, dUTPs may be substituted for dTTPs during the primer extension or other amplification reactions, such that oligonucleotide products comprise uracil containing nucleotides rather than thymine containing nucleotides. This uracil-containing section of the universal sequence may later be used together with a polymerase that will not accept or process uracil-containing templates to mitigate undesired amplification products.

Amplification reagents may include a universal primer, universal primer binding site, sequencing primer, sequencing primer binding site, universal read primer, universal read binding site, or other primers compatible with a sequencing device, e.g., an Illumina sequencer, Ion Torrent sequencer, etc. The amplification reagents may include P5, non cleavable 5'acrydite-P5, a cleavable 5' acrydite-SS-P5, R1c, Biotin R1c, sequencing primer, read primer, P5_Universal, P5_U, 52-BioR1-rc, a random N-mer sequence, a universal read primer, etc. In some cases, a primer may contain a modified nucleotide, a locked nucleic acid (LNA), an LNA nucleotide, a uracil containing nucleotide, a nucleotide containing a non-native base, a blocker oligonucleotide, a blocked 3' end, 3'ddCTP.

As described herein, in some cases oligonucleotides comprising barcodes are partitioned such that each bead is partitioned with, on average, less than one unique oligonucleotide sequence, less than two unique oligonucleotide sequences, less than three unique oligonucleotide sequences, less than four unique oligonucleotide sequences, less than five unique oligonucleotide sequences, or less than ten unique oligonucleotide sequences. Therefore, in some cases, a fraction of the beads does not contain an oligonucleotide template and therefore cannot contain an amplified oligonucleotide. Thus, it may be desirable to separate beads comprising oligonucleotides from beads not comprising oligonucleotides. In some cases, this may be done using a capture moiety.

In some embodiments, a capture moiety may be used with isolation methods such as magnetic separation to separate beads containing barcodes from beads, which may not contain barcodes. As such, in some cases, the amplification reagents may include capture moieties attached to a primer or probe. Capture moieties may allow for sorting of labeled beads from non-labeled beads to confirm attachment of primers and downstream amplification products to a bead. Exemplary capture moieties include biotin, streptavidin, glutathione-S-transferase (GST), cMyc, HA, etc. The capture moieties may be, or include, a fluorescent label or magnetic label. The capture moiety may comprise multiple molecules of a capture moiety, e.g., multiple molecules of biotin, streptavidin, etc. In some cases, an amplification reaction may make use of capture primers attached to a capture moiety (as described elsewhere herein), such that the primer hybridizes with amplification products and the capture moiety is integrated into additional amplified oligonucleotides during additional cycles of the amplification reaction. In other cases, a probe comprising a capture moiety may be hybridized to amplified oligonucleotides following the completion of an amplification reaction such that the capture moiety is associated with the amplified oligonucleotides.

A capture moiety may be a member of binding pair, such that the capture moiety can be bound with its binding pair during separation. For example, beads may be generated that comprise oligonucleotides that comprise a capture moiety that is a member of a binding pair (e.g., biotin). The beads may be mixed with capture beads that comprise the other member of the binding pair (e.g., streptavidin), such that the two binding pair members bind in the resulting mixture. The bead-capture bead complexes may then be separated from other components of the mixture using any suitable means, including, for example centrifugation and magnetic separation (e.g., including cases where the capture bead is a magnetic bead).

III. Barcode Libraries

Beads may contain one or more attached barcode sequences. The barcode sequences attached to a single bead may be identical or different. In some cases, each bead may be attached to about 1, 5, 10, 50, 100, 500, 1000, 5000, 10000, 20000, 50000, 100000, 500000, 1000000, 5000000, 10000000, 50000000, 100000000, 500000000, 1000000000, 5000000000, 10000000000, 50000000000, or 100000000000 identical barcode sequences. In some cases, each bead may be to about 1, 5, 10, 50, 100, 500, 1000, 5000, 10000, 20000, 50000, 100000, 500000, 1000000, 5000000, 10000000, 50000000, 100000000, 500000000, 1000000000, 5000000000, 10000000000, 50000000000, or 100000000000 different barcode sequences. In some cases, each bead may be attached to at least about 1, 5, 10, 50, 100, 500, 1000, 5000, 10000, 20000, 50000, 100000, 200000, 300000, 400000, 500000, 600000, 700000, 800000, 900000, 1000000, 2000000, 3000000, 4000000, 5000000, 6000000, 7000000, 8000000, 9000000, 10000000, 20000000, 30000000, 40000000, 50000000, 60000000, 70000000, 80000000, 90000000, 100000000, 200000000, 300000000, 400000000, 500000000, 600000000, 700000000, 800000000, 900000000, 1000000000, 2000000000, 3000000000, 4000000000, 5000000000, 6000000000, 7000000000, 8000000000, 9000000000, 10000000000, 20000000000, 30000000000, 40000000000, 50000000000, 60000000000, 70000000000, 80000000000, 90000000000, 100000000000 or more identical barcode sequences. In some cases, each bead may be attached to at least about 1, 5, 10, 50, 100, 500, 1000, 5000, 10000, 20000, 50000, 100000, 200000, 300000, 400000, 500000, 600000, 700000, 800000, 900000, 1000000, 2000000, 3000000, 4000000, 5000000, 6000000, 7000000, 8000000, 9000000, 10000000, 20000000, 30000000, 40000000, 50000000, 60000000, 70000000, 80000000, 90000000, 100000000, 200000000, 300000000, 400000000, 500000000, 600000000, 700000000, 800000000, 900000000, 1000000000, 2000000000, 3000000000, 4000000000, 5000000000, 6000000000, 7000000000, 8000000000, 9000000000, 10000000000, 20000000000, 30000000000, 40000000000, 50000000000, 60000000000, 70000000000, 80000000000, 90000000000, 100000000000 or more different barcode sequences. In some cases, each bead may be attached to less than about 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 500000, 1000000, 5000000, 10000000, 50000000, 1000000000, 5000000000, 10000000000, 50000000000, or 100000000000 identical barcode sequences. In some cases, each bead may be attached to less than about 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 500000, 1000000, 5000000, 10000000, 50000000, 1000000000, 5000000000, 10000000000, 50000000000, or 100000000000 different barcode sequences.

An individual barcode library may comprise one or more barcoded beads. In some cases, an individual barcode library may comprise about 1, 5, 10, 50, 100, 500, 1000, 5000, 10000, 20000, 50000, 100000, 500000, 1000000, 5000000, 10000000, 50000000, 100000000, 500000000, 1000000000, 5000000000, 10000000000, 50000000000, or 100000000000 individual barcoded beads. In some cases, each library may comprise at least about 1, 5, 10, 50, 100, 500, 1000, 5000, 10000, 20000, 50000, 100000, 200000, 300000, 400000, 500000, 600000, 700000, 800000, 900000, 1000000, 2000000, 3000000, 4000000, 5000000, 6000000, 7000000, 8000000, 9000000, 10000000, 20000000, 30000000, 40000000, 50000000, 60000000, 70000000, 80000000, 90000000, 100000000, 200000000, 300000000, 400000000, 500000000, 600000000, 700000000, 800000000, 900000000, 1000000000, 2000000000, 3000000000, 4000000000, 5000000000, 6000000000, 7000000000, 8000000000, 9000000000, 10000000000, 20000000000, 30000000000, 40000000000, 50000000000, 60000000000, 70000000000, 80000000000, 90000000000, 100000000000 or more individual barcoded beads. In some cases, each library may comprise less than about 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 500000, 1000000, 5000000, 10000000, 50000000, 100000000, 1000000000, 5000000000, 10000000000, 50000000000, or 100000000000 individual barcoded beads. The barcoded beads within the library may have the same sequences or different sequences.

In some embodiments, each bead may have a unique barcode sequence. However, the number of beads with unique barcode sequences within a barcode library may be limited by combinatorial limits. For example, using four different nucleotides, if a barcode is 12 nucleotides in length, than the number of unique constructs may be limited to $4^{12}=16777216$ unique constructs. Since barcode libraries may comprise many more beads than 1677216, there may be some libraries with multiple copies of the same barcode. In some embodiments, the percentage of multiple copies of the same barcode within a given library may be 1%, 2%, 3%, 4%, 5%, 6%, 7%, 8%, 9%, 10%, 15%, 20%, 25%, 30%, 40%, or 50%. In some cases, the percentage of multiple copies of the same barcode within a given library may be more than 1%, 2%, 3%, 4%, 5%, 6%, 7%, 8%, 9%, 10%, 15%, 20%, 25%, 30%, 40%, 50% or more. In some cases, the percentage of multiple copies of the same barcode within a given library may be less than 1%, 2%, 3%, 4%, 5%, 6%, 7%, 8%, 9%, 10%, 11%, 12%, 13%, 14%, 15%, 16%, 17%, 18%, 19%, 20%, 25%, 30%, 40%, or 50%.

In some embodiments, each bead may comprise one unique barcode sequence but multiple different random N-mers. In some cases, each bead may have one or more different random N-mers. Again, the number of beads with different random N-mers within a barcode library may be limited by combinatorial limits. For example, using four different nucleotides, if an N-mer sequence is 12 nucleotides in length, than the number of different constructs may be limited to $4^{12}=16777216$ different constructs. Since barcode libraries may comprise many more beads than 16777216, there may be some libraries with multiple copies of the same N-mer sequence. In some embodiments, the percentage of multiple copies of the same N-mer sequence within a given library may be 1%, 2%, 3%, 4%, 5%, 6%, 7%, 8%, 9%, 10%, 15%, 20%, 25%, 30%, 40%, or 50%. In some cases, the percentage of multiple copies of the same N-mer sequence within a given library may be more than 1%, 2%, 3%, 4%, 5%, 6%, 7%, 8%, 9%, 10%, 15%, 20%, 25%, 30%, 40%, 50% or more. In some cases, the percentage of multiple copies of the same N-mer sequence within a given library may be less than 1%, 2%, 3%, 4%, 5%, 6%, 7%, 8%, 9%, 10%, 11%, 12%, 13%, 14%, 15%, 16%, 17%, 18%, 19%, 20%, 25%, 30%, 40%, or 50%.

In some embodiments, the unique identifier sequence within the barcode may be different for each primer within each bead. In some cases, the unique identifier sequence within the barcode sequence may be the same for each primer within each bead.

IV. Samples

Types of Samples

The methods, compositions, devices, and kits of this disclosure may be used with any suitable sample or species. A sample (e.g., sample material, component of a sample material, fragment of a sample material, etc.) or species can be, for example, any substance used in sample processing, such as a reagent or an analyte. Exemplary samples can include one or more of whole cells, chromosomes, polynucleotides, organic molecules, proteins, nucleic acids, polypeptides, carbohydrates, saccharides, sugars, lipids, enzymes, restriction enzymes, ligases, polymerases, barcodes (e.g., including barcode sequences, nucleic acid barcode sequences, barcode molecules), adaptors, small molecules, antibodies, fluorophores, deoxynucleotide triphosphate (dNTPs), dideoxynucleotide triphosphates (ddNTPs), buffers, acidic solutions, basic solutions, temperature-sensitive enzymes, pH-sensitive enzymes, light-sensitive enzymes, metals, metal ions, magnesium chloride, sodium chloride, manganese, aqueous buffer, mild buffer, ionic buffer, inhibitors, oils, salts, ions, detergents, ionic detergents, non-ionic detergents, oligonucleotides, template nucleic acid molecules (e.g., template oligonucleotides, template nucleic acid sequences), nucleic acid fragments, template nucleic acid fragments (e.g., fragments of a template nucleic acid generated from fragmenting a template nucleic acid during fragmentation, fragments of a template nucleic acid generated from a nucleic acid amplification reaction), nucleotides, DNA, RNA, peptide polynucleotides, complementary DNA (cDNA), double stranded DNA (dsDNA), single stranded DNA (ssDNA), plasmid DNA, cosmid DNA, chromosomal DNA, genomic DNA (gDNA), viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA, proteases, locked nucleic acids in whole or part, locked nucleic acid nucleotides, nucleases, protease inhibitors, nuclease inhibitors, chelating agents, reducing agents, oxidizing agents, probes, chromophores, dyes, organics, emulsifiers, surfactants, stabilizers, polymers, water, pharmaceuticals, radioactive molecules, preservatives, antibiotics, aptamers, and the like. In summary, the samples that are used will vary depending on the particular processing needs.

Samples may be derived from human and non-human sources. In some cases, samples are derived from mammals, non-human mammals, rodents, amphibians, reptiles, dogs, cats, cows, horses, goats, sheep, hens, birds, mice, rabbits, insects, slugs, microbes, bacteria, parasites, or fish. Samples may be derived from a variety of cells, including but not limited to: eukaryotic cells, prokaryotic cells, fungi cells, heart cells, lung cells, kidney cells, liver cells, pancreas cells, reproductive cells, stem cells, induced pluripotent stem cells, gastrointestinal cells, blood cells, cancer cells, bacterial cells, bacterial cells isolated from a human microbiome sample, etc. In some cases, a sample may comprise the contents of a cell, such as, for example, the contents of a single cell or the contents of multiple cells. Examples of single cell applications of the methods and systems described herein are set forth in U.S. Pub. No. 20140378345. Samples may also be cell-free, such as circulating nucleic acids (e.g., DNA, RNA).

A sample may be naturally-occurring or synthetic. A sample may be obtained from any suitable location, including from organisms, whole cells, cell preparations and cell-free compositions from any organism, tissue, cell, or environment. A sample may be obtained from environmental biopsies, aspirates, formalin fixed embedded tissues, air, agricultural samples, soil samples, petroleum samples, water samples, or dust samples. In some instances, a sample may be obtained from bodily fluids, which may include blood, urine, feces, serum, lymph, saliva, mucosal secretions, perspiration, central nervous system fluid, vaginal fluid, or semen. Samples may also be obtained from manufactured products, such as cosmetics, foods, personal care products, and the like. Samples may be the products of experimental manipulation including recombinant cloning, polynucleotide amplification, polymerase chain reaction (PCR) amplification, purification methods (such as purification of genomic DNA or RNA), and synthesis reactions.

Methods of Attaching Barcodes to Samples

Barcodes (or other oligonucleotides, e.g. random N-mers) may be attached to a sample by joining the two nucleic acid segments together through the action of an enzyme. This may be accomplished by primer extension, polymerase chain reaction (PCR), another type of reaction using a polymerase, or by ligation using a ligase. See for example, FIGS. 2A, 2B and 2C and as discussed in the Examples.

When the ligation method is used to attach a sample to a barcode, the samples may or may not be fragmented prior to the ligation step. In some cases, the oligonucleotides (e.g., barcodes, random N-mers) are attached to a sample while the oligonucleotides are still attached to the beads. In some cases, the oligonucleotides (e.g., barcodes, random N-mers) are attached to a sample after the oligonucleotides are released from the beads, e.g., by cleavage of the oligonucleotides comprising the barcodes from the beads and/or through degradation of the beads.

The oligonucleotides may include one or more random N-mer sequences. A collection of unique random N-mer sequences may prime random portions of a DNA segment, thereby amplifying a sample (e.g., a whole genome). The resulting product may be a collection of barcoded fragments representative of the entire sample (e.g., genome).

The samples may or may not be fragmented before ligation to barcoded beads. DNA fragmentation may involve separating or disrupting DNA strands into small pieces or segments. A variety of methods may be employed to fragment DNA including restriction digest or various methods of generating shear forces. Restriction digest may utilize restriction enzymes to make intentional cuts in a DNA sequence by blunt cleavage to both strands or by uneven cleavage to generate sticky ends. Examples of shear-force mediated DNA strand disruption may include sonication, acoustic shearing, needle shearing, pipetting, or nebulization. Sonication, is a type of hydrodynamic shearing, exposing DNA sequences to short periods of shear forces, which may result in about 700 bp fragment sizes. Acoustic shearing applies high-frequency acoustic energy to the DNA sample within a bowl-shaped transducer. Needle shearing generates shear forces by passing DNA through a small diameter needle to physically tear DNA into smaller segments. Nebulization forces may be generated by sending DNA through a small hole of an aerosol unit in which resulting DNA fragments are collected from the fine mist exiting the unit.

In some cases, a ligation reaction is used to ligate oligonucleotides to sample. One example is illustrated in FIG. 2B (as discussed in the Examples). The ligation may involve joining together two nucleic acid segments, such as a barcode sequence and a sample, by catalyzing the formation of a phosphodiester bond. The ligation reaction may include a DNA ligase, such as an *E. coli* DNA ligase, a T4 DNA ligase, a mammalian ligase such as DNA ligase I, DNA ligase III, DNA ligase IV, thermostable ligases, or the like. The T4 DNA ligase may ligate segments containing DNA, oligonucleotides, RNA, and RNA-DNA hybrids. The ligation reaction may not include a DNA ligase, utilizing an alternative such as a topoisomerase. To ligate a sample to a barcode sequence, utilizing a high DNA ligase concentration and including PEG may achieve rapid ligation. The optimal temperature for DNA ligase, which may be 37° C., and the melting temperature of the DNA to be ligated, which may vary, may be considered to select for a favorable temperature for the ligation reaction. The sample and barcoded beads may be suspended in a buffer to minimize ionic effects that may affect ligation.

Although described in terms of ligation or direct attachment of a barcode sequence to a sample nucleic acid component, above, the attachment of a barcode to a sample nucleic acid, as used herein, also encompasses the attachment of a barcode sequence to a complement of a sample, or a copy or complement of that complement, e.g., when the barcode is associated with a primer sequence that is used to replicate the sample nucleic acid, as is described in greater detail elsewhere herein. In particular, where a barcode containing primer sequence is used in a primer extension reaction using the sample nucleic acid (or a replicate of the sample nucleic acid) as a template, the resulting extension product, whether a complement of the sample nucleic acid or a duplicate of the sample nucleic acid, will be referred to as having the barcode sequence attached to it.

In some cases, sample is combined with the barcoded beads (either manually or with the aid of a microfluidic device) and the combined sample and beads are partitioned, such as in a microfluidic device. The partitions may be aqueous droplets within a water-in-oil emulsion. When samples are combined with barcoded beads, on average less than two target analytes may be present in each fluidic droplet. In some embodiments, on average, less than three target analytes may appear per fluidic droplet. In some cases, on average, more than two target analytes may appear per fluidic droplet. In other cases, on average, more than three target analytes may appear per fluidic droplet. In some cases, one or more strands of the same target analyte may appear in the same fluidic droplet. In some cases, less than 1, 2, 3, 4, 5, 6, 7, 8, 9, 10, 50, 100, 1000, 5000, 10000, or 100000 target analytes are present within a fluidic droplet. In some cases, greater than 1, 2, 3, 4, 5, 6, 7, 8, 9, 10, 50, 100, 1000, 5000, 10000, or 100000 target analytes are present within a fluidic droplet. The partitions described herein are often characterized by having extremely small volumes. For example, in the case of droplet based partitions, the droplets may have overall volumes that are less than 1000 pL, less than 900 pL, less than 800 pL, less than 700 pL, less than 600 pL, less than 500 pL, less than 400 pL, less than 300 pL, less than 200 pL, less than 100 pL, less than 50 pL, less than 20 pL, less than 10 pL, or even less than 1 pL. Where co-partitioned with beads, it will be appreciated that the sample fluid volume within the partitions may be less than 90% of the above described volumes, less than 80%, less than 70%, less than 60%, less than 50%, less than 40%, less than 30%, less than 20%, or even less than 10% the above described volumes.

When samples are combined with barcoded beads, on average less than one bead may be present in each fluidic droplet. In some embodiments, on average, less than two beads may be present in each fluidic droplet. In some embodiments, on average, less than three beads may be present per fluidic droplet. In some cases, on average, more than one bead may be present in each fluidic droplet. In other cases, on average, more than two beads may appear be present in each fluidic droplet. In other cases, on average, more than three beads may be present per fluidic droplet. In some embodiments, a ratio of on average less than one barcoded bead per fluidic droplet may be achieved using limiting dilution technique. Here, barcoded beads may be diluted prior to mixing with the sample, diluted during mixing with the sample, or diluted after mixing with the sample.

The number of different barcodes or different sets of barcodes (e.g., different sets of barcodes, each different set coupled to a different bead) that are partitioned may vary depending upon, for example, the particular barcodes to be partitioned and/or the application. Different sets of barcodes may be, for example, sets of identical barcodes where the identical barcodes differ between each set. Or different sets of barcodes may be, for example, sets of different barcodes, where each set differs in its included barcodes. In some cases, different barcodes are partitioned by attaching different barcodes to different beads (e.g., gel beads). In some cases, different sets of barcodes are partitioned by disposing each different set in a different partition. In some cases, though a partition may comprise one or more different barcode sets. For example, each different set of barcodes may be coupled to a different bead (e.g., a gel bead). Each different bead may be partitioned into a fluidic droplet, such that each different set of barcodes is partitioned into a different fluidic droplet. For example, about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more different barcodes or different sets of barcodes may be partitioned. In some examples, at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900, 000, 1000000, 2000000, 3000000, 4000000, 5000000, 6000000, 7000000, 8000000, 9000000, 10000000, 20000000, 50000000, 100000000, or more different barcodes or different sets of barcodes may be partitioned. In some examples, less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 different barcodes or different sets of barcodes may be partitioned. In some examples, about 1-5, 5-10, 10-50, 50-100, 100-1000, 1000-10000, 10000-100000, 100000-1000000, 10000-1000000, 10000-10000000, or 10000-100000000 different barcodes or different sets of barcodes may be partitioned.

Barcodes may be partitioned at a particular density. For example, barcodes may be partitioned so that each partition contains about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 barcodes per partition. Barcodes may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more barcodes per partition. Barcodes may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 barcodes per partition. Barcodes may be partitioned such that each partition contains about 1-5, 5-10, 10-50, 50-100, 100-1000, 1000-10000, 10000-100000, 100000-1000000, 10000-1000000, 10000-10000000, or 10000-100000000 barcodes per partition. In some cases, partitioned barcodes may be coupled to one or more beads, such as, for example, a gel bead. In some cases, the partitions are fluidic droplets.

Barcodes may be partitioned such that identical barcodes are partitioned at a particular density. For example, identical barcodes may be partitioned so that each partition contains about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 identical barcodes per partition. Barcodes may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more identical barcodes per partition. Barcodes may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 identical barcodes per partition. Barcodes may be partitioned such that each partition contains about 1-5, 5-10, 10-50, 50-100, 100-1000, 1000-10000, 10000-100000, 100000-1000000, 10000-1000000, 10000-10000000, or 10000-100000000 identical barcodes per partition. In some cases, partitioned identical barcodes may be coupled to a bead, such as, for example, a gel bead. In some cases, the partitions are fluidic droplets.

Barcodes may be partitioned such that different barcodes are partitioned at a particular density. For example, different barcodes may be partitioned so that each partition contains about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 different barcodes per partition. Barcodes may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more different barcodes per partition. Barcodes may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 different barcodes per partition. Barcodes may be partitioned such that each partition contains about 1-5, 5-10, 10-50, 50-100, 100-1000, 1000-10000, 10000-100000, 100000-1000000, 10000-1000000, 10000-10000000, or 10000-100000000 different barcodes per partition. In some cases, partitioned different barcodes may be coupled to a bead, such as, for example, a gel bead. In some cases, the partitions are fluidic droplets.

The number of partitions employed to partition barcodes or different sets of barcodes may vary, for example, depending on the application and/or the number of different barcodes or different sets of barcodes to be partitioned. For example, the number of partitions employed to partition barcodes or different sets of barcodes may be about 5, 10, 50, 100, 250, 500, 750, 1000, 1500, 2000, 2500, 5000, 7500, or 10,000, 20000, 30000, 40000, 50000, 60000, 70000, 80000, 90000, 100,000, 200000, 300000, 400000, 500000, 600000, 700000, 800000, 900000, 1,000,000, 2,000,000, 3,000,000, 4,000,000, 5,000,000, 10000000, 20000000 or more. The number of partitions employed to partition barcodes or different sets of barcodes may be at least about 5, 10, 50, 100, 250, 500, 750, 1000, 1500, 2000, 2500, 5000, 7500, 10,000, 20000, 30000, 40000, 50000, 60000, 70000, 80000, 90000, 100,000, 200000, 300000, 400000, 500000, 600000, 700000, 800000, 900000, 1000000, 2000000, 3000000, 4000000, 5000000, 10000000, 20000000 or more. The number of partitions employed to partition barcodes or different sets of barcodes may be less than about 5, 10, 50, 100, 250, 500, 750, 1000, 1500, 2000, 2500, 5000, 7500, 10,000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, or 20000000. The number of partitions employed to partition barcodes may be about 5-10000000, 5-5000000, 5-1,000,000, 10-10,000, 10-5,000, 10-1,000, 1,000-6,000, 1,000-5,000, 1,000-4,000, 1,000-3,000, or 1,000-2,000. In some cases, the partitions may be fluidic droplets.

As described above, different barcodes or different sets of barcodes (e.g., each set comprising a plurality of identical barcodes or different barcodes) may be partitioned such that each partition generally comprises a different barcode or different barcode set. In some cases, each partition may comprise a different set of identical barcodes, such as an identical set of barcodes coupled to a bead (e.g., a gel bead). Where different sets of identical barcodes are partitioned, the number of identical barcodes per partition may vary. For example, about 100,000 or more different sets of identical barcodes (e.g., a set of identical barcodes attached to a bead) may be partitioned across about 100,000 or more different partitions, such that each partition comprises a different set of identical barcodes (e.g., each partition comprises a bead coupled to a different set of identical barcodes). In each partition, the number of identical barcodes per set of barcodes may be about 1,000,000 or more identical barcodes (e.g., each partition comprises 1,000,000 or more identical barcodes coupled to one or more beads). In some cases, the number of different sets of barcodes may be equal to or substantially equal to the number of partitions or may be less than the number of partitions. Any suitable number of different barcodes or different barcode sets, number of barcodes per partition, and number of partitions may be combined. Thus, as will be appreciated, any of the above-described different numbers of barcodes may be provided with any of the above-described barcode densities per partition, and in any of the above-described numbers of partitions.

Microfluidic Devices and Droplets

In some cases, this disclosure provides devices for making beads and for combining beads (or other types of partitions) with samples, e.g., for co-partitioning sample components and beads. Such a device may be a microfluidic device (e.g., a droplet generator). The device may be formed from any suitable material. In some examples, a device may be formed from a material selected from the group consisting of fused silica, soda lime glass, borosilicate glass, poly (methyl methacrylate) PMMA, PDMS, sapphire, silicon, germanium, cyclic olefin copolymer, polyethylene, polypropylene, polyacrylate, polycarbonate, plastic, thermosets, hydrogels, thermoplastics, paper, elastomers, and combinations thereof.

A device may be formed in a manner that it comprises channels for the flow of fluids. Any suitable channels may be used. In some cases, a device comprises one or more fluidic input channels (e.g., inlet channels) and one or more fluidic outlet channels. In some embodiments, the inner diameter of a fluidic channel may be about 10 μm, 20 μm, 30 μm, 40 μm, 50 μm, 60 μm, 65 μm, 70 μm, 75 μm, 80 μm, 85 μm, 90 μm, 100 μm, 125 μm, or 150 μm. In some cases, the inner diameter of a fluidic channel may be more than 10 μm, 20 μm, 30 μm, 40 μm, 50 μm, 60 μm, 65 μm, 70 μm, 75 μm, 80 μm, 85 μm, 90 μm, 100 μm, 125 μm, 150 μm or more. In some embodiments, the inner diameter of a fluidic channel may be less than about 10 μm, 20 μm, 30 μm, 40 μm, 50 μm, 60 μm, 65 μm, 70 μm, 75 μm, 80 μm, 85 μm, 90 μm, 100 μm, 125 μm, or 150 μm. Volumetric flow rates within a fluidic channel may be any flow rate known in the art.

As described elsewhere herein, the microfluidic device may be utilized to form beads by forming a fluidic droplet comprising one or more gel precursors, one or more cross-linkers, optionally an initiator, and optionally an aqueous surfactant. The fluidic droplet may be surrounded by an immiscible continuous fluid, such as an oil, which may further comprise a surfactant and/or an accelerator.

In some embodiments, the microfluidic device may be used to combine beads (e.g., barcoded beads or other type of first partition, including any suitable type of partition described herein) with sample (e.g., a sample of nucleic acids) by forming a fluidic droplet (or other type of second partition, including any suitable type of partition described herein) comprising both the beads and the sample. The fluidic droplet may have an aqueous core surrounded by an oil phase, such as, for example, aqueous droplets within a water-in-oil emulsion. The fluidic droplet may contain one or more barcoded beads, a sample, amplification reagents, and a reducing agent. In some cases, the fluidic droplet may include one or more of water, nuclease-free water, acetonitrile, beads, gel beads, polymer precursors, polymer monomers, polyacrylamide monomers, acrylamide monomers, degradable crosslinkers, non-degradable crosslinkers, disulfide linkages, acrydite moieties, PCR reagents, primers, polymerases, barcodes, polynucleotides, oligonucleotides, nucleotides, DNA, RNA, peptide polynucleotides, complementary DNA (cDNA), double stranded DNA (dsDNA), single stranded DNA (ssDNA), plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, probes, dyes, organics, emulsifiers, surfactants, stabilizers, polymers, aptamers, reducing agents, initiators, biotin labels, fluorophores, buffers, acidic solutions, basic solutions, light-sensitive enzymes, pH-sensitive enzymes, aqueous buffer, oils, salts, detergents, ionic detergents, non-ionic detergents, and the like. In summary, the composition of the fluidic droplet will vary depending on the particular processing needs.

The fluidic droplets may be of uniform size or heterogeneous size. In some cases, the diameter of a fluidic droplet may be about 1 μm, 5 μm, 10 μm, 20 μm, 30 μm, 40 μm, 45 μm, 50 μm, 60 μm, 65 μm, 70 μm, 75 μm, 80 μm, 90 μm, 100 μm, 250 μm, 500 μm, or 1 mm. In some cases, a fluidic droplet may have a diameter of at least about 1 μm, 5 μm, 10 μm, 20 μm, 30 μm, 40 μm, 45 μm, 50 μm, 60 μm, 65 μm, 70 μm, 75 μm, 80 μm, 90 μm, 100 μm, 250 μm, 500 μm, 1 mm or more. In some cases, a fluidic droplet may have a diameter of less than about 1 μm, 5 μm, 10 μm, 20 μm, 30 μm, 40 μm, 45 μm, 50 μm, 60 μm, 65 μm, 70 μm, 75 μm, 80 μm, 90 μm, 100 μm, 250 μm, 500 μm, or 1 mm. In some cases, fluidic droplet may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In some embodiments, the device may comprise one or more intersections of two or more fluid input channels. For example, the intersection may be a fluidic cross. The fluidic cross may comprise two or more fluidic input channels and one or more fluidic outlet channels. In some cases, the fluidic cross may comprise two fluidic input channels and two fluidic outlet channels. In other cases, the fluidic cross may comprise three fluidic input channels and one fluidic outlet channel. In some cases, the fluidic cross may form a substantially perpendicular angle between two or more of the fluidic channels forming the cross.

In some cases, a microfluidic device may comprise a first and a second input channel that meet at a junction that is fluidly connected to an output channel. In some cases, the output channel may be, for example, fluidly connected to a third input channel at a junction. In some cases, a fourth input channel may be included and may intersect the third input channel and outlet channel at a junction. In some cases, a microfluidic device may comprise first, second, and third input channels, wherein the third input channel intersects the first input channel, the second input channel, or a junction of the first input channel and the second input channel.

As described elsewhere herein, the microfluidic device may be used to generate gel beads from a liquid. For example, in some embodiments, an aqueous fluid comprising one or more gel precursors, one or more crosslinkers and optionally an initiator, optionally an aqueous surfactant, and optionally an alcohol within a fluidic input channel may enter a fluidic cross. Within a second fluidic input channel, an oil with optionally a surfactant and an accelerator may enter the same fluidic cross. Both aqueous and oil components may be mixed at the fluidic cross causing aqueous fluidic droplets to form within the continuous oil phase. Gel precursors within fluidic droplets exiting the fluidic cross may polymerize forming beads.

As described elsewhere herein, the microfluidic device (e.g., a droplet generator) may be used to combine sample with beads (e.g., a library of barcoded beads) as well as an agent capable of degrading the beads (e.g., reducing agent if the beads are linked with disulfide bonds), if desired. In some embodiments, a sample (e.g., a sample of nucleic acids) may be provided to a first fluidic input channel that is fluidly connected to a first fluidic cross (e.g., a first fluidic junction). Pre-formed beads (e.g., barcoded beads, degradable barcoded beads) may be provided to a second fluidic input channel that is also fluidly connected to the first fluidic cross, where the first fluidic input channel and second fluidic input channel meet. The sample and beads may be mixed at the first fluidic cross to form a mixture (e.g., an aqueous mixture). In some cases, a reducing agent may be provided to a third fluidic input channel that is also fluidly connected to the first fluidic cross and meets the first and second fluidic input channel at the first fluidic cross. The reducing agent can then be mixed with the beads and sample in the first fluidic cross. In other cases, the reducing agent may be premixed with the sample and/or the beads before entering the microfluidic device such that it is provided to the microfluidic device through the first fluidic input channel with the sample and/or through the second fluidic input channel with the beads. In other cases, no reducing agent may be added.

In some embodiments, the sample and bead mixture may exit the first fluidic cross through a first outlet channel that is fluidly connected to the first fluidic cross (and, thus, any fluidic channels forming the first fluidic cross). The mixture may be provided to a second fluidic cross (e.g., a second fluidic junction) that is fluidly connected to the first outlet channel. In some cases, an oil (or other suitable immiscible) fluid may enter the second fluidic cross from one or more separate fluidic input channels that are fluidly connected to the second fluidic cross (and, thus, any fluidic channels forming the cross) and that meet the first outlet channel at the second fluidic cross. In some cases, the oil (or other suitable immiscible fluid) may be provided in one or two separate fluidic input channels fluidly connected to the second fluidic cross (and, thus, the first outlet channel) that meet the first outlet channel and each other at the second fluidic cross. Both components, the oil and the sample and bead mixture, may be mixed at the second fluidic cross. This mixing partitions the sample and bead mixture into a plurality of fluidic droplets (e.g., aqueous droplets within a water-in-oil emulsion), in which at least a subset of the droplets that form encapsulate a barcoded bead (e.g., a gel bead). The fluidic droplets that form may be carried within the oil through a second fluidic outlet channel exiting from the second fluidic cross. In some cases, fluidic droplets exiting the second outlet channel from the second fluidic cross may be partitioned into wells for further processing (e.g., thermocycling).

In many cases, it will be desirable to control the occupancy rate of resulting droplets (or second partitions) with respect to beads (or first partitions). Such control is described in, for example, U.S. Pub. No. 20150292988, the full disclosure of which is incorporated herein by reference in its entirety for all purposes. In general, the droplets (or second partitions) will be formed such that at least 50%, 60%, 70%, 80%, 90% or more droplets (or second partitions) contain no more than one bead (or first partition). Additionally, or alternatively, the droplets (or second partitions) will be formed such that at least 50%, 60%, 70%, 80%, 90% or more droplets (or second partitions) include exactly one bead (or first partition). In some cases, the resulting droplets (or second partitions) may each comprise, on average, at most about one, two, three, four, five, six, seven, eight, nine, ten, eleven, twelve, thirteen, fourteen, fifteen, sixteen, seventeen, eighteen, nineteen, or twenty beads (or first partitions). In some cases, the resulting droplets (or second partitions) may each comprise, on average, at least about one, two, three, four, five, six, seven, eight, nine, ten, eleven, twelve, thirteen, fourteen, fifteen, sixteen, seventeen, eighteen, nineteen, twenty, or more beads (or first partitions).

In some embodiments, samples may be pre-mixed with beads (e.g., degradable beads) comprising barcodes and any other reagent (e.g., reagents necessary for sample amplification, a reducing agent, etc.) prior to entry of the mixture into a microfluidic device to generate an aqueous reaction mixture. Upon entry of the aqueous mixture to a fluidic device, the mixture may flow from a first fluidic input channel and into a fluidic cross. In some cases, an oil phase may enter the fluidic cross from a second fluidic input channel (e.g., a fluidic channel perpendicular to or substantially perpendicular to the first fluidic input channel) also fluidly connected to the fluidic cross. The aqueous mixture and oil may be mixed at the fluidic cross, such that an emulsion (e.g. a gel-water-oil emulsion) forms. The emulsion can comprise a plurality of fluidic droplets (e.g., droplets comprising the aqueous reaction mixture) in the continuous oil phase. In some cases, each fluidic droplet may comprise a single bead (e.g., a gel bead attached to a set of identical barcodes), an aliquot of sample, and an aliquot of any other reagents (e.g., reducing agents, reagents necessary for amplification of the sample, etc.). In some cases, though, a fluidic droplet may comprise a plurality of beads. Upon droplet formation, the droplet may be carried via the oil continuous phase through a fluidic outlet channel exiting from the fluidic cross. Fluidic droplets exiting the outlet channel may be partitioned into wells for further processing (e.g., thermocycling).

In cases where a reducing agent may be added to the sample prior to entering the microfluidic device or may be added at the first fluidic cross, the fluidic droplets formed at the second fluidic cross may contain the reducing agent. In this case, the reducing agent may degrade or dissolve the beads contained within the fluidic droplet as the droplet travels through the outlet channel leaving the second fluidic cross.

In some embodiments, a microfluidic device may contain three discrete fluidic crosses in parallel. Fluidic droplets may be formed at any one of the three fluidic crosses. Sample and beads may be combined within any one of the three fluidic crosses. A reducing agent may be added at any one of the three fluidic crosses. An oil may be added at any one of the three fluidic crosses.

The methods, compositions, devices, and kits of this disclosure may be used with any suitable oil. In some embodiments, an oil may be used to generate an emulsion. The oil may comprise fluorinated oil, silicon oil, mineral oil, vegetable oil, and combinations thereof.

In some embodiments, the aqueous fluid within the microfluidic device may also contain an alcohol. For example, an alcohol may be glycerol, ethanol, methanol, isopropyl alcohol, pentanol, ethane, propane, butane, pentane, hexane, and combinations thereof. The alcohol may be present within the aqueous fluid at about 5%, 6%, 7%, 8%, 9%, 10%, 11%, 12%, 13%, 14%, 15%, 16%, 17%, 18%, 19%, or 20% (v/v). In some cases, the alcohol may be present within the aqueous fluid at least about 5%, 6%, 7%, 8%, 9%, 10%, 11%, 12%, 13%, 14%, 15%, 16%, 17%, 18%, 19%, 20% or more (v/v). In some cases, the alcohol may be present within the aqueous fluid for less than about 5%, 6%, 7%, 8%, 9%, 10%, 11%, 12%, 13%, 14%, 15%, 16%, 17%, 18%, 19%, or 20% (v/v).

In some embodiments, the oil may also contain a surfactant to stabilize the emulsion. For example, a surfactant may be a fluorosurfactant, Krytox lubricant, Krytox FSH, an engineered fluid, HFE-7500, a silicone compound, a silicon compound containing PEG, such as bis krytox peg (BKP). The surfactant may be present at about 0.1%, 0.5%, 1%, 1.1%, 1.2%, 1.3%, 1.4%, 1.5%, 1.6%, 1.7%, 1.8%, 1.9%, 2%, 5%, or 10% (w/w). In some cases, the surfactant may be present at least about 0.1%, 0.5%, 1%, 1.1%, 1.2%, 1.3%, 1.4%, 1.5%, 1.6%, 1.7%, 1.8%, 1.9%, 2%, 5%, 10% (w/w) or more. In some cases, the surfactant may be present for less than about 0.1%, 0.5%, 1%, 1.1%, 1.2%, 1.3%, 1.4%, 1.5%, 1.6%, 1.7%, 1.8%, 1.9%, 2%, 5%, or 10% (w/w).

In some embodiments, an accelerator and/or initiator may be added to the oil. For example, an accelerator may be Tetramethylethylenediamine (TMEDA or TEMED). In some cases, an initiator may be ammonium persulfate or calcium ions. The accelerator may be present at about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% (v/v). In some cases, the accelerator may be present at least about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% (v/v) or more. In some cases, the accelerator may be present for less than about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% (v/v).

V. Amplification

DNA amplification is a method for creating multiple copies of small or long segments of DNA. The methods, compositions, devices, and kits of this disclosure may use DNA amplification to attach one or more desired oligonucleotide sequences to individual beads, such as a barcode sequence or random N-mer sequence. DNA amplification may also be used to prime and extend along a sample of interest, such as genomic DNA, utilizing a random N-mer sequence, in order to produce a fragment of the sample sequence and couple the barcode associated with the primer to that fragment.

For example, a nucleic acid sequence may be amplified by co-partitioning a template nucleic acid sequence and a bead comprising a plurality of attached oligonucleotides (e.g., releasably attached oligonucleotides) into a partition (e.g., a droplet of an emulsion, a microcapsule, or any other suitable type of partition, including a suitable type of partition described elsewhere herein). The attached oligonucleotides can comprise a primer sequence (e.g., a variable primer sequence such as, for example, a random N-mer, or a targeted primer sequence such as, for example, a targeted N-mer) that is complementary to one or more regions of the template nucleic acid sequence and, in addition, may also comprise a common sequence (e.g., such as a barcode sequence). The primer sequence can be annealed to the template nucleic acid sequence and extended (e.g., in a primer extension reaction or any other suitable nucleic acid amplification reaction) to produce one or more first copies of at least a portion of the template nucleic acid, such that the one or more first copies comprises the primer sequence and the common sequence. In cases where the oligonucleotides comprising the primer sequence are releasably attached to the bead, the oligonucleotides may be released from the bead prior to annealing the primer sequence to the template nucleic acid sequence. Moreover, in general, the primer sequence may be extended via a polymerase enzyme (e.g., a strand displacing polymerase enzyme as described elsewhere herein, an exonuclease deficient polymerase enzyme as described elsewhere herein, or any other type of suitable polymerase, including a type of polymerase described elsewhere herein) that is also provided in the partition. Furthermore, the oligonucleotides releasably attached to the bead may be exonuclease resistant and, thus, may comprise one or more phosphorothioate linkages as described elsewhere herein. In some cases, the one or more phosphorothioate linkages may comprise a phosphorothioate linkage at a terminal internucleotide linkage in the oligonucleotides.

In some cases, after the generation of the one or more first copies, the primer sequence can be annealed to one or more of the first copies and the primer sequence again extended to produce one or more second copies. The one or more second copies can comprise the primer sequence, the common sequence, and may also comprise a sequence complementary to at least a portion of an individual copy of the one or more first copies, and/or a sequence complementary to the variable primer sequence. The aforementioned steps may be repeated for a desired number of cycles to produce amplified nucleic acids.

The oligonucleotides described above may comprise a sequence segment that is not copied during an extension reaction (such as an extension reaction that produces the one or more first or second copies described above). As described elsewhere herein, such a sequence segment may comprise one or more uracil containing nucleotides and may also result in the generation of amplicons that form a hairpin (or partial hairpin) molecule under annealing conditions.

In another example, a plurality of different nucleic acids can be amplified by partitioning the different nucleic acids into separate first partitions (e.g., droplets in an emulsion) that each comprise a second partition (e.g., beads, including a type of bead described elsewhere herein). The second partition may be releasably associated with a plurality of oligonucleotides. The second partition may comprise any suitable number of oligonucleotides (e.g., more than 1,000 oligonucleotides, more than 10,000 oligonucleotides, more than 100,000 oligonucleotides, more than 1,000,000 oligonucleotides, more than 10,000,000 oligonucleotides, or any other number of oligonucleotides per partition described herein). Moreover, the second partitions may comprise any suitable number of different barcode sequences (e.g., at least 1,000 different barcode sequences, at least 10,000 different barcode sequences, at least 100,000 different barcode sequences, at least 1,000,000 different barcode sequences, at least 10,000,000 different barcode sequence, or any other number of different barcode sequences described elsewhere herein).

Furthermore, the plurality of oligonucleotides associated with a given second partition may comprise a primer sequence (e.g., a variable primer sequence, a targeted primer sequence) and a common sequence (e.g., a barcode sequence). Moreover, the plurality of oligonucleotides associated with different second partitions may comprise different barcode sequences. Oligonucleotides associated with the plurality of second partitions may be released into the first partitions. Following release, the primer sequences within the first partitions can be annealed to the nucleic acids within the first partitions and the primer sequences can then be extended to produce one or more copies of at least a portion of the nucleic acids with the first partitions. In general, the one or more copies may comprise the barcode sequences released into the first partitions.

Amplification within Droplets and Sample Indexing

Nucleic acid (e.g., DNA) amplification may be performed on contents within fluidic droplets. As described herein, fluidic droplets may contain oligonucleotides attached to beads. Fluidic droplets may further comprise a sample. Fluidic droplets may also comprise reagents suitable for amplification reactions which may include Kapa HiFi Uracil Plus, modified nucleotides, native nucleotides, uracil containing nucleotides, dTTPs, dUTPs, dCTPs, dGTPs, dATPs, DNA polymerase, Taq polymerase, mutant proof reading polymerase, 9 degrees North, modified (NEB), exo (−), exo (−) Pfu, Deep Vent exo (−), Vent exo (−), and acyclonucleotides (acyNTPS).

Oligonucleotides attached to beads within a fluidic droplet may be used to amplify a sample nucleic acid such that the oligonucleotides become attached to the sample nucleic acid. The sample nucleic acids may comprise virtually any nucleic acid sought to be analyzed, including, for example, whole genomes, exomes, amplicons, targeted genome segments e.g., genes or gene families, cellular nucleic acids, circulating nucleic acids, and the like, and, as noted above, may include DNA (including gDNA, cDNA, mtDNA, etc.) RNA (e.g., mRNA, rRNA, total RNA, etc.). Preparation of such nucleic acids for barcoding may generally be accomplished by methods that are readily available, e.g., enrichment or pull-down methods, isolation methods, amplification methods etc. In order to amplify a desired sample, such as gDNA, the random N-mer sequence of an oligonucleotide within the fluidic droplet may be used to prime the desired target sequence and be extended as a complement of the target sequence. In some cases, the oligonucleotide may be released from the bead in the droplet, as described elsewhere herein, prior to priming. For these priming and extension processes, any suitable method of DNA amplification may be utilized, including polymerase chain reaction (PCR), digital PCR, reverse-transcription PCR, multiplex PCR, nested PCR, overlap-extension PCR, quantitative PCR, multiple displacement amplification (MDA), or ligase chain reaction (LCR). In some cases, amplification within fluidic droplets may be performed until a certain amount of sample nucleic acid comprising barcode may be produced. In some cases, amplification may be performed for about 1, 2, 3, 4, 5, 6, 7, 8, 9, 10, 11, 12, 13, 14, 15, 16, 17, 18, 19, or 20 cycles. In some cases, amplification may be performed for more than about 1, 2, 3, 4, 5, 6, 7, 8, 9, 10, 11, 12, 13, 14, 15, 16, 17, 18, 19, 20 cycles, or more. In some cases, amplification may be performed for less than about 2, 3, 4, 5, 6, 7, 8, 9, 10, 11, 12, 13, 14, 15, 16, 17, 18, 19, or 20 cycles.

In some cases, a sample index can be added to a sample nucleic acid after the addition of the original barcode to the sample nucleic acid, with or without the use of partitions or the generation of additional partitions. In some cases, the sample index is added in bulk. In some cases, the addition of a sample index to a sample nucleic acid may occur prior to the addition of a barcode to the sample nucleic acid. In some cases, the addition of a sample index to a sample nucleic acid may occur simultaneous to or in parallel to the addition of a sample index to the sample nucleic acid.

In alternative aspects, additional sequence segments may be ligated to the 5' end of the partial hairpin structure where such sequence segments are not complementary to the non-overlapped portion of the hairpin structure. A partial hairpin structure, when subjected to primer extension conditions, may act as its own primer and have its 5' sequence extended, as shown by the dashed arrow, until it forms a complete or nearly complete hairpin structure, e.g., with little or no overhang sequence. This full hairpin structure will possess far greater duplex stability, thereby potentially negatively impacting the ability to disrupt the hairpin structure to prime its replication, even when employing higher affinity primers, e.g., LNA containing primers/probes.

In some cases, a microfluidic device (e.g., a microfluidic chip) may be useful in parallelizing sample indexing. Such a device may comprise parallel modules each capable of adding a barcode sequence and a sample index to nucleic acid molecules of a sample via primers comprising both the barcode sequence and the sample index. Each parallel module may comprise a primer set comprising a different sample index, such that the sample processed in each module is associated with a different sample index and set of barcodes. For example, a microfluidic device with 8 modules may be capable of sample indexing 8 different samples. Following barcoding and sample indexing via attachment of the sequences to a sample nucleic acid, bulk addition of additional sequences (e.g., R2, P7, other barcode sequences) via, for example, serial amplification can be used to generate sequencer-ready products as described elsewhere herein.

A sequencer-ready product may comprise a barcode sequence that can be used to align sequence reads and provide a sequence for a sample nucleic acid. The sequencer-ready product may be generated, for example, using PHASE amplification and subsequent bulk amplification as described elsewhere herein. Moreover, the barcode sequence may belong to a particular set of known barcode sequences. The set of barcode sequences may be associated with a particular sample, such that identification of the sample from which a particular sequencing read originates can be achieved via the read barcode sequence. Each sample can be associated with a set of known barcode sequences, with each barcode sequence set comprising barcode sequences that do not overlap with barcode sequence in other barcode sets associated with other samples. Thus, the uniqueness of a barcode sequence and its uniqueness amongst different sets of barcode sequences may be used for multiplexing.

In other cases, a sample index may be added to a sample nucleic acid prior to the addition of a barcode sequence to the sample nucleic acid. For example, a sample nucleic acid may be pre-amplified in bulk such that resulting amplicons are attached to a sample index sequence prior to barcoding. For example, sample may be amplified with a primer comprising a sample index sequence such that the sample index sequence can be attached to the sample nucleic acid. In some cases, the primer may be a random primer (e.g., comprising a random N-mer) and amplification may be random. Produced amplicons that comprise the sample index can then be barcoded using any suitable method, including barcoding methods described herein.

Sample nucleic acid molecules can be combined into partitions (e.g., droplets of an emulsion) with the primers described above. In some cases, each partition can comprise a plurality of sample nucleic acid molecules (e.g., smaller pieces of a larger nucleic acid). In some cases, no more than one copy of a unique sample nucleic acid molecule is present per partition. In some cases, each partition can generally comprise primers comprising an identical barcode sequence and a sample priming sequence (e.g., a variable random-Nmer, a targeted N-mer), with the barcode sequence generally differing between partitions. In such cases, each partition (and, thus, sample nucleic acid in the partition) can be associated with a unique barcode sequence and the unique barcode sequence can be used to determine a sequence for the barcoded sample nucleic acid generated in the partition.

In some cases, upon generation of barcoded sample nucleic acids, the barcoded sample nucleic acids can be released from their individual partitions, pooled, and subject to bulk amplification schemes to add additional sequences (e.g., additional sequencing primer binding sites, additional sequencer primer binding sites, additional barcode sequences, sample index sequences) common to all downstream sequencer-ready products. In cases where the partitions are droplets of an emulsion, the emulsion may be broken and the barcoded sample nucleic acids pooled. A sample index can be added in bulk to the released, barcoded sample nucleic acids, for example, using the serial amplification methods described herein. Where a sample index is added in bulk, each sequencer-ready product generated from the same sample will comprise the same sample index that can be used to identify the sample from which the read for the sequencer-ready product was generated. Where a sample index is added during barcoding, each primer used for barcoding may comprise an identical sample index sequence, such that each sequencer-ready product generated from the same sample will comprise the same sample index sequence.

Partitioning of sample nucleic acids to generate barcoded (or barcoded and sample indexed) sample nucleic acids and subsequent addition of additional sequences (e.g., including a sample index) to the barcoded sample nucleic acids can be repeated for each sample, using a different sample index for each sample. In some cases, a microfluidic droplet generator may be used to partition sample nucleic acids. In some cases, a microfluidic chip may comprise multiple droplet generators, such that a different sample can be processed at each droplet generator, permitting parallel sample indexing. Via each different sample index, multiplexing during sequencing can be achieved.

Upon the generation of sequencer-ready oligonucleotides, the sequencer-ready oligonucleotides can then be provided to a sequencing device for sequencing. Thus, for example, the entire sequence provided to the sequencing device may comprise one or more adaptors compatible with the sequencing device (e.g. P5, P7), one or more barcode sequences, one or more primer binding sites (e.g. Read1 (R1) sequence primer, Read2 (R2) sequencing primer, Index primer), an N-mer sequence, a universal sequence, the sequence of interest, and combinations thereof. The barcode sequence may be located at either end of the sequence. In some cases, the barcode sequence may be located between P5 and Read1 sequence primer binding site. In other cases, the barcode sequence may be located between P7 and Read 2 sequence primer binding site. In some cases, a second barcode sequence may be located between P7 and Read 2 sequence primer binding site. The index sequence primer binding site may be utilized in the sequencing device to determine the barcode sequence.

The configuration of the various components (e.g., adaptors, barcode sequences, sample index sequences, sample sequence, primer binding sites, etc.) of a sequence to be provided to a sequencer device may vary depending on, for example the particular configuration desired and/or the order in which the various components of the sequence is added. Any suitable configuration for sequencing may be used and any sequences can be added to oligonucleotides in any suitable order. Additional sequences may be added to a sample nucleic acid prior to, during, and after barcoding of the sample nucleic acid. For example, a P5 sequence can be added to a sample nucleic acid during barcoding and P7 can be added in bulk amplification following barcoding of the sample nucleic acid. Alternatively, a P7 sequence can be added to a sample nucleic acid during barcoding and a P5 sequence can be added in bulk amplification following barcoding of the sample nucleic acid. Example configurations displayed as examples herein are not intended to be limiting. Moreover, the addition of sequence components to an oligonucleotide via amplification is also not meant to be limiting. Other methods, such as, for example, ligation may also be used. Furthermore, adaptors, barcode sequences, sample index sequences, primer binding sites, sequencer-ready products, etc. described herein are not meant to be limiting. Any type of oligonucleotide described herein, including sequencer-ready products, may be generated for any suitable type of sequencing platform (e.g., Illumina sequencing, Life Technologies Ion Torrent, Pacific Biosciences SMRT, Roche 454 sequencing, Life Technologies SOLiD sequencing, etc.) using methods described herein.

Sequencer-ready oligonucleotides can be generated with any adaptor sequence suitable for a particular sequencing platform using methods described herein. For example, sequencer-ready oligonucleotides comprising one or more barcode sequences and P1 and A adaptor sequences useful in Life Technologies Ion Torrent sequencing may be generated using methods described herein. In one example, beads (e.g., gel beads) comprising an acrydite moiety linked to a P1 sequence via a disulfide bond may be generated. A barcode construct may be generated that comprises a P1 sequence, a barcode sequence, and a random N-mer sequence. The barcode construct may enter an amplification reaction (e.g., in a partition, such as a fluidic droplet) to barcode sample nucleic acid. Barcoded amplicons may then be subject to further amplification in bulk to add the A sequence and any other sequence desired, such as a sample index. Alternatively, P1 and A sequences can be interchanged such that A is added during sample barcoding and P1 is added in bulk. The complete sequence can then be entered into an Ion Torrent sequencer. Other adaptor sequences (e.g., P1 adaptor sequence for Life Technologies SOLiD sequencing, A and B adaptor sequences for Roche 454, etc.) for other sequencing platforms can be added in analogous fashion.

Although described herein as generating partial hairpin molecules, and in some cases, preventing formation of complete hairpins, in some cases, it may be desirable to provide complete hairpin fragments that include the barcode sequences described herein. In particular, such complete hairpin molecules may be further subjected to conventional sample preparation steps by treating the 3' and 5' end of the single hairpin molecule as one end of a double stranded duplex molecule in a conventional sequencing workflow. In particular, using conventional ligation steps, one could readily attach the appropriate adapter sequences to both the 3' and 5' end of the hairpin molecule in the same fashion as those are attached to the 3' and 5' termini of a duplex molecule. For example, in case of an Illumina based sequencing process, one could attach a standard Y adapter that includes the P5 and P7 adapters and R1 and R2 primer sequences, to one end of the hairpin as if it were one end of a duplex molecule, using standard Illumina protocols.

VII. Digital Processor

The methods, compositions, devices, and kits of this disclosure may be used with any suitable processor, digital processor or computer. The digital processor may be programmed, for example, to operate any component of a device and/or execute methods described herein. The digital processor may be capable of transmitting or receiving electronic signals through a computer network, such as for example, the Internet and/or communicating with a remote computer. One or more peripheral devices such as screen display, printer, memory, data storage, and/or electronic display adaptors may be in communication with the digital processor. One or more input devices such as keyboard, mouse, or joystick may be in communication with the digital processor. The digital processor may also communicate with detector such that the detector performs measurements at desired or otherwise predetermined time points or at time points determined from feedback received from pre-processing unit or other devices.

In one example a controller includes a computer that serves as the central hub for control assembly. The computer is in communication with a display, one or more input devices (e.g., a mouse, keyboard, camera, etc.), and optionally a printer. The control assembly, via its computer, is in communication with one or more devices: optionally a sample pre-processing unit, one or more sample processing units (such as a sequence, thermocycler, or microfluidic device), and optionally a detector. The control assembly may be networked, for example, via an Ethernet connection. A user may provide inputs (e.g., the parameters necessary for a desired set of nucleic acid amplification reactions or flow rates for a microfluidic device) into the computer, using an input device. The inputs are interpreted by the computer, to generate instructions. The computer communicates such instructions to the optional sample pre-processing unit, the one or more sample processing units, and/or the optional detector for execution.

Moreover, during operation of the optional sample pre-processing unit, one or more sample processing units, and/or the optional detector, each device may communicate signals back to computer. Such signals may be interpreted and used by computer to determine if any of the devices require further instruction. The computer may also modulate the sample pre-processing unit such that the components of a sample are mixed appropriately and fed, at a desired or otherwise predetermined rate, into the sample processing unit (such as the microfluidic device).

The computer may also communicate with a detector such that the detector performs measurements at desired or otherwise predetermined time points or at time points determined from feedback received from pre-processing unit or sample processing unit. The detector may also communicate raw data obtained during measurements back to the computer for further analysis and interpretation.

Analysis may be summarized in formats useful to an end user via a display and/or printouts generated by a printer. Instructions or programs used to control the sample pre-processing unit, the sample processing unit, and/or the detector; data acquired by executing any of the methods described herein; or data analyzed and/or interpreted may be transmitted to or received from one or more remote computers, via a network, which, for example, could be the Internet.

In some embodiments, the method of bead formation may be executed with the aid of a digital processor in communication with a droplet generator. The digital processor may control the speed at which droplets are formed or control the total number of droplets that are generated. In some embodiments, the method of attaching samples to barcoded beads may be executed with the aid of a digital processor in communication with the microfluidic device. Specifically, the digital processor may control the volumetric amount of sample and/or beads injected into the input channels and may also control the flow rates within the channels. In some embodiments, the method of attaching oligonucleotides, primers, and the like may be executed with the aid of a digital processor in communication with a thermocycler or other programmable heating element. Specifically, the digital processor may control the time and temperature of cycles during ligation or amplification. In some embodiments, the method of sequencing a sample may be executed with the aid of a digital processor in communication with a sequencing device.

VIII. Kits

In some cases, this disclosure provides a kit comprising a microfluidic device, a plurality of barcoded beads, and instructions for utilizing the microfluidic device and combining barcoded beads with customer sample to create fluidic droplets containing both. As specified throughout this disclosure, any suitable sample may be incorporated into the fluidic droplets. As described throughout this disclosure, a bead may be designed to be degradable or non-degradable. In this case, the kit may or may not include a reducing agent for bead degradation.

In some cases, this disclosure provides a kit comprising a plurality of barcoded beads, suitable amplification reagents, e.g., optionally including one or more of polymerase enzymes, nucleoside triphosphates or their analogues, primer sequences, buffers, and the like, and instructions for combining barcoded beads with customer sample. As specified throughout this disclosure, any suitable sample may be used. As specified throughout this disclosure, the amplification reagents may include a polymerase that will not accept or process uracil-containing templates. A kit of this disclosure may also provide agents to form an emulsion, including an oil and surfactant.

IX. Applications

Barcoding Sample Materials

The methods, compositions and systems described herein are particularly useful for attaching barcodes, and particularly barcode nucleic acid sequences, to sample materials and components of those sample materials. In general, this is accomplished by partitioning sample material components into separate partitions or reaction volumes in which are co-partitioned a plurality of barcodes, which are then attached to sample components within the same partition.

In an exemplary process, a first partition is provided that includes a plurality of oligonucleotides (e.g., nucleic acid barcode molecules) that each comprise a common nucleic acid barcode sequence. The first partition may comprise any of a variety of portable partitions, e.g., a bead (e.g., a degradable bead, a gel bead), a droplet (e.g., an aqueous droplet in an emulsion), a microcapsule, or the like, to which the oligonucleotides are releasably attached, releasably coupled, or are releasably associated. Moreover, any suitable number of oligonucleotides may be included in the first partition, including numbers of oligonucleotides per partition described elsewhere herein. For example, the oligonucleotides may be releasably attached to, releasably coupled to, or releasably associated with the first partition via a cleavable linkage such as, for example, a chemically cleavable linkage (e.g., a disulfide linkage, or any other type of chemically cleavable linkage described herein), a photocleavable linkage, and/or a thermally cleavable linkage. In some cases, the first partition may be a bead and the bead may be a degradable bead (e.g., a photodegradable bead, a chemically degradable bead, a thermally degradable bead, or any other type of degradable bead described elsewhere herein). Moreover, the bead may comprise chemically-cleavable cross-linking (e.g., disulfide cross-linking) as described elsewhere herein.

The first partition is then co-partitioned into a second partition, with a sample material, sample material component, fragment of a sample material, or a fragment of a sample material component. The sample material (or component or fragment thereof) may be any appropriate sample type, including the example sample types described elsewhere herein. In cases where a sample material or component of a sample material comprises one or more nucleic acid fragments, the one or more nucleic acid fragments may be of any suitable length, including, for example, nucleic acid fragment lengths described elsewhere herein. The second partition may include any of a variety of partitions, including for example, wells, microwells, nanowells, tubes or containers, or in preferred cases droplets (e.g., aqueous droplets in an emulsion) or microcapsules in which the first partition may be co-partitioned. In some cases, the first partition may be provided in a first aqueous fluid and the sample material, sample material component, or fragment of a sample material component may be provided in a second aqueous fluid. During co-partitioning, the first aqueous fluid and second aqueous fluid may be combined within a droplet within an immiscible fluid. In some cases, the second partition may comprise no more than one first partition. In other cases, the second partition may comprise no more than one, two, three, four, five, six, seven, eight, nine, or ten first partitions. In other cases, the second partition may comprise at least one, two, three, four, five, six, seven, eight, nine, ten, or more first partitions.

Once co-partitioned, the oligonucleotides comprising the barcode sequences may be released from the first partition (e.g., via degradation of the first partition, cleaving a chemical linkage between the oligonucleotides and the first partition, or any other suitable type of release, including types of release described elsewhere herein) into the second partition, and attached to the sample components co-partitioned therewith. In some cases, the first partition may comprise a bead and the crosslinking of the bead may comprise a disulfide linkage. In addition, or as an alternative, the oligonucleotides may be linked to the bead via a disulfide linkage. In either case, the oligonucleotides may be released from the first partition by exposing the first partition to a reducing agent (e.g., DTT, TCEP, or any other exemplary reducing agent described elsewhere herein).

As noted elsewhere herein, attachment of the barcodes to sample components includes the direct attachment of the barcode oligonucleotides to sample materials, e.g. through ligation, hybridization, or other associations. Additionally, in many cases, for example, in barcoding of nucleic acid sample materials (e.g., template nucleic acid sequences, template nucleic acid molecules), components or fragments thereof, such attachment may additionally comprise use of the barcode containing oligonucleotides that also comprise as priming sequences. The priming sequence can be complementary to at least a portion of a nucleic acid sample material and can be extended along the nucleic acid sample materials to create complements to such sample materials, as well as at least partial amplification products of those sequences or their complements.

In another exemplary process, a plurality of first partitions can be provided that comprise a plurality of different nucleic acid barcode sequences. Each of the first partitions can comprise a plurality of nucleic acid barcode molecules having the same nucleic acid barcode sequence associated therewith. Any suitable number of nucleic acid barcode molecules may be associated with each of the first partitions, including numbers of nucleic acid barcode molecules per partition described elsewhere herein. The first partitions may comprise any suitable number of different nucleic acid barcode sequences, including, for example, at least about 2, 10, 100, 500, 1000, 5000, 10000, 50000, 100000, 500000, 1000000, 5000000, 10000000, 50000000, or 1000000000, or more different nucleic acid barcode sequences.

In some cases, the plurality of first partitions may comprise a plurality of different first partitions where each of the different first partitions comprises a plurality of releasably attached, releasably coupled, or releasably associated oligonucleotides comprising a common barcode sequence, with the oligonucleotides associated with each different first partitions comprising a different barcode sequence. The number of different first partitions may be, for example, at least about 2, 10, 100, 500, 1000, 5000, 10000, 50000, 100000, 500000, 1000000, 5000000, 10000000, 50000000, or 1000000000, or more different first partitions.

The first partitions may be co-partitioned with sample materials, fragments of a sample material, components of a sample material, or fragments of a component(s) of a sample material into a plurality of second partitions. In some cases, a subset of the second partitions may comprise the same nucleic acid barcode sequence. For example, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or more of the second partitions may comprise the same nucleic acid barcode sequence. Moreover, the distribution of first partitions per second partition may also vary according to, for example, occupancy rates described elsewhere herein. In cases where the plurality of first partitions comprises a plurality of different first partitions, each different first partition may be disposed within a separate second partition.

Following co-partitioning, the nucleic acid barcode molecules associated with the first partitions can be released into the plurality of second partitions. The released nucleic acid barcode molecules can then be attached to the sample materials, sample material components, fragments of a sample material, or fragments of sample material components, within the second partitions. In the case of barcoded nucleic acid species (e.g., barcoded sample nucleic acid, barcoded template nucleic acid, barcoded fragments of one or more template nucleic acid sequences, etc.), the barcoded nucleic acid species may be sequenced as described elsewhere herein.

In another exemplary process, an activatable nucleic acid barcode sequence may be provided and partitioned with one or more sample materials, components of a sample material, fragments of a sample material, or fragments of a component(s) of a sample material into a first partition. With the first partition, the activatable nucleic acid barcode sequence may be activated to produce an active nucleic acid barcode sequence. The active nucleic acid barcode sequence can then be attached to the one or more sample materials, components of a sample material, fragments of a sample material, or fragments of a component(s) of a sample material.

In some cases, the activatable nucleic acid barcode sequence may be coupled to a second partition that is also partitioned in the first partition with the activatable nucleic acid barcode sequence. As described elsewhere herein, an activatable nucleic acid barcode sequence may be activated by releasing the activatable nucleic acid barcode sequence from an associated partition (e.g., a bead). Thus, in cases where an activatable nucleic acid barcode sequence is associated with a second partition (e.g., a bead) that is partitioned in a first partition (e.g., a fluidic droplet), the activatable nucleic acid barcode sequence may be activated by releasing the activatable nucleic acid barcode sequence from its associated second partition. In addition, or as an alternative, an activatable barcode may also be activated by removing a removable blocking or protecting group from the activatable nucleic acid barcode sequence.

In another exemplary process, a sample of nucleic acids may be combined with a library of barcoded beads (including types of beads described elsewhere herein) to form a mixture. In some cases, the barcodes of the beads may, in addition to a barcode sequence, each comprise one or more additional sequences such as, for example, a universal sequence and/or a functional sequence (e.g., a random N-mer or a targeted N-mer, as described elsewhere herein). The mixture may be partitioned into a plurality of partitions, with at least a subset of the partitions comprising at most one barcoded bead. Within the partitions, the barcodes may be released from the beads, using any suitable route, including types of release described herein. A library of barcoded beads may be generated via any suitable route, including the use of methods and compositions described elsewhere herein. In some cases, the sample of nucleic acids may be combined with the library of barcoded beads and/or the resulting mixture partitioned with the aid of a microfluidic device, as described elsewhere herein. In cases where the released barcodes also comprise a primer sequence (e.g., such as a targeted N-mer or a random N-mer as described elsewhere herein), the primer sequences of the barcodes may be hybridize with the sample nucleic acids and, if desired, an amplification reaction can be completed in the partitions.

Polynucleotide Sequencing

Generally, the methods and compositions provided herein are useful for preparation of oligonucleotide fragments for downstream applications such as sequencing. In particular, these methods, compositions and systems are useful in the preparation of sequencing libraries. Sequencing may be performed by any available technique. For example, sequencing may be performed by the classic Sanger sequencing method. Sequencing methods may also include: high-throughput sequencing, pyrosequencing, sequencing-by-ligation, sequencing by synthesis, sequencing-by-hybridization, RNA-Seq (Illumina), Digital Gene Expression (Helicos), next generation sequencing, single molecule sequencing by synthesis (SMSS) (Helicos), massively-parallel sequencing, clonal single molecule Array (Solexa), shotgun sequencing, Maxim-Gilbert sequencing, primer walking, and any other sequencing methods known in the art.

For example, a plurality of target nucleic acid sequences may be sequenced by providing a plurality of target nucleic sequences and separating the target nucleic acid sequences into a plurality of separate partitions. Each of the separate partitions can comprise one or more target nucleic acid sequences and a plurality of oligonucleotides. The separate partitions may comprise any suitable number of different barcode sequences (e.g., at least 1,000 different barcode sequences, at least 10,000 different barcode sequences, at least 100,000 different barcode sequences, at least 1,000,000 different barcode sequences, at least 10,000,000 different barcode sequences, or any other number of different barcode sequences as described elsewhere herein). Moreover, the oligonucleotides in a given partition can comprise a common barcode sequence. The oligonucleotides and associated common barcode sequence in a given partition can be attached to fragments of the one or more target nucleic acids or to copies of portions of the target nucleic acid sequences within the given partition. Following attachment, the separate partitions can then be pooled. The fragments of the target nucleic acids or the copies of the portions of the target nucleic acids and attached barcode sequences can then be sequenced.

In another example, a plurality of target nucleic acid sequences may be sequenced by providing the target nucleic acid sequences and separating them into a plurality of separate partitions. Each partition of the plurality of separate partitions can include one or more of the target nucleic acid sequences and a bead having a plurality of attached oligonucleotides. The oligonucleotides attached to a given bead may comprise a common barcode sequence. The oligonucleotides associated with a bead can be attached to fragments of the target nucleic acid sequences or to copies of portions of the target nucleic acid sequences within a given partition, such that the fragments or copies of the given partition are also attached to the common barcode sequence associated with the bead. Following attachment of the oligonucleotides to the fragments of the target nucleic acid sequences or the copies of the portions of the target nucleic acid sequences, the separate partitions can then be pooled. The fragments of the target nucleic acid sequences or the copies of the portions of the target nucleic acid sequences and any attached barcode sequences can then be sequenced (e.g., using any suitable sequencing method, including those described elsewhere herein) to provide barcoded fragment sequences or barcoded copy sequences. The barcoded fragment sequences or barcoded copy sequences can be assembled into one or more contiguous nucleic acid sequence based, in part, upon a barcode portion of the barcoded fragment sequences or barcoded copy sequences.

In some cases, varying numbers of barcoded-oligonucleotides are sequenced. For example, in some cases about 30%-90% of the barcoded-oligonucleotides are sequenced. In some cases, about 35%-85%, 40%-80%, 45%-75%, 55%-65%, or 50%-60% of the barcoded-oligonucleotides s are sequenced. In some cases, at least about 30%, 40%, 50%, 60%, 70%, 80%, or 90% of barcoded-oligonucleotides are sequenced. In some cases, less than about 30%, 40%, 50%, 60%, 70%, 80%, or 90% of the barcoded-oligonucleotides are sequenced.

In some cases, sequences from fragments are assembled to provide sequence information for a contiguous region of the original target polynucleotide that may be longer than the individual sequence reads. Individual sequence reads may be about 10-50, 50-100, 100-200, 200-300, 300-400, or more nucleotides in length. Examples of sequence assembly methods include those set forth in U.S. patent application Ser. No. 14/752,773, filed Jun. 26, 2014.

The identities of the barcodes may serve to order the sequence reads from individual fragments as well as to differentiate between haplotypes. For example, when combining individual sample fragments and barcoded beads within fluidic droplets, parental polynucleotide fragments may be separated into different droplets. With an increase in the number of fluidic droplets and beads within a droplet, the likelihood of a fragment from both a maternal and paternal haplotype contained within the same fluidic droplet associated with the same bead may become negligibly small. Thus, sequence reads from fragments in the same fluidic droplet and associated with the same bead may be assembled and ordered.

In at least one example, the present disclosure provides nucleic acid sequencing methods, systems compositions, and combinations of these that are useful in providing myriad benefits in both sequence assembly and read-length equivalent, but do so with very high throughput and reduced sample preparation time and cost.

In general, the sequencing methods described herein provide for the localized tagging or barcoding of fragments of genetic sequences. By tagging fragments that derive from the same location within a larger genetic sequence, one can utilize the presence of the tag or barcode to inform the assembly process as alluded to above. In addition, the methods described herein can be used to generate and barcode shorter fragments from a single, long nucleic acid molecule. Sequencing and assembly of these shorter fragments provides a long read equivalent sequence, but without the need for low throughput longer read-length sequencing technologies.

In accordance with the foregoing, a large genetic component, such as a long nucleic acid fragment, e.g., 1, 10, 20, 40, 50, 75, 100, 1000 or more kb in length, a chromosomal fragment or whole chromosome, or part of or an entire genome (e.g., genomic DNA) is fragmented into smaller first fragments. Typically, these fragments may be anywhere from about 1000 to about 100000 bases in length. In certain preferred aspects, the fragments will be between about 1 kb and about 100 kb, or between about 5 kb and about 50 kb, or from about 10 kb to about 30 kb, and in some cases, between about 15 kb and about 25 kb. Fragmentation of these larger genetic components may be carried out by any of a variety of convenient available processes, including commercially available shear based fragmenting systems, e.g., Covaris fragmentation systems, size targeted fragmentation systems, e.g., Blue Pippin (Sage Sciences), enzymatic fragmentation processes, e.g., using restriction endonucleases, or the like. As noted above, the first fragments of the larger genetic component may comprise overlapping or non-overlapping first fragments. Although described here as being fragmented prior to partitioning, it will be appreciated that fragmentation may optionally and/or additionally be performed later in the process, e.g., following one or more amplification steps, to yield fragments of a desired size for sequencing applications.

In preferred aspects, the first fragments are generated from multiple copies of the larger genetic component or portions thereof, so that overlapping first fragments are produced. In preferred aspects, the overlapping fragments will constitute greater than 1× coverage, greater than 2× coverage, greater than 5× coverage, greater than 10× coverage, greater than 20× coverage, greater than 40× coverage, or even greater coverage of the underlying larger genetic component or portion thereof. The first fragments are then segregated to different reaction volumes. In some cases, the first fragments may be separated so that reaction volumes contain one or fewer first fragments. This is typically accomplished by providing the fragments in a limiting dilution in solution, such that allocation of the solution to different reaction volumes results in a very low probability of more than one fragment being deposited into a given reaction volume. However, in most cases, a given reaction volume may include multiple different first fragments, and can even have 2, 5, 10, 100, 100 or even up to 10,000 or more different first fragments in a given reaction volume. Again, achieving a desired range of fragment numbers within individual reaction volumes is typically accomplished through the appropriate dilution of the solution from which the first fragments originate, based upon an understanding of the concentration of nucleic acids in that starting material.

The reaction volumes may include any of variety of different types of vessels or partitions. For example, the reaction volumes may include conventional reaction vessels, such as test tubes, reaction wells, microwells, nanowells, or they may include less conventional reaction volumes, such as droplets within a stabilized emulsion, e.g., a water in oil emulsion system. In preferred aspects, droplets are preferred as the reaction volumes for their extremely high multiplex capability, e.g., allowing the use of hundreds of thousands, millions, tens of millions or even more discrete droplet/reaction volumes within a single container. Within each reaction volume, the fragments that are contained therein are then subjected to processing that both derives sets of overlapping second fragments of each of the first fragments, and also provides these second fragments with attached barcode sequences. As will be appreciated, in preferred aspects, the first fragments are partitioned into droplets that also contain one or more microcapsules or beads that include the members of the barcode library used to generate and barcode the second fragments.

In preferred aspects, the generation of these second fragments is carried out through the introduction of primer sequences that include the barcode sequences and that are capable of hybridizing to portions of the first fragment and be extended along the first fragment to provide a second fragment including the barcode sequence. These primers may comprise targeted primer sequences, e.g., to derive fragments that overlap specific portions of the first fragment, or they may comprise universal priming sequences, e.g., random primers, that will prime multiple different regions of the first fragments to create large and diverse sets of second fragments that span the first fragment and provide multifold overlapping coverage. These extended primer sequences may be used as the second fragments, or they may be further replicated or amplified. For example, iterative priming against the extended sequences, e.g., using the same primer containing barcoded oligonucleotides. In certain preferred aspects, the generation of the second sets of fragments generates the partial hairpin replicates of portions of the first fragment, as described elsewhere herein that each include barcode sequences, e.g., for PHASE amplification as described herein. As noted elsewhere herein, the formation of the partial hairpin is generally desired to prevent repriming of the replicated strand, e.g., making a copy of a copy. As such, the partial hairpin is typically preferentially formed from the amplification product during annealing as compared to a primer annealing to the amplification product, e.g., the hairpin will have a higher Tm than the primer product pair.

The second fragments are generally selected to be of a length that is suitable for subsequent sequencing. For short read sequencing technologies, such fragments will typically be from about 50 bases to about 1000 bases in sequenceable length, from about 50 bases to about 900 bases in sequenceable length, from about 50 bases to about 800 bases in sequenceable length, from about 50 bases to about 700 bases in sequenceable length, from about 50 bases to about 600 bases in sequenceable length, from about 50 bases to about 500 bases in sequenceable length, from about 50 bases to about 400 bases in sequenceable length, from about 50 bases to about 300 bases in sequenceable length, from about 50 bases to about 250 bases in sequenceable length, from about 50 bases to about 200 bases in sequenceable length, or from about 50 bases to about 100 bases in sequenceable length, including the barcode sequence segments, and functional sequences that are subjected to the sequencing process.

Once the overlapping, barcoded second fragment sets are generated, they may be pooled for subsequent processing and ultimately, sequencing. For example, in some cases, the barcoded fragments may be subsequently subjected to additional amplification, e.g., PCR amplification, as described elsewhere herein. Likewise, these fragments may additionally, or concurrently, be provided with sample index sequences to identify the sample from which collections of barcoded fragments have derived, as well as providing additional functional sequences for use in sequencing processes.

In addition, clean up steps may also optionally be performed, e.g., to purify nucleic acid components from other impurities, to size select fragment sets for sequencing, or the like. Such clean up steps may include purification and/or size selection upon SPRI beads (such as Ampure® beads, available from Beckman Coulter, Inc.). In some cases, multiple process steps may be carried out in an integrated process while the fragments are associated with SPRI beads, e.g., as described in Fisher et al., Genome Biol. 2011:12(1): R1 (E-pub Jan. 4, 2011), which is incorporated herein by reference in its entirety for all purposes.

As noted previously, in many cases, short read sequencing technologies are used to provide the sequence information for the second fragment sets. Accordingly, in preferred aspects, second fragment sets will typically comprise fragments that, when including the barcode sequences, will be within the read length of the sequencing system used. For example, for Illumina HiSeq® sequencing, such fragments may be between generally range from about 100 bases to about 200 bases in length, when carrying out paired end sequencing. In some cases, longer second fragments may be sequenced when accessing only the terminal portions of the fragments by the sequencing process.

As will be appreciated, despite being based upon short sequence data, one can infer that two sequences sharing the same barcode likely originated from the same longer first fragment sequence, especially where such sequences are otherwise assemble-able into a contiguous sequence segment, e.g., using other overlapping sequences bearing the common barcode. Once the first fragments are assembled, they may be assembled into larger sequence segments, e.g., the full length genetic component.

In one exemplary process, one or more fragments of one or more template nucleic acid sequences may be barcoded using a method described herein. A fragment of the one or more fragments may be characterized based at least in part upon a nucleic acid barcode sequence attached thereto. Characterization of the fragment may also include mapping the fragment to its respective template nucleic acid sequence or a genome from which the template nucleic acid sequence was derived. Moreover, characterization may also include identifying an individual nucleic acid barcode sequence and a sequence of a fragment of a template nucleic acid sequence attached thereto.

In some cases, sequencing methods described herein may be useful in characterizing a nucleic acid segment or target nucleic acid. In some example methods, a nucleic acid segment may be characterized by co-partitioning the nucleic acid segment and a bead (e.g., including any suitable type of bead described herein) comprising a plurality of oligonucleotides that include a common nucleic acid barcode sequence, into a partition (including any suitable type of partition described herein, such as, for example, a droplet). The oligonucleotides may be releasably attached to the bead (e.g., releasable from the bead upon application of a stimulus to the bead, such as, for example, a thermal stimulus, a photo stimulus, and a chemical stimulus) as described elsewhere herein, and/or may comprise one or more functional sequences (e.g., a primer sequence, a primer annealing sequence, an immobilization sequence, any other suitable functional sequence described elsewhere herein, etc.) and/or one or more sequencing primer sequences as described elsewhere herein. Moreover, any suitable number of oligonucleotides may be attached to the bead, including numbers of oligonucleotides attached to beads described elsewhere herein.

Within the partition, the oligonucleotides may be attached to fragments of the nucleic segment or to copies of portions of the nucleic acid segment, such that the fragments or copies are also attached to the common nucleic acid barcode sequence. The fragments may be overlapping fragments of the nucleic acid segment and may, for example, provide greater than 2× coverage, greater than 5× coverage, greater than 10× coverage, greater than 20× coverage, greater than 40× coverage, or even greater coverage of the nucleic acid segment. In some cases, the oligonucleotides may comprise a primer sequence capable of annealing with a portion of the nucleic acid segment or a complement thereof. In some cases, the oligonucleotides may be attached by extending the primer sequences of the oligonucleotides to replicate at least a portion of the nucleic acid segment or complement thereof, to produce a copy of at least a portion of the nucleic acid segment comprising the oligonucleotide, and, thus, the common nucleic acid barcode sequence.

Following attachment of the oligonucleotides to the fragments of the nucleic acid segment or to the copies of the portions of the nucleic acid segment, the fragments of the nucleic acid segment or the copies of the portions of the nucleic acid segment and the attached oligonucleotides (including the oligonucleotide's barcode sequence) may be sequenced via any suitable sequencing method, including any type of sequencing method described herein, to provide a plurality of barcoded fragment sequences or barcoded copy sequences. Following sequencing, the fragments of the nucleic acid segment or the copies of the portions of the nucleic acid segment can be characterized as being linked within the nucleic acid segment at least in part, upon their attachment to the common nucleic acid barcode sequence. As will be appreciated, such characterization may include sequences that are characterized as being linked and contiguous, as well as sequences that may be linked within the same fragment, but not as contiguous sequences. Moreover, the barcoded fragment sequences or barcoded copy sequences generated during sequencing can be assembled into one or more contiguous nucleic acid sequences based at least in part on the common nucleic acid barcode sequence and/or a non-barcode portion of the barcoded fragment sequences or barcoded copy sequences.

In some cases, a plurality of nucleic acid segments (e.g., fragments of at least a portion of a genome, as described elsewhere herein) may be co-partitioned with a plurality of different beads in a plurality of separate partitions, such that each partition of a plurality of different partitions of the separate partitions contains a single bead. The plurality of different beads may comprise a plurality of different barcode sequences (e.g., at least 1,000 different barcode sequences, at least 10,000 different barcode sequences, at least 100,000 different barcode sequences, at least 1,000,000 different barcodes sequences, or any other number of different barcode sequences as described elsewhere herein). In some cases, two or more, three or more, four or more, five or more, six or more, seven or more of the plurality of separate partitions may comprise beads that comprise the same barcode sequence. In some cases, at least 0.01%, 0.1%, 1%, 5%, 10%, 15%, 20%, 25%, 30%, 35%, 40%, 45%, 50%, 55%, 60%, 65%, 70%, 75%, 80%, 85%, 90%, 95%, or 99% of the separate partitions may comprise beads having the same barcode sequence. Moreover, each bead may comprise a plurality of attached oligonucleotides that include a common nucleic acid barcode sequence.

Following co-partitioning, barcode sequences can be attached to fragments of the nucleic acid segments or to copies of portions of the nucleic acid segments in each partition. The fragments of the nucleic acid segments or the copies of the portions of the nucleic acid segments can then be pooled from the separate partitions. After pooling, the fragments of the nucleic acid segments or copies of the portions of the nucleic acid segments and any associated barcode sequences can be sequenced (e.g., using any suitable sequencing method, including those described herein) to provide sequenced fragment or sequenced copies. The sequenced fragments or sequenced copies can be characterized as deriving from a common nucleic acid segment, based at least in part upon the sequenced fragments or sequenced copies comprising a common barcode sequence. Moreover, sequences obtained from the sequenced fragments or sequenced copies may be assembled to provide a contiguous sequence of a sequence (e.g., at least a portion of a genome) from which the sequenced fragments or sequenced copies originated. Sequence assembly from the sequenced fragments or sequenced copies may be completed based, at least in part, upon each of a nucleotide sequence of the sequenced fragments and a common barcode sequence of the sequenced fragments.

In another example method, a target nucleic acid may be characterized by partitioning fragments of the target nucleic acid into a plurality of droplets. Each droplet can comprise a bead attached to a plurality of oligonucleotides comprising a common barcode sequence. The common barcode sequence can be attached to fragments of the fragments of the target nucleic acid in the droplets. The droplets can then be pooled and the fragments and associated barcode sequences of the pooled droplets sequenced using any suitable sequencing method, including sequencing methods described herein. Following sequencing, the fragments of the fragments of the target nucleic acid may be mapped to the fragments of the target nucleic acid based, at least in part, upon the fragments of the fragments of the target nucleic acid comprising a common barcode sequence.

The application of the methods, compositions and systems described herein in sequencing may generally be applicable to any of a variety of different sequencing technologies, including NGS sequencing technologies such as Illumina MiSeq, HiSeq and X10 Sequencing systems, as well as sequencing systems available from Life Technologies, Inc., such as the Ion Torrent line of sequencing systems. While discussed in terms of barcode sequences, it will be appreciated that the sequenced barcode sequences may not include the entire barcode sequence that is included, e.g., accounting for sequencing errors. As such, when referring to characterization of two barcode sequences as being the same barcode sequence, it will be appreciated that this may be based upon recognition of a substantial portion of a barcode sequence, e.g., varying by fewer than 5, 4, 3, 2 or even a single base.

Sequencing from Small Numbers of Cells

Methods provided herein may also be used to prepare polynucleotides contained within cells in a manner that enables cell-specific information to be obtained. The methods enable detection of genetic variations from very small samples, such as from samples comprising about 10-100 cells. In some cases, about 1, 5, 10, 20, 30, 40, 50, 60, 70, 80, 90 or 100 cells may be used in the methods described herein. In some cases, at least about 1, 5, 10, 20, 30, 40, 50, 60, 70, 80, 90 or 100 cells may be used in the methods described herein. In other cases, at most about 5, 10, 20, 30, 40, 50, 60, 70, 80, 90 or 100 cells may be used in the methods described herein.

In an example, a method may comprise partitioning a cellular sample (or crude cell extract) such that at most one cell (or extract of one cell) is present within a partition, e.g., fluidic droplet, and is co-partitioned with the barcode oligonucleotides, e.g., as described above. Processing then involves lysing the cells, fragmenting the polynucleotides contained within the cells, attaching the fragmented polynucleotides to barcoded beads, pooling the barcoded beads, and sequencing the resulting barcoded nucleic acid fragments.

As described elsewhere herein, the barcodes and other reagents may be encapsulated within, coated on, associated with, or dispersed within a bead (e.g. gel bead). The bead may be loaded into a fluidic droplet contemporaneously with loading of a sample (e.g. a cell), such that each cell is contacted with a different bead. This technique may be used to attach a unique barcode to oligonucleotides obtained from each cell. The resulting tagged oligonucleotides may then be pooled and sequenced, and the barcodes may be used to trace the origin of the oligonucleotides. For example, oligonucleotides with identical barcodes may be determined to originate from the same cell, while oligonucleotides with different barcodes may be determined to originate from different cells.

The methods described herein may be used to detect a specific gene mutation that may indicate the presence of a disease, such as cancer. For example, detecting the presence of a V600 mutation in the BRAF gene of a colon tissue sample may indicate the presence of colon cancer. In other cases, prognostic applications may include the detection of a mutation in a specific gene or genes that may serve as increased risk factors for developing a specific disease. For example, detecting the presence of a BRCA1 mutation in a mammary tissue sample may indicate a higher level of risk to developing breast cancer than a person without this mutation. In some examples, this disclosure provides methods of identifying mutations in two different oncogenes (e.g., KRAS and EGRF). If the same cell comprises genes with both mutations, this may indicate a more aggressive form of cancer. In contrast, if the mutations are located in two different cells, this may indicate that the cancer may be more benign, or less advanced.

Analysis of Gene Expression

Methods of the disclosure may be applicable to processing samples for the detection of changes in gene expression. A sample may comprise a cell, mRNA, or cDNA reverse transcribed from mRNA. The sample may be a pooled sample, comprising extracts from several different cells or tissues, or a sample comprising extracts from a single cell or tissue.

Cells may be placed directly into a fluidic droplet and lysed. After lysis, the methods of the disclosure may be used to fragment and barcode the oligonucleotides of the cell for sequencing. Oligonucleotides may also be extracted from cells prior to introducing them into a fluidic droplet used in a method of the disclosure. Reverse transcription of mRNA may be performed in a fluidic droplet described herein, or outside of such a fluidic droplet. Sequencing cDNA may provide an indication of the abundance of a particular transcript in a particular cell over time, or after exposure to a particular condition.

Partitioning Polynucleotides from Cells or Proteins

In one example the compositions, methods, devices, and kits provided in this disclosure may be used to encapsulate cells or proteins within the fluidic droplets. In one example, a single cell or a plurality of cells (e.g., 2, 10, 50, 100, 1000, 10000, 25000, 50000, 10000, 50000, 1000000, or more cells) may be loaded onto, into, or within a bead along with a lysis buffer within a fluidic droplet and incubated for a specified period of time. The bead may be porous, to allow washing of the contents of the bead, and introduction of reagents into the bead, while maintaining the polynucleotides of the one or more cells (e.g. chromosomes) within the fluidic droplets. The encapsulated polynucleotides of the one or more cells (e.g. chromosomes) may then be processed according to any of the methods provided in this disclosure, or known in the art. This method can also be applied to any other cellular component, such as proteins.

Epigenetic Applications

Compositions, methods, devices, and kits of this disclosure may be useful in epigenetic applications. For example, DNA methylation can be in indicator of epigenetic inheritance, including single nucleotide polymorphisms (SNPs). Accordingly, samples comprising nucleic acid may be treated in order to determine bases that are methylated during sequencing. In some cases, a sample comprising nucleic acid to be barcoded may be split into two aliquots. One aliquot of the sample may be treated with bisulfite in order to convert unmethylated cytosine containing nucleotides to uracil containing nucleotides. In some cases, bisulfite treatment can occur prior to sample partitioning or may occur after sample partitioning. Each aliquot may then be partitioned (if not already partitioned), barcoded in the partitions, and additional sequences added in bulk as described herein to generate sequencer-ready products. Comparison of sequencing data obtained for each aliquot (e.g., bisulfite-treated sample vs. untreated sample) can be used to determine which bases in the sample nucleic acid are methylated.

In some cases, one aliquot of a split sample may be treated with methylation-sensitive restriction enzymes (MSREs). Methylation specific enzymes can process sample nucleic acid such that the sample nucleic acid is cleaved as methylation sites. Treatment of the sample aliquot can occur prior to sample partitioning or may occur after sample partitioning and each aliquot may be partitioned used to generate barcoded, sequencer-ready products. Comparison of sequencing data obtained for each aliquot (e.g., MSRE-treated sample vs. untreated sample) can be used to determine which bases in the sample nucleic acid are methylated.

Low Input DNA Applications

Compositions and methods described herein may be useful in the analysis and sequencing of low polynucleotide input applications. Methods described herein, such as PHASE, may aid in obtaining good data quality in low polynucleotide input applications and/or aid in filtering out amplification errors. These low input DNA applications include the analysis of samples to sequence and identify a particular nucleic acid sequence of interest in a mixture of irrelevant or less relevant nucleic acids in which the sequence of interest is only a minority component, to be able to individually sequence and identify multiple different nucleic acids that are present in an aggregation of different nucleic acids, as well as analyses in which the sheer amount of input DNA is extremely low. Specific examples include the sequencing and identification of somatic mutations from tissue samples, or from circulating cells, where the vast majority of the sample will be contributed by normal healthy cells, while a small minority may derive from tumor or other cancer cells. Other examples include the characterization of multiple individual population components, e.g., in microbiome analysis applications, where the contributions of individual population members may not otherwise be readily identified amidst a large and diverse population of microbial elements. In a further example, being able to individually sequence and identify different strands of the same region from different chromosomes, e.g., maternal and paternal chromosomes, allows for the identification of unique variants on each chromosome. Additional examples of low polynucleotide input applications of the compositions, methods, and systems described herein are set forth in U.S. Provisional Patent Application No. 62/017,580, filed Jun. 26, 2014.

The advantages of the methods and systems described herein are clearer upon a discussion of the problems confronted in the present state of the art. In analyzing the genetic makeup of sample materials, e.g., cell or tissue samples, most sequencing technologies rely upon the broad amplification of target nucleic acids in a sample in order to create enough material for the sequencing process. Unfortunately, during these amplification processes, majority present materials will preferentially overwhelm portions of the samples that are present at lower levels. For example, where a genetic material from a sample is comprised of 95% normal tissue DNA, and 5% of DNA from tumor cells, typical amplification processes, e.g., PCR based amplification, will quickly amplify the majority present material to the exclusion of the minority present material. Furthermore, because these amplification reactions are typically carried out in a pooled context, the origin of an amplified sequence, in terms of the specific chromosome, polynucleotide or organism will typically not be preserved during the process.

In contrast, the methods and systems described herein partition individual or small numbers of nucleic acids into separate reaction volumes, e.g., in droplets, in which those nucleic acid components may be initially amplified. During this initial amplification, a unique identifier may be coupled to the components to the components that are in those separate reaction volumes. Separate, partitioned amplification of the different components, as well as application of a unique identifier, e.g., a barcode sequence, allows for the preservation of the contributions of each sample component, as well as attribution of its origin, through the sequencing process, including subsequent amplification processes, e.g., PCR amplification.

The term "about," as used herein and throughout the disclosure, generally refers to a range that may be 15% greater than or 15% less than the stated numerical value within the context of the particular usage. For example, "about 10" would include a range from 8.5 to 11.5.

As will be appreciated, the instant disclosure provides for the use of any of the compositions, libraries, methods, devices, and kits described herein for a particular use or purpose, including the various applications, uses, and purposes described herein. For example, the disclosure provides for the use of the compositions, methods, libraries, devices, and kits described herein in partitioning species, in partitioning oligonucleotides, in stimulus-selective release of species from partitions, in performing reactions (e.g., ligation and amplification reactions) in partitions, in performing nucleic acid synthesis reactions, in barcoding nucleic acid, in preparing polynucleotides for sequencing, in sequencing polynucleotides, in polynucleotide phasing (see e.g., U.S. Provisional Patent Application No. 62/017,808, filed Jun. 26, 2014), in sequencing polynucleotides from small numbers of cells, in analyzing gene expression, in partitioning polynucleotides from cells, in mutation detection, in neurologic disorder diagnostics, in diabetes diagnostics, in fetal aneuploidy diagnostics, in cancer mutation detection and forensics, in disease detection, in medical diagnostics, in low input nucleic acid applications, such as circulating tumor cell (CTC) sequencing, in a combination thereof, and in any other application, method, process or use described herein.

Any concentration values provided herein are provided as admixture concentration values, without regard to any in situ conversion, modification, reaction, sequestration or the like. Moreover, where appropriate, the sensitivity and/or specificity of methods (e.g., sequencing methods, barcoding methods, amplification methods, targeted amplification methods, methods of analyzing barcoded samples, etc.) described herein may vary. For example, a method described herein may have specificity of greater than 50%, 70%, 75%, 80%, 85%, 86%, 87%, 88%, 89%, 90%, 91%, 92%, 93%, 94%, 95%, 96%, 97%, 98%, 99%, or 99.5% and/or a sensitivity of greater than 50%, 70%, 75%, 80%, 85%, 86%, 87%, 88%, 89%, 90%, 91%, 92%, 93%, 94%, 95%, 96%, 97%, 98%, 99%, or 99.5%.

Additional Sequencing Approaches

A wide variety of different sequencing technologies are practiced across broad ranging industries, including biotechnology, pharmaceutical research, medical diagnostics, agriculture, basic research, food safety and so on. These technologies include the older Sanger sequencing methods where nested fragments of template nucleic acids terminated with the four different nucleotides bearing distinguishable labels are separated by their size and identified as to their terminating nucleotide by the distinguishable label.

Sequencing methods also include more recent "sequencing by synthesis", or SBS, methods where the iterative addition of specific nucleotides in a template dependent, polymerase mediated extension reaction are identified and used to provide the underlying sequence of the template nucleic acid. These SBS processes are generally divided into (1) short read sequencing technologies, e.g., employed in Illumina HiSeq, MiSeq, and NextSeq sequencing systems, as well as the Ion Torrent Proton and PGM systems, available from Thermo Fisher, and (2) long read sequencing technologies such as single molecule, real time, or SMRT® sequencing systems available from Pacific Biosciences.

The short read technologies generally utilize an ensemble approach where patches or clusters of identical nucleic acid template molecules arrayed on substrates are observed or detected in separate cycles of nucleotide addition, in order to identify the added bases in a stepwise fashion. By providing large numbers of clusters each representing different molecules, one can sequence large numbers of different nucleic acid fragments during a sequencing run. Further, by relying upon the consensus of the identified base added over all of the molecules within a given cluster, i.e., having hundreds of thousands of molecules, any low level inaccuracy of the extension reaction, e.g., incorporating an incorrect base, is overwhelmed by the correct base addition, leading to very high accuracy rates for sequence reads. However, because of inherent inefficiencies in the extension reactions, extension of the various template molecules within any given cluster can, over time, go out of phase with one another, resulting in an inability to accurately call bases after a few hundred bases of read length, even in an ensemble approach.

By contrast, the long read, single molecule SBS methods, such as SMRT sequencing, detect individual bases within a single nucleic acid molecule. SMRT sequencing, for example, relies upon the observation of incorporation of individual bases in a replication of a template molecule, as the template is being replicated by a single DNA polymerase enzyme, where the sequential addition of bases to the duplicating strand are observable using special optical detection techniques and fluorophore labeled nucleotides. By observing replication of a single long nucleic acid template molecule, one can obtain very long read lengths, e.g., on the order of 10s of thousands of bases. However, as these techniques observe replication of a single nucleic acid molecule, any mistakes made in the polymerase reaction are observed and incorporated into the perceived read. Furthermore, in order to avoid confounding sequence information, highly accurate polymerases, e.g., that possess proofreading capabilities, are not used. This results in single pass accuracies of only on the order of 85% of base calls being correct. Remedies for this deficiency in single pass accuracy employ the template molecules in a circular structure, such that multiple passes by the single polymerase around the circular molecule may be made, mimicking an ensemble approach to improving accuracy, e.g., multiple sequencing passes over the same molecule of sequence provide a higher consensus accuracy for that sequence.

In still other approaches, individual template molecules would be directly read out as the molecule itself passes through a detecting zone, e.g., in a nanopore sequencing system. Again, while these systems have been described in proof of principle experiments, they are generally not commercially available, and are generally prone to inaccuracy and production of noisy data.

For most of these sequencing technologies, there are significant steps that are taken up front of the actual sequencing process, in order to provide template nucleic acids in a sequenceable format for the sequencing system being used. These involve conventional process steps of purifying the nucleic acids to be sequenced away from other material in a sample, e.g., extracting it from cells or tissue, purifying away contaminating proteins, enzymes and other cellular debris, as well as steps of incorporating operable components onto the nucleic acids in order to allow for sequencing, such as primer sequences, adapter sequences, hairpin sequences and identifier sequences, such as oligonucleotide barcodes or sample index oligonucleotides. A number of different process steps have evolved for preparing sequenceable libraries of nucleic acid molecules (also termed "sequencing libraries" herein), many of which are highly dependent upon the sequencing system being used.

Additional Barcoding Libraries

In one example, a partitioning and barcoding process is used to derive long-range sequence information from template nucleic acids without the need for long read sequencing processes. In brief, long fragments of nucleic acids from sample, e.g., cells or tissue, are partitioned into discrete aqueous droplets in an aqueous:oil emulsion. Beads bearing populations of barcoded primer sequences are co-partitioned into these droplets along with the sample fragments, polymerization reaction components, e.g., polymerase enzyme, nucleoside triphosphates, Mg2+, and the like. The barcoded primers are released from the beads and allowed to prime along portions of the template nucleic acids to produce replicate fragments of the template. As a result, each partition or droplet can include replicate fragments of the original starting fragments, but where each fragment includes a barcode sequence that is attributable to the single bead partitioned into a given droplet. These replicate fragments are then further processed, e.g., to attach additional functional sequences, such as amplification primer sequences, other sequencer specific sequences, e.g., flow cell attachment sequences, sequencing primer sequences, and the like, as well as to amplify the number of fragments in order to put them through the sequencing processes.

Sequencing of the replicated, barcoded fragments then yields short sequence reads that also include a barcode sequence. This barcode sequence can then be used, along with sequence information, to attribute the associated fragment sequence to an originating starting fragment, thereby providing long range sequence information, e.g., as to the originating long fragment, from short read sequences. By ensuring that replicate fragments cover the entire originating fragment, even multiple times, one can readily assemble the sequence into virtual long reads of the originating fragment. In addition, even without complete multifold coverage used for complete de novo sequencing, the presence of common barcodes on different short sequences can allow the inference of longer range linkage between the two different short sequences, providing numerous advantages over short read sequencing alone, e.g., in genome mapping, structural variant detection, identification of phased variants (see, e.g., U.S. Patent Application No. 62/072,214, filed Oct. 29, 2014, which is incorporated herein by reference in its entirety for all purposes), as well as other valuable long range sequence linkage information. These methods and their applications are discussed in detail in, for example, co-pending U.S. patent application Ser. No. 14/316,383, filed Jun. 26, 2014, 62/017,808, filed Jun. 26, 2014, 62/072,214, filed Oct. 29, 2014, 62/072,164, filed Oct. 29, 2014, and 62/017,558, filed Jun. 26, 2014, the full disclosures of which are each incorporated herein by reference in their entireties for all purposes.

Additional Fragmentation and Barcoding

As described herein, provided are methods, and systems for preparing improved sequencing libraries from sample nucleic acids. The improved sequencing libraries provide one or more of more uniform coverage, lower sequence error rates, higher amplification rates of the original sequence, and lower chimera generation rates.

Figure 19A:
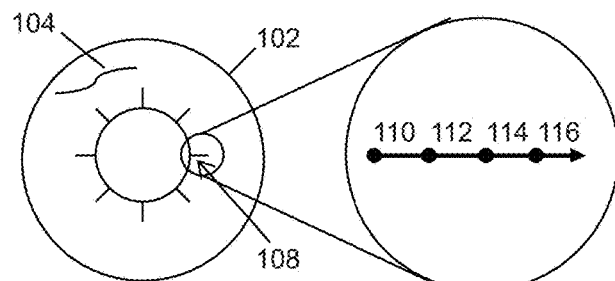
FIG. 19A schematically illustrates an overview of a process for preparation of barcoded sequencing libraries.

As noted above, a method for providing barcoded replicate fragments of template nucleic acids to use as a sequencing library is described in detail in co-pending U.S. patent application Ser. No. 14/316,383, filed Jun. 26, 2014, and previously incorporated herein by reference. Briefly, and as shown in FIG. 19A-F, oligonucleotides that include a barcode sequence are co-partitioned in, e.g., a droplet 102 in an emulsion, along with a sample nucleic acid 104. The oligonucleotides 108 may be provided on a bead 106 that is co-partitioned with the sample nucleic acid 104, which oligonucleotides are preferably releasable from the bead 106, as shown in FIG. 19A. The oligonucleotides 108 include a barcode sequence 112, in addition to one or more functional sequences, e.g., sequences 110, 114 and 116. For example, oligonucleotide 108 is shown as comprising barcode sequence 112, as well as sequence 110 that may function as an attachment or immobilization sequence for a given sequencing system, e.g., a P5 sequence used for attachment in flow cells of an Illumina Hiseq or Miseq system. As shown, the oligonucleotides also include a primer sequence 116, which may include a universal, random or targeted N-mer for priming replication of portions of the sample nucleic acid 104. Also included within oligonucleotide 108 is a sequence 114 which may provide a sequencing priming region, such as a "read1" or R1 priming region, that is used to prime polymerase mediated, template directed sequencing by synthesis reactions in sequencing systems. In many cases, the barcode sequence 112, immobilization sequence 110 and R1 sequence 114 may be common to all of the oligonucleotides attached to a given bead. The primer sequence 116 may vary for random N-mer primers, or may be common to the oligonucleotides on a given bead for certain targeted applications. Although described with reference to the specific positioning and type of functional sequence segment elements within the barcode oligonucleotides, it will be appreciated that the position and nature of the functional segments within a barcode oligonucleotide may vary. For example, primer sequences for different sequencing systems may be employed in place of the P5, read1, etc. primers. Likewise, as noted elsewhere herein, targeted primer sequences may be provided to permit attachment of barcode sequences to targeted portions of a genome or sample genetic material. Additionally, in some cases, the positional context of the different segments may be changed. For example, in some cases, it may be desirable to position the barcode sequence segment 5' of the sequence read primer or R1 segment 114, e.g., between segments 114 and 116, so that the barcode can be sequenced in a first pass or initial sequence read, e.g., following priming of the read1 sequence during the sequencing of the resultant barcoded fragments, as opposed to obtaining the barcode read on a subsequent sequencing read of a reverse complement. This and a variety of other variations are envisioned by the present disclosure.

Figure 19B:
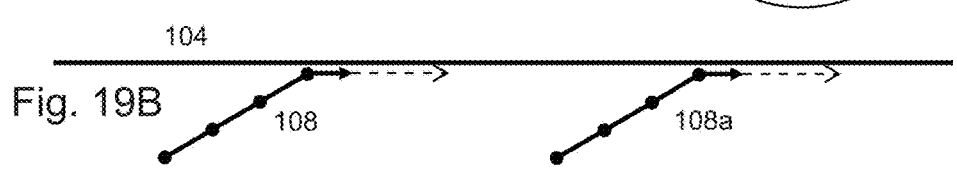
FIGS. 19B-19F schematically illustrate steps of a process for preparation of barcoded sequencing libraries.
Figure 19C:
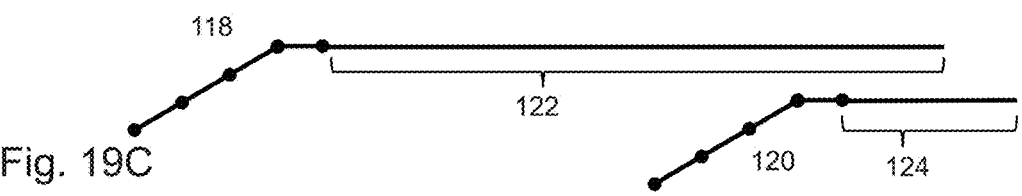

Based upon the presence of primer sequence 116, the oligonucleotides are able to prime the sample nucleic acid as shown in FIG. 19B, which allows for extension of the oligonucleotides 108 and 108a using polymerase enzymes and other extension reagents also co-partitioned with the bead 106 and sample nucleic acid 104. As described elsewhere herein, these polymerase enzymes may include thermostable polymerases, e.g., where initial denaturation of double stranded sample nucleic acids within the partitions is desired. Alternatively, denaturation of sample nucleic acids may precede partitioning, such that single stranded target nucleic acids are deposited into the partitions, allowing the use of non-thermostable polymerase enzymes, e.g., Klenow, phi29, PolI, and the like, where desirable. As shown in FIG. 19C, following extension of the oligonucleotides that, for random N-mer primers, can anneal to multiple different regions of the sample nucleic acid 104; multiple overlapping complements or fragments of the nucleic acid are created, e.g., fragments 118 and 120. Although including sequence portions that are complementary to portions of sample nucleic acid, e.g., sequences 122 and 124 (also referred to as "inserts"), these constructs are generally referred to herein as comprising fragments of the sample nucleic acid 104, having the attached barcode sequences. In some cases, it may be desirable to artificially limit the size of the replicate fragments that are produced in order to maintain manageable fragment sizes from the first amplification steps. In some cases, this may be accomplished by mechanical means, as described above, e.g., using fragmentation systems like a Covaris system, or it may be accomplished by incorporating random extension terminators, e.g., at low concentrations, to prevent the formation of excessively long fragments.

Figure 19D:
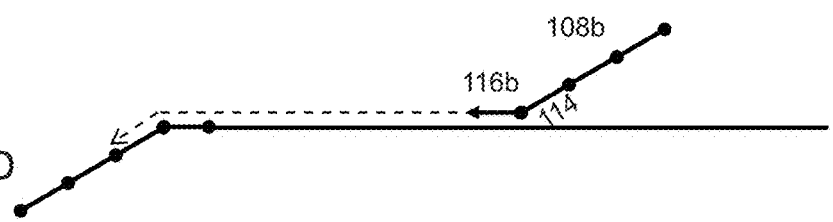
Figure 19E:
Figure 19F:
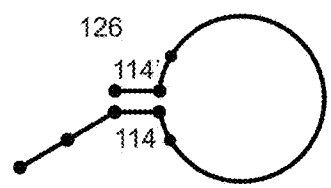

These fragments may then be subjected to sequence analysis, or they may be subjected to further processing, e.g., to amplify the amount of nucleic acids available for sequencing, e.g., as shown in the process illustrated in FIG. 19D and/or provide additional functional sequences. For example, additional oligonucleotides, e.g., oligonucleotide 108b, also released from bead 106, may prime the fragments 118 and 120. In particular, again, based upon the presence of the random N-mer primer 116b in oligonucleotide 108b (which in many cases can be different from other random N-mers in a given partition, e.g., primer sequence 116), the oligonucleotide anneals with the fragment 118, and is extended to create a complement 126 to at least a portion of fragment 118 which includes sequence 128, that comprises a duplicate of a portion of the sample nucleic acid sequence. Extension of the oligonucleotide 108b continues until it has replicated through the oligonucleotide portion 108 of fragment 118. As illustrated in FIG. 19D, the oligonucleotides may be configured to prompt a stop in the replication by the polymerase at a desired point, e.g., after replicating through sequences 116 and 114 of oligonucleotide 108 that is included within fragment 118. In some cases, this is achieved through the incorporation of nucleotide or nucleotide analogues that are not processed by the polymerase being used for the replication reaction. For example, in many cases, uracil containing bases may be included in the primer sequences to stop replication by a polymerase that does not read through uracil containing bases. This may be done in order to provide for the generation of partial hairpin sequences, e.g., that have partial internal complementarity, in order to prevent excessive replication of copies and the associated bias, e.g., partial hairpins would be removed, at least in part, from subsequent replication steps.

As described herein, this may be accomplished by different methods, including, for example, the incorporation of different nucleotides and/or nucleotide analogues that are not capable of being processed by the polymerase enzyme used. For example, this may include the inclusion of uracil containing nucleotides within the sequence to cause a non-uracil tolerant polymerase to cease replication of that region. As a result, a fragment 126 is created that includes the full-length oligonucleotide 108b at one end, including the barcode sequence 112, the attachment sequence 110, the R1 primer region 114, and the random n-mer sequence 116b.

At the other end of the sequence can be included the complement 116' to the random n-mer of the first oligonucleotide 108, as well as a complement to all or a portion of the R1 sequence, shown as sequence 114'. The R1 sequence 114 and its complement 114' are then able to hybridize together to form a partial hairpin structure 128. As will be appreciated because the random-n-mers differ among different oligonucleotides, these sequences and their complements generally would not be expected to participate in hairpin formation, e.g., sequence 116', which is the complement to random N-mer 116, would generally not be expected to be complementary to random n-mer sequence 116b. This generally would not be the case for other applications, e.g., targeted primers, where the N-mers may be common among oligonucleotides within a given partition.

By forming these partial hairpin structures, it allows for the removal of a large number of first level duplicates of the sample sequence from further replication, e.g., reducing the prevalence of iterative copying of copies. The partial hairpin structure also provides a useful structure for subsequent processing of the created fragments, e.g., fragment 126. Additionally, the use of U-containing oligonucleotides and non-U processing polymerases in the barcoding process reduces the amount of primer-dimer artifacts during that barcoding process (e.g., as little or no extension would occur across a U-containing primer that is serving as a template for extension), that would otherwise reduce the efficiency of the process.

Figure 20A:
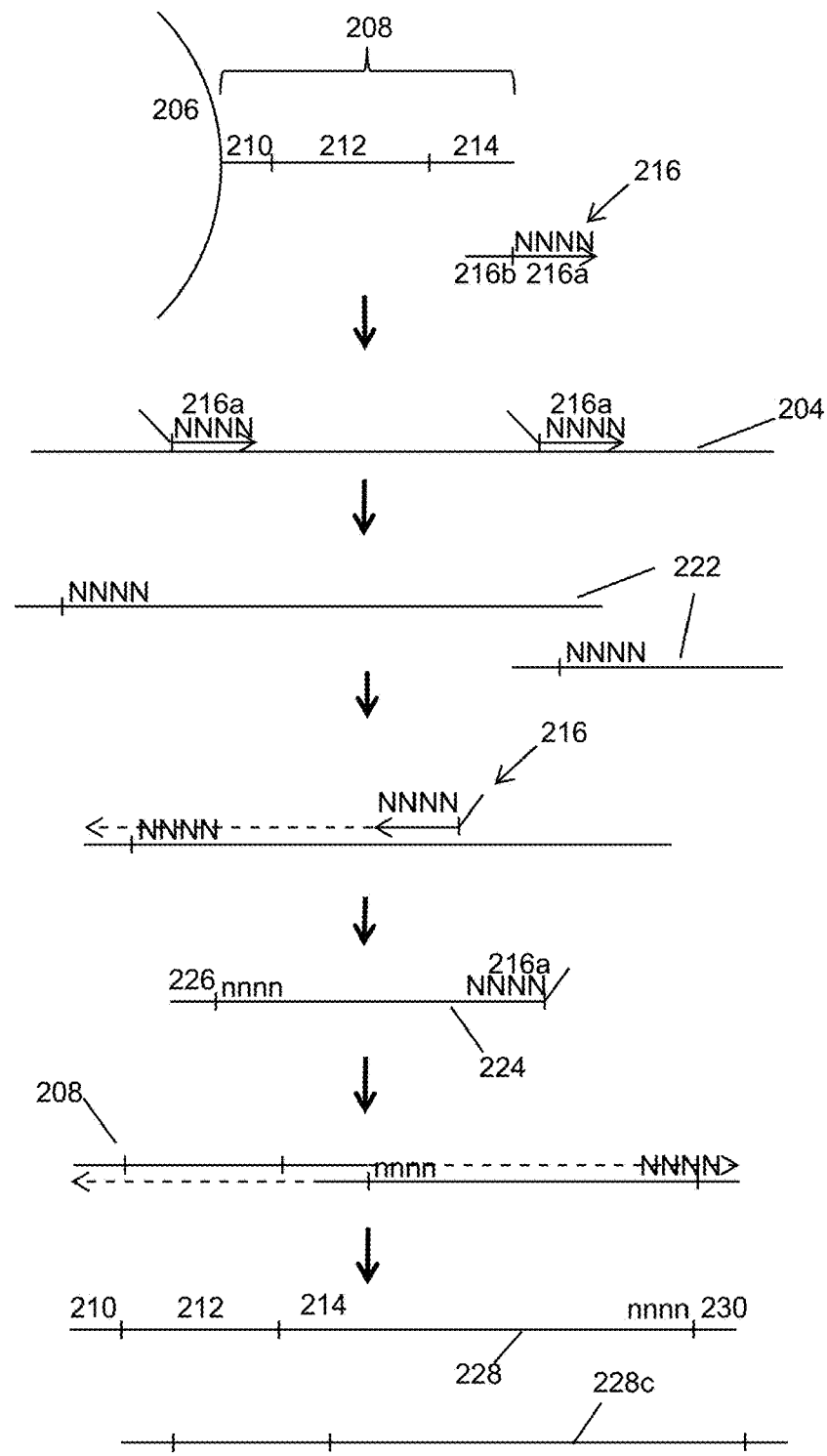
FIG. 20A, FIG. 20B and FIG. 20C schematically illustrate alternative processes for preparing barcoded sequencing libraries.

In one example of an improved approach, a partitioning method as described above is employed, but with a separate primer oligonucleotide added to the reaction mix that also includes sufficient functional sequence elements to be able to permit barcode attachment, but which not part of the barcode oligonucleotide. This approach is schematically illustrated in FIG. 20A. As shown, a bead 206 bearing the barcode oligonucleotide 208 to be co-partitioned with the sample nucleic acid fragment includes oligonucleotides that have a barcode sequence as well as one or more additional sequences, e.g., attachment sequence 210 (e.g., P5), barcode sequence 212, and sequencing primer sequence 214 (e.g., R1). As noted above, the barcode portion 212 of the sequence can vary among different beads, while at least one of the additional sequences is constant across the various different beads. In the example shown, the oligonucleotides 208 on the bead 206 include a variable barcode portion 212 and one or more constant portions, which, as shown include, e.g., attachment sequence 210 and sequencing primer segment 214. Also co-partitioned with the barcode oligonucleotides is a separate primer oligonucleotide 216 that includes a primer sequence portion 216a as well as a portion 216b that is identical to at least a portion of the constant portion, e.g., sequencing primer 214, of barcode oligonucleotide 208. While primer sequence portion 216a is illustrated as a random N-mer primer, it will again be appreciated that specific primer sequences could also be employed, e.g., targeting specific priming sequences or sequences adjacent to regions of interest in the genome, for use in generating sequencing libraries for targeted genes, gene panels, or portions of the genome, or primer sequences that are less than completely random, e.g., as described elsewhere herein.

Once co-partitioned along with the template nucleic acid 204, the primer sequence portion 216a can anneal to portions of the template 204, and be extended to create replicate fragments 222 of the template 204 that include both the priming sequence 216a and the additional sequence segment 216b that is identical to at least a portion of a constant portion, e.g., sequence 214, of barcode oligonucleotide 208. Following the initial extension, a second primer sequence 216 anneals to the newly created replicate fragment 222, and is extended to create a complementary replicate fragment 224 that includes sequence portion 226 that is complementary to at least a portion of constant sequence segment 214, e.g., at the 5' terminus) on barcode oligonucleotide 208 (as well as a complement to the original primer sequence— shown as nnnn) The barcode oligonucleotide is then able to anneal to the complementary sequence portion 226 through constant segment 214, and extension of that sequence results in a replicate copy 228 of the sample nucleic acid sequence with an attached barcode sequence 212, as well as the attached constant portions, e.g., attachment sequence 210 and sequencing primer sequence 214, and a complementary sequence 230 to the partial constant sequence 216b. As shown, both the barcode oligonucleotide 208 and replicate fragment 224 are extended to yield both replicate copy 228, and its complement 228c. As will be appreciated, in some cases, the 5' terminus of the barcode oligonucleotide may be provided with a blocking group to prevent extension, e.g., preventing the generation of fragment 228, and only allowing replication of the barcode oligonucleotide onto fragment 224. This may be done in some instances in order to avoid the barcode oligonucleotide priming in a less controlled fashion against the underlying sample nucleic acids, e.g., the genome, which could result in suboptimal library generation. A variety of blocking groups or other non-extendible nucleotide groups may be employed, including blocked nucleic acids, dideoxy terminated nucleic acids, and the like.

Use of a separate primer sequence with the ability to attach barcode sequences to it, in process, can provide advantages of controllability to the priming operation that is separate from the barcode library itself. In particular, a barcode library may be constructed that is universally applicable for different applications, where those different applications may benefit from different priming strategies, e.g., other than purely random n-mer priming. The application specific primer sequences may then be added to the reaction mix, rather than having to reconstruct an entire barcode library including primer sequences, to pursue the desired application. In particular, one could readily substitute targeted primer sequences, biased primer sequences, e.g., GC biased, AT biased, or other structured primer sequences, e.g., having defined sub-motifs, sub-biases as to segments of the primer sequence, etc., in order to optimize the library generation process to the given application.

As discussed in greater detail below, additional processing steps may be carried out on barcoded replicate nucleic acid fragments, e.g., fragments 228 and 228c shown in FIG. 20A, in order to provide additional functional sequences on those replicate fragments or copies or complements of those fragments. For example, in some cases as described below, additional amplification steps can be carried out that couple additional functional sequences used for sequencing processes, onto the end of the barcoded fragment, e.g., at end 230 of barcoded fragment 228. However, in certain aspects, the attachment of additional sequences may be incorporated into the barcoding replication process so as to yield fragments that include both the barcode oligonucleotide portion and other functional sequences at the opposing end of the replicate fragment. By way of example, one may include, within the original barcoding reaction mixture, a second set of primer sequences that include a priming sequence, e.g., a random n-mer primer sequence that is coupled to the desired additional functional sequences, e.g., the R2 and P7 sequences discussed elsewhere herein, allowing for a single step reaction process for both barcoding a fragment at one end, and attaching additional functional sequences at the other end. The presence of functional sequences on both ends of the barcoded fragments can then allow facile further processing of the fragments. For example one may use these functional sequences in the anteparallel amplification of the barcoded fragments.

Figure 20B:
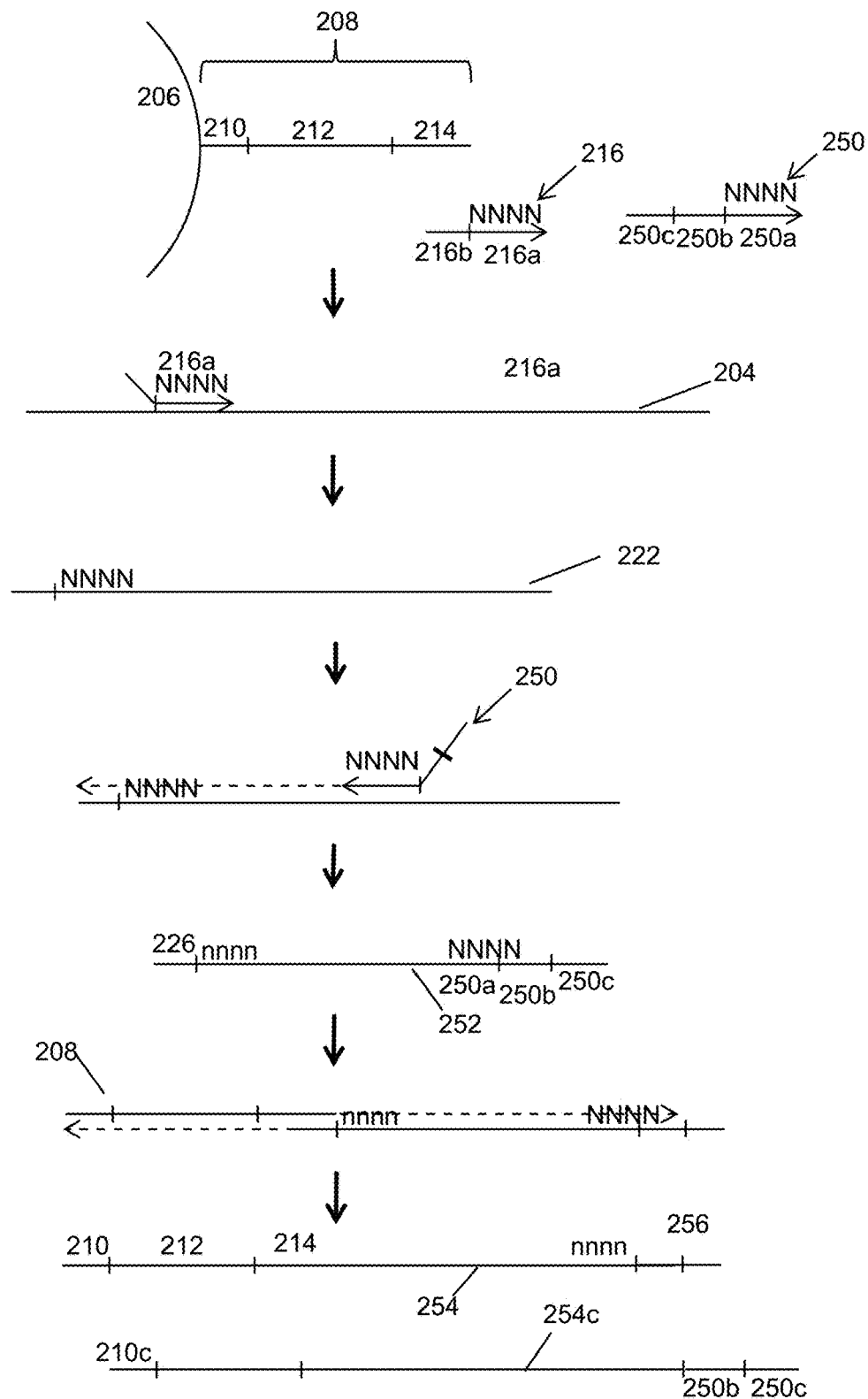

This is schematically illustrated in FIG. 20B, and with reference to FIG. 20A where second primer oligonucleotide 250 is introduced into the reaction mixture along with the barcode oligonucleotides 208 and template 204. Second primer set 250 includes the additional desired functional sequences 250b and 250c, which may be a read2 priming sequence and a P7 attachment sequence, respectively, in addition to the primer sequence, e.g., random n-mer 250a.

Again, as with the process shown in FIG. 20A, first primer set 216 anneals to the template and extends along a portion of the template 204 to produce a first replicate fragment 222. The second primer set 250 then anneals to replicate fragment 222 and extends along that replicate fragment to produce a complementary copy 252 that includes those functional sequence elements 250b and 250c, as well as a complement to at least a portion of segment 214 on the barcode oligonucleotide 208. The barcode oligonucleotide 208 can then anneal to replicate fragment 252, where extension of the barcode oligonucleotide (and fragment 252), can produce a barcoded replicate fragment 254 and its complement 254c, both of which can include the sequence segments included in the barcode oligonucleotide or their complements, as well as those additional functional sequences delivered by the second primer set 250, or their complements. As will be appreciated, the presence of first and second primer sets in the same reaction mixture can potentially result in a set of replicate fragments that includes a number of structures, including the desired structures, where the insert segment is flanked on one side by the first primer set or its complement and on the other side by the second primer set or its complement. However, other arrangements can also be present, including those where only one of either of the first or the second primer sets flank both sides of an insert segment. In general, this could be resolvable during a sequencing process, or by a subsequent amplification process in which only sequences carrying both ends of the desired sequence are present are amplified, e.g., using P5 and P7 as the amplification primer sequences. For example, with respect to replicate fragment 254c, one could selectively amplify this segment by priming against the P7 sequence represented by segment 250c, while priming against the complement to the P5 sequence segment (e.g., segment 210), as represented by segment 210c.

As will be appreciated, this simplified process described in FIG. 20B, may also be applied in a modified version of the process shown in FIGS. 19A-F. In particular, two different primer sets may be presented in the barcoding reaction mix in order to provide a "one pot" reaction that results in barcoded fragments having functional sequences at both ends.

Figure 20C:
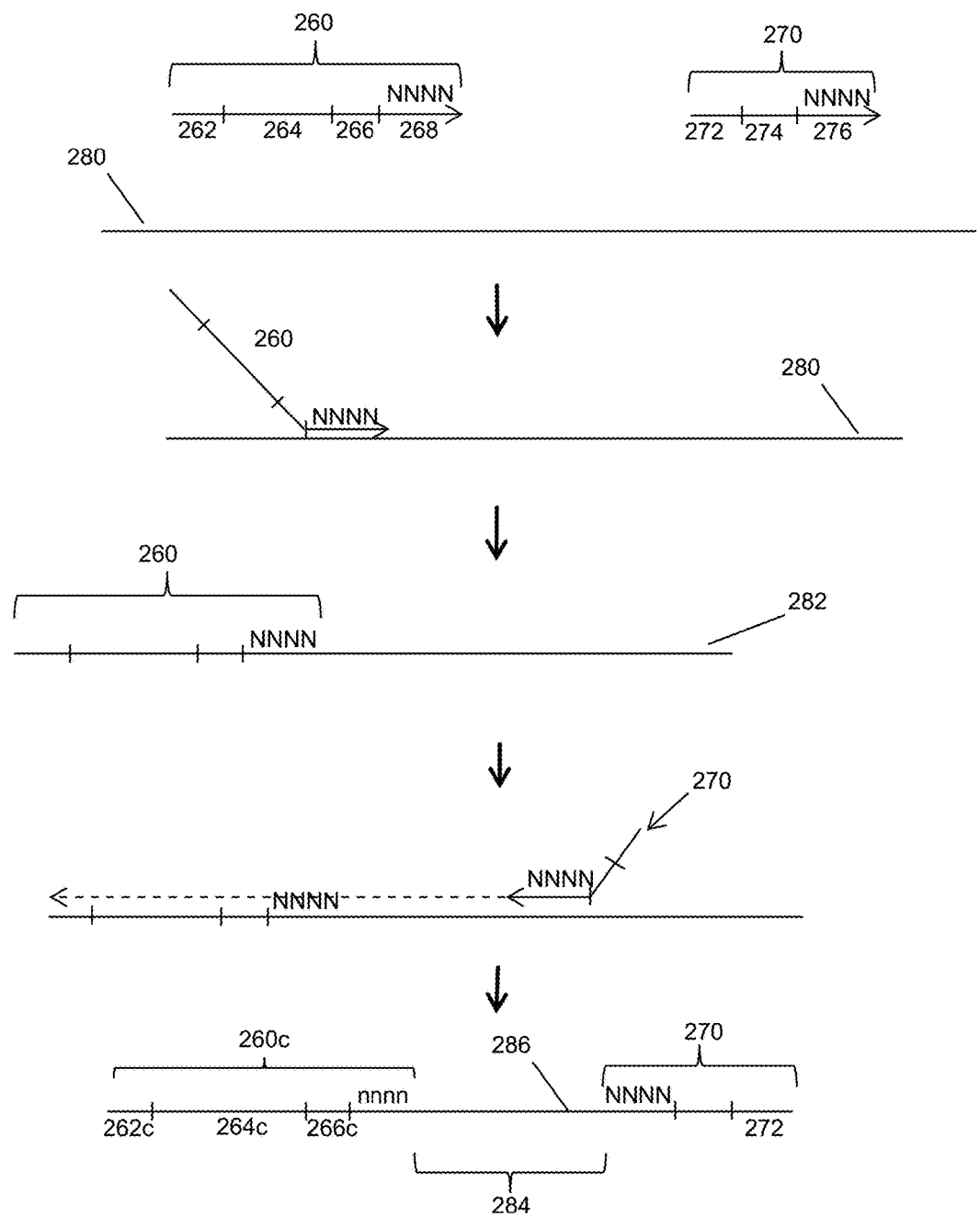

This is schematically illustrated in FIG. 20C. As shown, a template nucleic acid sequence 280, is co-partitioned along with a barcode/primer oligonucleotide 260 and a second adapter/primer sequence 270. The barcode/primer 260 is preferably partitioned, releasably attached to a bead, and as a member of a diverse barcode library, e.g., as described above. Adapter/primer sequence 270, as it can typically include defined or common functional sequences, may be partitioned in bulk, e.g., along with the nucleic acid template 280, or other reagents added to the partitioning process, e.g., enzymes, nucleotides, etc. In some cases, however, the adapter/primer 270 may be partitioned releasably attached to the same or a different bead from the barcode/primer 260.

Each of the barcode/primer 260 and adapter/primer 270 may include additional functional sequences, in addition to the barcode and primer portions. For example, barcode/primer sequence 260 is shown as including barcode sequence 264, and a random n-mer primer sequence 268, but also includes one or more additional functional sequences, such as a flow cell attachment sequence, sequencing read primer sequence, and the like. For ease of discussion, the example illustrated in FIG. 20C is described where barcode primer 260 includes a P5 attachment sequence 262, a barcode sequence 264, a first sequence read primer, e.g., a read1 primer sequence used in Illumina sequencing processes, and a random sample priming sequence or n-mer 268. The adapter primer 270 is described in terms of including a P7 attachment sequence 272, e.g., as used in Illumina sequencing, a second sequence read primer, e.g., Read2 primer 274, and a random priming sequence or n-mer 276.

Upon initiation of a primer extension reaction, e.g., upon one or more of mixing the requisite reagents, release of the barcode primer from the beads and/or commencement of thermal cycling of the reaction mixture, the primer sequences, e.g., 268 and 276, can anneal with the template nucleic acid 280 (only shown as primer 268 annealing), and be extended along the template creating a replicated portion of the template that is attached to the barcode/primer as extension product 282. Although not shown, along with extension product 282, extension products can be created based upon extension of adapter/primer 270 that has annealed to the template sequence.

Following this first extension, the extension product then serves as a template for subsequent rounds of primer annealing and extension. As shown, adapter/primer 270 anneals to extension product 282, and is extended to replicate the portion of the extension product 282 that includes a complementary portion to the original template sequence (shown as insert segment 284), and the original barcode/primer, to create extension product 286, that includes a complement to the original barcode primer, shown as segment 260c. Again, although not shown, a similar complementary reaction can be carried out to replicate the extension products created from extension of the adapter/primer sequence along the template, which could result in the barcode primer at one end of an insert sequence, and the complement of the adapter/primer sequence at the other end of the insert.

As will be appreciated, and as alluded to above, in some cases, the same sequence or its complement could be present on both ends of an insert in roughly 50% of the extension products. Conveniently, however, the products of the barcoding and adapter attachment processes described above, e.g., including extension product 286, and those 'products' that have the same sequence or its complement on each end, may be subjected to additional processing. In particular, in at least one example, the products may be subjected to anteparallel amplification by priming against both of the P5 and P7 sequences using a PCR process. As a result, those fragments that include both the P5 and P7 sequences, or their complements can be rapidly, and exponentially amplified, which the other 'products' will not.

As will be appreciated, specific reference to the functional sequences and their complements in this example is illustrative, and not limiting. In practice, a particular sequence or its complement, may be chosen for any of the sequence segments designated above, e.g., P5, P7, read1, read2, etc., depending upon the desired end state of the desired products.

As will be appreciated, in some cases, the process of generating barcoded replicate fragments from a long template nucleic acid can have variations in the amount of coverage of the underlying nucleic acid fragment, e.g., some areas being represented by more replicate fragments than others, and that variation in coverage can translate into the sequencing coverage for that template. Generally, it is desirable to generate replicate fragments that represent more even coverage over the full length of the template nucleic acid, or meet a minimum coverage threshold as to significant portions of the template sequence.

As alluded to above, in some cases, the make up of the primer portion of the oligonucleotide, e.g., primer segment 116 of the barcode oligonucleotide shown in FIG. 19A, or a primer segment 216 shown in FIG. 20A and FIG. 20B, may be adjusted to enhance library preparation. In particular, in some cases, the make up of the primer sequence used to anneal to the template nucleic acid can be controlled in order to provide for more uniform sampling of the template sequence, and as a result, more even sequence coverage. In particular, by controlling the relative GC content of the primer sequence, whether it is a random primer sequence or a more targeted primer sequence, one can enhance the resulting sequencing coverage. In some aspects the primer sequences are provided with greater than a 50% GC content, preferably, greater than 60% GC content, greater than 70% GC content or even 80% GC content or greater. In preferred aspects, the GC content of the primer may be from 50% to about 90% and any range defined thereby, or from about 50% to about 60%, from about 60% to about 70%, from about 70% to about 80%, or from about 80% to about 90%.

In some cases, blends of primer subpopulations, each having a different GC percentage may be employed, e.g., where the primers contained in the overall mix have a range of GC concentrations from greater than 50% to 90% or greater. In many cases, the primers can range from greater than 50% GC up to about 80% GC. These primer populations may span the entire range of GC concentrations in the stated range, or they may constitute set subpopulations of primers each having a distinct GC percentage.

For example, in some cases, subpopulations of primers may be blended to create mixtures having set subpopulations of GC concentrations in the primers, e.g., a primer subpopulation that has 60% GC blended with a primer subpopulation that has 80% GC. As will be appreciated, in such cases, the blends may include two, three, four or more different subpopulations of primer constructs, e.g., having differing GC content. Typically, such subpopulations may be from 50% GC to 90% GC, while each subpopulation may be from 1% to 99% of the blend. In preferred aspects, the subpopulations may have a GC content of between about 50% and 80% GC, inclusive, and each subpopulation can make up from 10% to 90% of the total primer population, from 20% to 80%, 30% to 70%, 40% to 60%, or even 50% for each subpopulation.

In addition to the above-described processes for improving library preparation, one may also utilize modifications to the polymerase reactions in order to provide improved libraries, e.g., with more even coverage, lower error and lower chimera formation. In particular, in at least one example, one may utilize different polymerases in combination, in order to improve the reaction products. In particular, by using polymerases that have different but complementary properties, one can produce higher quality libraries. By way of example, a blend of a first polymerase that provides very low error rates in replicating template sequence fragments, and a second polymerase that provides more even coverage or higher reaction rate or greater processivity, can provide a reaction that provides improved libraries. In one specific example, a blend of a highly accurate and processive polymerase such as the 9° North polymerase, retaining its wild type exonuclease activity (exo+) may be blended with another archeal polymerase such as Deep Vent polymerase, available from NEB provides sequencing libraries having more uniform coverage and lower error rates than either polymerase used alone.

Figure 21:
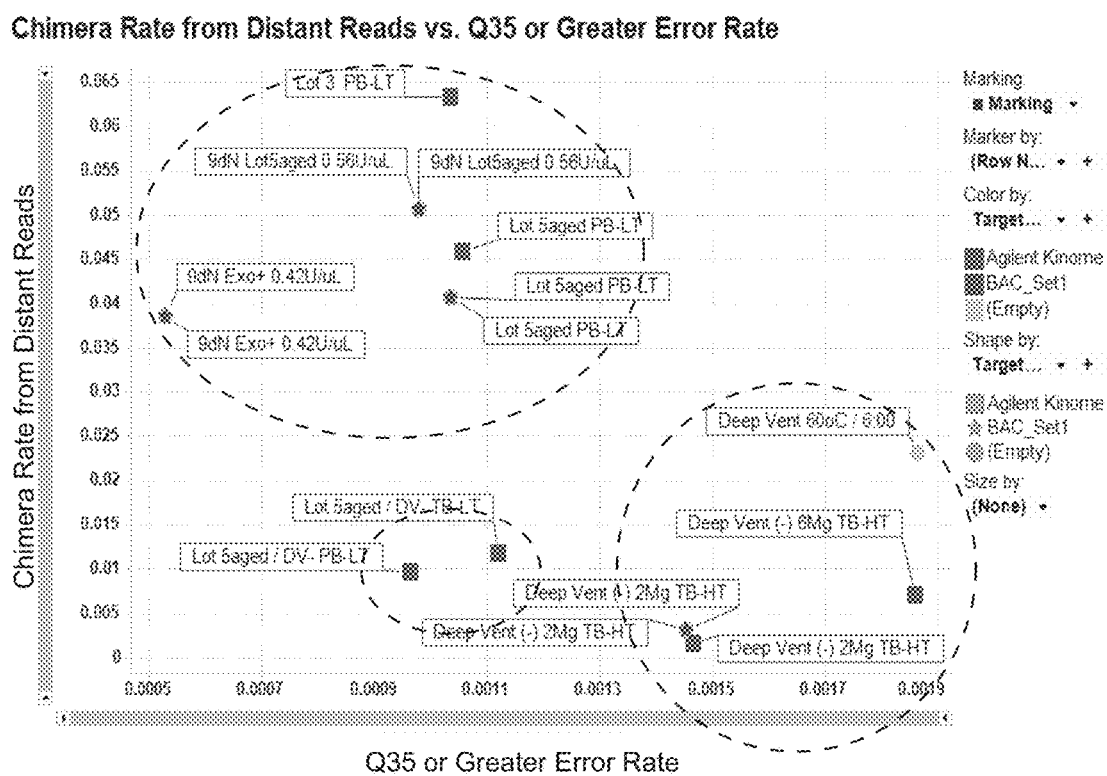
FIG. 21 illustrates a comparison of different enzyme performances in preparing sequencing libraries.

FIG. 21 shows comparison of chimera and Q35 error rates of different polymerase enzymes. As shown, the 9° N (exo+) polymerase demonstrates a relatively low Q35 error rate, but a relatively high chimera rate when used on its own (see circle A). In contrast, the Deep Vent polymerase illustrates a relatively higher error rate, but a relatively lower chimera rate (See circle B). When both enzymes are used in a blend of both enzymes, benefits are seen over either alone in both chimera rate and error rate (See circle C).

In addition to the processing described above, the methods described herein may also be used for selective barcoding of targeted genomic libraries. One approach for barcoding targeted genomic libraries, e.g., sequencing libraries that include targeted genetic regions, e.g., genes, gene panels, exomes, kinomes, etc., using the barcoding methods alluded to herein are described in Provisional U.S. Patent Application No. 62/073,659, filed Oct. 31, 2014, and incorporated herein by reference in its entirety for all purposes. In particular, the methods described utilize the barcoding approaches described herein in order to attach barcodes to genome (or sample) wide fragments, in order to provide an indicator of original molecular context or attribution. Once the fragments are barcoded, they may be selected for using conventional targeting processes, e.g., pull-downs, e.g., using conventional kits, e.g., pull down panels, exome kits etc., such as the SureSelect® exome kits available from Agilent Technologies, Inc. In an alternative approach, the barcodes may be attached to the targeting sequences (also referred to as target baits or targeted primers) using the methods described herein and illustrated with reference to FIG. 24, which are then used to create the targeted sequencing libraries that include the barcode sequences, e.g., using process steps described herein. As will be appreciated, although described as attaching the barcode sequences to targeted primers, the methods described may be used in attaching the barcode oligonucleotides to virtually any sequence, e.g., any targeted, random, universal, or other primer sequence or probe, without the need to incorporate a sample priming sequence, e.g., a radon n-mer or targeted primer, on the barcode oligonucleotide on the bead. In one example, a barcoded bead library, as described above, is used to deliver a population of common barcode sequences to an individual partition, e.g., as a droplet in an emulsion. The bead may be co-partitioned along with a sample nucleic acid as described above. Additionally, the bead can be co-partitioned with a targeted primer sequence, e.g., a sequence that is the same as or complementary to a specific targeted sequence of interest. The targeted primer sequence can typically include a portion that allows it to hybridize to a downstream portion of the barcode oligonucleotide, in order for the barcoded primer to be extended along the barcode oligonucleotide, thus replicating the barcode into the targeted primer sequence. Replication of the now barcoded targeting sequence can create a barcoded, targeted primer sequence that can interrogate the sample nucleic acid for the targeted region, and produce replicate fragments that include the barcode sequence.

Figure 24:
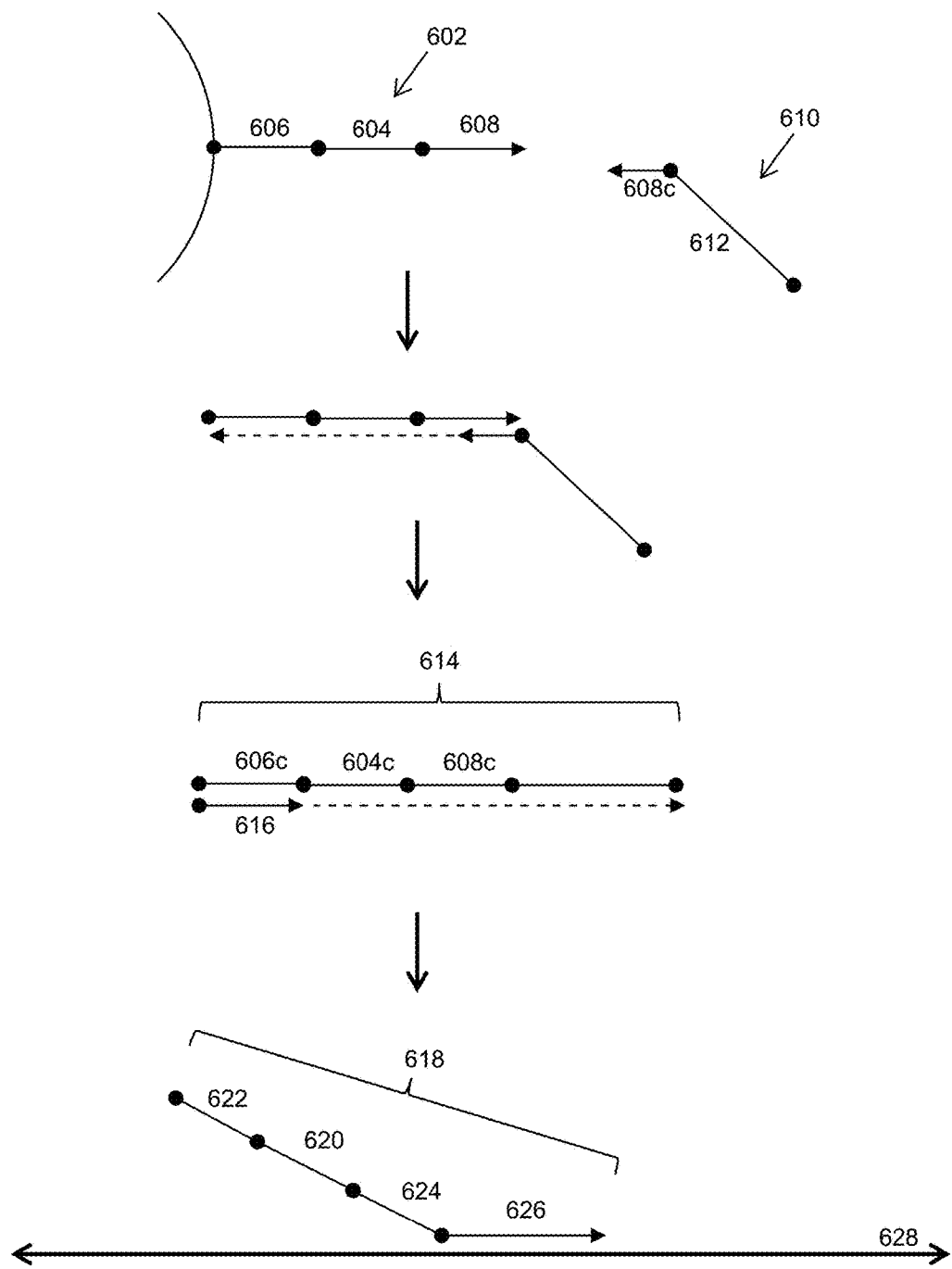
FIG. 24 schematically illustrates an alternative library generation process.

An example of this process is schematically illustrated in FIG. 24. As shown, a barcoded bead from a barcode bead library as described elsewhere herein, is provided with a barcode containing oligonucleotide 602, that includes a barcode segment 604 along with additional functional sequences, e.g., an attachment/primer sequence 606, such as a P5 attachment sequence, as well as a first known sequence segment, e.g., a known primer sequence 608, such as a Read1 primer sequence. Additional functional sequences may optionally be included, e.g., random primer sequences and the like, as discussed elsewhere herein, when, for example, a more universal barcode bead library is used for many different applications or processes. An additional targeted primer oligonucleotide 610 is also co-partitioned along with the barcode oligonucleotide 602. The targeted primer oligonucleotide 610 includes a first portion 612 that provides a complement sequence to a targeted primer sequence, e.g., a sequence for priming known sequence portion that is proximal in the sample sequence to a sequence region of interest (referred to as a targeted primer). As shown, the targeted primer oligonucleotide 610 also includes a portion, shown as segment 608c, that is complementary to a portion of the barcode oligonucleotide 602 that is 3' of the barcode segment 604, such as a portion of the Read1 primer segment 608.

As shown, annealing of the targeted primer oligonucleotide 610 to the portion of the barcode oligonucleotide 602 and subsequent extension, e.g., using the polymerase reaction within the partition, then creates a reverse complement of the barcode oligonucleotide (shown as 614) with complements of its various segments (e.g., 604c, 606c and 608c) with the targeted primer sequence 612 attached, shown as completed oligonucleotide 614. Further replication of oligonucleotide 614, e.g., using a P5 primer sequence 616 to prime replication of oligonucleotide 614, e.g., that is identical to segment 606 and complementary to segment 606c, results in the production of a complementary oligonucleotide 618 that includes the barcode segment 620 (that is identical to barcodes segment 604, as the complement of the complement), the functional segments, e.g., P5 segment 622 (identical to segment 606) and read1 primer segment 624 (identical to segment 608), and the targeted primer sequence 626 (complementary to targeted segment 612). The targeted primer sequence 626 is then able to prime against the targeted portions of a sample nucleic acid 628, that is also co-partitioned with the barcode oligonucleotides 602 and the targeted primer oligonucleotides 610, in the same manner described above for use of the random n-mer primers for generating barcoded libraries.

As a result, a sequencing library may be created that is specifically selected for the targeted sequences and which includes both the barcodes that are indicative of original molecular context, and one or more desired functional sequences, e.g., primers, such as P5, read1, etc.

As will be appreciated, the targeted primer oligonucleotides may be co-partitioned along with the barcode oligonucleotides by providing such oligonucleotides in a bulk solution, e.g., and co-partitioning along with other reagents, e.g., polymerases, dNTPs, etc. Alternatively, different targeted oligonucleotides or groups of targeted oligonucleotides may be predisposed on beads similar to those in the barcode bead libraries described herein, where the barcode beads and targeted primer beads may be co-partitioned together into a single partition, e.g., a droplet.

In still a further alternative process, barcoded libraries may be prepared in a similar fashion to the processes described above, but through the ligation of the barcode oligonucleotides to the partitioned fragment nucleic acids. Generally speaking, a fragment library can be created within a partition from the long fragments contained within that partition, in order to preserve the molecular context. The fragment library can be prepared in a fashion that leaves the fragments available for ligation with the barcoded oligonucleotides co-partitioned with those fragments, e.g., via a bead based delivery system as described herein. In certain cases, a ligation based process can avoid the possibility of amplification based anomalies, such as priming biases, that could potentially be associated with an extension based barcoding approach.

Figure 25:
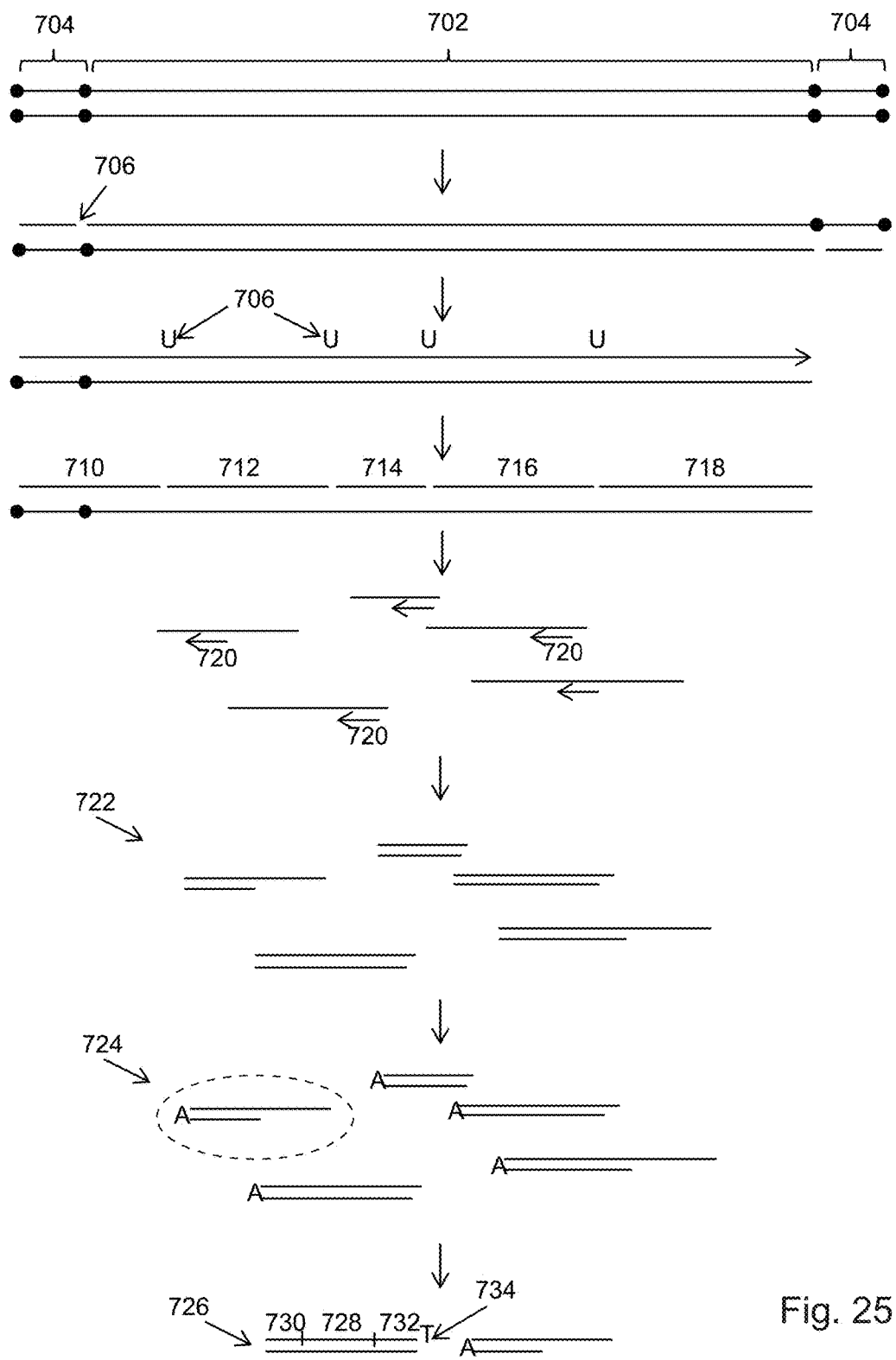
FIG. 25 schematically illustrates a library barcoding process utilizing ligation processes in place of primer extension processes.

One example of such an approach is schematically illustrated in FIG. 25. As shown, a sample nucleic acid fragment 702 is partitioned into a droplet or other partition. The long fragment 702 is fragmented into shorter fragments within the partition. As illustrated, this fragmenting step is carried out by first replicating the long fragment using a high fidelity polymerase enzyme, e.g., a phi29 DNA polymerase. The replicating step may be carried out by priming off of a known terminal sequence segment that may be provided as an adapter sequence ligated to the originating fragment, e.g., during a pre-partitioning sample prep step. Alternatively, and as illustrated, an adapter sequence, e.g., adapter sequences 704, may be provided on the originating double stranded fragment, that provides a known nicking site 706 within each strand. Following treatment with an appropriate nicking enzyme, a DNA polymerase capable of priming off of the nicked strand, e.g., phi29 polymerase, may be used to replicate one strand while displacing the other strand. This replication can be carried out with a low level concentration of removable nucleotides, e.g., UTP, in order to create a replicate with randomly dispersed uracil containing bases 708 dispersed throughout its sequence. By using an enzyme to cleave at the uracil base, e.g., uracil DNA glycosylase (UDG), e.g., as found in the Uracil Specific Excision Reagent, or USER (available from New England Biolabs), or other reagents, one can create a set of fragments of the replicate, e.g., fragments 710, 712, 714, 716 and 718.

Further fragments may be generated by allowing the phi29 polymerase to extend these fragments from the nicking points, both displacing the first set of fragments, and creating further replicate copies that incorporate uracil containing bases at randomly dispersed intervals, which can then be fragmented as above. Alternatively, a random priming and extension process, e.g., using random n-mer primers, e.g., hexamers, 7-mers, 8-mers, 9-mers, 10-mers or larger, may be used to generate random fragments from the originating fragment, by annealing to random locations on the originating fragment, and being extended by a present polymerase, e.g., phi29 or the like. While these alternative priming mechanisms may be employed, by priming off of random nicking sites, e.g., as described above, one can reduce priming bias that may come from exogenously introduced primers, thus allowing creation of a less biased fragment library from the originating fragment.

Once these fragment libraries are generated, they may be further replicated using, e.g., random hexamer primers 720 also co-partitioned with the fragments. The replication of these fragments using the short primer sequences 720 can result in the creation of double stranded, blunt ended fragments 722 of varying lengths. Once the blunt ended fragments 722 are created, they may be processed in order to attach double stranded barcode oligonucleotides that are co-partitioned with the fragments, e.g., via the bead based delivery systems described herein. For example, as shown, the blunt ended fragments 722 are first a-tailed, using, e.g., Klenow polymerase. The A-tailed fragments 724 are then ligated to the double stranded barcode oligonucleotides 726, e.g., including a barcode segment 728, as well as functional sequences, such as P5 sequence 730 and R1 segment 732, along with the complementary T base 734 at the ligation point, using a standard ligation enzyme system, e.g., a T4 ligase. As a result, a barcoded, double stranded fragment is created. The barcoded fragment may then be subjected to additional processing as described elsewhere herein, e.g., to amplify and attach adapter sequences at the other end.

Additional Processing of Barcoded Libraries

Improvements in library preparation may additionally or alternatively be achieved through process steps following the initial barcoding steps, described above. For example, following the creation of barcoded replicate fragments of the template nucleic acid, e.g., as described above, additional processing may be carried out with the barcoded fragments, e.g., to further amplify those fragments and/or to provide additional functional sequences on those fragments or copies thereof, e.g., additional sequencing primers, sample index sequences and the like.

In many cases, the barcoded replicate fragments may be further processed to both provide greater quantities of barcoded nucleic acids for sequencing, and also to attach additional functional nucleic acid sequence segments to the library members in order to efficiently process the library on a sequencing system. Because this additional processing occurs after the attachment of the barcode sequences to the fragments, e.g., preserving the linkage information of fragments generated from a given nucleic acid molecule within a given partition by virtue of the common included barcode sequences, the subsequent processing may be carried out as a pooled reaction, e.g., where the contents of the various partitions are pooled together for bulk processing.

By way of example, as described in U.S. patent application Ser. No. 14/316,383, filed Jun. 26, 2014, and previously incorporated herein by reference, the barcoded fragment nucleic acids, e.g., fragment 126 in FIG. 19E, can be subjected to additional processing to amplify the presence of those fragments, as well as to attach additional functional sequences for use in sequencing processes. For example, once the barcoded fragments 126 are prepared within individual partitions, the various separate partitions may be ruptured (e.g., by breaking the aqueous in oil emulsion), resulting in a pooling of all of the barcoded fragments that originated from different partitions and bearing different barcode sequences. The amplification of the barcoded fragment 126 may then be carried out by priming against the replicated functional sequence, e.g., the R1 complementary sequence 114', where the primer for this amplification also includes additional functional sequences, e.g., the P7 and R2 sequences, or their complements. As a result, the produced sequences can include on each end the requisite functional sequences or their complements. Further, one may amplify by anteparallel priming by also using a primer against the original functional sequence 110, as the primer annealing sequence, to initiate anteparallel amplification, e.g., PCR.

Figure 22:
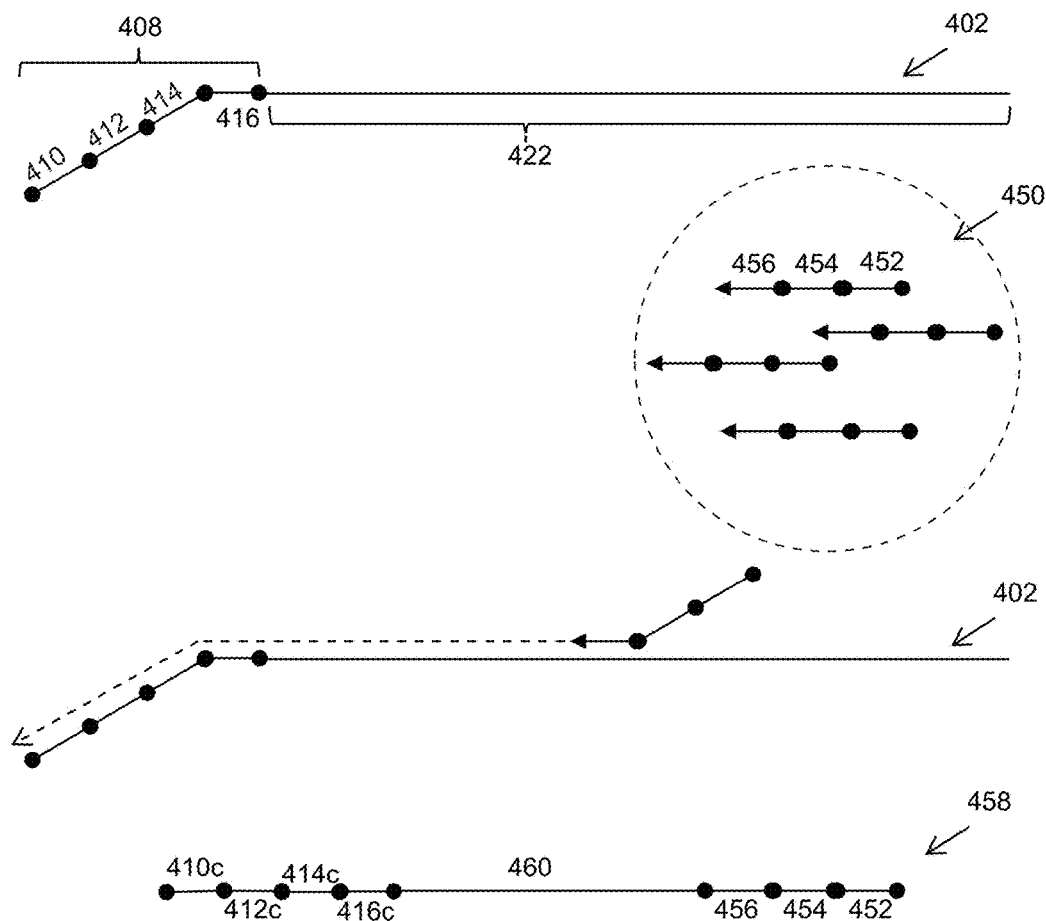
FIG. 22 schematically illustrates processing of barcoded fragments of nucleic acids in preparation of sequencing libraries.

One exemplary process is illustrated in FIG. 22, and with reference to FIGS. 19A-F. In particular, assuming a barcoding process as shown in FIGS. 19A-F, one could obtain a barcoded set of nucleic acid fragments 402 in FIG. 22, that would be a pooled set of fragments, e.g., from multiple partitions, and bearing multiple different barcode sequences on the attached barcode oligonucleotide 408, including the barcode sequence(s) 412 along with the other functional sequences, e.g. attachment sequence 410 and sequencing primer 414, attached to the sample fragment or insert 422.

A second set of primer sequences 450 would then be introduced into the reaction mixture. As shown, the second set of primer sequences 450 includes additional functional sequences used in sequence libraries, e.g., for attachment to sequencer flow cells, e.g., the P7 sequence 452, and for priming of the second reading step for the sequencer, e.g., R2 priming sequence 454. Also included in these primer sequences could be a set of random priming sequences, e.g., random n-mer 456, as well as optional sample index sequences (not shown), that would be common for any given sample. The random n-mer 456 *c* randomly prime against the barcoded fragments 402 in the reaction mixture, and extension of these primers would produce a replicate copy 458 of the barcoded fragment 402, including a complementary replicate of the barcode oligonucleotide 408, e.g., including a complement to barcode sequence 412 (shown as segment 412*c*) and complements to any functional sequences included in that barcoded fragment, e.g., P5 attachment sequence 410 (shown as complementary sequence 410c) and R1 primer sequence 414 (shown as complementary sequence 414c).

Following this replication, the resulting fragments 458, now including functional sequences at both ends, e.g., the P5 and P7 sequences (segments 410 and 452, respectively) of an insert sequence segment 460. These completed fragments may then be subjected to additional amplification steps, e.g., PCR, using the known terminal segments of the fragments, e.g., the P5 and P7 sequences or their respective complements such as segments 410c and 452, as priming regions for anteparallel amplification.

As will be appreciated, in some cases following the initial generation of barcoded fragments, it may be desirable to purify the barcoded fragments away from the reaction mixture that was used to produce them, e.g., using SPRI beads, etc. For example, when using a polymerase that is incapable of processing through uracil containing bases, e.g., as described above with reference to FIGS. 19A-F, it may be useful to swap out that polymerase for a different polymerase to be used to further process the fragments, allowing replication of the uracil containing portion of the barcode oligonucleotides as shown in FIG. 22. A variety of different, highly processive, highly accurate polymerases may be employed in this process, including for example, thermally stable polymerases, e.g., taq, 9° North, Deep Vent polymerases, as well as non-thermally stable polymerases, e.g., Bst, Klenow, phi29, and the like. In some cases, e.g., as described above for hairpin or partial hairpin structures, it may also be desirable to utilize polymerases in the subsequent amplification steps that possess one or more of strand displacing activity, uracil tolerance, proof reading capability, e.g., including exonuclease activity, and the like.

Likewise, following the second replication step, e.g., as illustrated in FIG. 22, it may be desirable to purify the replicated fragments 458 prior to subjecting them to further PCR or other amplification in order to remove extraneous primers sequences, e.g., primers 450, from participating in the selected amplification of the resultant fragments 458.

Although illustrated as incorporating the functional sequence segments in the primer set 450, it will be appreciated that some of these sequences may be incorporated in subsequent process steps. For example, in some cases, the primer set 450 might not include a functional sequence like a P7 sequence, e.g., segment 452. Following replication of the barcoded fragments, one can add additional functional sequences to the resulting library of fragments, e.g., fragment 458. Again, addition of other sequences can be accomplished through a ligation step, e.g., as described below with reference to FIG. 23, or alternatively, it could be introduced as a component of a primer sequence used in a subsequent amplification of the resulting fragment 458. In particular, an additional sequence could be provided attached to a primer sequence that can prime against a portion of the fragment, e.g., segment 454 (assuming the absence of fragment 452). Amplification of the fragment 458 can then carry with it the sequence segment added through the primer.

Figure 23:
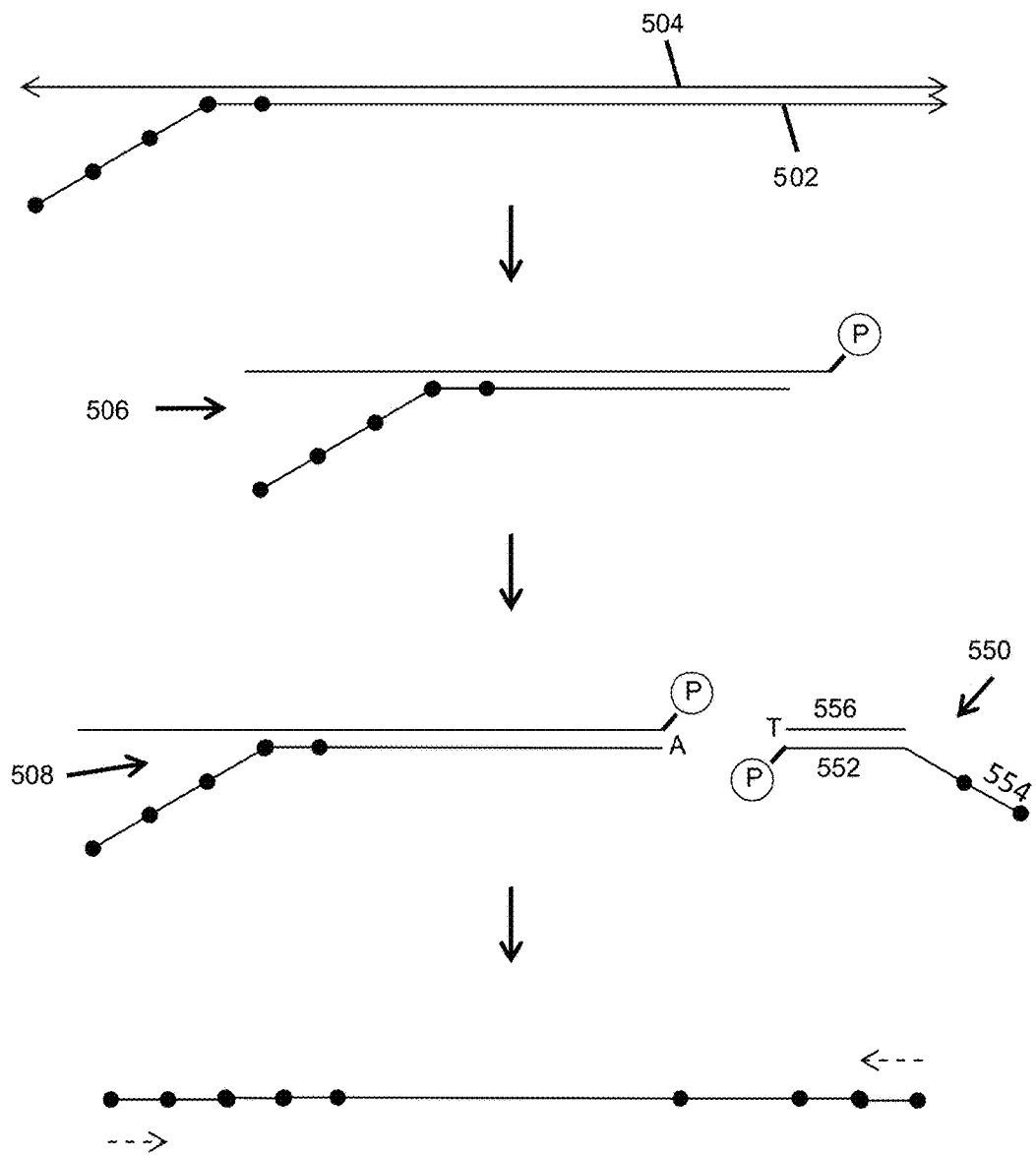
FIG. 23 schematically illustrates alternative processes for further processing fragment nucleic acids in the preparation of sequencing libraries.

In another exemplary process, subsequent processing of the initial barcoded fragments, e.g., fragment 118 or 402 from FIG. 19A-F or 22, respectively, can be achieved through a shearing and ligation process to provide finished fragments bearing the requisite functional sequences. This process is schematically illustrated in FIG. 23. As shown, a collection of barcoded, double stranded nucleic acid fragments 502 is produced from the initial barcoding step, e.g., as shown in any of FIGS. 19 and 20. The fragments and their associated complementary strands 504, e.g., the templates from which they were replicated, are then subjected to a shearing process, e.g., using enzymatic, mechanical and/or acoustic shearing processes, e.g., Covaris AFA shearing processes, to produce sheared double stranded fragments 506.

The sheared double stranded fragments 506 are then blunt ended using, e.g., one or more of fill-in reactions, e.g., using Klenow, and/or nuclease treatments. Following blunting, an A base is added to the 3' terminus, e.g., using a Taq or other non-proofreading polymerase in the presence of dATP, to yield the A-tailed, blunt ended double stranded fragments 508. Adapter 550, which includes a T-base at its 3' terminus, is then added to the mix in the presence of appropriate ligation mixture, e.g., T-4 ligases and associated reagents. As shown, the adapter 550 includes the additional functional sequences needed for application to the sequencer of choice, e.g., the Read2 primer (complement) 552 and P7 (complement) 554 sequences. Also included is a partially complementary sequence having a 3' T-base overhang (shown as partial R2 segment 556), in order to allow efficient ligation with the barcoded fragments.

Following ligation, the resulting library element 558 includes the insert sequence 560, e.g., derived from the original sample template sequence, the first set of functional sequences, e.g., P5 510 and R1 514 sequences, the barcode sequence 512, and a second set of functional sequences, e.g., R2 and P7 sequences or their complements (segments 552 and 554, respectively). Also included are the original primer sequences 516 from the barcoding oligonucleotides.

As described above, the resulting barcoded fragments may then be further amplified by priming amplification, e.g., anteparallel amplification like PCR, using the known end sequence segments, e.g., P5 sequence 510 and P7 sequence 554, as the priming targets.

As will be appreciated, in some cases, the shearing step described above can produce fragments where the original barcoded sequence has been sheared off, or can produce fragments that result from sheared fragments that did not include the barcode fragments.

Because these fragments lack a complete set of functional sequences, e.g., both of P5 and P7, or any other functional sequences used to prime subsequent amplification steps, even following ligation of the second set of functional sequences, e.g., through adapter 550, they would not be amplified in subsequent steps, which rely on the presence of both sets of sequences, e.g., P5 and P7 sequences, for successful amplification. Restated, although incorrectly ligated fragments may initially be created, they may not be subsequently amplified and, as a result, can fall below the noise level of the system upon sequencing.

A number of additional or alternative processes may be employed in further processing the barcode library elements. For example, when starting with barcoded nucleic acid fragments, e.g., fragment 126 in FIG. 19E-F, or other similar barcoded fragments, one may attach additional functional sequences to the end of the fragment, e.g., the non-barcoded end, via a number of methods. For example, as noted above, this may be achieved through the amplification of the total sequence from the non-barcoded end using a primer that includes additional functional sequences, such that the extension products of such primer include not only a copy of the barcoded fragment 126, but also the functional sequences attached to the primer. Likewise, additional sequences may be simply ligated to the end of the sequence to add functional sequences.

A number of other process steps may be employed in further processing, amplifying, and/or appending additional sequences to the barcoded fragments described herein. For example, in some cases, rather than creating a partial hairpin, e.g., using uracil containing bases in the barcode oligonucleotides to block complete replication, non-uracil containing barcode oligonucleotides may be used to permit formation of complete hairpin molecules. By selectively removing a portion of the 3' terminus, one may create a ligation site for the additional functional sequences for the various fragments. For example, by incorporating the complement to a nicking enzyme recognition site in a common known portion of the barcode oligonucleotide, e.g., in the R1 primer segment, described above, one could indirectly create a nicking site in the downstream portion of the hairpin duplex. Treatment of the hairpin with the requisite nicking enzyme could yield a partial hairpin structure having a portion of single stranded DNA that is known, which known sequence portion may be used as a landing spot for ligation of an additional functional sequence(s) to the 3' end of the partial hairpin, e.g., read2, P7, sample indices, etc.

In an alternative, but related approach, one may create a complete hairpin structure using the approach outlined in FIGS. 19A-F, but employing a polymerase enzyme that is capable of processing through uracil containing bases. In such case, a fragment that results from initial extension of a barcode containing primer oligonucleotide, e.g., uracil containing oligonucleotide 108, is completely replicated through the extension of a second barcode containing primer oligonucleotide, e.g., oligonucleotide 108b, such that the complete replicate includes barcode oligonucleotide 108b (including the uracil bases) at one end, and a complement of the original barcode oligonucleotide 108 (without uracil containing bases) at the other, which would include a complement to the barcode segment 112, and the functional sequences, e.g., 110 and 114. One could then cleave the resulting replicate fragment at the uracil containing bases, e.g., using a UDG enzyme or the like, to leave a portion of the barcode oligonucleotide 108b on the end of the fragment, e.g., segment 114. The other end, meanwhile, can still retain the complement to the original barcode oligonucleotide, including the complement to the barcode sequence and functional sequences. By leaving a known segment attached to the digested end, one is provided with a handle at which to ligate the second side adapter sequence, e.g., including other functional sequences, e.g., sequencer specific attachment and primer sequences, sample index sequences, and the like.

In still other aspects, one may exploit the hairpin structure of the barcoded fragments created in a barcoding process. For example, in some cases, it may be desirable to create a barcoded fragment that forms into a complete hairpin structure, as noted above. With reference to the process described above and shown in FIGS. 19A-F, for example, one could provide complete barcoded hairpin structures by allowing complete replication of the barcode/primer sequence, with or without additional functional sequences included. The termini of the duplexed portion of the hairpin may then be treated as a terminus of a standard duplex in duplex adapter attachment process (see, e.g., Illumina Truseq Sample Preparation Guide (Illumina, Inc. part #15026486 Rev C), and U.S. Pat. No. 8,053,192), the full disclosures of which are incorporated herein by reference in their entirety for all purposes), to attach the additional functional sequences to the hairpin. In particular, the Truseq adapter includes both the P5-Read2 sequence in a partial hybrid structure with the P7-Read2 sequence, based upon at least partial complementarity between the read1 and read2 primer sequences. As a result, the duplex portion of the adapter may be attached, e.g., ligated, to the duplex end of the hairpin structure, to attach the P5-Read 1 sequence to the 5' end of the hairpin molecule, and P7-R2 to the 3' end of the hairpin. As described above, once the duplex adapter is attached to the duplex end of the hairpin, it may be amplified, e.g., using an ante-parallel, PCR amplification process by priming against the P5 and P7 sequences. As will be appreciated, one could attach a variety of different additional functional and other sequences to the ends of the hairpin structure using partial or completely complementary and duplexed structures that are ligated to the hairpin, using this approach.

Alternative processes may likewise be used to modify complete hairpins that include the barcode oligonucleotide structure. In particular, rather than generating partial hairpin structures, one could incorporate a selective nicking site into the complementary duplex structure that allows nicking of the 5' portion of the duplex, which when digested, can yield a partial hairpin structure, which may then be processed as discussed above.

Additional Systems and Kits

Although primarily described in terms of the library generation and preparation processes, it will be appreciated that also provided herein are process systems, reagents, consumables and reagent and consumable kits used for carrying out the above-described processes. For example, overall systems may include the reagents necessary for carrying out the above-described reaction processes, e.g., including barcoding reagents such as barcode oligonucleotide libraries disposed on partitionable beads, e.g., as described in in detail in, for example, co-pending U.S. patent application Ser. No. 14/316,383, filed Jun. 26, 2014, 62/017,808, filed Jun. 26, 2014, 62/072,214, filed Oct. 29, 2014, 62/072, filed Oct. 29, 2014, and 62/017,558, filed Jun. 26, 2014, previously incorporated herein by reference in their entireties for all purposes. Also included in such systems may be other reagents used in the process, such as partitioning fluids, e.g., fluorinated oils, nucleoside triphosphates, and the like, as well as partitioning systems used to co-partition sample nucleic acids with the barcode reagents, including both microfluidic consumable components in which partitions are generated as well as instruments used to drive and control the operation of the microfluidic devices.

As noted, kits are also provided herein that include the reagents necessary for carrying out the reaction processes described herein. Typically such kits can include the barcoding reagents including the requisite barcode oligonucleotide bearing bead libraries, and appropriate enzymatic reaction reagents, e.g., appropriate polymerase enzymes, monomers, and other reagents, e.g., UDG, USER or the like, for carrying out the desired reaction. The kits likewise may also contain the requisite partitioning reagents, such as the non-aqueous partitioning fluids, e.g., fluorinated oils, and the like. Finally, the kits can also typically include user instructions for directing the user to carry out the desired reaction process as described in detail above.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. For example, particle delivery can be practiced with array well sizing methods as described. All publications, patents, patent applications, and/or other documents cited in this application are incorporated by reference in their entirety for all purposes to the same extent as if each X. Examples

Example 1

Molecular Barcoding of Priming Free Amplification Templates

It is contemplated that a number of approaches would be effective for molecular barcoding templates resulting from priming free amplification for sequencing. The reactions and reagents for achieving molecular barcoding can be part of the same reaction and run simultaneously with the priming free amplification of templates. The approach can include adaptors as well. For example adaptor designs can include partial R1 sequence from Illumina's primer design, followed by a preferred barcode sequence followed by a random Nmer (sequence size varies between 2-20 bases). These adaptors can be double stranded and include a barcode and R1 sequence with the Nmer arranged as a 3' overhang.

Figure 2A:
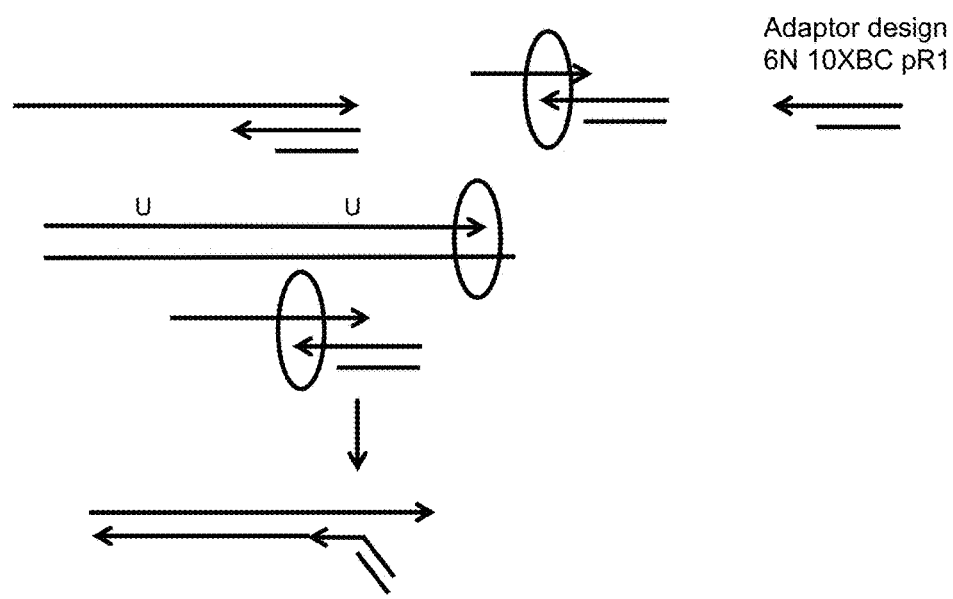
FIG. 2A is a diagram illustrating barcoding of templates using an extension barcoding approach.
Figure 2B:
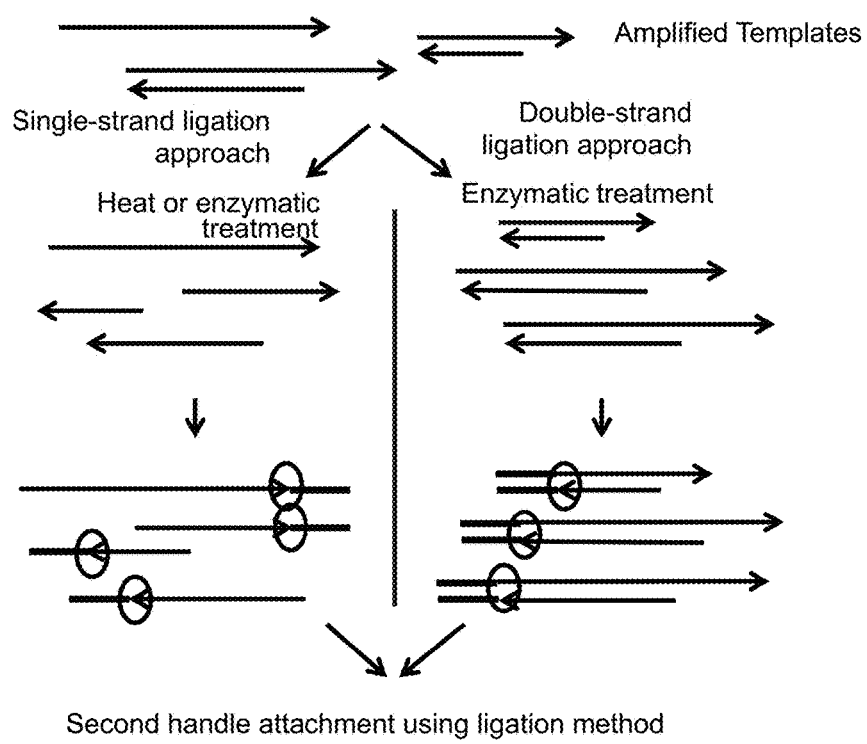
FIG. 2B is a diagram illustrating barcoding of single or double stranded templates using a ligation approach.

In a first approach, as shown in FIG. 2A, barcoding the templates can be achieved using an extension barcoding approach. Stand displacement and high processivity of phi29 DNA polymerase releases amplified fragments thereby enabling recycling of the template for further amplification. The single strand fragments that are generated during stand displacement can be converted to dsDNA but the hexamer or Nmer part of the adaptor by the same polymerase.

Another approach to molecular barcoding is shown in FIG. 2B. Amplified templates generated as described in FIG. 1 are molecular barcoded optionally by a single stranded or double stranded template to barcode ligation approach. As shown, the template DNA molecules are converted to either single stranded (using temperature/enzyme; see left half of figure) or double stranded (using enzyme; see right half of figure). The molecular barcodes, e.g., oligonucleotides are attached through a ligation process using a ssDNA ligase (ovals) or dsDNA ligase (ovals) or other nucleic acid modifying enzymes. Additional oligonucleotides serving as molecular handles may be added to the first barcode tag in subsequent ligations.

Figure 2C:
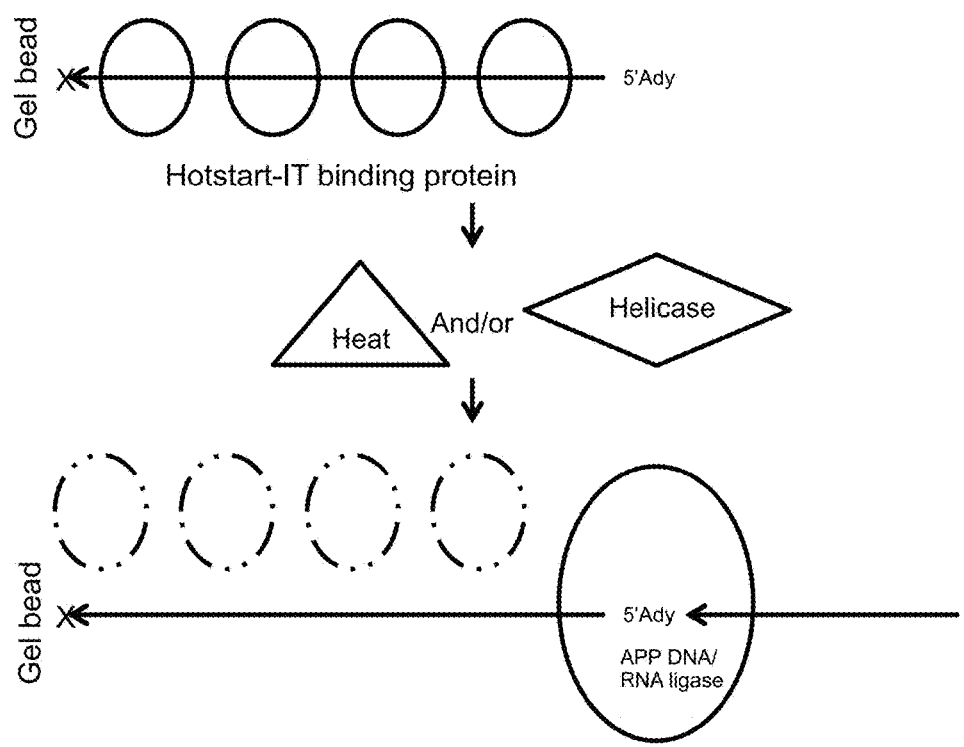
FIG. 2C is a diagram illustrating barcoding of single stranded library molecules using and APP DNA/RNA ligase approach.

An additional approach to molecular barcoding the templates is shown in FIG. 2C. In this scheme, a single strand DNA molecule (with barcode/primer sequence) is attached to the bead from 3'end. The 5' end of the oligo is pre-adenylated (either chemically or enzymatically). The oligo can be sequestered using Hotstart-IT binding protein if desired which can be released using heat. For barcoding the single-stranded library molecules (single strands generated by heat treatment or helicase), APP DNA/RNA ligase will ligate 5' pre-adenylated oligo with 3' end of the library molecule. This process is very specific as oligo-oligo ligation can be avoided by blocking the 3' end and library molecules cannot self ligate as they are not adenylated.

APP DNA/RNA ligase can be a thermostable 5' App DNA/RNA Ligase including a point mutant of catalytic lysine of RNA ligase from *Methanobacterium thermoautotrophicum*. This enzyme is ATP independent. It requires a 5' pre-adenylated linker for ligation to the 3'-OH end of either RNA or single stranded DNA (ssDNA).

A further approach to molecular barcoding the templates uses a topoisomerase enzyme. For example, topoisomerase I from Vaccinia virus binds to duplex DNA at specific sites and cleaves the phosphodiester backbone after 5'-CCCTT in one strand. Here molecular barcoding can be achieved where at an adapter sequence (e.g., an oligonucleotide) is pre-bound to a topoisomerase enzyme. The amplified templates can be prepared for blunt end ligation using, for example, the Klenow fragment of DNA polymerase.

Example 2

Priming Free Amplification by Polymerization at Nick Sites Results in Thymidine (T) Base Bias Experiments were conducted using an amplification protocol with (A) or without primer (B).

(A) Amplification Protocol with Primer Formulation:
1× Thermopol Buffer (NEB), 0.2 mM dNTP Mix (10 mM each), 0.3 uM Primer*, 0.07% (v/v) Glycerol, 0.5% (w/v) Synperonic-F108, 1 mM DTT, 0.1 ng/µL gDNA Template, 0.4 U/µL 9° N Polymerase.

*Primer Seq:

(SEQ ID NO: 1)
TAGAUCGCACACUCUUUCCCUACACGACGCUCTTCCGATCTNNNNNNNNNNN

Thermocycling Protocol:
1.) 4° C./∞
2.) 98° C./5:00 mins-ramp 2° C./S
3.) 4° C./0:30 sec-ramp 2° C./S
4.) 45° C./0:01 sec-ramp 0.1° C./s
5.) 70° C./0:20 sec-ramp 2° C./S
6.) 98° C./0:30 sec-ramp 2° C./S
7.) go to Step 2, 14×
8.) 4° C./∞

(B) Amplification Protocol without Primer (Priming Free Amplification by Polymerization) Formulation:
50 mM Tris, pH 7.5, 10 mM (NH4)2SO4, 0.50% SymPeronic, 1 mM dNTP, 0.03 mM dUTP, 7% Glycerol, 25 uM Hexamer, 17 mM DTT, ing gDNA, 10 ug/ml BSA, 0.01% Triton X, 0.006 U/ul UDG, 30 U/ul EndoIV, 0.2 uM Phi29 DNA Pol Thermocycling Protocol:
1.) 30° C./3 hours
2.) 65° C./10:00 mins
3.) 4° C./∞

Using a priming free amplification by polymerization reaction, dUTP's (U) were incorporated into templates. Excision of "U" was achieved with a lyase enzyme creating a nick in the template which resulted in an initiation site for the polymerase. Since the initiation occurred as a result of the U excision, there is a bias for the base Thymidine (T) that's reflected in the sequences observed.

Figure 3:
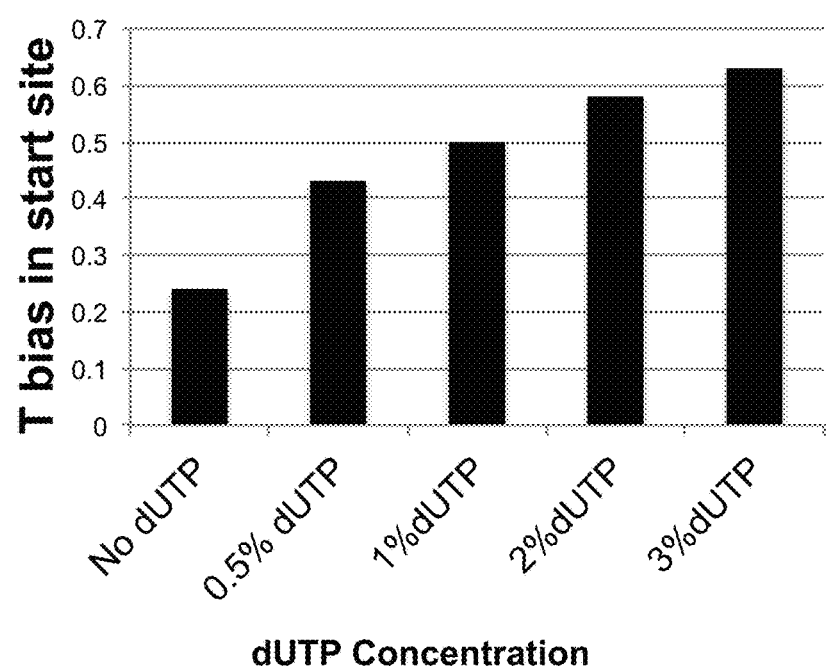
FIG. 3 shows results of testing for T base bias based on whole genome sequencing data.

As shown in FIG. 3, testing for T base bias based on whole genome sequencing data revealed a bias for T base. The T base bias scaled proportionately with dUTP concentration tested, strongly supporting that most initiation was driven by U incorporation/excision. The T base bias was revealed when the sequences were aligned to a reference sequence.

The results shown in FIG. 3 validated the concept of polymerase initiation from the created nick sites rather than the primer based extensions.

Example 3

GC Coverage: Primed Amplification vs. Priming Free Amplification

Figure 4A:
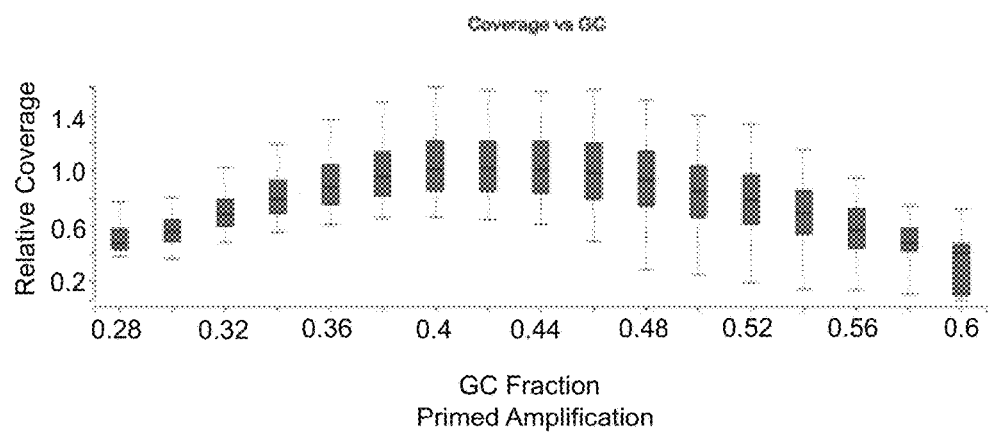
FIG. 4A is a plot of a primed amplification showing coverage evenness over 1000 base pairs binned GC content of the human genome.
Figure 4B:
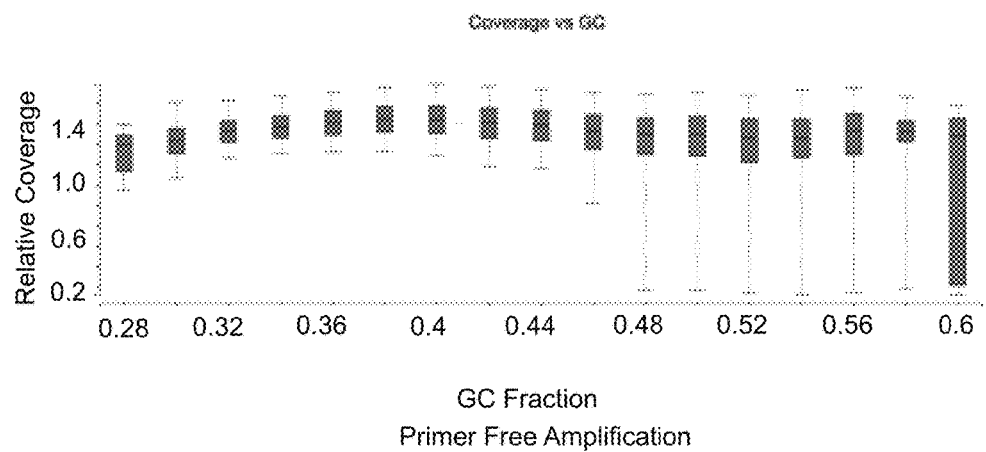
FIG. 4B is a plot of a primer free amplification showing coverage evenness over 1000 base pairs binned GC content of the human genome.
Figure 5A:
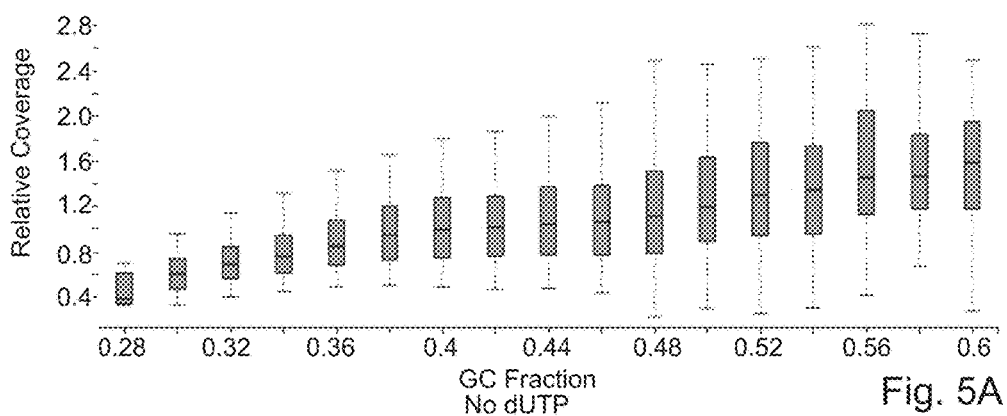
FIG. 5A is a GC coverage plot for a reaction with no dUTP added.
Figure 5B:
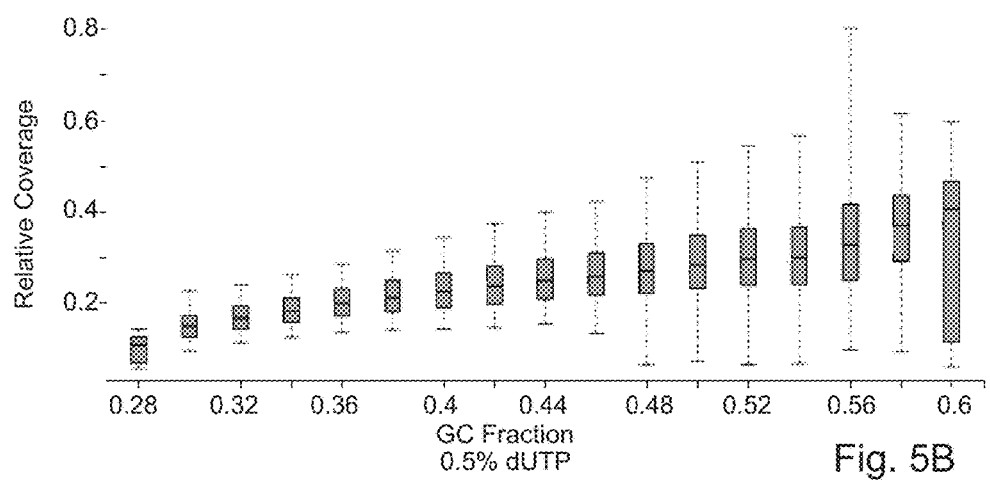
FIG. 5B is a GC coverage plot for a reaction with 0.5% dUTP added.
Figure 5C:
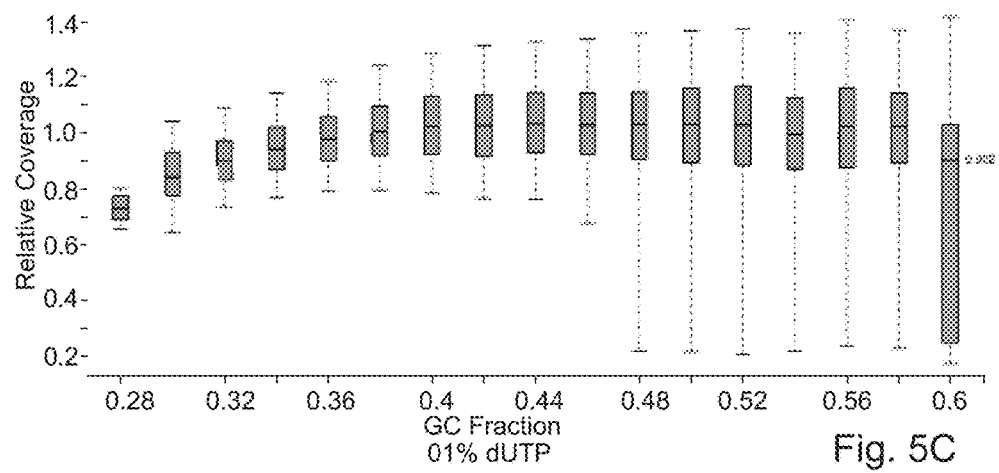
FIG. 5C is a GC coverage plot for a reaction with 1% dUTP added.
Figure 5D:
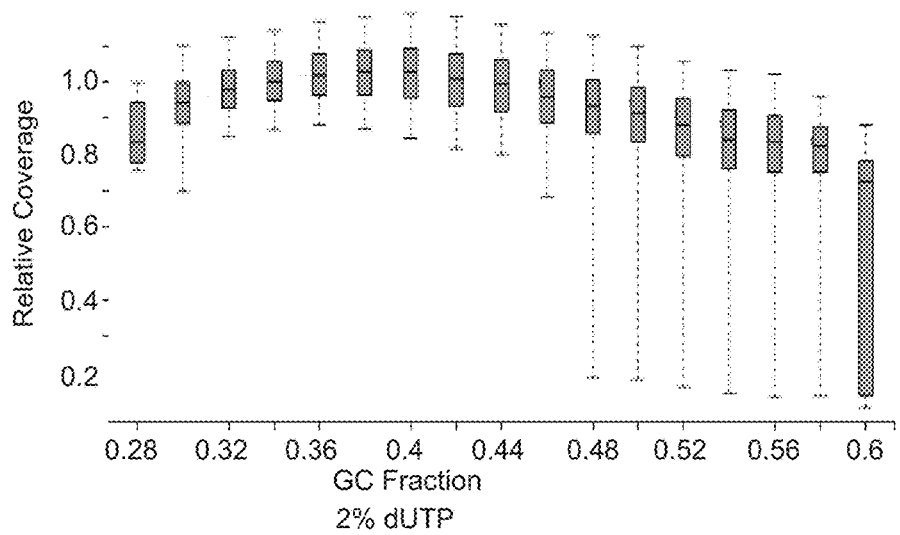
FIG. 5D is a GC coverage plot for a reaction with 2% dUTP added.
Figure 5E:
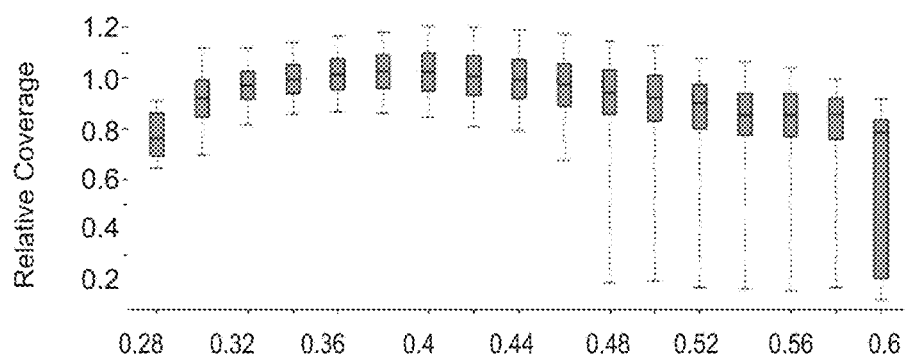
FIG. 5E is a GC coverage plot for a reaction with 3% dUTP added.

The two plots in FIGS. 4A and 4B show coverage evenness over 1000 bp binned GC content of the human genome. As can be seen from the plots, the primed amplification reaction (FIG. 4A) does not have even coverage whereby the low GC and high GC genome regions are poorly represented as compared to regions with GC content of 0.35-0.5. In comparison, the primer free amplification method (FIG. 4B) shows even coverage across broad range of GC contents.

Example 4

Titration of dUTP for Effect on GC Coverage

GC coverage plots illustrated in FIGS. 5A-5E shows the evenness of coverage using sequencing across different parts of the genome binned by their GC content. The data shows that GC coverage is more skewed towards high GC when there is no dUTP present (FIG. 5A), and it becomes more even with higher dUTP (>1%). Results for no dUTP, 0.5%, 1%, 2% and 3% dUTP are shown in FIGS. 5A, 5B, 5C, 5D and 5E respectively. In sum, it was observed that use of >1% dUTP, when compared to no dUTP (FIG. 5A) or 0.5% dUTP (FIG. 5B), advantageously results in even coverage of various GC bins.

Example 5

Titration of dUTP for Chimera Reduction

Figure 6:
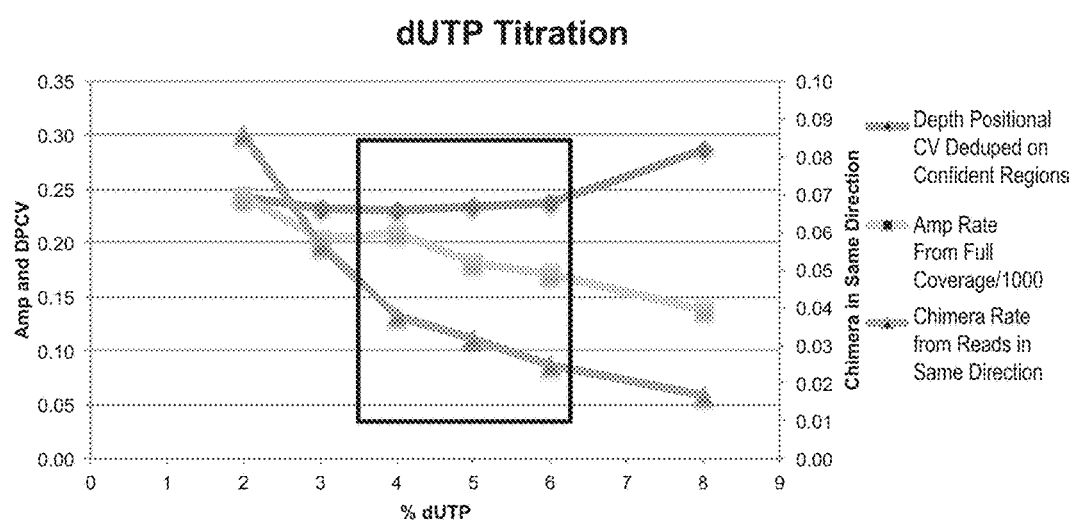
FIG. 6 shows the results of titration of dUTP and the effect on chimera rate, Depth Positional CV (DPCV).

In a priming free amplification by polymerization reaction, dUTP concentration during amplification was titrated and the effect on chimera rate from reads in the same direction, Depth Positional Coefficient of Variation (DPCV) deduped on confident regions and amplification (amp) rate from full coverage over 1000 bases were studied. As shown in FIG. 6, in a range from about 3.5% to about 5.5% dUTP, significant reduction in chimera rate was observed while both DPCV and amp rate remained relatively strong and stable.

Example 6

Addition of DTT Reduces DPCV

Figure 7:
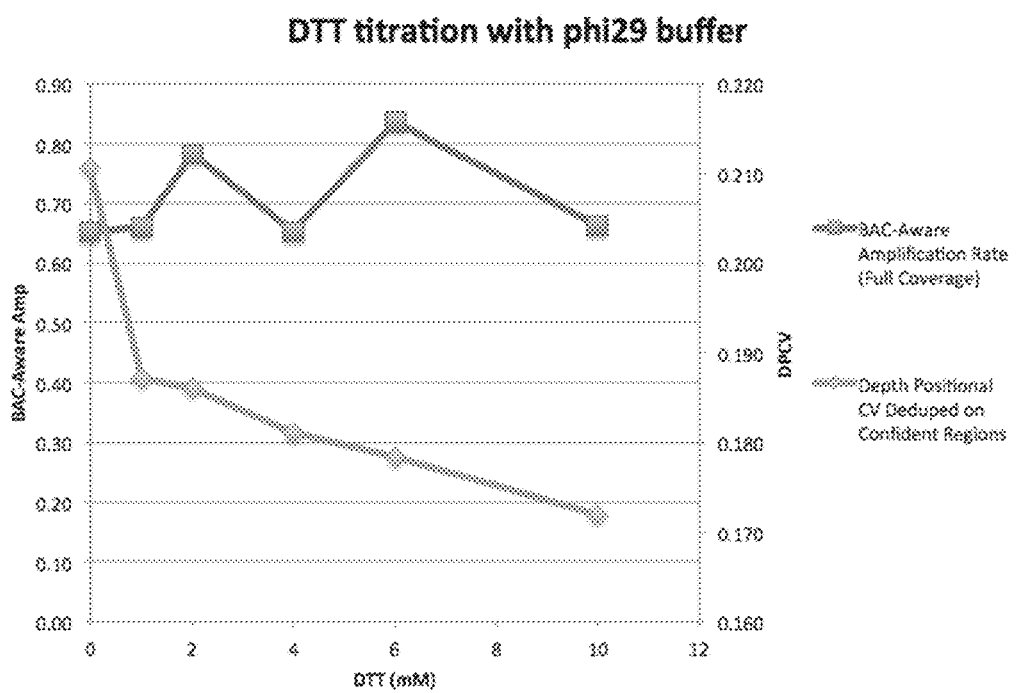
FIG. 7 shows the results of DTT addition on DPCV and amplification rate.

DTT addition was tested for the effect on DPCV and amplification rate in priming free amplification by polymerization reactions. As shown in FIG. 7, addition of DTT was tested over a concentration range of 1.0 mM to 10 mM. Advantageously, across the range of tested DTT concentrations, beneficial reduction in DPCV was observed without appreciable effect on the amplification rate. Higher concentrations of DTT resulted in even more reduction in DPCV. As such DPCV was improved with the addition of DTT without adversely affecting amplification rate.

Example 7

Polymerization Conditions Optimization for Whole Genome Analysis

Figure 8A:
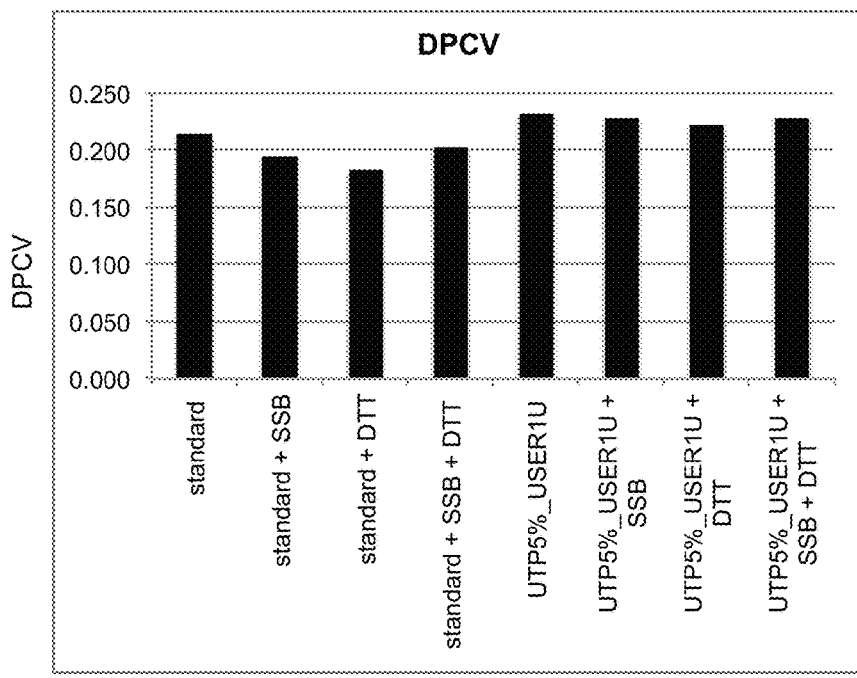
FIG. 8A shows the effect of SSB, DTT or both on DPCV using standard conditions.
Figure 8B:
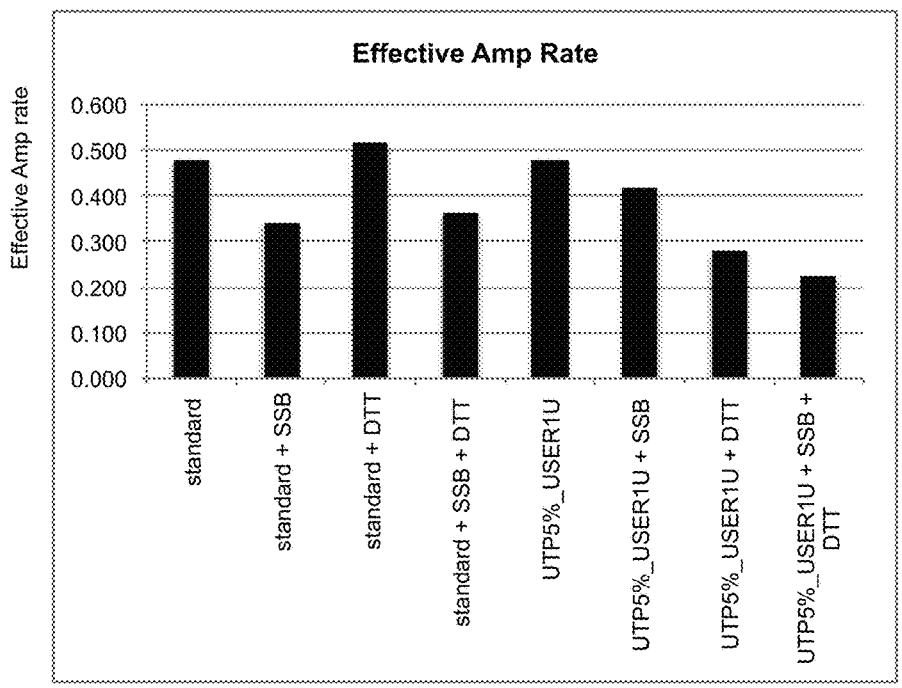
FIG. 8B shows the effect of addition of SSB on amplification rate.
Figure 8C:
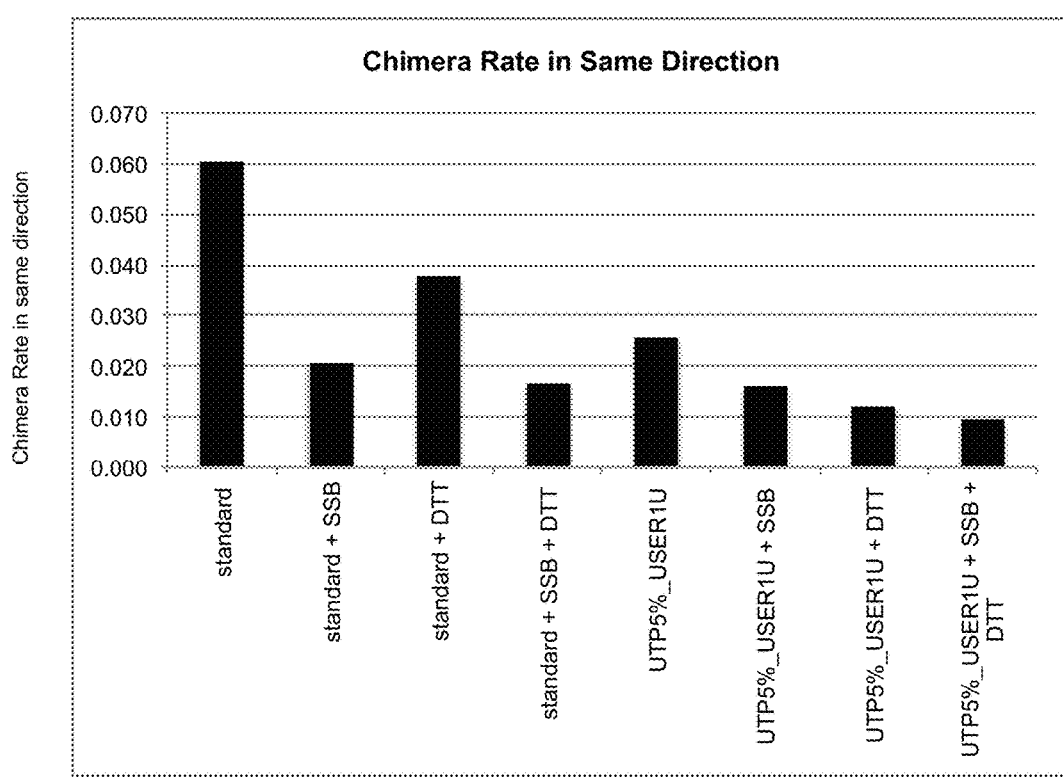
FIG. 8C shows the effect of addition of SSB on chimera reduction.

Various reaction components for priming free amplification by polymerization reactions were tested in a number of combinations to determine optimized polymerization for whole genome template sample. As shown in FIG. 8A, the standard condition including addition of SSB, DTT or both had lower DPCV as compared to similar condition with higher dUTP (5%) concentration. As shown in FIG. 8B, the data suggested that addition of SSB reduced amplification rate, which was reduced even further in presence of 5% dUTP. As shown in FIG. 8C SSB reduces chimeras as compared to conditions where SSB was omitted. DTT also reduced amp rate.

Example 8

Polymerization Reaction Time Course

Figure 9:
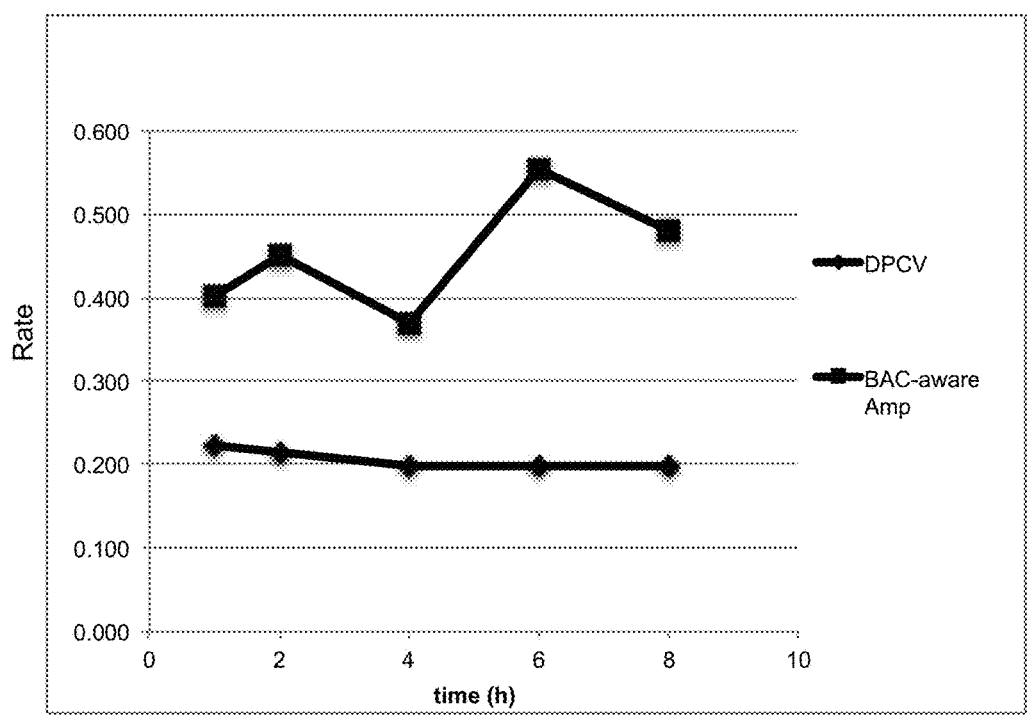
FIG. 9 shows the effect of time on DPCV and amplification rates.
Figure 12A:
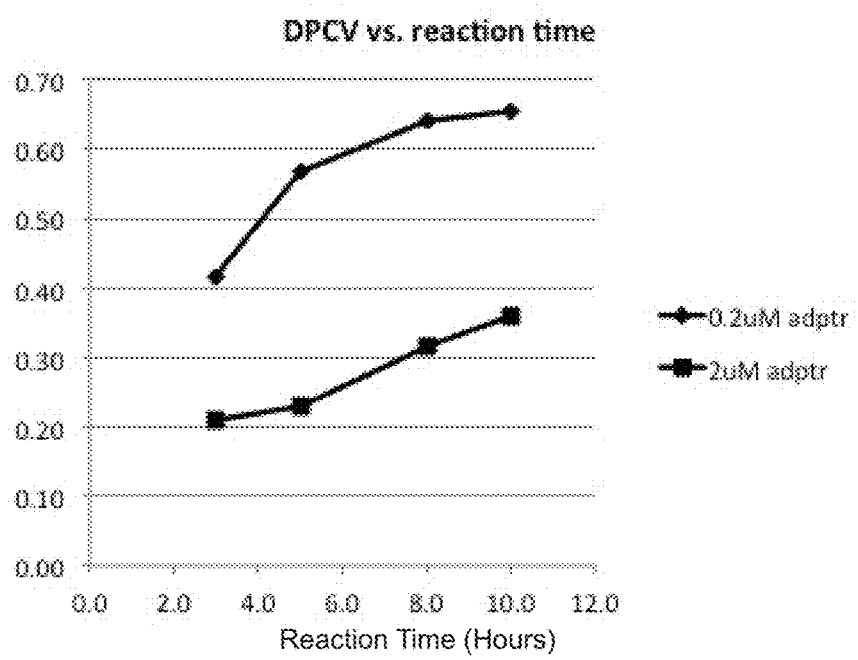
FIG. 12A shows the effect of barcoding ligation reaction time on DPCV.
Figure 12B:
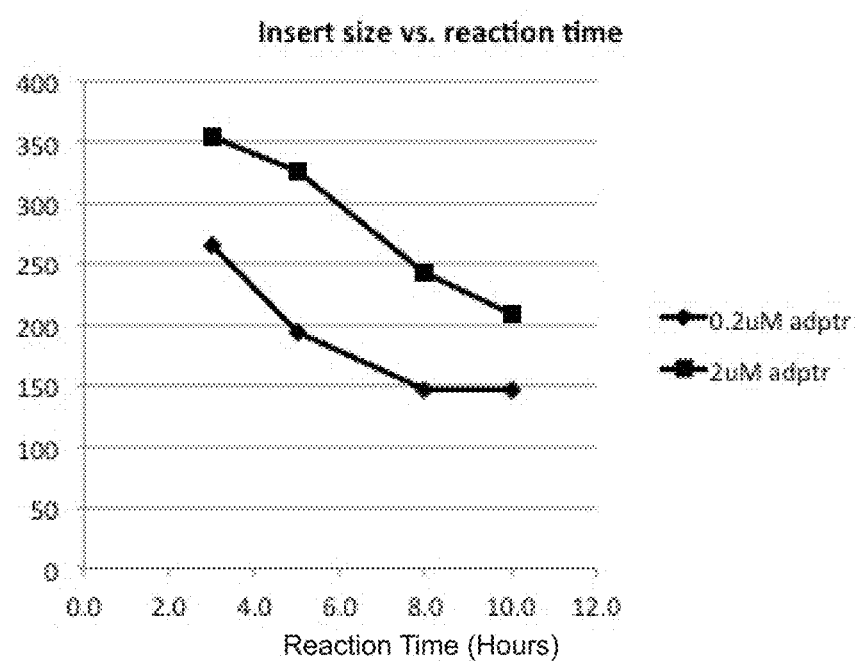
FIG. 12B shows the effect of barcoding ligation reaction time on insert size.
Figure 12C:
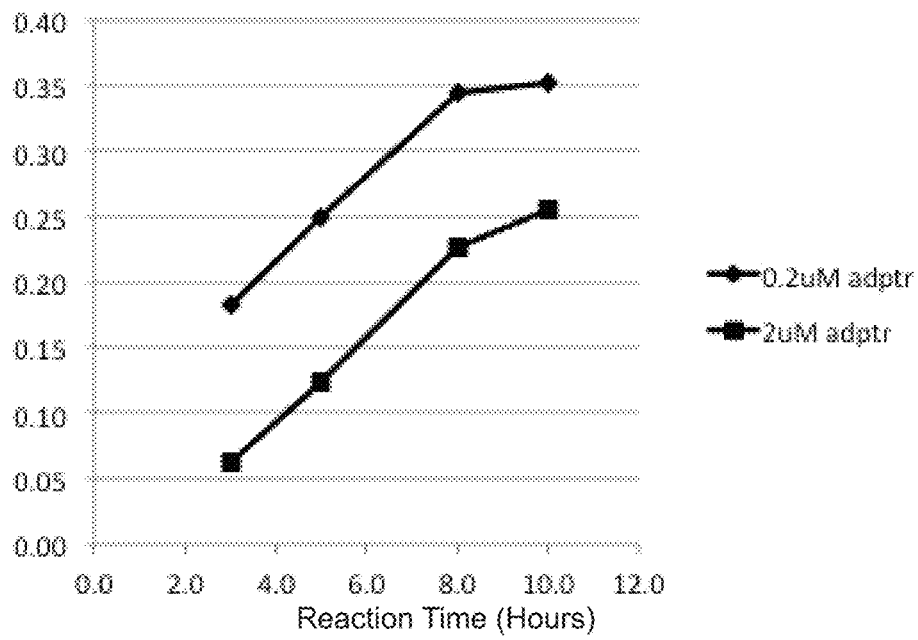
FIG. 12C shows the effect of barcoding ligation reaction time on chimeras.
Figure 12D:
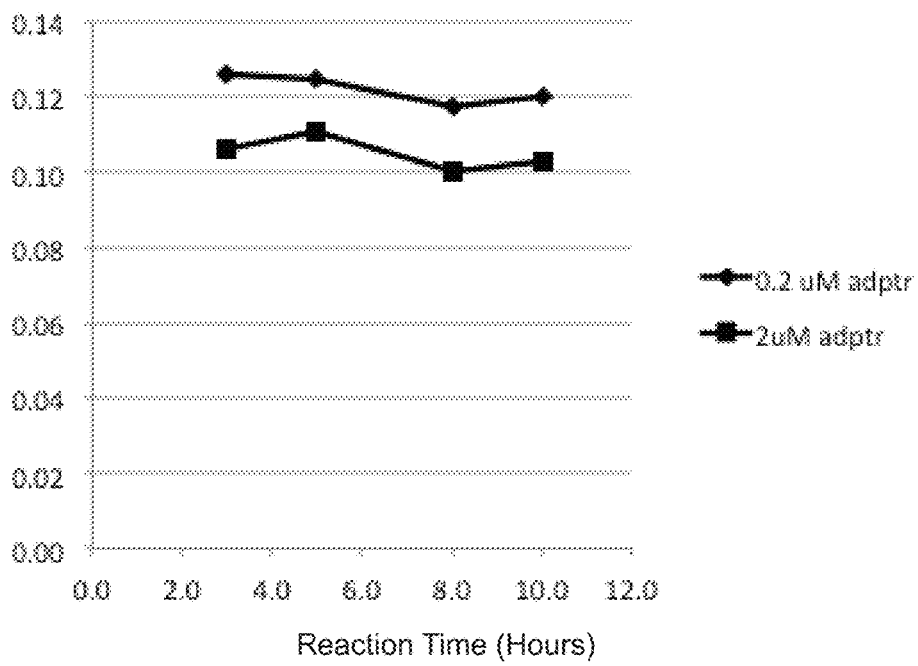
FIG. 12D shows the effect of barcoding ligation reaction time on unmapped fraction.
Figure 12E:
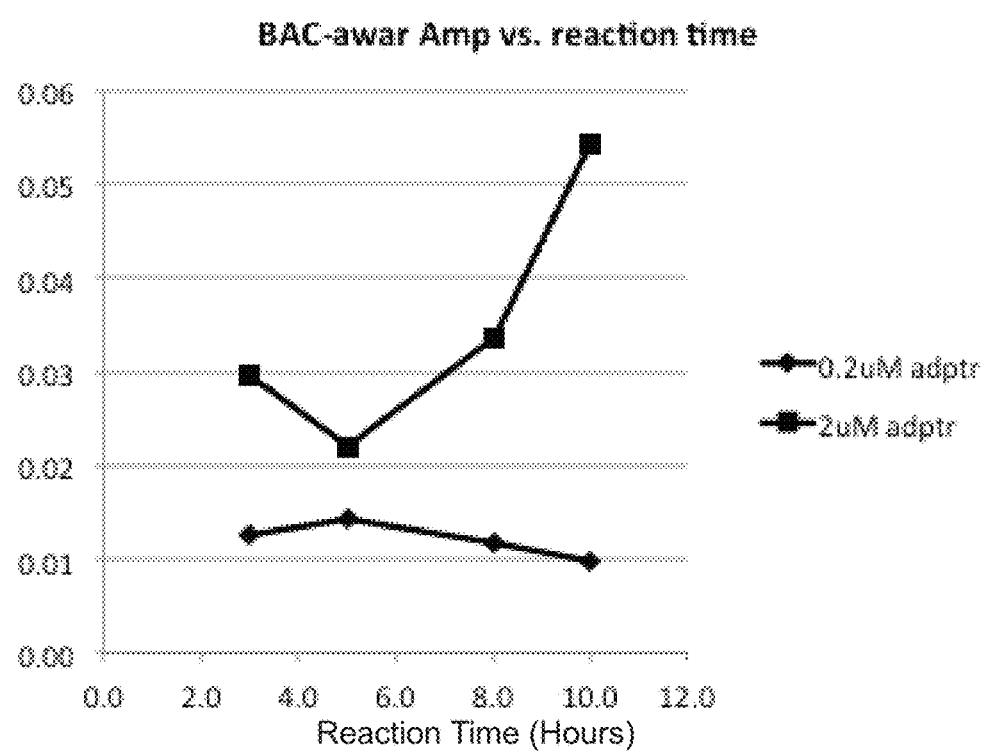
FIG. 12E shows the effect of barcoding ligation reaction time on amplification rate.

In a bulk priming free amplification by polymerization reaction using phi29 polymerase at 32 nM, both DPCV and amplification rate were measured over time, up to 8 hours. As shown in FIG. 9, the DPCV improves (is reduced) slightly from 1 to 4 hours (0.22 to 0.20) and essentially plateaus over the remaining 4 hours. The amplification rate (shown as BAC-aware Amp) remained relatively flat across the entire time series tested. Additional phi29, testing at 80 nM did not significantly impact the above results (data not shown).

Example 9

Effect of Template Denaturation on DPCV and Amplification Rate

To test the effect of template denaturation on DPCV and amplification rate in priming free amplification by polymerization reactions, three conditions where tested in blank GEMs: i) no denaturation (no heat), ii) NaOH denaturation and iii) heat denaturation. Experiments were performed in duplicate. As shown in FIG. 10, the results of the experiment indicated that DPCV is fairly stable in all conditions tested but amplification is substantially lower when the template is not denatured. As tested, either NaOH or heat denaturation can effectively be used for successful polymerization. However, a slight advantage for heat denaturation was observed.

Example 10

Titration of Adaptor Concentration

The suitable range for adaptor concentration for molecular barcoding was tested by titration of and adaptor and measuring DPCV and dup rate. The tested conditions were 0.4 U/uL Phi29 DNA polymerase, 54 nM-500 nM adaptor 12 (duplex pR1 in-line BC adaptor).

As shown in FIG. 11, both DPCV and dup rate was stable between the tested range of 54 nM-500 nM adaptor, although an increase in unmapped fraction was observed as adaptor concentration increased.

It is expected from these results that the suitable range of adaptor concentration might be extendable to 1 nM-10 uM by including SSB (single stranded binding protein) or other additives to reduce the unmapped fraction.

The table in FIG. 11 shows the effect of adaptor concentration on dup rate (measure of library complexity) and DPCV (measure of coverage evenness). The first column shows the adaptor concentration used with 'LL ctrl' sample has no adaptors. The third column shows the depth of sequencing (deduped—duplicates are removed before calculating this number). The fourth column shows the dup rate post downsampling all the samples to 0.25× coverage, this number is also calculated using the barcode information. The fifth column shows DPCV, measure of coverage evenness. The results shown indicated that across a broad range of adaptor concentrations, the dup rate and DPCV remains relatively flat suggesting the reaction's tolerance to broad range of adaptor concentrations.

Example 11

Effect of Barcoding Ligation Reaction Time

This experiment was designed to study the effect of reaction duration on different sequencing matrices. The study was conducted at two different adaptor (adptr) concentrations, 0.2 uM and 2 uM.

FIG. 12 panel A shows: DPCV reduces with shorter reaction time; panel B shows: insert size increases with shorter reaction time; panel C shows: chimeras are reduced with shorter reaction time; panel D shows:unmapped fraction is unaffected as a function of time; and panel E shows: at lower adaptor concentration, the amplification (Amp) rate is flat, higher adaptor concentration shows increase in amplification after 4 hours. Based on these results, 3 hours of reaction time can be interpreted to be optimum of most matrices.

Example 12

T4 Ligase Molecular Barcoding of Priming Free Amplification Products

FIG. 13 shows the results of control experiments to test the specificity of T4 ligase based barcoding. The readout is P5/P7 quants. P5/P7 quant of >5 is considered positive. The results show that it is necessary to have ligase, template, and adaptor present to make a useful set of barcoded templates (e.g., a library of templates for sequencing). Absence of any of the three components results in an inadequate set of barcoded templates for use, for example as a library of amplified templates for sequencing.

Example 13

Figure 14A:
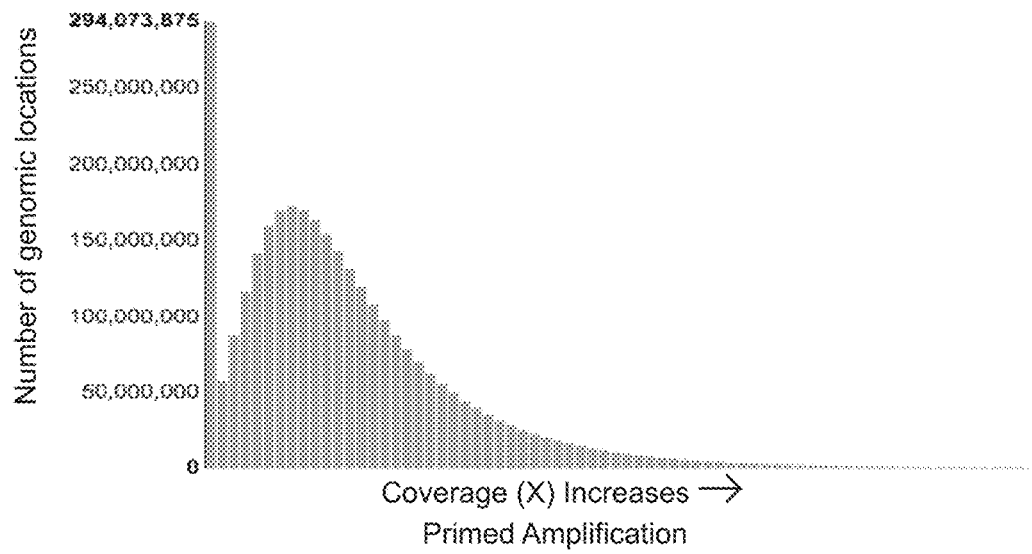
FIG. 14A is a histogram illustrating evenness of sequencing coverage in a primed amplification reaction.
Figure 14B:
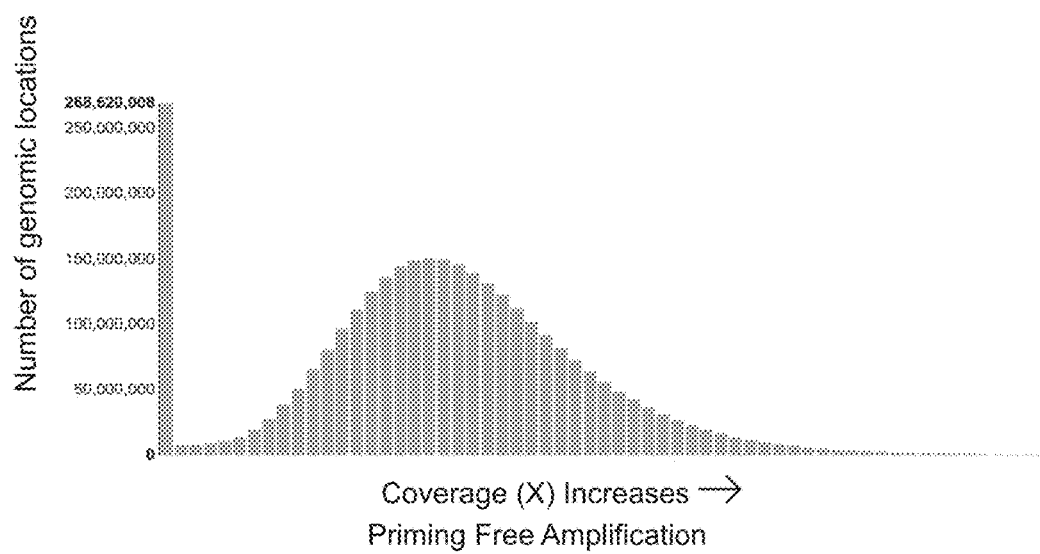
FIG. 14B is a histogram illustrating evenness of sequencing coverage in a primer free amplification.

Evenness of Sequencing Coverage—Primed Amplification vs. Priming Free Amplification FIGS. 14A and 14B are histograms comparing the coverage evenness between primed amplification (FIG. 14A) and priming free amplification (FIG. 14B). The y-axis in both figures is the number of genomic locations. The x-axis plots increasing coverage from left (0) to the right. The data clearly shows the improved coverage eveness advantage observed in the priming free amplification protocol, which had a more poissonian distribution when compared to the distribution for primed amplification.

Example 14

Concentration of nMer (uM) Effect on DPCV

Figure 15:
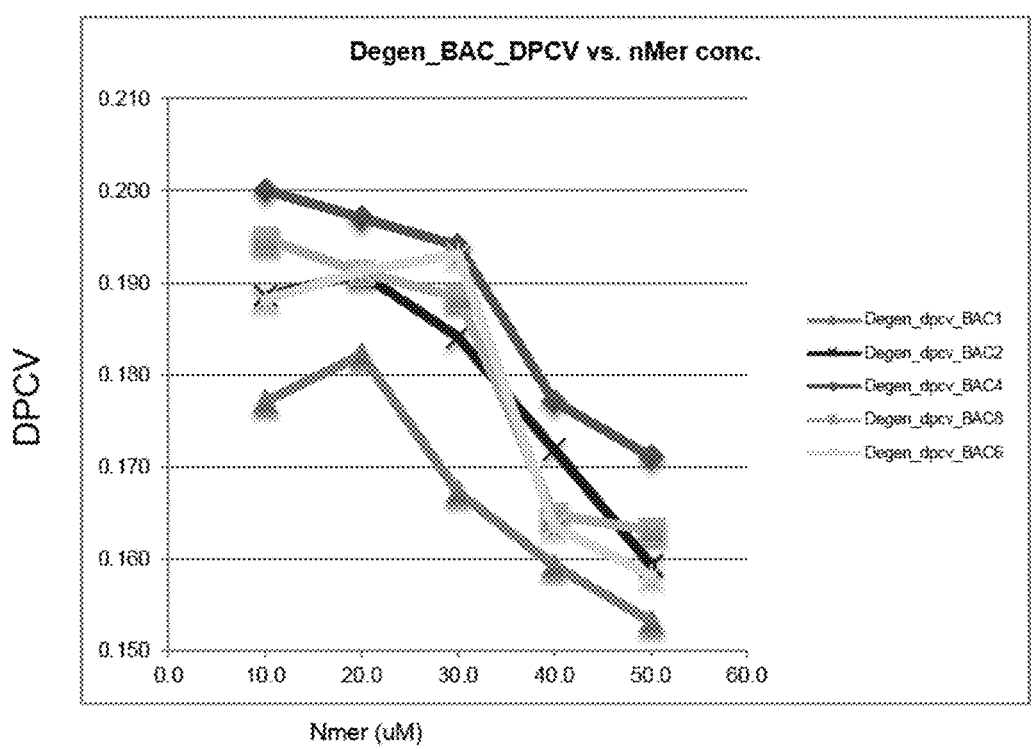
FIG. 15 shows the effect of nMer concentration (uM) on five different barcoded template library samples.

The effect of nMer concentration (uM) was tested on five different barcoded template library samples prepared as described above. As shown in FIG. 15, at higher concentrations of nMer, above 30 uM, advantageously reduced DPCV in four out of five samples was observed. At 40 uM and 50 uM, every sample showed reduced DPCV with the greatest reduction being observed at 50 uM nMer concentration. The results indicated that higher rather than lower concentrations of nMer are required for improved DPCV reduction.

Example 15

SPRI Stringency Cut Effect on DPCV

Figure 16:
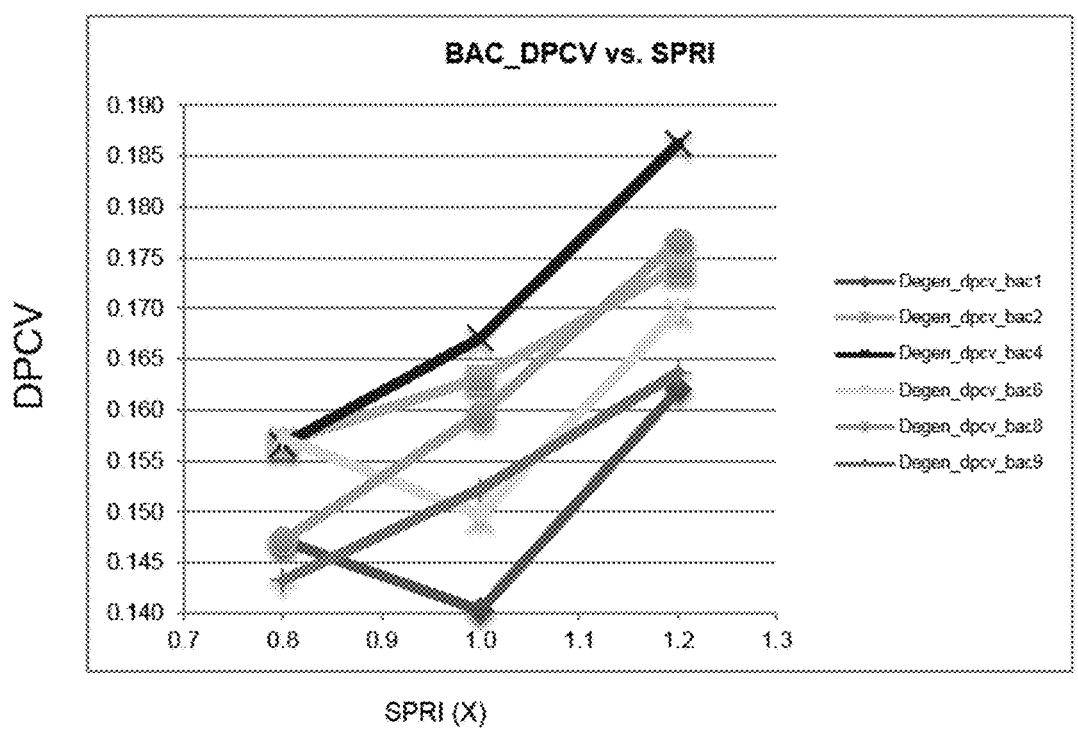
FIG. 16 shows the effect of SPRI (Solid Phase Reversible Immobilization) stringency cut on six different barcoded template library samples.

The effect of SPRI (Solid Phase Reversible Immobilization) stringency cut was tested on six different barcoded template library samples as described above. As shown in FIG. 16, more stringent SPRI cuts advantageously resulted in reduced DPCV.

Example 16

Total Reaction Time Effect on DPCV

Figure 17:
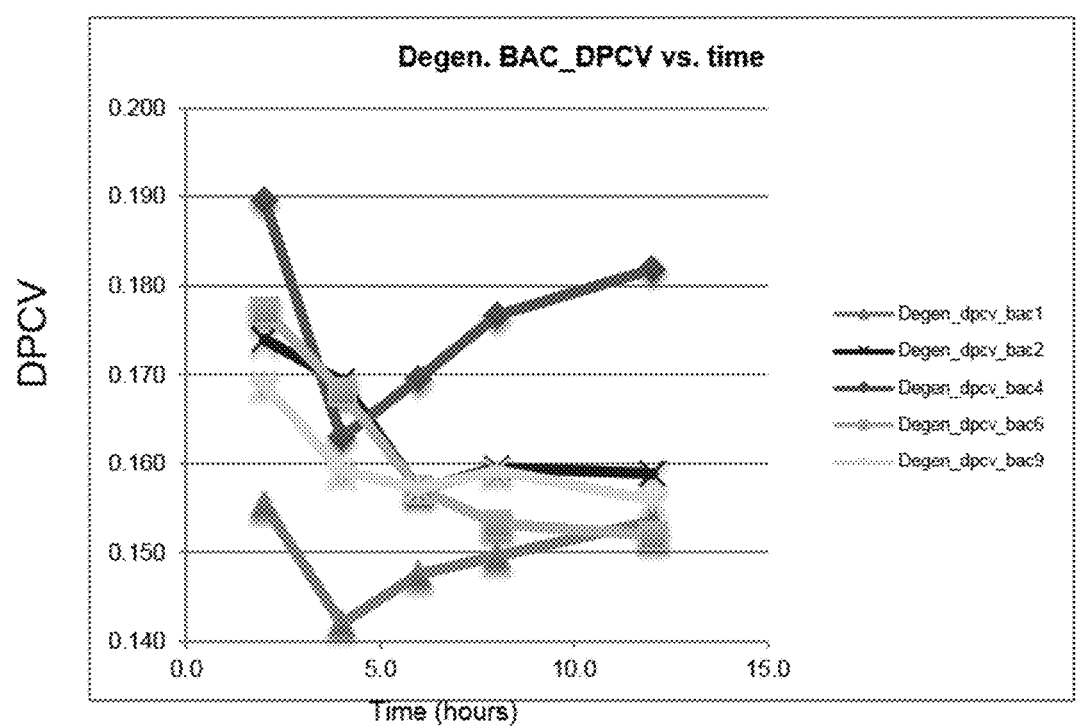
FIG. 17 shows the effect of total reaction time on DPCV on five different barcoded template library samples.

The effect of total reaction time on DPCV was tested on five different barcoded template library samples as described above. As shown in FIG. 17, under the instant test conditions, the DPCV is relatively unaffected by time. Time points tested ranged from 2 hours to over 10 hours.

Example 17

USER Concentration Effect on DPCV

Figure 18:
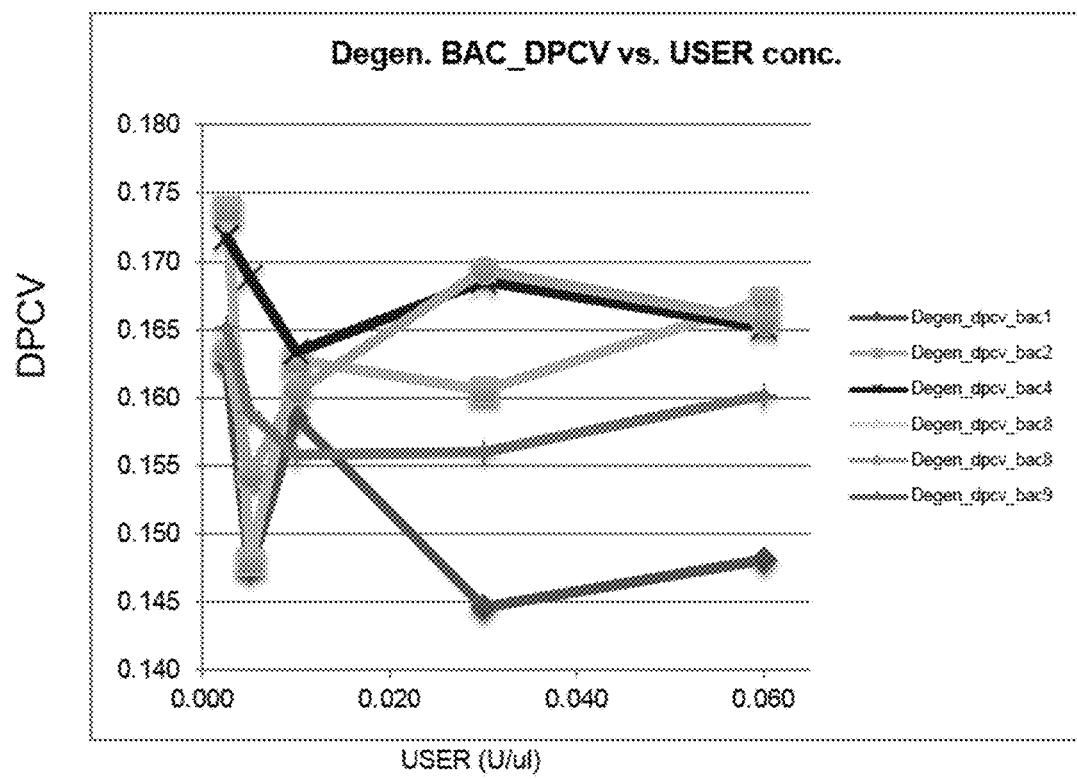
FIG. 18 shows the effect of Uracil-Specific Excision Reagent (USER®) concentration on DPCV for six different barcoded template library samples.

The effect of USER™ (Uracil-Specific Excision Reagent; New England Biolabs® Inc. (NEB), Ipswich, Mass.) concentration on DPCV was tested on six different barcoded template library samples as described above. As shown in FIG. 18, under the experimental test conditions, on average the DPCV is relatively unaffected by USER concentration.

It should be understood from the foregoing that, while particular implementations have been illustrated and described, various modifications may be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A method of preparing a barcoded nucleic acid molecule, comprising:
   (a) providing a template nucleic acid molecule, deoxynucleotide triphosphates (dNTPs), deoxyuridine triphosphates (dUTPs), a random primer, a polymerase, an enzyme capable of excising uracil, and a bead comprising a plurality of oligonucleotide barcode molecules releasably attached thereto;
   (b) subjecting the template nucleic acid molecule, the polymerase, dNTPs, dUTPs and the random primer to conditions sufficient to synthesize a double stranded nucleic acid molecule comprising a first strand, wherein said first strand comprises a uracil;
   (c) excising the uracil from the double stranded nucleic acid molecule with the enzyme to provide a nick in the double stranded nucleic acid molecule;
   (d) subjecting the double stranded nucleic acid molecule to a nucleic acid extension reaction under conditions sufficient to yield a plurality of single stranded nucleic acid fragments; and
   (e) using an oligonucleotide barcode molecule of the plurality of oligonucleotide barcode molecules and a single stranded nucleic acid fragment of the plurality of single stranded nucleic acid fragments to generate a barcoded nucleic acid molecule.

2. The method of claim 1, wherein (a)-(e) are performed in a single reaction volume.

3. The method of claim 1, wherein the bead, the template nucleic acid molecule, dNTPs, dUTPs, the random primer, the polymerase, and the enzyme are provided in a partition.

4. The method of claim 3, wherein the partition is a droplet in an emulsion.

5. The method of claim 1, wherein the bead is a degradable bead selected from the group consisting of a chemically degradable bead, a photodegradable bead, and a thermally degradable bead.

6. The method of claim 5, wherein the bead is a chemically degradable bead, and wherein the chemically degradable bead comprises chemically reducible cross-linkers.

7. The method of claim 6, wherein the chemically reducible cross-linkers comprise disulfide linkages.

8. The method of claim 1, wherein, in (d), the nucleic acid extension reaction is isothermal.

9. The method of claim 1, wherein, in (e), the barcoded nucleic acid molecule is generated through use of a ligating enzyme, a polymerase enzyme, or a topoisomerase.

10. The method of claim 9, wherein the ligating enzyme is an adenosine triphosphate (ATP) independent enzyme.

11. The method of claim 10, wherein each of the plurality of oligonucleotide barcode molecules is adenylated and wherein the ATP independent enzyme is a thermostable 5' App DNA/RNA ligase.

12. The method of claim 9, wherein the topoisomerase is topoisomerase I.

13. The method of claim 9, wherein the ligating enzyme comprises a T4 DNA ligase.

14. The method of claim 1, wherein each of the plurality of oligonucleotide barcode molecules comprises a barcode sequence that is at least 4 nucleotides in length.

15. The method of claim 1, wherein the bead comprises at least 1,000,000 oligonucleotide barcode molecules releasably attached thereto.

16. The method of claim 1, wherein each of the plurality of oligonucleotide barcode molecules comprises one or more functional sequences.

17. The method of claim 16, wherein the one or more functional sequences are selected from an adapter sequence, a primer sequence, a primer annealing sequence, an attachment sequence, and a sequencing primer sequence.

18. The method of claim 16, wherein the one or more functional sequences comprise a blocking group.

19. The method of claim 16, wherein the one or more functional sequences comprise a random N-mer sequence 5 to 500 nucleotides in length.

20. The method of claim 1, further comprising releasing oligonucleotide barcode molecules of the plurality of oligonucleotide barcode molecules from the bead.

21. The method of claim 20, wherein the releasing comprises degrading the bead.

22. The method of claim 20, wherein the releasing comprises using a reducing agent to cleave a disulfide linkage between the plurality of oligonucleotide barcode molecules and the bead.

23. The method of claim 22, wherein the reducing agent is dithiothreitol (DTT) or tris(2-carboxyethyl) phosphine (TCEP).

24. The method of claim 1, wherein, in (a), dNTPs are provided at a concentration that is greater than a concentration of dUTPs.

25. The method of claim 1, further comprising sequencing the barcoded nucleic acid molecule or a derivative thereof.

26. The method of claim 1, wherein (b) comprises (i) coupling the random primer to the template nucleic acid molecule and (ii) extending the random primer to synthesize the first strand comprising the uracil.

27. The method of claim 17, wherein each of the plurality of oligonucleotide barcode molecules comprises a primer sequence and wherein, in (e), the barcoded nucleic acid molecule is generated by nucleic acid extension of the primer sequence.

28. The method of claim 1, wherein, in (d), the polymerase engages the double stranded nucleic acid molecule at the nick, wherein the nucleic acid extension reaction comprises a primer independent extension process, and wherein the polymerase comprises strand displacement activity.

29. The method of claim 1, wherein the primer is a random N-mer sequence 5 to 500 nucleotides in length.

30. The method of claim 29, wherein the random N-mer sequence is 5 to 25 nucleotides in length.

31. The method of claim 19, wherein the random N-mer sequence is 5 to 25 nucleotides in length.

32. The method of claim 18, further comprising performing a releasing operation to remove the blocking group, wherein the releasing operation comprises applying a stimulus selected from the group consisting of a thermal stimulus and a chemical stimulus.

33. The method of claim 27, wherein in (e), the nucleic acid extension is isothermal.

34. The method of claim 1, wherein each of the plurality of barcode oligonucleotide molecules is releasably attached to the bead through a labile bond.

35. The method of claim 34, wherein the labile bond is selected from the group consisting of a thermally cleavable bond, a chemically labile bond, and a photo-sensitive bond.

36. The method of claim 34, wherein the labile bond comprises a linkage selected from the group consisting of an ester linkage, a vicinal diol linkage, a Diels-Alder linkage, a sulfone linkage, a silyl ester linkage, a glycosidic linkage, a peptide linkage, and a phosphodiester linkage.

37. The method of claim 3, wherein the partition is a well.

* * * * *

UNITED STATES PATENT AND TRADEMARK OFFICE
CERTIFICATE OF CORRECTION

PATENT NO. : 10,221,436 B2
APPLICATION NO. : 14/990276
DATED : March 5, 2019
INVENTOR(S) : Paul Hardenbol et al.

Page 1 of 1

It is certified that error appears in the above-identified patent and that said Letters Patent is hereby corrected as shown below:

On the Title Page

Item (72), seventh inventor's Name:
In Column 1, please change "Kamila Belhocine" to --Zahra Kamila Belhocine--.

Signed and Sealed this
Nineteenth Day of May, 2020

Andrei Iancu
*Director of the United States Patent and Trademark Office*

SEQUENCE LISTING

<160> NUMBER OF SEQ ID NOS: 1

<210> SEQ ID NO 1

```
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (42)..(51)
<223> OTHER INFORMATION: a, c, t, g, u, unknown or other

<400> SEQUENCE: 1
tagaucgcac acucuuuccc uacacgacgc ucttccgatc tnnnnnnnnn n        51
```